US011844795B2

United States Patent

(12) United States Patent
Blanchette et al.

(10) Patent No.: US 11,844,795 B2
(45) Date of Patent: *Dec. 19, 2023

(54) COMBINATION THERAPY FOR CANCER TREATMENT

(71) Applicant: Ipsen Biopharm Ltd., Wrexham (GB)

(72) Inventors: Sarah F. Blanchette, Lynnfield, MA (US); Daryl C. Drummond, Lincoln, MA (US); Jonathan Basil Fitzgerald, Arlington, MA (US); Victor Moyo, Ringoes, NJ (US)

(73) Assignee: Ipsen Biopharm Ltd.

( * ) Notice: Subject to any disclaimer, the term of this patent is extended or adjusted under 35 U.S.C. 154(b) by 0 days.

This patent is subject to a terminal disclaimer.

(21) Appl. No.: 17/703,312

(22) Filed: Mar. 24, 2022

(65) Prior Publication Data

US 2023/0074866 A1 Mar. 9, 2023

Related U.S. Application Data

(63) Continuation of application No. 16/586,609, filed on Sep. 27, 2019, which is a continuation of application
(Continued)

(51) Int. Cl.
*A61K 31/436* (2006.01)
*A61K 31/4745* (2006.01)
(Continued)

(52) U.S. Cl.
CPC ........ *A61K 31/4745* (2013.01); *A61K 9/0019* (2013.01); *A61K 9/127* (2013.01);
(Continued)

(58) Field of Classification Search
CPC .................................................. A61K 31/4745
See application file for complete search history.

(56) References Cited

U.S. PATENT DOCUMENTS 4,604,463 A 8/1986 Miyasaka et al.
5,013,556 A 5/1991 Woodle et al.
(Continued)

FOREIGN PATENT DOCUMENTS

CA 2412790 A1 1/2002
CN 1829741 A 9/2006
(Continued)

OTHER PUBLICATIONS

Hubner et al, You are here: 2015 / Proffered paper sessions, https://abstracts.ncri.org.uk/abstract/expanded-analyses-of-napoli-1-phase-3-study-of-nal-iri-mm-398-with-or-without-5-fluorouracil-5fu-and-leucovorin-lv-versus-5-fluorouracil-and-leucovorin- 5fulv-in-metastatic-pancreatic-canc/ (Year: 2015).*
(Continued)

*Primary Examiner* — Benjamin J Packard
(74) *Attorney, Agent, or Firm* — McNeill Baur PLLC

(57) ABSTRACT

Combination therapies for treating cancer comprising administration of a topoisomerase-1 inhibitor and a PARP inhibitor are provided. The topoisomerase-1 inhibitor can be delivered as a liposomal formulation that provides for prolonged accumulation of the topoisomerase-1 inhibitor within a tumor relative to outside of the tumor. Therapeutic benefit can thereby be obtained by delaying the administration of the PARP inhibitor after each administration of a liposomal irinotecan formulation until the accumulation of the topoisomerase inhibitor in the tumor is sufficiently greater than outside the tumor to result in increased efficacy of the PARP inhibitor and topoisomerase inhibitor within the tumor, while reducing the peripheral toxicity of the combination therapy. The therapies disclosed herein are useful in the treatment of human cancers with solid tumors, including cervical cancer.

15 Claims, 31 Drawing Sheets

Related U.S. Application Data

No. 15/852,551, filed on Dec. 22, 2017, now Pat. No. 10,478,428, which is a continuation of application No. 15/337,274, filed on Oct. 28, 2016, now Pat. No. 9,895,365, which is a continuation of application No. PCT/US2016/047827, filed on Aug. 19, 2016.

(60) Provisional application No. 62/323,422, filed on Apr. 15, 2016, provisional application No. 62/308,924, filed on Mar. 16, 2016, provisional application No. 62/269,511, filed on Dec. 18, 2015, provisional application No. 62/269,756, filed on Dec. 18, 2015, provisional application No. 62/207,709, filed on Aug. 20, 2015, provisional application No. 62/207,760, filed on Aug. 20, 2015.

(51) Int. Cl.

| | |
|---|---|
| ***A61K 31/04*** | (2006.01) |
| ***A61K 31/166*** | (2006.01) |
| ***A61K 31/416*** | (2006.01) |
| ***A61K 31/4184*** | (2006.01) |
| ***A61K 31/475*** | (2006.01) |
| ***A61K 31/502*** | (2006.01) |
| ***A61K 31/55*** | (2006.01) |
| ***A61K 9/127*** | (2006.01) |
| ***A61K 47/20*** | (2006.01) |
| ***A61K 47/06*** | (2006.01) |
| ***A61K 9/00*** | (2006.01) |
| ***A61K 31/454*** | (2006.01) |
| ***A61K 31/5025*** | (2006.01) |
| ***A61K 45/06*** | (2006.01) |

(52) U.S. Cl.

CPC ............ *A61K 9/1271* (2013.01); *A61K 31/04* (2013.01); *A61K 31/166* (2013.01); *A61K 31/416* (2013.01); *A61K 31/4184* (2013.01); *A61K 31/436* (2013.01); *A61K 31/454* (2013.01); *A61K 31/475* (2013.01); *A61K 31/502* (2013.01); *A61K 31/5025* (2013.01); *A61K 31/55* (2013.01); *A61K 45/06* (2013.01); *A61K 47/06* (2013.01); *A61K 47/20* (2013.01)

(56) References Cited

U.S. PATENT DOCUMENTS

| | | | |
|---|---|---|---|
| 5,077,056 | A | 12/1991 | Bally et al. |
| 5,192,549 | A | 3/1993 | Barenolz et al. |
| 5,316,771 | A | 5/1994 | Barenholz et al. |
| 5,538,954 | A | 7/1996 | Koch et al. |
| 5,543,152 | A | 8/1996 | Webb et al. |
| 5,593,622 | A | 1/1997 | Yoshioka et al. |
| 5,676,971 | A | 10/1997 | Yoshioka et al. |
| 5,783,568 | A | 7/1998 | Schlessinger et al. |
| 5,785,987 | A | 7/1998 | Hope et al. |
| 5,846,458 | A | 12/1998 | Yoshioka et al. |
| 6,110,491 | A | 8/2000 | Kirpotin |
| 6,210,707 | B1 | 4/2001 | Papahadjopoulos et al. |
| 6,214,388 | B1 | 4/2001 | Benz et al. |
| 6,241,999 | B1 | 6/2001 | Ye et al. |
| 6,355,268 | B1 | 3/2002 | Slater et al. |
| 6,403,569 | B1 | 6/2002 | Achterrath |
| 6,465,008 | B1 | 10/2002 | Slater et al. |
| 6,511,676 | B1 | 1/2003 | Boulikas |
| 6,545,010 | B2 | 4/2003 | Bissery |
| 6,720,001 | B2 | 4/2004 | Chen et al. |
| 6,787,132 | B1 | 9/2004 | Gabizon et al. |
| 6,794,370 | B2 | 9/2004 | Achterrath |
| 7,022,336 | B2 | 4/2006 | Papahadjopoulos et al. |
| 7,060,828 | B2 | 6/2006 | Madden et al. |
| 7,135,177 | B2 | 11/2006 | Benz et al. |
| 7,219,016 | B2 | 5/2007 | Rimm et al. |
| 7,244,448 | B2 | 7/2007 | Madden et al. |
| 7,244,826 | B1 | 7/2007 | Marks et al. |
| 7,507,407 | B2 | 3/2009 | Benz et al. |
| 7,829,113 | B2 | 11/2010 | Okada et al. |
| 7,842,676 | B2 | 11/2010 | Janoff et al. |
| 7,846,440 | B2 | 12/2010 | Schoeberl et al. |
| 7,846,473 | B2 | 12/2010 | Yoshino et al. |
| 7,850,990 | B2 | 12/2010 | Tardi et al. |
| 7,871,620 | B2 | 1/2011 | Benz et al. |
| 7,892,554 | B2 | 2/2011 | Marks et al. |
| 8,067,432 | B2 | 11/2011 | Anderson et al. |
| 8,147,867 | B2 | 4/2012 | Hong et al. |
| 8,329,213 | B2 | 12/2012 | Hong et al. |
| 8,496,961 | B2 | 7/2013 | Hong et al. |
| 8,658,203 | B2 | 2/2014 | Drummond et al. |
| 8,703,181 | B2 | 4/2014 | Hong et al. |
| 8,992,970 | B2 | 3/2015 | Hong et al. |
| 9,339,497 | B2 | 5/2016 | Bayever et al. |
| 9,364,473 | B2 | 6/2016 | Bayever et al. |
| 9,452,162 | B2 | 9/2016 | Bayever et al. |
| 9,492,442 | B2 | 11/2016 | Bayever et al. |
| 9,511,155 | B2 | 12/2016 | Drummond et al. |
| 9,616,081 | B2 | 4/2017 | Okabe |
| 9,717,723 | B2 | 8/2017 | Hong et al. |
| 9,717,724 | B2 | 8/2017 | Bayever et al. |
| 9,724,303 | B2 | 8/2017 | Hong et al. |
| 9,730,891 | B2 | 8/2017 | Hong et al. |
| 9,737,528 | B2 | 8/2017 | Drummond et al. |
| 9,782,349 | B2 | 10/2017 | Hong et al. |
| 9,895,365 | B2 | 2/2018 | Blanchette et al. |
| 10,350,201 | B2 | 7/2019 | Hong et al. |
| 10,413,510 | B2 | 9/2019 | Hong et al. |
| 10,456,360 | B2 | 10/2019 | Drummond et al. |
| 10,478,428 | B2 | 11/2019 | Blanchette et al. |
| 10,722,508 | B2 | 7/2020 | Hong et al. |
| 10,980,795 | B2 | 4/2021 | Bayever et al. |
| 10,993,914 | B2 | 5/2021 | Drummond et al. |
| 11,052,079 | B2 | 7/2021 | Hong et al. |
| 11,071,726 | B2 | 7/2021 | Fitzgerald et al. |
| 11,318,131 | B2 | 5/2022 | Adiwijaya et al. |
| 11,344,552 | B2 | 5/2022 | Bayever et al. |
| 11,369,597 | B2 | 6/2022 | Bayever et al. |
| 2002/0035091 | A1 | 3/2002 | Govindarajan et al. |
| 2002/0102298 | A1 | 8/2002 | Needham |
| 2002/0146450 | A1 | 10/2002 | Slater et al. |
| 2002/0192275 | A1 | 12/2002 | Zalipsky et al. |
| 2003/0138481 | A1 | 7/2003 | Zadi |
| 2004/0002505 | A1 | 1/2004 | Ozawa et al. |
| 2004/0071768 | A1 | 4/2004 | Sarris et al. |
| 2007/0110798 | A1 | 5/2007 | Drummond et al. |
| 2007/0219268 | A1 | 9/2007 | Hausheer |
| 2007/0265324 | A1 | 11/2007 | Wernet et al. |
| 2008/0108135 | A1 | 5/2008 | Marks et al. |
| 2009/0123419 | A1 | 5/2009 | Sherman et al. |
| 2009/0149397 | A1 | 6/2009 | Ossovskaya et al. |
| 2010/0056761 | A1 | 3/2010 | Schoeberl et al. |
| 2010/0068255 | A1 | 3/2010 | Benz et al. |
| 2011/0059076 | A1 | 3/2011 | McDonagh et al. |
| 2011/0104256 | A1 | 5/2011 | Wang et al. |
| 2011/0123523 | A1 | 5/2011 | Schoeberl et al. |
| 2012/0003160 | A1 | 1/2012 | Wolf et al. |
| 2012/0034295 | A1 | 2/2012 | Spiegel et al. |
| 2012/0045524 | A1 | 2/2012 | Wernet et al. |
| 2012/0269812 | A1 | 10/2012 | Baum et al. |
| 2012/0282325 | A1 | 11/2012 | Tong et al. |
| 2013/0209481 | A1 | 8/2013 | Zhou et al. |
| 2013/0236459 | A1 | 9/2013 | Baum et al. |
| 2013/0274281 | A1 | 10/2013 | Bradley |
| 2014/0065204 | A1 | 3/2014 | Hayes et al. |
| 2014/0170075 | A1* | 6/2014 | Drummond .......... A61K 31/704 424/9.32 |
| 2015/0182460 | A1 | 7/2015 | Hong et al. |
| 2015/0182521 | A1 | 7/2015 | Bayever et al. |
| 2015/0328156 | A1 | 11/2015 | Bayever et al. |
| 2015/0374682 | A1 | 12/2015 | Bayever et al. |
| 2016/0030341 | A1 | 2/2016 | Hong et al. |
| 2016/0030342 | A1 | 2/2016 | Hong et al. |
| 2016/0058704 | A1 | 3/2016 | Tardi et al. |

(56) References Cited

U.S. PATENT DOCUMENTS

| | | | |
|---|---|---|---|
| 2016/0074382 A1 | 3/2016 | Bayever et al. |
| 2016/0206615 A1 | 7/2016 | Tangutoori et al. |
| 2016/0303264 A1 | 10/2016 | Hendricks et al. |
| 2016/0346272 A1 | 12/2016 | Bayever et al. |
| 2017/0049767 A1 | 2/2017 | Blanchette et al. |
| 2017/0049775 A1 | 2/2017 | Bayever et al. |
| 2017/0202840 A1 | 7/2017 | Bayever et al. |
| 2017/0333421 A1 | 11/2017 | Adiwijaya et al. |

FOREIGN PATENT DOCUMENTS

| | | |
|---|---|---|
| CN | 101878229 A | 11/2010 |
| CN | 1980637 B | 2/2014 |
| WO | 1997028156 A1 | 8/1997 |
| WO | 2000023052 A1 | 4/2000 |
| WO | 2003013536 A2 | 2/2003 |
| WO | 2003030864 A1 | 4/2003 |
| WO | 2003101474 A1 | 12/2003 |
| WO | 2004017940 A3 | 4/2004 |
| WO | 2004093795 A3 | 11/2004 |
| WO | 2005000900 A1 | 1/2005 |
| WO | 2005107712 A1 | 11/2005 |
| WO | 2006110816 A2 | 10/2006 |
| WO | 2007076117 A2 | 7/2007 |
| WO | 2008114274 A1 | 9/2008 |
| WO | 2009040426 A1 | 4/2009 |
| WO | 2009126920 A3 | 3/2010 |
| WO | 2010125462 A2 | 11/2010 |
| WO | 2011066684 A1 | 6/2011 |
| WO | 2011153010 A1 | 12/2011 |
| WO | 2011160110 A1 | 12/2011 |
| WO | 2012012454 A1 | 1/2012 |
| WO | 2012031293 A1 | 3/2012 |
| WO | 2012078695 A2 | 6/2012 |
| WO | 2012079582 A1 | 6/2012 |
| WO | 2012146610 A1 | 11/2012 |
| WO | 2013006547 A2 | 1/2013 |
| WO | 2013138371 A1 | 9/2013 |
| WO | 2013158803 A1 | 10/2013 |
| WO | 2013188586 A1 | 12/2013 |
| WO | 2014113167 A1 | 7/2014 |
| WO | 2014157444 A1 | 10/2014 |
| WO | 2016094402 A1 | 6/2016 |
| WO | 2016168451 A1 | 10/2016 |
| WO | 2017031442 A1 | 2/2017 |
| WO | 2017031445 A1 | 2/2017 |
| WO | 2017034957 A1 | 3/2017 |
| WO | 2017066726 A1 | 4/2017 |
| WO | 2017172678 A1 | 10/2017 |
| WO | 2017199093 A1 | 11/2017 |
| WO | 2018083470 A1 | 5/2018 |

OTHER PUBLICATIONS

EP3266456: Proprietor's Response to O1 Submission in Response to Proprietor's Reply to Opposition, dated Nov. 18, 2022, 5 pages.

EP3266456: Proprietor's Response to O2 and O3 Submissions in Response to Proprietor's Reply to Opposition, dated Dec. 9, 2022, 5 pages.

EP3337467: Sandoz AG Opposition dated Sep. 9, 2021, 24 pages.

EP3337467: Sandoz AG Opposition dated Sep. 9, 2021, D1 (Lorusso P, et al., "Phase I Study of the Safety, Pharmacokinetics (PK), and Pharmacodynamics (PD) of the Poly(ADP-ribose) Polymerase (PARP) Inhibitor Veliparib (ABT-888; V) in Combination with Irinotecan (CPT-11; Ir) in Patients (pts) with Advanced Solid Tumors," J Clin Oncol. 29(15) Suppl:3000 (2011), 2 pages).

EP3337467: Sandoz AG Opposition dated Sep. 9, 2021, D1a (Lorusso P, et al., "Phase I Study of the Safety, Pharmacokinetics, and Pharmacodynamics of the Poly(ADP-ribose) Polymerase (PARP) Inhibitor Veliparib (ABT-888) in Combination with Irinotecan (CPT-11) in Patients with Advanced Solid Tumors," Presentation presented at American Society of Clinical Oncology 2011 Meeting, 37 pages).

EP3337467: Sandoz AG Opposition dated Sep. 9, 2021, D2 (Berlin J, et al., "A Phase 1 Dose-Escalation Study of Veliparib with Bimonthly FOLFIRI in Patients with Advanced Solid Tumors," J Clin Oncol. 32(15) Suppl:2574 (2014), 4 pages).

EP3337467: Sandoz AG Opposition dated Sep. 9, 2021, D3 (Tahara M, et al., "The Use of Olaparib (AZD2281) Potentiates SN-38 Cytotoxicity in Colon Cancer Cells by Indirect Inhibition of Rad51-Mediated Repair of DNA Double-Strand Breaks," Mol Cancer Ther. 13(5):1170-80 (2014)).

EP3337467: Sandoz AG Opposition dated Sep. 9, 2021, D4 (Neijzen R, et al., "Irinophore C™, a Lipid Nanoparticle Formulation of Irinotecan, Improves Vascular Function, Increases the Delivery of Sequentially Administered 5-FU in HT-29 Tumors, and Controls Tumor Growth in Patient Derived Xenografts of Colon Cancer," J Control Release. 199:72-83 (2015), Epub 2014).

EP3337467: Sandoz AG Opposition dated Sep. 9, 2021, D5 (Clinical Trials Identifier NCT01770353: May 5, 2015 update submitted, "A Pilot Study in Patients Treated with MM-398 to Determine Tumor Drug Levels and to Evaluate the Feasibility of Ferumoxytol Magnetic Resonance Imaging to Measure Tumor Associated Macrophages." 5 pages).

EP3337467: Sandoz AG Opposition dated Sep. 9, 2021, D6 (Shah M, et al., "The Relevance of Drug Sequence in Combination Chemotherapy," Drug Resist Updat. 3(6):335-356 (2000).

EP3337467: Sandoz AG Opposition dated Sep. 9, 2021, D7 (O'Sullivan C, et al., "Beyond Breast and Ovarian Cancers: PARP Inhibitors for BRCA Mutation-Associated and BRCA-Like Solid Tumors," Front Oncol. 4:42 doi: 10.3389/fonc.2014.00042 (2014), 13 pages).

EP3337467: Sandoz AG Opposition dated Sep. 9, 2021, D8 (ONIVYDE package insert, revision Oct. 22, 2015, 18 pages).

EP3337467: Sandoz AG Opposition dated Sep. 9, 2021, D9 (Carnevale J and Ko A, "MM-398 (Nanoliposomal Irinotecan): Emergence of a Novel Therapy for the Treatment of Advanced Pancreatic Cancer," Future Oncol. 12(4):453-64 (2016). Epub 2015).

EP3337467: Sandoz AG Opposition dated Sep. 9, 2021, D10 (Clinical Trials Identifier NCT02631733: Dec. 15, 2015 submitted, "A Phase I Study of a Combination of MM-398 and Veliparib in Solid Tumors." 7 pages).

EP3337467: Sandoz AG Opposition dated Sep. 9, 2021, D11 (Koshkaryev A, et al., "Differential Tissue Clearance Results in Improved Therapeutic Index for Irinotecan Liposome Injection (ONIVYDE) When Combined with the PARP Inhibitor Veliparib in Preclinical Cervical Tumors," In: Proceedings of the 107th Annual Meeting of the American Association for Cancer Research; Apr. 16-20, 2016; Cancer Res. 76(14 Suppl):Abstract nr 2075 (2016), 2 pages).

EP3337467: Sandoz AG Opposition dated Sep. 9, 2021, D12 (Livraghi L, et al., "PARP Inhibitors in the Management of Breast Cancer: Current Data and Future Prospects," BMC Med. 13:188; doi: 10.1186/s12916-015-0425-1 (2015), 16 pages)).

EP3337467: Proprietor's Submission in Response to Oppositions, dated Feb. 3, 2022, including main request and auxiliary requests 1-23, 140 pages.

EP3337467: Proprietor's Submission in Response to Oppositions, dated Feb. 3, 2022, D13 (Written transcript of the presentation associated with D1a: Lorusso P, et al., "Phase I Study of the Safety, Pharmacokinetics, and Pharmacodynamics of the Poly(ADP-ribose) Polymerase (PARP) Inhibitor Veliparib (ABT-888) in Combination with rinotecan (CPT-11) in Patients with Advanced Solid Tumors," American Society of Clinical Oncology 2011 Meeting), 7 pages).

EP3337467: Proprietor's Submission in Response to Oppositions, dated Feb. 3, 2022, D14 (Shah M, et al., "A Phase I Clinical Trial of the Sequential Combination of Irinotecan Followed by Flavopiridol," Clin Cancer Res. 11(10):3836-45 (2005)).

EP3337467: Proprietor's Submission in Response to Oppositions, dated Feb. 3, 2022, D15 (Sadetzki S, et al., "Childhood Exposure to External lonising Radiation and Solid Cancer Risk," Br J Cancer. 100(7):1021-25 (2009).

EP3337467: Proprietor's Submission in Response to Oppositions, dated Feb. 3, 2022, D16 (Practical Medical Oncology Textbook, Eds. Russio A, et al., Springer Nature Switzerland AG, Table of Contents, pp. I-XI (2021)).

(56) References Cited

OTHER PUBLICATIONS

EP3337467: Proprietor's Submission in Response to Oppositions, dated Feb. 3, 2022, D17 (CAMPTOSAR package insert, 2014, 39 pages).
EP3337467: Sandoz AG Response to Proprietor's Reply to the Notice of Opposition dated Mar. 23, 2022, 13 pages.
EP3337467: Sandoz AG Response to Proprietor's Reply to the Notice of Opposition dated Mar. 23, 2022, D18 (Kristeleit R, et al., "Phase 1/2 of Oral Rucaparib: Final Phase 1 Results," J Clin Oncol. 32(15_suppl):2573 (2014), 2 printed pages).
EP3337467: Proprietor's Response to Sandoz's Submission in Response to Proprietor's Reply to Opposition, dated Apr. 29, 2022, 16 pages.
EP3337467: Proprietor's Response to Sandoz's Submission in Response to Proprietor's Reply to Opposition, dated Apr. 29, 2022, D19 (excerpt from Jena V and Matic N, "Metastatic Cancer Chemistry," LP Inc. Publisher, North Carolina, Jan. 2016, pp. 12-13).
EP3337467: Proprietor's Response to Sandoz's Submission in Response to Proprietor's Reply to Opposition, dated Apr. 29, 2022, D20 (National Cancer Institute, "Metastatic Cancer: When Cancer Spreads. What is Metastatic Cancer?" Retrieved from https://www.cancer.gov/types/metastatic-cancer#/what, Apr. 18, 2022, 4 printed pages).
EP3337467: Proprietor's Response to Sandoz's Submission in Response to Proprietor's Reply to Opposition, dated Apr. 29, 2022, D20a (National Cancer Institute, "Metastatic Cancer: What is Metastatic Cancer?" The Wayback Machine Archive of https://www.cancer.gov/types/metastatic-cancer#/what, May 17, 2015, 2 printed pages).
EP3337467: Summons to attend oral proceedings including preliminary opinion of the Opposition Division dated Jun. 21, 2022, 16 pages.
EP3337478: Proprietor's Submission in Response to Oppositions, dated Dec. 7, 2021, including main request and auxiliary requests 1-3, 62 pages.
EP3337478: Proprietor's Submission in Response to Oppositions, dated Dec. 7, 2021, D18 (Wainberg Z, et al., "First-line Liposomal Irinotecan With Oxaliplatin, 5-Fluorouracil and Leucovorin (NALIRIFOX) in Pancreatic Ductal Adenocarcinoma: A Phase I/II Study," Eur J Cancer. 151:14-24 (2021)).
EP3337478: Proprietor's Submission in Response to Oppositions, dated Dec. 7, 2021, D19 (Declaration of Dr. Bin Zhang, including Annex A and Annex B, 15 pages).
EP3337478: Proprietor's Submission in Response to Oppositions, dated Dec. 7, 2021, D20 (Eisenhauer E, et al., "New Response Evaluation Criteria in Solid Tumours: Revised RECIST Guideline (version 1.1)," Eur J Cancer. 45(2):228-47 (2009)).
EP3337478: Proprietor's Submission in Response to Oppositions, dated Dec. 7, 2021, D21 (Jang G, et al., "Comparison of RECIST Version 1.0 and 1.1 in Assessment of Tumor Response by Computed Tomography in Advanced Gastric Cancer," Chin J Cancer Res. 25(6):689-694 (2013)).
EP3337478: Proprietor's Submission in Response to Oppositions, dated Dec. 7, 2021, D22 (Kim J, et al., "Comparison of RECIST 1.0 and RECIST 1.1 in Patients with Metastatic Cancer: A Pooled Analysis," J Cancer. 6(4):387-393 (2015)).
EP3337478: Proprietor's Submission in Response to Oppositions, dated Dec. 7, 2021, D23 (Trial Protocol for Conroy T, et al., "FOLFIRINOX versus Gemcitabine for Metastatic Pancreatic Cancer," N Engl J Med. 364(19):1817-25 (2011), 88 pages).
EP3337478: Proprietor's Submission in Response to Oppositions, dated Dec. 7, 2021, D24 (Package leaflet for Campto 20 mg/mL concentration for solution for infusion irinotecan hydrochloride, trihydrate, last revised May 2021, 11 pages).
EP3337478: Sandoz AG Response to Proprietor's Reply to the Notice of Opposition dated Feb. 1, 2022, 17 pages.
EP3337478: Sandoz AG Response to Proprietor's Reply to the Notice of Opposition dated Feb. 1, 2022, D25 (Tsai C, et al., "Nanovector-Based Therapies in Advanced Pancreatic Cancer," J Gastroint Oncol 2(3):185-94 (2011).
EP3337478: Sandoz AG Response to Proprietor's Reply to the Notice of Opposition dated Feb. 1, 2022, D26 (Yoo C, et al., "A Randomised Phase II Study of Modified FOLFIRI.3 vs Modified FOLFOX as Second-Line Therapy in Patients with Gemcitabine-Refractory Advanced Pancreatic Cancer," Br J Cancer. 101(10):1658-63 (2009)).
EP3337478: Sandoz AG Response to Proprietor's Reply to the Notice of Opposition dated Feb. 1, 2022, D27 Kalra A, et al., "Preclinical Activity of Nanoliposomal Irinotecan Is Governed by Tumor Deposition and Intratumor Prodrug Conversion," Cancer Res. 74(23):7003-13 (2014).
EP3337478: Proprietor's Response to Sandoz AG's Submission of Feb. 1, 2022, dated Feb. 28, 2022, 17 pages.
EP3337478: Summons to attend oral proceedings including preliminary opinion of the Opposition Division dated Apr. 13, 2022, 12 pages.
EP3337478: Sandoz AG (Opponent 1) Response to Preliminary Opinion of the Opposition Division, dated Nov. 22, 2022, 11 pages.
EP3337478: Proprietor Response to Preliminary Opinion of the Opposition Division, dated Nov. 24, 2022, 7 pages.
EP3337478: Proprietor Response to Preliminary Opinion of the Opposition Division, dated Nov. 24, 2022, D28 (Mahaseth H, et al., "Modified FOLFIRINOX Regimen With Improved Safety and Maintained Efficacy in Pancreatic Adenocarcinoma," Pancreas. 42(8):1311-5 (2013)).
EP3337478: Proprietor Response to Preliminary Opinion of the Opposition Division, dated Nov. 24, 2022, D29 (Blazer M, et al., "Tolerability and Efficacy of Modified FOLFIRINOX (mFOLFIRINOX) in Patients with Borderline-Resectable Pancreatic Cancer (BRPC) and Locally Advanced Unresectable Pancreatic Cancer (LAURPC)," J Clin Oncol. 32(3_suppl):275 (2014), 4 printed pages).
EP3337478: Proprietor Response to Preliminary Opinion of the Opposition Division, dated Nov. 24, 2022, D30 (Gunturu K, et al., "Single-Institution Experience with FOLFIRINOX in Advanced Pancreatic Cancer (PC)," J Clin Oncol. 30(4_suppl):330 (2012), 4 printed pages).
EP3337478: Proprietor Response to Preliminary Opinion of the Opposition Division, dated Nov. 24, 2022, D31 (Metges J, et al., "Efficacy and Safety of FOLFIRINOX in Patients with Metastatic Pancreatic Cancer," J Clin Oncol. 32(3_suppl):305 (2014), 4 printed pages).
EP3337478: Proprietor Response to Preliminary Opinion of the Opposition Division, dated Nov. 24, 2022, D32 (Alessandretti M, et al., "Safety and Efficacy of Modified Dose-Attenuated FOLFIRINOX Chemotherapy in Patients Over 65 Years with Advanced Pancreatic Adenocarcinoma," J Clin Oncol. 31(15_suppl):e15176 (2013), 4 printed pages).
EP3337478: EPO Notice of Sandoz AG Opposition dated May 6, 2021, 5 pages.
EP3337478: Sandoz AG Opposition dated May 6, 2021, 22 pages.
EP3337478: Sandoz AG Opposition dated May 6, 2021, D1 (History of Changes for Study NCT02551991, retrieved from ClinicalTrials.gov archive on May 3, 2021, 4 pages).
EP3337478: Sandoz AG Opposition dated May 6, 2021, D2 (Abstract O-0003. Von Hoff D, et al., "NAPOLI 1: Randomized Phase 3 Study of MM-398 (nal-IRI), With or Without 5-Fluorouracil and Leucovorin, Versus 5-Fluorouracil and Leucovorin, in Metastatic Pancreatic Cancer Progressed on or Following Gemcitabine-Based Therapy." Ann Oncol. 25(Suppl 2):ii105 (2014)).
EP3337478: Sandoz AG Opposition dated May 6, 2021, D3 (Marsh R, et al., "Pancreatic Cancer and FOLFIRINOX: A New Era and New Questions," Cancer Med. 4(6):853-63 (2015).
EP3337478: Sandoz AG Opposition dated May 6, 2021, D4 (ONIVYDE [MM-398] package insert, revision Oct. 22, 2015, 18 pages).
EP3337478: Sandoz AG Opposition dated May 6, 2021, D5 (Carnevale J and Ko A, "MM-398 (Nanoliposomal Irinotecan): Emergence of a Novel Therapy for the Treatment of Advanced Pancreatic Cancer," Future Oncol. 12(4):453-64 (2016). Epub 2015).
EP3337478: Sandoz AG Opposition dated May 6, 2021, D6 (Dean A, et al., Abstract TPS482. "A Randomized, Open-Label Phase II Study of Nanoliposomal Irinotecan (nal-IRI)-Containing Regimens Versus nab-Paclitaxel Plus Gemcitabine in Patients With Previously

(56) References Cited

OTHER PUBLICATIONS

Untreated Metastatic Pancreatic Adenocarcinoma (mPAC)," J Clin Oncol. 34(4_Suppl):tps482 (2016), DOI: 10.1200/jco.2016.34.4_suppl.tps482, 5 printed pages).
EP3337478: Sandoz AG Opposition dated May 6, 2021, D7 (Zhang H, "Onivyde for the Therapy of Multiple Solid Tumors," Onco Targets Ther. 9:3001-3007 (2016).
EP3337478: Sandoz AG Opposition dated May 6, 2021, D8 (Gaddy D, et al., "Abstract 4830: Preclinical Anti-tumor Activity of Nanoliposomal Irinotecan (Nal-IRI, MM-398) + 5-FU + Oxaliplatin in Pancreatic Cancer." In: Proceedings of the 107th Annual Meeting of the American Association for Cancer Research; Apr. 16-20, 2016; New Orleans, LA. Cancer Res. 76(14 Suppl): Abstract nr 4830 (2016), 4 printed pages).
EP3337478: Sandoz AG Opposition dated May 6, 2021, D9 (Parhi P, et al., "Nanotechnology-Based Combinational Drug Delivery: An Emerging Approach for Cancer Therapy," Drug Discov Today. 17(17-18):1044-52 (2012)).
EP3337478: EPO Notice of Generics [UK] Limited Opposition dated May 12, 2021, 5 pages.
EP3337478: Generics [UK] Limited Opposition dated May 12, 2021, 9 pages.
EP3337478: Generics [UK] Limited Opposition dated May 12, 2021, D10 (Conroy T, et al., "FOLFIRINOX versus Gemcitabine for Metastatic Pancreatic Cancer," N Engl J Med. 364(19):1817-25 (2011).
EP3337478: Generics [UK] Limited Opposition dated May 12, 2021, D11 (Gourgou-Bourgade S, et al., "Impact of FOLFIRINOX Compared With Gemcitabine on Quality of Life With Metastatic Pancreatic Cancer: Results From the PRODIGE 4/ACCORD 11 Randomized Trial," J Clin Oncol. 31(1):23-9 (2013). Epub 2012.).
EP3337478: Generics [UK] Limited Opposition dated May 12, 2021, D12 (Ko A, et al., "A Multinational Phase 2 Study of Nanoliposomal Irinotecan Sucrosofate (PEP02, MM-398) for Patients with Gemcitabine-Refractory Metastatic Pancreatic Cancer," Br J Cancer. 109(4):920-5 (2013).
EP3337478: Generics [UK] Limited Opposition dated May 12, 2021, D13 (Hann B, et al., Abstract 5648. "Lipidic Nanoparticle CPT-11 in a Bioluminescent Orthotopic Pancreas Cancer Model," Cancer Res. 67(9 Suppl):5648 (2007), 4 printed pages).
EP3337478: Generics [UK] Limited Opposition dated May 12, 2021, D14 (Chang T, et al., "Phase I Study of Nanoliposomal Irinotecan (PEP02) in Advanced Solid Tumor Patients," Cancer Chemother Pharmacol. 75(3):579-86 (2015)).
EP3337478: Generics [UK] Limited Opposition dated May 12, 2021, D15 (Chen L, et al., "Phase I Study of Liposome Irinotecan (PEP02) in Combination with Weekly Infusion of 5-FU/LV in Advanced Solid Tumors," J Clin Oncol., 2010 ASCO Annual Meeting Abstracts, 28(15_suppl) (May 20 Suppl):e13024 (2010), 4 printed pages).
EP3337478: Generics [UK] Limited Opposition dated May 12, 2021, D16 (Pubmed abstract retrieved on May 6, 2021 for Mahaseth H, et al., "Modified FOLFIRINOX Regimen With Improved Safety and Maintained Efficacy in Pancreatic Adenocarcinoma," Pancreas. 42(8):1311-5 (2013), 2 printed pages).
EP3337478: Generics [UK] Limited Opposition dated May 12, 2021, D17 (Drummond D, et al., "Development of a Highly Active Nanoliposomal Irinotecan Using a Novel Intraliposomal Stabilization Strategy," Cancer Res. 66(6):3271-77 (2006)).
EP3337478: Proprietor Response to Preliminary Opinion of the Opposition Division, dated Nov. 24, 2022, D33 (James E, et al., "Interim Analysis of a Phase II Study of Dose-Modified FOLFIRINOX (mFOLFIRINOX) in Locally Advanced (LAPC) and Metastatic Pancreatic Cancer (MPC)," J Clin Oncol. 32(3_suppl):256 (2014), 4 printed pages).
EP3337478: Proprietor Response to Preliminary Opinion of the Opposition Division, dated Nov. 24, 2022, D34 (Ipsen, "Onivyde Regimen Demonstrated Statistically Significant Improvement in Overall Survival in Previously Untreated Metastatic Pancreatic Ductal Adenocarcinoma," Nov. 9, 2022. Retrieved from https://www.ipsen.com/websites/Ipsen_Online/wp-content/uploads/2022/11/08224906/Ipsen-Onivyde-Press-Release-11-2022.pdf, 5 pages).
EP3337478: Generics [UK] Limited (Opponent 2) Response to Proprietor's Reply to Notices of Opposition and to Preliminary Opinion of the Opposition Division, dated Nov. 24, 2022, 8 pages.
KHAPZORY (levoleucovrin) package insert, revised Oct. 2018, accessed from accessdata.fda.gov/drugsatfda_docs/label/2018/211226s000lbl.pdf, 9 pages.
Kim G, et al., "Clinical Pathway Implications and Real-World Characteristics and Outcomes for Patients With Metastatic Pancreatic Ductal Adenocarcinoma (mPDAC) Treated With First Line Category 1 National Comprehensive Cancer Network (NCCN) Regimens." Poster presented at the European Society for Medical Oncology (ESMO) Virtual Congress 2020, Sep. 19-21, 2020, 6 pages.
Kim G, et al., "Impact of Treatment Sequence on Overall Survival in Metastatic Pancreatic Cancer Patients Treated with Liposomal Irinotecan in the Real-World Setting." Poster presented at the Hematology Oncology Pharmacy Association (HOPA) Annual Conference, Tampa, FL, Mar. 11-14, 2020, 7 pages.
Kim G, et al., Abstract 1564P. "Clinical Pathway Implications and Real-World Characteristics and Outcomes for Patients With Metastatic Pancreatic Ductal Adenocarcinoma (mPDAC) Treated With First Line Category 1 National Comprehensive Cancer Network (NCCN) Regimens," Ann Oncol. 31(Suppl_4):S881-S897 10.1016/annonc/annonc285 (2020), 2 printed pages.
Kim G, et al., Abstract e16740. "Real-World Use of Liposomal Irinotecan-Based Regimens Among Patients (pts) With Metastatic Pancreatic Adenocarcinoma (mPDAC) in the United States (U.S.)," J Clin Oncol. 38(15_Suppl):e16740 DOI: 10.1200/JCO.2020.38.15_suppl.e16740 (2020), 2 printed pages.
Kim H, et. al., "Phase II Study of Palliative S-1 in Combination With Cisplatin as Second-Line Chemotherapy for Gemcitabine-Refractory Pancreatic Cancer Patients," Oncol Lett. 3(6):1314-8 (2012).
Kim J, et al., "Efficient Prioritization of Potential Diagnostic Biomarkers Using a Systems Pharmacology Approach: Case Study of MM-398 (Irinotecan sucrosofate liposome injection)." Presentation presented at the Pharmacokinetics JK 2013 Meeting, Oct. 31, 2013, Harrogate, North Yorkshire, 34 pages.
Kim J, et al., "Efficient Prioritization of Potential Diagnostic Biomarkers Using a Systems Pharmacology Approach: Case Study of MM-398, an Irinotecan Sucrosofate Liposome Injection)." Abstract for Pharmacokinetics UK 2013 Meeting, Oct. 30-Nov. 1, 2013, Harrogate, North Yorkshire, 2 pages.
Kim J, et al., "Sustained Intratumoral Activation of MM-398 Results in Superior Activity over Irinotecan Demonstrated by Using a Systems Pharmacology Approach." Poster presented at the AACR Pancreatic Cancer Symposium, Jun. 18-21, 2012, New York, New York, 8 pages.
Kim J, et al., "Systems Pharmacology Modeling Identifies Unique Parameters That Drive Tumor SN38 Levels for Liposomal Irinotecan (MM-398) Compared to Irinotecan." Poster presented at 14th International Conference on Systems Biology; Copenhagen, Denmark; Aug. 29-Sep. 4, 2013, 11 pages.
Kim J, et al., "Systems Pharmacology Modeling Identifies Unique Parameters That Drive Tumor SN38 Levels for Liposomal Irinotecan (MM-398) Compared to Irinotecan." Abstract presented at 14th International Conference on Systems Biology; Copenhagen, Denmark; Aug. 29-Sep. 4, 2013, 1 page.
Kim J, et al., Abstract A6. "Sustained Intratumoral Activation of MM-398 Results in Superior Activity Over Irinotecan Demonstrated by Using a Systems Pharmacology Approach," In: Proceedings of the AACR Special Conference on Chemical Systems Biology: Assembling and Interrogating Computational Models of the Cancer Cell by Chemical Perturbations; Jun. 27-30, 2012; Boston, MA. Cancer Res. 2012;72(13 Suppl):Abstract nr A6, 3 printed pages.
Kim J, et. al., "Systems Pharmacology Based Biomarker Potentially Predicts Clinical Anti-Cancer Activity of MM-398, Nanoliposomal Irinotecan, nal-IRI." Poster presented at American Conference on Pharmacometrics, October, 12-15 2014, 10 pages.

(56) References Cited

OTHER PUBLICATIONS

Kim Y, et. al., "Phase II Study of 5-Fluorouracil and Paclitaxel in Patients With Gemcitabine-Refractory Pancreatic Cancer," Cancer Chemother Pharmacol. 63(3):529-33 (2009). Epub 2008.
Kindler H, et. al., "Arsenic Trioxide in Patients With Adenocarcinoma of the Pancreas Refractory to Gemcitabine: A Phase II Trial of the University of Chicago Phase II Consortium," Am J Clin Oncol. 31(6):553-6 (2008).
Kindler H, et. al., "Gemcitabine Plus Bevacizumab Compared With Gemcitabine Plus Placebo in Patients With Advanced Pancreatic Cancer: Phase III Trial of the Cancer and Leukemia Group B (CALGB 80303)," J Clin Oncol. 28(22):3617-22 (2010).
Kipps E, et. al., "Liposomal Irinotecan in Gemcitabine-Refractory Metastatic Pancreatic Cancer: Efficacy, Safety and Place in Therapy," Ther Adv Med Oncol. 9(3):159-70 (2017).
Kirpotin D, et al. "Antibody Targeting of Long-Circulating Lipidic Nanoparticles Does Not Increase Tumor Locatlization but Does Increase Internalization in Animal Models," Cancer Res. 66(13):6732-40 (2006).
Kirpotin D, et al., "Building and Characterizing Antibody-Targeted Lipidic Nanotherapeutics," Methods Enzymol. 502:139-66 (2012).
Kirpotin D, et al., "Targeting of Liposomes to Solid Tumors: The Case of Sterically Stabilized Anti-HER2 Immunoliposomes," J Liposome Res. 7:391-417 (1997).
Kirpotin D, et al., Chapter 4.7, "Targeting of Sterically Stabilized Liposomes to Cancers Overexpressing HER2/neu Proto-Oncogene," In Medical Applications of Liposomes, Lasic D and Papahadjopoulos D, eds., pp. 325-345 (1998).
Klapdor R and Fenner C, "Irinotecan(Campto R): Efficacy as Third/Forth Line Therapy in Advanced Pancreatic Cancer," Anticancer Res. 20(6D): 5209-12 (2000).
Klapdor R, et. al., "Reflections on Treatment Strategies for Palliative Chemotherapy of Pancreatic Cancer," Anticancer Res. 27(4A): 1789-94 (2007).
Kline C, et. al., "Preliminary Observations Indicate Variable Patterns of Plasma 5-Fluorouracil (5-FU) Levels During Dose Optimization of Infusional 5-FU in Colorectal Cancer Patients," Cancer Biol Ther. 12(7):557-68 (2011).
Klinz S, et al., "Identifying Differential Mechanisms of Action for MM-398/PEP02, a Novel Nanotherapeutic Encapsulation of Irinotecan." Poster presented at MCR, Nov. 12-16, 2011, 8 pages.
Klinz S, et al., "Identifying Differential Mechanisms of Action for MM-398/PEP02, a Novel Nanotherapeutic Encapsulation of Irinotecan," Mol Cancer Ther. 10(11 Suppl): Abstract C207. Molecular Targets and Therapeutics Meeting (2011), 2 printed pages.
Klinz S, et al., "Nanoliposomal Irinotecan (nal-IRI) is an Active Treatment and Reduces Hypoxia as Measured Through Longitudinal Imaging Using [18F]FAZA-PET in an Orthotopic Patient-Derived Tumorgraft Model of Pancreatic Cancer." Poster presented at AACR Pancreatic meeting Orlando, FL, May 12-15, 2016, 10 pages.
Klinz S, et al., Abstract C293: "Irinotecan Sucrosofate Liposome Injection, MM-398, Demonstrates Superior Activity and Control of Hypoxia as Measured Through Longitudinal Imaging Using [18F] FAZA PET Compared to Free Irinotecan in a Colon Adenocarcinoma Xenografl Model." Poster presented at AACR-NCI-EORTC International Conference on Molecular Targets and Cancer Therapeutics on Oct. 19, 2013, 7 pages.
Klinz S, et al., Abstract e16205. "DNA Damage With Liposomal Irinotecan (nal-IRI) in Pancreatic Cancer Xenografts: Multimodal Analysis of Deposition Characteristics," J Clin Oncol. 36(15_Suppl):e16205 DOI: 10.1200/JCO.2018.36.15_suppl.e16205 (2018), 2 printed pages.
Klinz S, et al., "MM-302 a HER2-targeted Liposomal Doxorubicin, Shows Binding/Uptake and Efficacy in HER2 2+ Cells and Xenograft Models," Cancer Res. 71:Abstract 3637 (2011), 1 printed page.
Ko A, "Nanomedicine Developments in the Treatment of Metastatic Pancreatic Cancer: Focus on Nanoliposomal Irinotecan," Int J Nanomedicine. 11:1225-35 (2016).
Ko A, et al., "A Multinational Phase 2 Study of Nanoliposomal Irinotecan Sucrosofate (PEP02, MM-398) for Patients with Gemcitabine-Refractory Metastatic Pancreatic Cancer," Br J Cancer. 109(4):920-5 (2013).
Ko A, et al., "A Multinational Phase II Study of PEP02 (Liposome Irinotecan) for Patients with Gemcitabine-Refractory Metastatic Pancreatic Cancer," J Clin Oncol. 29:2011 (Suppl; Abstract 4069). 2011 ASCO Annual Meeting (2011), 2 printed pages.
Ko A, et al., "A Multinational Phase II Study of PEP02 (MM-398), Liposome Irinotecan, for Patients with Gemcitabine-refractory Metastatic Pancreatic Cancer." Poster presented at the American Society of Clinical Oncology meeting, Jun. 3-Jun. 7, 2011, Chicago, Illinois, 9 pages.
Ko A, et al., "Excess Toxicity Associated with Docetaxel and Irinotecan in Patients with Metastatic, Gemcitabine-Refractory Pancreatic Cancer: Results of a Phase II Study," Cancer Invest. 26(1):47-52 (2008).
Ko A, et. al., "A Phase II Study of Bevacizumab Plus Erlotinib for Gemcitabine-Refractory Metastatic Pancreatic Cancer," Cancer Chemother Pharmacol. 66(6):1051-7 (2010).
Koeller J, et al., Abstract e16751. "Trends in Real-World Clinical Outcomes Among Patients (pts) With Metastatic Pancreatic Adenocarcinoma (mPDAC) Treated With Liposomal Irinotecan Based Regimens in the United States (US)," J Clin Oncol. 38(15_Suppl):e16751 DOI: 10.1200/JCO.2020.38.15_suppl.e16751 (2020), 2 printed pages.
Köhne C, et al., "Randomized Phase III Study of High-Dose Fluorouracil Given as a Weekly 24-Hour Infusion With or Without Leucovorin Versus Bolus Fluorouracil Plus Leucovorin in Advanced Colorectal Cancer: European Organization of Research and Treatment of Cancer Gastrointestinal Group Study 40952," J Clin Oncol. 21(20):3721-8 (2003).
Koizumi W, at al., "Phase I/II Study of Bi-weekly Irinotecan plus Cisplatin in the Treatment of Advanced Gastric Cancer," Anticancer Res. 25(2B):1257-62 (2005).
Korn R, "Advanced Imaging with Ferumoxytol MRI to Predict Drug Delivery." Presentation presented at Pancreatic Cancer 2014, Feb. 22, 2014, 23 pages.
Koshkaryev A, et al., "Differential Tissue Clearance Results in Improved Therapeutic Index for Nanoliposomal Irinotecan (nal-IRI; Onivyde) when Combined with the PARP Inhibitor Veliparib." Poster presented at AACR Meeting on Apr. 16-20, 2016, 5 pages.
Kozuch P, et al., "Irinotecan Combined with Gemcitabine, 5-Fluorouracil, Leucovorin, and Cisplatin (G-FLIP) is an Effective and Noncrossresistant Treatment for Chemotherapy Refractory Metastatic Pancreatic Cancer," Oncologist. 6(6):488-95 (2001).
Krauss W, et al., "Emerging Antibody-Based HER2 (ErbB2/neu) Therapeutics," Breast Dis. 11:113-24 (2000).
Kraut E, et. al., Abstract 2017. "Final Results of a Phase I Study of Liposome Encapsulated SN-38 (LE-SN38): Safety, Pharmacogenomics, Pharmacokinetics, and Tumor Response," J Clin Oncol. 23(16_Suppl):2017 (2005), 3 printed pages.
Krauze M, et al., "Convection-Enhanced Delivery of Nanoliposomal CPT-11 (Irinotecan) and PEGylated Liposomal Doxorubicin (Doxil) in Rodent Intracranial Brain Tumor Xenografts," Neuro Oncol. 9(4):393-403 (2007).
Kulke M, et. al., "A Phase II Trial of Irinotecan and Cisplatin in Patients with Metastatic Neuroendocrine Tumors," Dig Dis Sci. 51(6):1033-8 (2006).
Kulke M, et. al., "Capecitabine Plus Erlotinib in Gemcitabine-Refractory Advanced Pancreatic Cancer," J Clin Oncol. 25(30):4787-92 (2007).
Kulke M, et. al., "Randomized Phase II Study of Gemcitabine Administered at a Fixed Dose Rate or in Combination With Cisplatin, Docetaxel, or Irinotecan in Patients With Metastatic Pancreatic Cancer: CALGB 89904," J Clin Oncol. 27(33):5506-12 (2009).
Kummar S, et al. "Phase I Study of PARP Inhibitor ABT-888 in Combination with Topotecan in Adults with Refractory Solid Tumors and Lymphomas," Cancer Res. 71(17):5626-34 (2011), Epub Jul. 27, 2011.
Lakatos G, et al., "Prognostic Value of Baseline Biliary Stents on Outcomes in Patients With Metastatic Pancreatic Ductal Adenocarcinoma (mPDAC) in the NAPOLI-1 Trial." Poster pre-

(56) References Cited

OTHER PUBLICATIONS sented at the European Society for Medical Oncology 20th World Congress on Gastrointestinal Cancer, Barcelona, Spain, Jun. 20-23, 2018, 10 pages.
U.S. Appl. No. 14/964,239: Nov. 4, 2016 Nonfinal Office Action, 21 pages.
U.S. Appl. No. 14/964,239: Apr. 26, 2017 Examiner Interview Summary, 2 pages.
U.S. Appl. No. 14/964,239: Jun. 21, 2017 Nonfinal Office Action, 16 pages.
U.S. Appl. No. 14/964,239: Dec. 11, 2017 Nonfinal Office Action, 15 pages.
U.S. Appl. No. 14/964,571: Feb. 13, 2017 Nonfinal Office Action, 8 pages.
U.S. Appl. No. 14/964,571: Nov. 1, 2017 Final Office Action, 14 pages.
U.S. Appl. No. 14/964,571: Sep. 25, 2018 Nonfinal Office Action, 12 pages.
U.S. Appl. No. 14/964,571: Jun. 12, 2019 Final Office Action, 15 pages.
U.S. Appl. No. 14/965,140: Mar. 10, 2016 Nonfinal Office Action, 24 pages.
U.S. Appl. No. 14/965,140: Jul. 13, 2016 Interview Summary and Nonfinal Office Action, 14 pages.
U.S. Appl. No. 14/965,140: Dec. 19, 2016 Nonfinal Office Action, 9 pages.
U.S. Appl. No. 14/966,458: Dec. 6, 2016 Nonfinal Office Action, 34 pages.
U.S. Appl. No. 14/966,458: Apr. 27, 2017 Examiner Interview Summary, 2 pages.
U.S. Appl. No. 14/979,666: Dec. 9, 2016 Nonfinal Office Action, 20 pages.
U.S. Appl. No. 15/059,640: Dec. 2, 2016 Nonfinal Office Action, 9 pages.
U.S. Appl. No. 15/227,561: Jul. 14, 2017 Nonfinal Office Action, 25 pages.
U.S. Appl. No. 15/227,561: Apr. 26, 2018 Nonfinal Office Action, 13 pages.
U.S. Appl. No. 15/227,561: Dec. 10, 2018 Final Office Action, 18 pages.
U.S. Appl. No. 15/227,631: Jul. 17, 2017 Nonfinal Office Action, 24 pages.
U.S. Appl. No. 15/227,631: Apr. 10, 2018 Nonfinal Office Action, 13 pages.
U.S. Appl. No. 15/227,631: Aug. 31, 2018 Nonfinal Office Action, 15 pages.
U.S. Appl. No. 15/227,631: Dec. 19, 2018 Final Office Action, 15 pages.
U.S. Appl. No. 15/241,106: Oct. 28, 2016 Pre-Interview Communication, 4 pages.
U.S. Appl. No. 15/241,106: Dec. 29, 2016 Nonfinal Office Action, 15 pages.
U.S. Appl. No. 15/241,106: Jul. 10, 2017 Final Office Action, 16 pages.
U.S. Appl. No. 15/241,128: Nov. 25, 2016 Nonfinal Office Action, 6 pages.
U.S. Appl. No. 15/296,536: Mar. 8, 2017 Nonfinal Office Action, 6 pages.
U.S. Appl. No. 15/331,393: Jan. 19, 2017 Pre-Interview Communication, 4 pages.
U.S. Appl. No. 15/331,393: Mar. 20, 2017: Examiner's Interview Summary and First Action Interview Office Action Summary, 5 pages.
U.S. Appl. No. 15/331,648: Jan. 19, 2017 Pre-Interview Communication, 4 pages.
U.S. Appl. No. 15/331,648: Mar. 17, 2017 Examiner's Interview Summary, 3 pages.
U.S. Appl. No. 15/337,274: Mar. 25, 2017 Nonfinal Office Action, 10 pages.
U.S. Appl. No. 15/341,377: Jan. 30, 2017 Nonfinal Office Action, 12 pages.
U.S. Appl. No. 15/341,377: Apr. 18, 2017 Final Office Action, 13 pages.
U.S. Appl. No. 15/341,619: Apr. 3, 2017 Pre-Interview Communication, 3 pages.
U.S. Appl. No. 15/363,761: Jan. 18, 2017 Nonfinal Office Action, 15 pages.
U.S. Appl. No. 15/363,761: Aug. 1, 2017 Final Office Action, 18 pages.
U.S. Appl. No. 15/363,761: Dec. 14, 2017 Examiner Interview Summary, 3 pages.
U.S. Appl. No. 15/363,923: Feb. 1, 2017 Nonfinal Office Action, 24 pages.
U.S. Appl. No. 15/363,923: Sep. 13, 2017 Final Office Action, 29 pages.
U.S. Appl. No. 15/363,978: Feb. 7, 2017 Nonfinal Office Action, 16 pages.
U.S. Appl. No. 15/363,978: Aug. 21, 2017 Final Office Action, 19 pages.
U.S. Appl. No. 15/363,978: Dec. 14, 2017 Examiner Interview Summary, 3 pages.
U.S. Appl. No. 15/364,021: Mar. 9, 2017 Nonfinal Office Action, 18 pages.
U.S. Appl. No. 15/364,021: Oct. 4, 2017 Final Office Action, 20 pages.
U.S. Appl. No. 15/375,039: Feb. 16, 2018 Nonfinal Office Action, 11 pages.
U.S. Appl. No. 15/403,441: Dec. 21, 2017 Nonfinal Office Action, 9 pages.
U.S. Appl. No. 15/645,645: Dec. 1, 2017 Nonfinal Office Action, 16 pages.
U.S. Appl. No. 15/652,513: Dec. 20, 2017 Nonfinal Office Action, 13 pages.
U.S. Appl. No. 15/661,868: Dec. 1, 2017 Nonfinal Office Action, 15 pages.
Macarulla Mercadé T, et al., Abstract 410. "Subgroup Analysis by Baseline (BL) Weight-Associated Parameters: A phase III Study of Liposomal Irinotecan (nal-IRI)±5-Fluorouracil/Leucovorin (5-FU/LV) in Patients (pts) With Metastatic Pancreatic Ductal Adenocarcinoma (mPDAC) Previously Treated With Gemcitabine-Based (Gem) Therapy," J Clin Oncol. 36(4_Suppl):410 DOI: 10.1200/JCO.2018.36.4_suppl.410 (2018), 6 printed pages.
Macarulla Mercadé T, et al., Abstract 733P. "NAPOLI-1 Phase III Trial Outcomes by Prior Surgery, and Disease Stage, in Patients With Metastatic Pancreatic Ductal Adenocarcinoma (mPDAC)," Ann Oncol. 29(Supp_8)viii249-viii250 doi: 10.1093/annonc/mdy282 (2018).
Macarulla Mercadé T, et al., Abstract O-004. "Selected Subgroup Analyses of Liposomal Irinotecan (nal-IRI) in Patients With Metastatic Pancreatic Ductal Adenocarcinoma (mPDAC) in the Global NAPOLI-1 Phase III Trial," Ann Oncol. 29(Suppl_5)v101 doi:10.1093/annonc/mdy149 (2018).
Macarulla Mercadé T, et al., Abstract P-150. "Prognostic Effect of Primary Tumour Location in the NAPOLI-1 Phase 3 Study in Metastatic Pancreatic Ductal Adenocarcinoma (mPDAC)," Ann Oncol. 29(Suppl_5)v41-v42 doi:10.1093/annonc/mdy151 (2018).
Macarulla Mercadé T, et al., Abstract P-152. "The Effect of Best Response to Prior Anticancer Therapy on Efficacy Outcomes in the NAPOLI-1 Trial of Patients With Metastatic Pancreatic Ductal Adenocarcinoma (mPDAC) Previously Treated with Gemcitabine-Based Therapy," Ann Oncol. 29(Suppl_5):v42 doi:10.1093/annonc/mdy151 (2018).
Macarulla T, et al., "Integrated Population Pharmacokinetic Modelling of Liposomal Irinotecan in Patients With Various Tumour Types, Including Untreated Metastatic Pancreatic Cancer (mPC)." Poster presented at the European Society for Medical Oncology (ESMO) Congress 2019, Barcelona, Spain, Sep. 27-Oct. 1, 2019, 6 pages.
Macarulla T, et al., "Subgroup Analysis by Prior Lines of Metastatic Therapy in NAPOLI-1, A Global, Randomized Phase 3 Study of Liposomal Irinotecan ± 5-Fluorouracil and Leucovorin, vs. 5-Fluorouracil and Leucovorin in Patients With Metastatic Pancre-

(56) References Cited

OTHER PUBLICATIONS atic Ductal Adenocarcinoma Who Have Progressed Following Gemcitabine-Based Therapy." Poster presented at the American Society of Clinical Oncology (ASCO) Annual Conference, Chicago, IL, Jun. 2-6, 2017, 7 pages.
Macarulla T, et al., Abstract 4127. "Subgroup Analysis by Prior Lines of Metastatic Therapy (mtx) in NAPOLI-1: A Global, Randomized Phase 3 Study of Liposomal Irinotecan (nal-IRI) ± 5-Fluorouracil and Leucovorin (5-FU/LV), vs. 5-FU/LV in Patients (pts) With Metastatic Pancreatic Ductal Adenocarcinoma (mPDAC) Who Have Progressed Following Gemcitabine-Based Therapy," J Clin Oncol. 35(15_Suppl): 4127 DOI: 10.1200/JCO.2017.35.15_suppl.4127 (2017), 2 printed pages.
Macarulla T, et al., Abstract 691P. "Integrated Population Pharmacokinetic Modelling of Liposomal Irinotecan in Patients With Various Tumour Types, Including Untreated Metastatic Pancreatic Cancer (mPC)," Ann Oncol. 30(Suppl_5):v263 doi:10.1093/annonc/mdz247 (2019).
Mackenzie M, et. al., "A Phase I Study of OSI-211 and Cisplatin as Intravenous Infusions Given on Days 1, 2 and 3 Every 3 Weeks in Patients With Solid Cancers," Ann Oncol. 15(4):665-70 (2004).
Maddison J, et al., "Sucralfate," In Small Animal Clinical Pharmacology at p. 474, published by W. B. Saunders (2002).
Mahaseth H, et al., "Modified FOLFIRINOX Regimen With Improved Safety and Maintained Efficacy in Pancreatic Adenocarcinoma," Pancreas. 42(8):1311-5 (2013).
Makrilia N, et al., "Treatment for Refractory Pancreatic Cancer. Highlights from the '2011 ASCO Gastrointestinal Cancers Symposium'. San Francisco, CA, USA, Jan. 20-22, 2011," J Pancreas. 12(2):110-3 (2011).
Malet-Martino M and Martino R, "Clinical Studies of Three Oral Prodrugs of 5-Fluorouracil (Capecitabine, UFT, S-1): A Review," Oncologist. 7(4):288-323 (2002).
Mamot C, et al., "Epidermal Growth Factor Receptor (EGFR)-Targeted Immunoliposomes Mediate Specific and Efficient Drug Delivery to EGFR- and EGFRvIII-Overexpressing Tumor Cells," Cancer Res. 63(12):3154-61 (2003).
Mamot C, et al., "Epidermal Growth Factor Receptor-Targeted Immunoliposomes Significantly Enhance the Efficacy of Multiple Anticancer Drugs In Vivo," Cancer Res. 65(24):11631-8 (2005).
Mamot C, et al., "Extensive Distribution of Liposomes in Rodent Brains and Brain Tumors Following Convection-Enhanced Delivery," J Neurooncol. 68(1):1-9 (2004).
Mamot C, et al., "Liposome-Based Approaches to Overcome Anticancer Drug Resistance," Drug Resist Updat. 6(5):271-9 (2003).
Mancini R and Modlin J, "Chemotherapy Administration Sequence: A Review of the Literature and Creation of a Sequencing Chart," J Hematol Oncol Pharm. 1(1):17-25 (2011).
Mans D, et al., "Sequence-Dependent Growth Inhibition and DNA Damage Formation by the Irinotecan-5-Fluorouracil Combination in Human Colon Carcinoma Cell Lines," Eur J Cancer. 35(13):1851-61 (1999).
Markham C, et al., "A Phase II Irinotecan-Cisplatin Combination in Advanced Pancreatic Cancer," Br J Cancer. 89(10):1860-4 (2003).
Martin L, et. al., "VEGF Remains an Interesting Target in Advanced Cancreas Cancer (APCA): Results of a Multi-Institutional Phase II Study of Bevacizumab, Gemcitabine, and Infusional 5-Fluorouracil in Patients With APCA," Ann Oncol. 23(11):2812-20 (2012).
Masuda N, et al., "CPT-11: A New Derivative of Camptothecin for the Treatment of Refractory or Relapsed Small-Cell Lung Cancer," J Clin Oncol. 10(8):1225-9 (1992).
Mathé G, et al., "A Phase I Trial of Trans-1-diamino-cyclohexane Oxalate-platinum (I-OHP)," Biomed Pharmacother, 40(10):372-376 (1986).
Mathé G, et al., "Oxalato-platinum or 1-OHP, a Third-Generation Platinum Complex: An Experimental and Clinical Appraisal and Preliminary Comparison with Cis-platinum and Carboplatinum," Biomed Pharmacother, 43(4):237-50 (1989).
Mathijssen R, et al., "Clinical Pharmacokinetics and Metabolism of Irinotecan (CPT-11)," Clin Cancer Res. 7(8):2182-94 (2001).
Matrisian , et. al., "The Past, Present, and Future of Pancreatic Cancer Clinical Trials," American Society of Clinical Oncology Educational Book. 35:e205-15 (2016).
Matsusaka S, et. al., "Differential Effects of Two Fluorouracil Administration Regimens for Colorectal Cancer," Oncol Rep. 10(1):109-13 (2003).
Maxwell F, et al., "CA 19-9 levels in patients with metastatic pancreatic adenocarcinoma receiving first-line therapy with liposomal irinotecan plus 5-fluorouracil/leucovorin and oxaliplatin (NAPOX)," Poster presented at the American Association for Cancer Research (AACR) Special Conference on Pancreatic Cancer: Advances in Science and Clinical Care, Sep. 6-9, 2019, Boston, MA, 7 pages.
Mayer L, et. al., "Ratiometric Dosing of Anticancer Drug Combinations: Controlling Drug Ratios After Systemic Administration Regulates Therapeutic Activity in Tumor-Bearing Mice," Mol Cancer Ther. 5(7):1854-63 (2006).
McNamara M, et al., "NET-02: A Multi-Centre, Randomized, Phase II Trial of Liposomal Irinotecan (nal-IRI) and 5-Fluorouracil (5-FU)/Folinic Acid or Docetaxel as Second-Line Therapy in Patients (pts) With Progressive Poorly Differentiated Extra-Pulmonary Neuroendocrine Carcinoma (PD-EP-NEC)." Poster presented at the 17th Annual European Neuroendocrine Tumor Society (ENETS) Conference for the Diagnosis and Treatment of Neuroendocrine Tumor Disease, Virtual Conference, Mar. 11-13, 2020, 4 pages.
McNamara M, et al., Abstract P04. "NET-02: A Phase II Trial of Liposomal Irinotecan (nal-IRI) and 5-Fluorouracil (5-FU)/Folinic Acid or Docetaxel as Second-Line Therapy in Patients (pts) With Progressive Poorly Differentiated Extra-Pulmonary Neuroendocrine Carcinoma (PD-EP-NEC)," In Abstracts of the 17th Annual European Neuroendocrine Tumor Society (ENETS) Conference for the Diagnosis and Treatment of Neuroendocrine Tumor Disease, Virtual Conference, Mar. 11-13, 2020, p. 374.
Meerum Terwogt J, et. al., "Phase I and Pharmacokinetic Study of SPI-77, a Liposomal Encapsulated Dosage Form of Cisplatin," Cancer Chemother Pharmacol. 49(3):201-10 (2002).
Melis M, et al., "Can We Downstage Regionally Advanced Pancreatic Cancer to Resectable: a Phase I/II Study of Induction Oxaliplatin and 5FU Chemo-Radiation," 52nd Annual Meeting for Society for Surgery of the Alimentary Tract, May 6-10, 2011, http://meetings.ssat.com/abstracts/11ddw/P57.cgi, Abstract P57, 1 printed page.
Melisi D, et al., Abstract B04. "Effects of Nanoliposomal Irinotecan (nal-IRI; MM-398) ± 5-Fluorouracil and Leucavorin (5-FU/LV) on Quality of Life (QoL) in Patients (pts) With Metastatic Pancreatic Adenocarcinoma (mPAC) Previously Treated With Gemcitabine-Based Therapy: Results From the Phase 3 NAPOLI-1 Study," Ann Oncol. 27(Supp_4):iv18 doi:10.1093/annonc/mdw333.4 (2016).
Merrimack Pharmaceuticals, "Merrimack Announces Inclusion of ONIVYDE (irinotecan liposome injection) as a Category 1 Treatment Option in the 2016 NCCN Guidelines for Pancreatic Adenocarcinoma," Mar. 24, 2016. Retrieved from http://investors.merrimack.com/news-releases/news-release-details/merrimack-announces-inclusion-onivyder-irinotecan-liposome, 2 printed pages.
Merrimack Pharmaceuticals, "Merrimack Pharmaceuticals Initiates Cross-Tumor Study to Investigate Potential Predictive Response Markers for a Developmental Nanotherapeutic Chemotherapy," Dec. 19, 2012. Retrieved from http://investors.merrimack.com/news-releases/news-release-details/merrimack-pharmaceuticals-initiates-cross-tumor-study, 2 printed pages.
Messerer C, et al., "Liposomal Irinotecan: Formulation Development and Therapeutic Assessment in Murine Kenograft Models of Colorectal Cancer," Clin Cancer Res. 10(19):6638-49 (2004).
Messerer C, et. al., "Liposomal Encapsulation of Irinotecan and Potential for the Use of Liposomal Drug in the Treatment of Liver Metastases Associated with Advanced Colorectal Cancer," MS Thesis, University of British Columbia, 2000, 90 pages.
Miles D, et al., "Combination Versus Sequential Single-Agent Therapy in Metastatic Breast Cancer," Oncologist. 7(suppl 6):13-19 (2002).
Miller M, et al. "Predicting Therapeutic Nanomedicine Efficacy Using a Companion Magnetic Resonance Imaging Nanoparticule," Sci Transl Med. 7:314ra183 (2015), pp. 1-12, Editor's Summary (1 page), and Supplementary Materials (24 pages).

(56) References Cited

OTHER PUBLICATIONS

Miller M, et al., "Tumour-Associated Macrophages Act as a Slow-Release Reservoir of Nano-Therapeutic Pt(IV) Pro-Drug," Nat. Commun. 6:8692, doi: 10.1038/ncomms9692, 13 pages (2015), Supplementary Figures 1-9 (9 pages), Supplementary Table 1 (1 page), and Supplementary References (1 page).
Minami H, et al., "Irinotecan Pharmacokinetics/Pharmacodynamics and UGT1A Genetic Polymorphisms in Japanese: Roles of UGT1A1*6 and *28," Pharmacogenet Genomics. 17(7):497-504 (2007).
Mirtsching B, et al., "Irinotecan-induced Immune Thrombocytopenia," Am J Med Sci. 347(2):167-9 (2014).
Mizuno N., "Randomized Phase II Trial of S-1 versus S-1 Plus Irinotecan (IRIS) in Patients with Gemcitabine-Refractory Pancreatic Cancer," J Clin Oncol. 31(Suppl 4):Abstract 263 (2013), 2 printed pages.
Mohammad A, et al., "Liposomal Irinotecan Accumulates in Metastatic Lesions, Crosses the Blood-Tumor Barrier (BTB), and Prolongs Survival in an Experimental Model of Brain Metastases of Triple Negative Breast Cancer," Pharm Res. 35(2):31; doi.org/10.1007/s11095-017-2278-0 (2018), 10 pages.
Moore M, et. al., "Erlotinib Plus Gemcitabine Compared With Gemcitabine Alone in Patients With Advanced Pancreatic Cancer: A Phase III Trial of the National Cancer Institute of Canada Clinical Trials Group," J Clin Oncol. 25(15):1960-6 (2007).
Morgan R, et al., "Human Cell Line (COLO 357) of Metastatic Pancreatic Adenocarcinoma," Int J Cancer 25(5):591-8 (1980).
Morise M, et al., "Low-dose Irinotecan as a Second-line Chemotherapy for Recurrent Small Cell Lung Cancer," Jpn J Clin Oncol. 44(9):846-51 (2014).
Mukhtar R, et al., "Elevated PCNA+ Tumor-Associated Macrophages in Breast Cancer are Associated with Early Recurrence and Non-Caucasian Ethnicity," Breast Cancer Res Treat. 130(2):635-44 (2011).
EP2861210: Notice of Opposition dated Feb. 5, 2018, 6 pages.
EP2861210: Opposition dated Feb. 5, 2018, Annex to Notice of Opposition, Facts and Arguments, 8 pages.
EP2861210: Opposition dated Feb. 5, 2018, D1 (FUSILEV package insert, 2008, 7 pages).
EP2861210: Opposition dated Feb. 5, 2018, D2 (Gebbia V, et al., "Irinotecan Plus Bolus/Infusional 5-Fluorouracil and Leucovorin in Patients With Pretreated Advanced Pancreatic Carcinoma: A Multicenter Experience of the Gruppo Oncologico Italia Meridionale," Am J Clin Oncol. 33(5):461-64 (2010).
EP2861210: Opposition dated Feb. 5, 2018, D3 (Zaniboni A, et al., "FOLFIRI as Second-Line Chemotherapy for Advanced Pancreatic Cancer: A Giscad Multicenter Phase II Study," Cancer Chemother Pharmacol 69(6):1641-5 (2012).
EP2861210: Opposition dated Feb. 5, 2018, D4 (Neuzillet C, et al., "FOLFIRI Regimen in Metastatic Pancreatic Adenocarcinoma Resistant to Gemcitabine and Platinum-Salts," World J Gastroenterol. 18(33):4533-41 (2012)).
EP2861210: Opposition dated Feb. 5, 2018, D5 (Yoo C, et al., "A Randomised Phase II Study of Modified FOLFIRI.3 vs Modified FOLFOX as Second-Line Therapy in Patients with Gemcitabine-Refractory Advanced Pancreatic Cancer," Br J Cancer. 101(10):1658-63 (2009)).
EP2861210: Opposition dated Feb. 5, 2018, D6 (Taïeb J., "FOLFIRI. 3, A New Regimen Combining 5-Fluorouracil, Folinic Acid and Irinotecan, For Advanced Pancreatic Cancer: Results of an Association des Gastro-Enterologues Oncologues (Gastroenterologist Oncologist Association) Multicenter Phase II Study," Ann Oncol. 18(3)498-503 (2007), epub Dec. 8, 2006).
EP2861210: Opposition dated Feb. 5, 2018, D7 (Chen L, et al., "Phase I Study of Liposome Encapsulated Irinotecan (PEP02) in Advanced Solid Tumor Patients," J Clin Oncol., 2008 ASCO Annual Meeting Proceedings (Post-Meeting Edition), 26(15S) (May 20 Suppl):2565 (2008), 2 pages).
EP2861210: Opposition dated Feb. 5, 2018, D8 (Infante J, et al., "Phase I and Pharmacokinetic Study of IHL-305 (PEGylated Liposomal Irinotecan) in Patients With Advanced Solid Tumors," Cancer Chemother Pharmacol. 70(5):699-705 (2012)).
EP2861210: Opposition dated Feb. 5, 2018, D9 (Waterhouse D, et al., "Lipid-Based Nanoformulation of Irinotecan: Dual Mechanism of Action Allows for Combination Chemo/Angiogenic Therapy," Nanomedicine 6(9):1645-54 (2011)).
EP2861210: Opposition filed Feb. 5, 2018, D10 (CAMPTOSAR package insert, 2012, 39 pages).
EP2861210: Opposition filed Feb. 5, 2018, D11 (Hoskins J, et al., "UGT1A1*28 Genotype and Irinotecan-Induced Neutropenia: Dose Matters," J Natl Cancer Inst. 99(17):1290-95 (2007).
EP2861210: Opposition dated Feb. 5, 2018, D12 (Tsai C, et al., "Nanovector-Based Therapies in Advanced Pancreatic Cancer," J Gastroint Oncol 2(3):185-94 (2011)).
EP2861210: Opposition dated Feb. 5, 2018, D13 (Ko A, et al., "A Multinational Phase II Study of Liposome rinotecan (PEP02) for Patients with Gemcitabine-Refractory Metastatic Pancreatic Cancer," J Clin Oncol. 29:2011 (Suppl; Abstract 237). 2011 ASCO Annual Meeting (2011), 2 printed pages).
EP2861210: Opposition dated Feb. 5, 2018, D15 (Clinical Trials Identifier NCT01494506: Jan. 25, 2013 version, "A Randomized, Open Label Phase 3 Study of MM-398, With or Without 5-Fluorouracil and Leucovorin, Versus 5 Fluorouracil and Leucovorin in Patients With Metastatic Pancreatic Cancer Who Have Failed Prior Gemcitabine-based Therapy," Retrieved from ClinicalTrials.gov archive, 1 printed page).
EP2861210: Communication of Notices of Opposition (R. 79(1) EPC), dated Feb. 16, 2018, 1 page.
EP2861210: Response to EP Opposition Proceedings filed Aug. 24, 2018, 22 pages.
EP2861210: Response to EP Opposition Proceedings filed Aug. 24, 2018, D15a (Clinical Trials Identifier NCT01494506: Dec. 16, 2011 version, "A Randomized, Open Label Phase 3 Study of MM-398 Versus 5-Fluorouracil and Leucovorin in Patients With Metastatic Pancreatic Cancer." Retrieved from ClinicalTrials.gov archive, 3 printed pages).
EP2861210: Response to EP Opposition Proceedings filed Aug. 24, 2018, D17 (European Commission Implementing Decision granting marketing authorisation for Onivyde, Oct. 14, 2016), 39 pages.
EP2861210: Response to EP Opposition Proceedings filed Aug. 24, 2018, D18 (FDA News Release, "FDA Approves New Treatment for Advanced Pancreatic Cancer." Retrieved from http://ww.fda.gov/NewsEvents/Newsroom/PressAnnouncements/ucm468654.htm, Oct. 22, 2015, 3 printed pages).
EP2861210: Response to EP Opposition Proceedings filed Aug. 24, 2018, D19 (Wang-Gillam A, et al., "Nanoliposomal Irinotecan with Flourouracil and Folinic Acid in Metastatic Pancreatic Cancer After Previous Gemcitabine-Based Therapy (NAPOLI-1): A Global, Randomised, Open-Label, Phase 3 Trial," Lancet, 387(10018):545-57 (2016). Epub doi: 10.1016/S0140-6736(15)00986-1, pp. 1-13 (2015).
EP2861210: Response to EP Opposition Proceedings filed Aug. 24, 2018, D20 (MHRA Public Assessment Report for 5-Fluorouracil, 2006, 60 pages).
EP2861210: Summons to attend oral proceedings including preliminary opinion of the Opposition Division dated Jan. 30, 2019, 12 pages.
EP2861210: Opponent submission in opposition proceedings made following summons to attend oral proceedings, dated May 10, 2019, 20 pages.
EP2861210: Opponent submission in opposition proceedings made following summons to attend oral proceedings, dated May 10, 2019, D1b (Leucovorin calcium injection product label, Nov. 2011, 2 pages).
EP2861210: Opponent submission in opposition proceedings made following summons to attend oral proceedings, dated May 10, 2019, D22 (Chen L, et al., "Phase I Study of Liposome Irinotecan (PEP02) in Combination with Weekly Infusion of 5-FU/LV in Advanced Solid Tumors," J Clin Oncol., 2010 ASCO Annual Meeting Abstracts, 28(15_suppl) (May 20 Suppl):e13024 (2010), 1 page).
EP2861210: Proprietor's Auxiliary Requests in Opposition Proceedings filed Jun. 28, 2019, including cover letter and clean and marked-up AR1, AR2, and AR3, 12 pages.
EP2861210: Minutes of the oral proceedings before the Opposition Division, dated Aug. 28, 2019, 9 pages.

(56) References Cited

OTHER PUBLICATIONS

EP2861210: Opposition Division's decision to revoke patent, dated Aug. 28, 2019, 27 pages.
EP2861210: Proprietor's statement of grounds of appeal to opposition decision dated Dec. 30, 2019, 35 pages.
EP2861210: Proprietor's Main and Auxiliary Requests Mr, AR1, AR2, and AR3 with Proprietor's Statement of Grounds of Appeal in Opposition Proceedings filed Dec. 30, 2019, 4 pages.
EP2861210: Proprietor's statement of grounds of appeal to opposition decision dated Dec. 30, 2019, D23 (Declaration of Amy McKee M.D.) including D23A (Hoos W, et al., "Pancreatic Cancer Clinical Trials and Accrual in the United Sates." J Clin Oncol. 31(27):3432-8 (2013) and accompanying Appendix Table A1, Table A2, and Figure A1) and D23B (BIO Industry Analysis: Clinical Development Success Rates 2006-2015, Jul. 2016), 44 total pages.
EP2861210: Proprietor's statement of grounds of appeal to opposition decision dated Dec. 30, 2019, D24 (Declaration of Bruce Belanger, Ph.D.), 2 pages.
EP2861210: Reply to proprietor's grounds of appeal following opposition and cover letter, dated Jul. 27, 2020, 35 pages.
EP2861210: Reply to proprietor's grounds of appeal to opposition decision dated Jul. 27, 2020, D15c (EU clinical trial database for NAPOLI-1 study from Oct. 12, 2012, corresponds to D15b), 10 pages.
EP2861210: Reply to proprietor's grounds of appeal to opposition decision dated Jul. 27, 2020, D25 (Chen P, et al., "Comparing Routes of Delivery for Nanoliposomal Irinotecan Shows Superior Anti-Tumor Activity of Local Administration in Treating Intracranial Glioblastoma Xenografts," Neuro Oncol. 15(2):189-97 (2013), Epub Dec. 21, 2012).
EP2861210: Reply to proprietor's grounds of appeal to opposition decision dated Jul. 27, 2020, D26 (Drummond D, et al., "Development of a Highly Active Nanoliposomal Irinotecan Using a Novel Intraliposomal Stabilization Strategy," Cancer Res. 66(6):3271-77 (2006)).
EP2861210: Reply to proprietor's grounds of appeal to opposition decision dated Jul. 27, 2020, D27 (Roy A, et al., "A Randomized Phase II Study of PEP02 (MM-398), Irinotecan or Docetaxel as a Second-Line Therapy in Patients With Locally Advanced or Metastatic Gastric or Gastro-Oesophageal Junction Adenocarcinoma," Ann Oncol. 24(6):1567-73 (2013)).
EP2861210: Reply to proprietor's grounds of appeal to opposition decision dated Jul. 27, 2020, D28 (Svenson S, "Clinical Translation of Nanomedicines," Current Opinion in Solid State and Materials Science. 16(6):287-294 (2012), article in press version, 7 pages).
EP2861210: Reply to proprietor's grounds of appeal to opposition decision dated Jul. 27, 2020, D29 (Makrilia N, et al., "Treatment for Refractory Pancreatic Cancer. Highlights from the '2011 ASCO Gastrointestinal Cancers Symposium'. San Francisco, CA, USA, Jan. 20-22, 2011," J Pancreas. 12(2):110-3 (2011)).
EP2861210: Reply to proprietor's grounds of appeal to opposition decision dated Jul. 27, 2020, D30 (Chen L, et al., "Phase I Study of Biweekly Liposome Irinotecan (PEP02, MM-398) in Metastatic Colorectal Cancer Failed on First-line Oxaliplatin-based Chemotherapy," J Clin Oncol. 30(4_suppl):Abstract 613 (2012), 5 printed pages.).
EP2861210: Reply to proprietor's grounds of appeal to opposition decision dated Jul. 27, 2020, D31 (Cunningham D, et al., "Randomized Phase II Study of PEP02, Irinotecan, or Docetaxel as a Second-Line Therapy in Gastric or Gastroesophageal Junction Adenocarcinoma," J Clin Oncol. 29(4_supp):Abstract 6 (2011), 5 printed pages).
EP2861210: Reply to proprietor's grounds of appeal to opposition decision dated Jul. 27, 2020, D32 (Gerber D, "Miscellaneous Agents—Cytotoxics and Hormonal Agents," J Thorac Oncol. 7(12 Suppl 5):S387-9 (2012)).
EP2861210: Reply to proprietor's grounds of appeal to opposition decision dated Jul. 27, 2020, D33 (Noble C, et al., "Novel Nanoliposomal CPT-11 Infused by Convection-Enhanced Delivery in Intracranial Tumors: Pharmacology and Efficacy," Cancer Res. 66(5):2801-6 (2006).
EP2861210: Reply to proprietor's grounds of appeal to opposition decision dated Jul. 27, 2020, D34 (Krauze M, et al., "Convection-Enhanced Delivery of Nanoliposomal CPT-11 (Irinotecan) and PEGylated Liposomal Doxorubicin (Doxil) in Rodent Intracranial Brain Tumor Xenografts," Neuro Oncol. 9(4):393-403 (2007).
EP2861210: Reply to proprietor's grounds of appeal to opposition decision dated Jul. 27, 2020, D35 (Mullard A, "How Much Do Phase III Trials Cost?" Nat Rev Drug Discov. 17(11):777 (2018)).
EP2861210: Reply to proprietor's grounds of appeal to opposition decision dated Jul. 27, 2020, D36 (The Medicines for Human Use (Clinical Trials) Regulations, 2004, 86 pages).
Colbern G, et al., "Encapsulation of the Topoisomerase I Inhibitor GL147211C in Pegylated (STEALTH) Liposomes: Pharmacokinetics and Antitumor Activity in HT29 Colon Tumor Xenografts," Clin Cancer Res. 4(12):3077-82 (1998).
Colucci G, et. al., "Randomized Phase III Trial of Gemcitabine Plus Cisplatin Compared With Single-Agent Gemcitabine as First-Line Treatment of Patients With Advanced Pancreatic Cancer: The GIP-1 Study," J Clin Oncol. 28(10):1645-51 (2010).
Comella P, et. al., "Irinotecan Plus Leucovorin-Modulated 5-Fluorouracil I.V. Bolus Every Other Week May Be a Suitable Therapeutic Option Also for Elderly Patients With Metastatic Colorectal Carcinoma," Br J Cancer. 89(6):992-6 (2003).
Conroy T et al., Abstract 4010. "Randomized Phase III Trial Comparing FOLFIRINOX (F: 5FU/Leucovorin [LV], Irinotecan [I}, and Oxaliplatin [O]) Versus Gemcitibine (G) as First-Line Treatment for Metastatic Pancreatic Adenocarcinoma (MPA): Preplanned Interim Analysis Results of the PRODIGE 4/ACCORD 11 Trial" J Clin Oncol. 28(15_Suppl):4010 (2010), 3 printed pages.
Conroy T, et al., "FOLFIRINOX versus Gemcitabine for Metastatic Pancreatic Cancer," N Engl J Med. 364(19):1817-25 (2011).
Conroy T, et al., "Irinotecan Plus Oxaliplatin and Leucovorin-Modulated Fluorouracil in Advanced Pancreatic Cancer—A Groupe Tumeurs Digestives of the Fédération Nationale des Centres de Lutte Contre le Cancer Study," J Clin Oncol. 23(6):1228-36 (2005).
Cortés J, et al., Abstract CT154. "Multicenter Open-Label, Phase II Trial, to Evaluate the Efficacy and Safety of Liposomal Irinotecan (nal-IRI) for Progressing Brain Metastases in Patients with HER2-Negative Breast Cancer (The Phenomenal Study)," In Proceedings of the American Association for Cancer Research Annual Meeting 2018; Apr. 14-18, 2018; Chicago, Illinois. Cancer Res. 2018;78(13 Suppl):Abstract nr CT154, 3 printed pages.
Custodio A, et. al., "Second-Line Therapy for Advanced Pancreatic Cancer: A Review of the Literature and Future Directions," Cancer Treat Rev. 35(8):676-84 (2009).
Daleke D, et al., "Endocytosis of Liposomes by Macrophages: Binding, Acidification and Leakage of Liposomes Monitored by a New Fluorescence Assay," Biochim Biophys Acta. 1024(2):352-66 (1990).
DaunoXome (daunorubicin citrate liposome injection) package insert, rev. Dec. 2011, 11 pages.
Davidson D, et al., "The PARP Inhibitor ABT-888 Synergizes Irinotecan Treatment of Colon Cancer Cell Lines," Invest New Drugs. 31(2);461-8 (2013) DOI: 10.1007/s10637-012-9886-7; Epub Oct. 9, 2012, 8 pages.
Dawidczyk C, et al., "State-of-the-art in Design Rules for Drug Delivery Platforms: Lessons Learned from FDA-Approved Nanomedicines," J Control Release. 187:133-44 (2014).
Dayyani F, et al., Abstract B14. "CA 19-9 levels in patients with metastatic pancreatic adenocarcinoma receiving first-line therapy with liposomal irinotecan plus 5-fluorouracil/leucovorin and oxaliplatin (NAPOX)," In Proceedings of the AACR Special Conference on Pancreatic Cancer: Advances in Science and Clinical Care; Sep. 6-9, 2019; Boston, MA; Cancer Res. 2019; 79(24 Suppl): Abstract nr B14, 3 printed pages.
De Jong F, et al., "Effects of nal-IRI (MM-398; a Liposomal Formulation of Irinotecan) ± 5-Fluorouracil (5-FU) on Quality of Life (QoL) in NAPOLI-1: A Phase 3 Study in Patients With Metastatic Pancreatic Ductal Adenocarcinoma Previously Treated With Gemcitabine," Poster presented at the Australian Gastro-

(56) References Cited

OTHER PUBLICATIONS

Intestinal Trials Group, 18th Annual Scientific Meeting, Melbourne, Australia, Sep. 14-16, 2016, 10 pages.
De Jong F, et al., Abstract. "Effects of nal-IRI (MM-398; a Liposomal Formulation of Irinotecan) ± 5-Fluorouracil (5-FU) on Quality of Life (QoL) in NAPOLI-1: A Phase 3 Study in Patients With Metastatic Pancreatic Ductal Adenocarcinoma (mPDAC) Previously Treated With Gemcitabine," Australian Gastro-Intestinal Trials Group, 18th Annual Scientific Meeting, Melbourne, Australia, Sep. 14-16, 2016, 2 pages.
Dean A, et al., "A Phase 2, Open-Label Dose-Exploration Study of Liposomal Irinotecan (nal-IRI) Plus 5-Flurouracil/Leucovorin (5-FU/LV) plus Oxaliplatin (OX) in Patients With Previously Untreated Metastatic Pancreatic Cancer." Poster presented at the American Society of Clinical Oncology Annual Conference, Chicago, IL, Jun. 1-5, 2018, 11 pages.
Dean A, et al., "A Randomized, Open-label, Phase 2 Study of Nanoliposomal Irinotecan (nal-IRI)-containing Regimens versus nab-Paclitaxel Plus Gemcitabine in Patients with Previously Untreated, Metastatic Pancreatic Adenocarcinoma (mPAC)." Poster presented at the Gastrointestinal Cancers Symposium ASCO 2016, 11 pages.
Dean A, et al., "A Randomized, Open-label, Phase 2 Study of Nanoliposomal Irinotecan (nal-IRI)-containing Regimens versus nab-Paclitaxel Plus Gemcitabine in Patients with Previously Untreated, Metastatic Pancreatic Adenocarcinoma (mPAC)." Poster handout at the Gastrointestinal Cancers Symposium ASCO 2016, 2 pages.
Dean A, et al., "First-Line (1L) Liposomal Irinotecan + 5-Fluorouracil/Leucovorin (5-FU/LV) + Oxaliplatin (OX) in Patients With Locally Advanced or Metastatic Pancreatic Ductal Adenocarcinoma: Exploratory Subgroup Analyses of Survival by Changes in CA 19-9 Levels." Poster presented at the European Society for Medical Oncology (ESMO) Virtual Congress 2020, Sep. 19-21, 2020, 7 pages.
Dean A, et al., "First-Line Liposomal Irinotecan + 5-Fluorouracil/Leucovorin + Oxaliplatin in Patients With Pancreatic Ductal Adenocarcinoma: Results From a Phase 1/2 Study." Presentation presented at the Clinical Oncology Society of Australia (COSA): Virtual meeting, Nov. 11-13, 2020, 10 pages.
Dean A, et al., "Nanoliposomal Irinotecan (nal-IRI)-Containing Regimens Versus nab-paclitaxel Plus Gemcitabine as First-Line Therapy in Patients With Metastatic Pancreatic Adenocarcinoma (mPAC): A Randomized, Open-Label Phase 2 Study." Poster presented at the 18th European Society of Medical Oncology World Congress on Gastrointestinal Cancer; Barcelona, Spain; Jun. 29-Jul. 2, 2016, 14 pages.
Dean A, et al., "NAPOLI-3: An Open-Label, Randomized, Phase III Study of First-Line Liposomal Irinotecan + 5-Fluorouracil/Leucovorin + Oxaliplatin Versus nab-Paclitaxel + Gemcitabine in Patients With Metastatic Pancreatic Ductal Adenocarcinoma." Presentation presented at the Clinical Oncology Society of Australia (COSA): Virtual meeting, Nov. 11-13, 2020, 10 pages.
Dean A, et al., Abstract 1529P. "First-Line (1L) Liposomal Irinotecan + 5-Fluorouracil/Leucovorin (5-FU/LV) + Oxaliplatin (OX) in Patients With Locally Advanced or Metastatic Pancreatic Ductal Adenocarcinoma (mPDAC): Exploratory Subgroup Analyses of Survival by Changes in CA 19-9 Levels," Ann Oncol. 31(Suppl_4):S881-S897 10.1016/annonc/annonc285 (2020), 3 printed pages.
Dean A, et al., Abstract 222. "First-Line Liposomal Irinotecan + 5-Fluorouracil/Leucovorin + Oxaliplatin in Patients With Pancreatic Ductal Adenocarcinoma: Results From a Phase 1/2 Study," Asia-Pac J Clin Oncol. 16(Suppl. 3):118-119 (2020).
Dean A, et al., Abstract 407. "NAPOLI-3: An Open-Label, Randomized, Phase III Study of First-Line Liposomal Irinotecan + 5-Fluorouracil/Leucovorin + Oxaliplatin Versus nab-Paclitaxel + Gemcitabine in Patients With Metastatic Pancreatic Ductal Adenocarcinoma," Asia-Pac J Clin Oncol. 16(Suppl. 8):202-3 (2020).
Dean A, et al., Abstract 4111. "A Phase 1/2, Open-Label Dose-Escalation Study of Liposomal Irinotecan (nal-IRI) Plus 5-Fluorouracil/Leucovorin (5-FU/LV) and Oxaliplatin (OX) in Patients with Previously Untreated Metastatic Pancreatic Cancer (mPAC)," J Clin Oncol. 36(15_Suppl):4111 10.1200/JCO.2018.36.15_suppl.4111 (2018), 1 page.
Dean A, et al., Abstract P-287. "Nanoliposomal Irinotecan (nal-IRI)-Containing Regimens Versus nab-paclitaxel Plus Gemcitabine as First-Line Therapy in Patients With Metastatic Pancreatic Adenocarcinoma (mPAC): A Randomized, Open-Label Phase 2 Study." Annals of Oncology. 27(Suppl 2):ii1-i85 (2016), 1 page.
Dean A, et al., Abstract. "Expanded Analyses of NAPOLI-1: Phase 3 Study of MM-398 (nal-IRI), With or Without 5-Fluorouracil and Leucovorin (5-FU/LV), Versus 5-FU/LV, in Metastatic Pancreatic Cancer (mPAC) Previously Treated With Gemcitabine-Based Therapy," 18th Annual Scientific Meeting of the Australasian Gastro-Intestinal Trials Group (AGITG), Melbourne, Australia, Sep. 14-16, 2016, 2 pages.
Dean A, et al., Abstract. "Liposomal Irinotecan (nal-IRI, MM-398)-Containing Regimens Versus nab-Paclitaxel Plus Gemcitabine as First-Line Therapy in Patients With Metastatic Pancreatic Adenocarcinoma (mPAC): A Randomized, Open-Label Phase 2 Study," 18th Annual Scientific Meeting of the Australasian Gastro-Intestinal Trials Group (AGITG), Melbourne, Australia, Sep. 14-16, 2016, 2 pages.
Delord J, et al., "Population Pharmacokinetics of Oxaliplatin," Cancer Chemother Pharmacol. 51(2):127-31 (2003), Epub Dec. 4, 2002.
Delord J, et. al., "A Phase I Clinical and Pharmacokinetic Study of Capecitabine (Xeloda®) and Irinotecan Combination Therapy (XELIRI) in Patients With Metastatic Gastrointestinal Tumours," Br J Cancer. 92(5):820-6 (2005).
Derksen J, et. al., "Interaction of Immunoglobulin-Coupled Liposomes with Rat Liver Macrophages In Vitro," Exp Cell Res. 168(1):105-15 (1987).
Dewhirst M, et al., "Microvascular Studies on the Origins of Perfusion-Limited Hypoxia," Br J Cancer Suppl. 27:S247-51 (1996).
Dickinson P, et al., "Canine Model of Convection-Enhanced Delivery of Liposomes Containing CPT-11 Monitored with Real-Time Magnetic Resonance Imaging," J. Neurosurg. 108(5):989-98 (2008).
Dickinson P, et al., "Canine Spontaneous Glioma: A Translational Model System for Convection-Enhanced Delivery," Neuro Oncol. 12(9):928-40; Epub 10:1093/neuonc/noq046, 1-13 (2010).
Dicko A, et al., "Intra and Inter-Molecular Interactions Dictate the Aggregation State of Irinotecan Co-Encapsulated with Floxuridine Inside Liposomes," Pharm Res. 25(7):1702-13 (2008).
Dieguez G, et al., "Real-World Rates of Hematologic Laboratory Abnormalities and Associated Cost Among Metastatic Pancreatic Cancer Therapeutic Regimens," Poster presented at the American Society of Clinical Oncology Gastrointestinal Cancers Symposium (ASCO GI), San Francisco, CA, Jan. 23-25, 2020, 6 pages.
Dieguez G, et al., Abstract 670. "Real-World Rates of Hematology Lab Abnormalities and Associated Cost Among Metastatic Pancreatic Cancer (mPC) Therapeutic Regimens," J Clin Oncol. 38(4_Suppl):670 DOI: 10.1200/JCO.2020.38.4_suppl.670 (2020), 2 printed pages.
Doris J, et al., Abstract CT12. "The Cost of Adverse Events for FDA-Approved/NCCN Category 1 Treatments for Medicare Fee-For-Service (FFS) Patients With Metastatic Pancreatic Cancer: Focus on Liposomal Irinotecan-Based Regimens," Hematology Oncology Pharmacy Association (HOPA) Annual Conference, Mar. 11-14, 2020, available at eventscribe.com/2020/posters/HOPAahead/SplitViewer.asp?PID=Njg0NzA2NjU1NjE, (2020), 2 pages.
Dos Santos N, et al., "Improved Retention of Idarubicin After Intravenous Injection Obtained for Cholesterol-Free Liposomes," Biochim Biophys Acta. 1561(2):188-201 (2002).
Dósa E, et al., "Magnetic Resonance Imaging of Intracranial Tumors: Intra-Patient Comparison of Gadoteridol and Ferumoxytol," Neuro Oncol. 13(2):251-60 (2011) doi: 10.1093/neuonc/noq172. Epub 2010.
Douillard J, et al., "Irinotecan Combined with Fluorouracil Compared with Fluorouracil Alone as First-line Treatment for Metastatic Colorectal Cancer: A Multicentre Randomised Trial," Lancet. 355(9209):1041-7 (2000).

(56) References Cited

OTHER PUBLICATIONS

DOXIL package insert, revision Apr. 16, 2015, retrieved from https://www.accessdata.fda.gov/drugsatfda_docs/label/2015/050718s048lbl.pdf, 28 pages.
DOXIL package insert, revision Aug. 30, 2013, retrieved from https://www.accessdata.fda.gov/drugsatfda_docs/label/2013/050718s045lbl.pdf, 35 pages.
DOXIL package insert, revision Jun. 10, 2008, retrieved from https://www.accessdata.fda.gov/drugsatfda_docs/label/2008/050718s033lbl.pdf, 34 pages.
Drummond D, et al., "Clinical Development of Histone Deacetylase Inhibitors as Anticancer Agents, " Annu Rev Pharmacol Toxicol. 45:495-528 and C1-C2 (2005).
Drummond D, et al., "Development of a Highly Active Nanoliposomal Irinotecan Using a Novel Intraliposomal Stabilization Strategy," Cancer Res. 66(6):3271-77 (2006).
Drummond D, et al., "Development of a Highly Stable and Targetable Nanoliposomal Formulation of Topotecan," J Control Release. 141(1):13-21 (2010). Epub 2009.
Drummond D, et al., "Improved Pharmacokinetics and Efficacy of a Highly Stable Nanoliposomal Vinorelbine," J Pharmacol Exp Ther. 328(1):321-30 (2009). Epub 2008.
Drummond D, et al., "Liposome Targeting to Tumors using Vitamin and Growth Factor Receptors," Vitam Horm. 60:285-332 (2000).
Abra R, et al., "The Next Generation of Liposome Delivery Systems: Recent Experience With Tumor-Targeted, Sterically-Stabilized Immunoliposomes and Active-Loading Gradients," J Liposome Res. 12(1-2):1-3 (2002).
Abrams T, et al., "Patterns of Chemotherapy Use in a U.S.-Based Cohort of Patients with Metastatic Pancreatic Cancer," Oncologist. 22(8):925-933 (2017).
ABRAXANE package insert, revision Dec. 23, 2011, retrieved from https://www.accessdata.fda.gov/drugsatfda_docs/label/2011/021660s025s026s029lbl.pdf, 13 pages.
ABRAXANE package insert, revision Jul. 21, 2015, retrieved from https://www.accessdata.fda.gov/drugsatfda_docs/label/2015/021660s041lbl.pdf, 24 pages.
Abushahin L, et al., "Multivariable Analysis of Real-World Clinical Outcomes Associated With Dose Reductions (DRs) for Patients (pts) With Metastatic Pancreatic Ductal Adenocarcinoma (mPDAC) Treated with Liposomal rinotecan." Poster presented at the European Society for Medical Oncology Virtual Congress Sep. 19-21, 2020, 6 pages.
Abushahin L, et al., Abstract 1534P. "Multivariable Analysis of Real-World Clinical Outcomes Associated With Dose Reductions (DRs) for Patients (pts) With Metastatic Pancreatic Ductal Adenocarcinoma (mPDAC) Treated with Liposomal Irinotecan" Ann Oncol. 31(Suppl_4):S881-S897 10.1016/annonc/annonc285 (2020), 2 printed pages.
Abushahin L, et al., Abstract e16780. "Real-World Dosing, Management, and Clinical Outcomes of Patients (pts) With Metastatic Pancreatic Adenocarcinoma (mPDAC) Treated With Liposomal Irinotecan," J Clin Oncol. 38(15_Suppl):e16780 DOI: 10.1200/JCO.2020.38.15_suppl.e16780 (2020), 2 printed pages.
Adiwijaya B, et al., "Population Pharmacokinetics of Liposomal Irinotecan in Patients With Cancer," Clin Pharmacol Ther. 102(6):997-1005 (2017).
Ahmad I, et al., "Antibody-Targeted Delivery of Doxorubicin Entrapped in Sterically Stabilized Liposomes Can Eradicate Lung Cancer in Mice," Cancer Res. 53(7):1484-8 (1993).
Ahn D, et al., "Real-World Dosing Patterns of Patients With Metastatic Pancreatic Cancer (mPC) Treated With Liposomal Irinotecan (nal-IRI) in US Oncology Clinics." Poster presented at the European Society for Medical Oncology (ESMO), Munich, Germany, Oct. 19-23, 2018, 8 pages.
Ahn D, et al., Abstract 735P. "Real-World Dosing Patterns of Patients (pts) With Metastatic Pancreatic Cancer (mPC) Treated With Liposomal Irinotecan (nal-IRI) in US Oncology Clinics," Ann Oncol. 29(Suppl_8):viii251 doi:10.1093/annonc/mdy282 (2018).
Alagoz M, et al., "DNA Repair and Resistance to Topoisomerase I Inhibitors: Mechanisms, Biomarkers and Therapeutic Targets," Curr Med Chem. 19(23):3874-85 (2012).
Alberts S, et al. "Gemcitabine and Oxaliptatin for Metastatic Pancreatic Adenocarcinoma: A North Central Cancer Treatment Group Phase II Study," Ann Oncol. 14(4):580-5 (2003).
Alcindor T, et al., "Oxaliplatin: A Review in the Era of Molecularly Targeted Therapy," Curr Oncol. 18(1):18-25 (2011).
Alese O, et al., "A Phase I/II Study of Trifluridine/Tipiracil (TAS-102) in Combination With Nanoliposomal Irinotecan (NAL-IRI) in Advanced GI Cancers." Poster presented at Chan E, et al., "A Phase 1/2 Study Combining MM-151 + nal-IRI + 5-FU + Leucovorin in RAS/RAF Wild-Type Metastatic Colorectal Cancer." Poster presented at the American Society of Clinical Oncology (ASCO) Annual Meeting, Chicago, Illinois, Jun. 1-5, 2018, 1 page.
Alese O, et al., Abstract TPS4155. "A Phase I/II Study of Trifluridine/Tipiracil (TAS-102) in Combination With Nanoliposomal Irinotecan (NAL-IRI) in Advanced GI Cancers," J Clin Oncol. 36(15_Suppl):TPS4155 DOI: 10.1200/JCO.2018.36.15_suppl.TPS4155 (2018), 5 printed pages.
Alfert M, et al., "A Selective Staining Method for the Basic Proteins of Cell Nuclei," Proc Natl Acad Sci USA. 39(10):991-9 (1953).
Allegrini G, et. al., "A Pharmacokinetic and Pharmacodynamic Study on Metronomic Irinotecan in Metastatic Colorectal Cancer Patients," Br J Cancer. 98(8):1312-19 (2008).
Alves Da Silva A, et. al., "Standardization of the Infusion Sequence of Antineoplastic Drugs Used in the Treatment of Breast and Colorectal Cancers," Einstein (Sao Paulo). 16(2):eRW4074 doi: 10.1590/S1679-45082018RW4074 (2018), 9 pages.
American Chemical Society (ACS), http://www.cancer.org/cancer/pancreaticcancer/detailedguide/pancreatic-cancer-what-is-pancreatic-cancer, retrieved Dec. 1, 2016, 4 printed pages.
American Chemical Society (ACS), http://www.cancer.org/cancer/pancreaticcancer/detailedguide/pancreatic-cancer-what-is-pancreatic-cancer, retrieved Dec. 10, 2017, 7 printed pages.
Amodeo S, et al., "Can we downstage locally advanced pancreatic cancer to resectable? A phase I/II study of Induction oxaliplatin and 5-FU chemoradiation," J Gastrointest Oncol. 9(5):922-35 (2018).
Amzal B, et al., "Imputing Missing Values to Estimate Health-Related Quality of Life (HR-QoL) in Metastatic Pancreatic Cancer Treated With 5-Fluorouracil and Leucovorin, With and Without Liposomal Irinotecan (nal-IRI)." Poster presented at the International Society for Pharmacoeconomics and Outcomes Research (ISPOR) Annual Meeting, Boston, MA, May 20-24, 2017, 6 pages.
Amzal B, et al., Abstract PCN179. "Imputing Missing Values to Estimate Health-Related Quality of Life (HR-QoL) in Metastatic Pancreatic Cancer (mpc) Treated With 5-Fluorouracil and Leucovorin, With and Without Liposomal rinotecan (nal-IRI)," Value in Health. 20(5):A119 (2017).
Anders C, et al., "Phase 1 Expansion Study of Irinotecan Liposome Injection (nal-IRI) in Patients with Metastatic Breast Cancer (mBC): Findings from the Cohort with Active Brain Metastasis (BM)." Presentation presented at the Society for Neuro-Oncology Inaugural Conference on Brain Metasteses, Aug. 16-17, 2019, New York, NY, 11 pages.
Anders C, et al., Abstract e12003. "Pharmacokinetic (PK) Characterization of Irinotecan Liposome Injection in Patients (pts) With Metastatic Breast Cancer (mBC)," J Clin Oncol. 37(15_Suppl):e12003 DOI: 10.1200/JCO.2019.37.15_suppl.e12003 (2019), 2 printed pages.
Anders C, et al., Abstract TRLS-06. "Phase 1 Expansion Study of Irinotecan Liposome Injection (nal-IRI) in Patients with Metastatic Breast Cancer (mBC): Findings from the Cohort with Active Brain Metastasis (BM)," Neuro-Oncology Advances. 1(Suppl 1):i9 doi.org/10.1093/noajnl/vdz014.039 (2019).
Andre T, et. al., "Phase III Study Comparing a Semimonthly With a Monthly Regimen of Fluorouracil and Leucovorin as Adjuvant Treatment for Stage II and III Colon Cancer Patients: Final Results of GERCOR C96.1," Clin Oncol. 25(24):3732-8 (2007).
Aranda E, et. al., "Randomized Study of Weekly Irinotecan Plus High-Dose 5-Fluorouracil (FUIRI) Versus Biweekly Irinotecan Plus 5-Fluorouracil/Leucovorin (FOLFIRI) as First-Line Chemotherapy

(56) References Cited

OTHER PUBLICATIONS for Patients With Metastatic Colorectal Cancer: A Spanish Cooperative Group for the Treatmentof Digestive Tumors Study," Ann Oncol. 20(2):251-7 (2009).
Araneo M, et. al., "Biweekly Low-Dose Sequential Gemcitabine, 5-Fluorouracil, Leucovorin, and Cisplatin (GFP): A Highly Active Novel Therapy for Metastatic Adenocarcinoma of the Exocrine Pancreas," Cancer Invest. 21(4):489-96 (2003).
Ardizzoni A, et al., "Topotecan, A New Active Drug in the Second-Line Treatment of Small-Cell Lung Cancer: A Phase II Study in Patients with Refractory and Sensitive Disease," J Clin Oncol. 15(5):2090-6 (1997).
Assaf E, et al., "5-Fluorouracil/Leucovorin Combined with Irinotecan and Oxaliplatin (FOLFIRINOX) as Second-Line Chemotherapy in Patients with Metastatic Pancreatic Adenocarcinoma," Oncology. 80(5-6):301-6 (2011).
Atkins K, et al., "A Phase I Study of Nanoliposomal Irinotecan and 5-Fluorouracil/Folinic Acid in Combination With Interleukin-1-alpha Antagonist for Advanced Pancreatic Cancer Patients With Cachexia (OnFX)." Poster presented at the American Society of Clinical Oncology Gastrointestinal Cancers Symposium (ASCO GI), San Francisco, CA, Jan. 23-25, 2020, 1 page.
Atkins K, et al., Abstract TPS780. "A Phase I Study of Nanoliposomal Irinotecan and 5-Fluorouracil/Folinic Acid in Combination With Interleukin-1-alpha Antagonist for Advanced Pancreatic Cancer Patients With Cachexia (OnFX)," J Clin Oncol. 38(4_Suppl):TPS780 DOI: 10.1200/JCO.2020.38.4_suppl.TPS780 (2020), 2 printed pages.
Author Unknown, "From Antinutrient to Phytonutrient: Phytic Acid Gains Respect." HighBeam Research, Environmental Nutrition, Apr. 1, 2004, 2 printed pages. URL: http://www.highbeam.com/doc/1G1-116341390.html/print (accessed Nov. 4, 2011).
Awasthi N, et al., "Antitumor Efficacy of a Liposomal Formulation of Irinotecan in Preclinical Gastric Cancer Models: Augmenting Its Response by Antiangiogenic Agents." Poster presented at the Annual Meeting of the American Association for Cancer Research 2020, Philadelphia, PA, Apr. 27-28, 2020 and Jun. 22-24, 2020, 6 pages.
Awasthi N, et al., Abstract 553. "Antitumor Efficacy of a Liposomal Formulation of Irinotecan in Preclinical Gastric Cancer Models: Augmenting Its Response by Antiangiogenic Agents," In Proceedings of the Annual Meeting of the American Association for Cancer Research 2020; Apr. 27-28, 2020 and Jun. 22-24, 2020. Cancer Res. 2020;80(16 Suppl):Abstract nr 553, DOI: 10.1158/1538-7445.AM2020-553, 2 printed pages.
Azrak R, et al., "Therapeutic Synergy Between Irinotecan and 5-Fluorouracil against Human Tumor Xenografts," Clin Cancer Res. 10(3):1121-9 (2004).
Baker J, et al., "Irinophore C, a Novel Nanoformulation of Irinotecan, Alters Tumor Vascular Function and Enhances the Distribution of 5-Fluorouracil and Doxorubicin," Clin Cancer Res. 14(22):7260-71 (2008).
Barbier S, et al., Abstract e16724. "Differentiation of Liposomal Irinotecan From Dose-Dense Non-Liposomal Irinotecan in Patient-Derived Pancreatic Cancer Xenograft Tumor Models," J Clin Oncol. 38(15_Suppl):e16724 DOI: 10.1200/JCO.2020.38.15_suppl.e16724 (2020), 5 printed pages.
Barenholz Y, "Development of Liposomal Drugs and Nano-Drugs: From Academic Research via Incubators and Startups to FDA and EMA Approved Products. Part I: Science and Technology," Presentation presented at Barcelona NanoMed, Mar. 4-5, 2014, 89 pages.
Barenholz Y, "Doxil®—The First FDA-Approved Nano-Drug: Lessons Learned," J Control Release. 160(2):117-34 (2012).
Barone C, et. al., "Schedule-Dependent Activity of 5-Fluorouracil and Irinotecan Combination in the Treatment of Human Colorectal Cancer: In Vitro Evidence and a Phase I Dose-Escalating Clinical Trial," Br J Cancer. 96(1):21-8 (2007). Epub 2006.
Barzi A, et al., Abstract e16229. "Real World Outcomes of Metastatic Pancreatic Cancer (mPC) Patients (pts) Treated With Liposomal Irinotecan (nal-IRI) in the US," J Clin Oncol. 36(15_Suppl):e16229 DOI: 10.1200/JCO.2018.36.15_suppl.e16229 (2018), 2 printed pages.
Basu S, et. al., "Development and Validation of an UPLC-MS/MS Method for the Quantification of Irinotecan, SN 38 and SN-38 Glucuronide in Plasma, Urine, Feces, Liver and Kidney: Application to a Pharmacokinetic Study of Irinotecan in Rats," J Chromatogr B Analyt Technol Biomed Life Sci. 1015-1016: 34-41 (2016).
Batist G, et al., "Safety Pharmacokinetics, and Efficacy of CPX-1 Liposome Injection in Patients with Advanced Solid Tumors," Clin Cancer Res. 15(2):692-700 (2009).
Batist G, et al., Abstract 2014. "Phase 1 Study of CPX-1, A Fixed Ratio Formulation of Irinotecan (IRI) and Floxuridine (FLOX), in Patients With Advanced Solid Tumors," J Clin Oncol. 24(18_suppl):2014 (2006), 2 printed pages.
Batist G, et al., Abstract 2549. "Ratiometric Dosing of Irinotecan (IRI) and Floxuridine (FLOX) in a Phase I Trial: A New Approach for Enhancing the Activity of Combination Chemotherapy," J Clin Oncol. 25(18_suppl):2549 (2007), 5 printed pages.
Becker C, et al., "Multivariate Analysis of Health-Related Quality of Life (HR-QoL) in Metastatic Pancreatic Cancer Treated with 5-Fluorouracil and Leucovorin (5-FU/LV), With and Without Liposomal Irinotecan (nal-IRI)." Poster presented at the International Society for Pharmacoeconomics and Outcomes Research (ISPOR) Annual Meeting, Boston, MA, May 20-24, 2017, 7 pages.
Becker C, et al., Abstract PCN182. "Multivariate Analysis of Health-Related Quality of Life (HR-QoL) in Metastatic Pancreatic Cancer (mPC) Treated with 5- Fluorouracil and Leucovorin, With and Without Liposomal Irinotecan (nal-IRI)," Value in Health. 20(5):A120 (2017).
Siegel R, et al., "Cancer Statistics, 2015," CA Cancer J Clin. 65(1):5-29 (2015).
Siveke J, et al., "Subgroup Analysis by Measurable Metastatic Lesion (ML) Number and Selected Lesion Locations (LL) at Baseline (BL) in NAPOLI-1: A Phase 3 Study of Liposomal Irinotecan (nal-IRI)±5-Fluorouracil/Leucovorin (5-FU/LV) in Patients With Metastatic Pancreatic Ductal Adenocarcinoma Previously Treated With Gemcitabine-Based Therapy." Poster presented at the American Society of Clinical Oncology Gastrointestinal Cancers Symposium (ASCO GI), San Francisco, CA, Jan. 18-20, 2018, 8 pages.
Siveke J, et al., Abstract 460. "Subgroup Analysis by Measurable Metastatic Lesion (ML) Number and Selected Lesion Locations (LL) at Baseline (BL) in NAPOLI-1: A Phase III Study of Liposomal Irinotecan (nal-IRI) ±5-Fluorouracil/Leucovorin (5-FU/LV) in Patients (pts) With Metastatic Pancreatic Ductal Adenocarcinoma (mPDAC) Previously Treated With Gemcitabine-Based Therapy," J Clin Oncol. 36(4_Suppl):460 DOI: 10.1200/JCO.2018.36.4_suppl.460 (2018), 2 printed pages.
Siveke J, et al., Abstract ID0596. "Expanded Analyses of NAPOLI-1: Phase 3 Study of nal-IRI (MM-398), With or Without 5-Fluorouracil (5FU) and Leucovorin (LV), Versus 5-Fluorouracil and Leucovorin (5FU/LV), in Metastatic Pancreatic Cancer (mPAC) Previously Treated With Gemcitabine-Based Therapy," Oncol Res Treat. 39(Suppl 1):170 (2016).
Siveke J, et al., Abstract P863. "Effects of Nanoliposomal Irinotecan (nal-IRI;MM-398) ± 5-Fluorouracil und Leucavorin (5-FU/LV) on Quality of Life (QoL) in NAPOLI-1: A Phase 3 Study in Patients (pts) With Metastatic Pancreatic Adenocarcinoma (mPAC) Previously Treated With Gemcitabine-Based Therapy," Oncol Res Threat. 39(Suppl 3):259 (2016).
Skof E, et. al., "Capecitabine Plus Irinotecan (XELIRI Regimen) Compared to 5-FU/LV Plus Irinotecan (FOLFIRI Regimen) as Neoadjuvant Treatment for Patients With Unresectable Liver-Only Metastases of Metastatic Colorectal Cancer: A Randomised Prospective Phase II Trial," BMC Cancer. 9:120 doi: 10.1186/1471-2407-9-120 (2009), 9 pages.
Slatter J, et al., "Pharmacokinetics, Metabolism, and Excretion of Irinotecan (CPT-11) Following I.V. Infusion of [14C]CPT-11 in Cancer Patients," Drug Metab Dispos. 28(4):423-33 (2000).
Soares H, et al., "A Phase II Study of Capecitabine Plus Docetaxel in Gemcitabine-Pretreated Metastatic Pancreatic Cancer Patients: CapTere," Cancer Chemother Pharmacol. 73(4):839-45 (2014).
Sohal D et. al., "Metastatic Pancreatic Cancer: ASCO Clinical Practice Guideline Update," J Clin Oncol. 36(24):2545-2556 and appendix (2018).

(56) References Cited

OTHER PUBLICATIONS

Sohal D, et. al., "Metastatic Pancreatic Cancer: American Society of Clinical Oncology Clinical Practice Guideline," J Clin Oncol. 34(23):2784-96 and Appendix (2016).
Sohal D, et. al., "Reply to A. Wang-Gillam et al," J Clin Oncol. 35(6):690-1 (2017). Epub 2016.
Son J, et al., "Glutamine Supports Pancreatic Cancer Growth Through a Kras-Regulated Metabolic Pathway," Nature. 496(7443):101-5 (2013), author manuscript version, 16 pages.
Sousa C and Kimmelman A, "The Complex Landscape of Pancreatic Cancer Metabolism," Carcinogenesis. 35(7):1441-50 (2014).
Spigel D, et al., "Liposomal Irinotecan in Adults with Small Cell Lung Cancer Who Progressed on Platinum-Based Therapy: Subgroup Analyses by Platinum Sensitivity." Poster presented at the International Association for the Study of Lung Cancer (IASLC) 2020 North America Conference on Lung Cancer (NACLC): virtual meeting, Oct. 16-17, 2020, 9 pages.
Spigel D, et al., "RESILIENT Part 1, An Open-Label, Safety Run-In of Liposomal Irinotecan in Adults With Small Cell Lung Cancer (SCLC) Who Have Progressed With Platinum-Based First-Line Therapy: Subgroup Analyses by Platinum Sensitivity." Poster presented at the American Society of Clinical Oncology (ASCO) Annual Conference, virtual format, May 29-Jun. 2, 2020, 6 pages.
Spigel D, et al., Abstract 9069. "RESILIENT Part I, An Open-Label, Safety Run-In of Liposomal Irinotecan in Adults With Small Cell Lung Cancer (SCLC) Who Have Progressed With Platinum-Based First-Line (1L) Therapy: Subgroup Analyses by Platinum Sensitivity," J Clin Oncol. 38(15_Suppl):9069 DOI: 10.1200/JCO.2020.38.15_suppl.9069 (2020), 2 printed pages.
Spigel D, et al., Abstract MO01.39. "Liposomal Irinotecan in Adults with Small Cell Lung Cancer Who Progressed on Platinum-Based Therapy: Subgroup Analyses by Platinum Sensitivity," IASLC 2020 North America Conference on Lung Cancer Abstracts, p. 80 (2020).
Starling N, et. al., "A Dose Escalation Study of Gemcitabine Plus Oxaliplatin in Combination With Imatinib for Gemcitabine-Refractory Advanced Pancreatic Adenocarcinoma," Ann Oncol. 23(4):942-7 (2012). Epub 2011.
Stathis A and Moore M, "Advanced Pancreatic Carcinoma: Current Treatment and Future Challenges," Nat Rev Clin Oncol. 7(3):163-72 (2010).
Stathopoulos G and Boulikas T, "Lipoplatin Formulation Review Article," J Drug Deliv. 2012:581363, Article ID 581363, doi: 10.1155/2012/581363, Epub 2011, 10 pages.
Stathopoulos G, et. al., "A Multicenter Phase III Trial Comparing Irinotecan-Gemcitabine (IG) With Gemcitabine (G) Monotherapy as First-Line Treatment in Patients With Locally Advanced or Metastatic Pancreatic Cancer," Br J Cancer. 95(5):587-92 (2006).
Stathopoulos G, et. al., "Liposomal Oxaliplatin in the Treatment of Advanced Cancer: A Phase I Study," Anticancer Res. 26(2B):1489-93 (2006).
Stathopoulos G, et. al., "Lipsomal Cisplatin Combined With Gemcitabine in Pretreated Advanced Pancreatic Cancer Patients: A phase I-II Study," Oncol Rep. 15(5):1201-4 (2006).
Stein S, et al., "Final Analysis of a Phase II Study of Modified FOLFIRINOX in Locally Advanced and Metastatic Pancreatic Cancer," Br J Cancer. 114(7):737-43 (2016).
Stylianopoulos T and Jain R, "Combining Two Strategies to Improve Perfusion and Drug Delivery in Solid Tumors," Proc Natl Acad Sci USA. 110(46):18632-7 (2013).
Tahara M, et al., "The Use of Olaparib (AZD2281) Potentiates SN-38 Cytotoxicity in Colon Cancer Cells by Indirect Inhibition of Rad51-Mediated Repair of DNA Double-Strand Breaks," Mol Cancer Ther. 13(5):1170-80 (2014).
Taïeb J., "FOLFIRI.3, A New Regimen Combining 5-Fluorouracil, Folinic Acid and Irinotecan, for Advanced Pancreatic Cancer: Results of an Association des Gastro-Enterologues Oncologues (Gastroenterologist Oncologist Association) Multicenter Phase II Study," Ann Oncol. 18(3):498-503 (2007), epub Dec. 8, 2006.
Takada T et al., "Comparison of 5-Fluorouracil, Doxorubicin and Mitomycin C with 5-Fluorouracil Alone in the Treatment of Pancreatic-Biliary Carcinomas," Oncology. 51(5):396-400 (1994).
Takahara N, et al., "Uridine Disphosphate Glucuronosyl Transferase 1 Family Polypeptide A1 Gene (UGT1A1) Polymorphisms are Associated with Toxicity and Efficacy in Irinotecan Monotherapy for Refractory Pancreatic Cancer," Cancer Chemother Pharmacol. 71(1):85-92 (2013), Epub Sep. 29, 2012.
Takahara N, et al., "A Retrospective Study of S-1 and Oxaliplatin Combination Chemotherapy in Patients With Refractory Pancreatic Cancer," Cancer Chemother Pharmacol. 72(5):985-90 (2013).
Takano S, et. al., "Metronomic Treatment of Malignant Glioma Xenografts with Irinotecan (CPT-11) Inhibits Angiogenesis and Tumor Growth," J Neurooncol. 99(2):177-85 (2010).
Tanaka R, et al., "Synergistic Interaction Between Oxaliplatin and SN-38 in Human Gastric Cancer Cell Lines In Vitro," Oncol Rep. 14(3):683-8 (2005).
Tardi P, et al., "Drug Ratio-Dependent Antitumor Activity of Irinotecan and Cisplatin Combinations In Vitro and In Vivo," Mol Cancer Ther. 8(8):2266-75 (2009).
Tardi P, et al., "Liposomal Encapsulation of Topotecan Enhances Anticancer Efficacy in Murine and Human Kenograft Models," Cancer Res. 60(13):3389-93 (2000).
Tardi P, et. al., "Coencapsulation of Irinotecan and Floxuridine Into Low Cholesterol-Containing Liposomes That Coordinate Drug Release In Vivo," Biochim Biophys Acta. 1768(3):678-87 (2007). Epub 2006.
Tempero M, et. al., "NCCN Clinical Practice Guidelines in Oncology: Pancreatic Adenocarcinoma," Version 1.2012. National Comprehensive Cancer Network, Inc. (2011), 79 pages.
Tempero M, et. al., "NCCN Clinical Practice Guidelines in Oncology: Pancreatic Adenocarcinoma," Version 2.2012. National Comprehensive Cancer Network, Inc. (2011), 94 pages.
Tempero M, et. al., "NCCN Clinical Practice Guidelines in Oncology: Pancreatic Adenocarcinoma," Version 2.2014. National Comprehensive Cancer Network, Inc. (2014), 122 pages.
Tempero M, et. al., "Pancreatic Adenocarcinoma: Clinical Practice Guidelines in Oncology," J Natl Compr Canc Netw. 8(9):972-1017 (2010).
Tentori L, et al., "Influence of MLH1 on Colon Cancer Sensitivity to Poly(ADP-ribose) Polymerase Inhibitor Combined with Irinotecan," Int J Oncol. 43(1):210-8 (2013).
Thota R, et. al., "Treatment of Metastatic Pancreatic Adenocarcinoma: A Review," Oncology. 28(1):70-4 (2014). Available at cancernetwork.com/view/treatment-metastatic-pancreatic-adenocarcinoma-review, 6 printed pages.
Todaka A, et. al., "S-1 Monotherapy as Second-line Treatment for Advanced Pancreatic Cancer after Gemcitabine Failure," Jpn J Clin Oncol. 40(6):567-72 (2010).
Togawa A, et. al., "Treatment With an Oral Fluoropyrimidine, S-1, Plus Cisplatin in Patients Who Failed Postoperative Gemcitabine Treatment for Pancreatic Cancer: A Pilot Study," Int J Clin Oncol. 12(4):268-73 (2007).
Tomicki S, et al., "Utilization of Hospital Inpatient Services Among Patients With Metastatic Pancreatic Cancer With Commercial and Medicare Insurance Treated With FDA-Approved/NCCN Category 1 Regimens." Poster presented at the Academy of Managed Care Pharmacy, Nexus (AMCP, Nexus): virtual meeting, week of Oct. 19, 2020, 6 pages.
Toutain P and Bousquet-Melou A, "Plasma terminal half-life," J Vet Pharmacol Ther. 27(6):427-39 (2004).
Tsai C, et al., "Nanovector-Based Therapies in Advanced Pancreatic Cancer," J Gastroint Oncol 2(3):185-94 (2011).
Tsavaris N, et. al., "Second-Line Treatment With Oxaliplatin, Leucovorin and 5-Fluorouracil in Gemcitabine-Pretreated Advanced Pancreatic Cancer: A Phase II Study," Invest New Drugs. 23(4):369-75 (2005).
Tsubamoto H, et al., "Combination Chemotherapy with Itraconazole for Treating Metastatic Pancreatic Cancer in the Second-line or Additional Setting,". Anticancer Res. 35(7):4191-6 (2015).
Ueno H, et al., "A Phase II Study of Weekly Irinotecan as First-Line Therapy for Patients with Metastatic Pancreatic Cancer," Cancer Chemother Pharmacol. 59(4):447-54 (2007), Epub Jul. 20, 2006.

(56) References Cited

OTHER PUBLICATIONS

Ulrich-Pur H, et al., "Irinotecan Plus Raltitrexed vs Raltitrexed Alone in Patients with Gemcitabine-Pretreated Advanced Pancreatic Adenocarcinoma," Br J Cancer. 88(8):1180-4 (2003).
Hosein P, et al., "A Retrospective Study of Neoadjuvant FOLFIRINOX in Unresectable or Borderline-Resectable Locally Advanced Adenocarcinoma," BMC Cancer. 12:199, pp. 1-7 (2012).
Hoskins J, et al., "UGT1A1*28 Genotype and Irinotecan-Induced Neutropenia: Dose Matters," J Natl Cancer Inst. 99(17):1290-95 (2007).
Hsu M and Juliano R, "Interactions of Liposomes With the Reticuloendothelial System. II: Nonspecific and Receptor-Mediated Uptake of Liposomes by Mouse Peritoneal Macrophages," Biochim Biophys Acta. 720(4):411-419 (1982).
Hsueh C-T, et al., "Nanovectors for Anti-Cancer Drug Delivery in the Treatment of Advanced Pancreatic Adenocarcinoma," World J Gastroenterol. 22(31):7080-90 (2016).
Huang S, et al., "Liposomes and Hyperthermia in Mice: Increased Tumor Uptake and Therapeutic Efficacy of Doxorubicin in Sterically Stabilized Liposomes," Cancer Res. 54(8):2186-91 (1994).
Huang S, et al., "Light Microscopic Localization of Silver Enhanced Liposome-Entrapped Colloidal Gold in Mouse Tissues," Biochim Biophys Acta. 1069(1):117-21 (1991).
Huang S, et al., "Microscopic Localization of Sterically Stabilized Liposomes in Colon-Carcinoma Bearing Mice," Cancer Res. 52(19):5135-43 (1992).
Huang S, et al., "Pharmacokinetics and Therapeutics of Sterically Stabilized Liposomes in Mice Bearing C-26 Colon Carcinoma," Cancer Res. 52(24):6774-81 (1992).
Huber R, et al., "Efficacy of a Toxicity-Adjusted Topotecan Therapy in Recurrent Small Cell Lung Cancer," Eur Respir J. 27(6):1183-9 (2006).
Hubner R, et al., "Effects of nal-IRI (MM-398) ± 5-Fluorouracil on Quality of Life (QoL) in NAPOLI-1: A Phase 3 Study in Patients With Metastatic Pancreatic Ductal Adenocarcinoma (mPDAC) Previously Treated with Gemcitabine- Based Therapy." Poster presented at the 18th European Society of Medical Oncology World Congress on Gastrointestinal Cancer; Barcelona, Spain; Jun. 29-Jul. 2, 2016, 9 pages.
Hubner R, et al., "Effects of nal-IRI (MM-398) ± 5-Fluorouracil on Quality of Life (QoL) in NAPOLI-1: A Phase 3 Study in Patients With Metastatic Pancreatic Ductal Adenocarcinoma (mPDAC) Previously Treated With Gemcitabine," Presentation presented at the European Society for Medical Oncology (ESMO) World Congress on Gastrointestinal Cancer, Barcelona, Spain, Jun. 29-Jul. 2, 2016, 13 pages.
Hubner R, et al., "Prognostic Value of Baseline Neutrophil-to-Lymphocyte Ratio (NLR) for Predicting Clinical Outcome in Metastatic Pancreatic Ductal Adenocarcinoma (mPDAC) Patients Treated With Liposomal Irinotecan (nal-IRI) + 5-Fluorouracil and Leucovorin (5-FU/LV) vs 5-FU/LV Alone." Poster presented at the European Society for Medical Oncology (ESMO) Annual Congress, Madrid, Spain, Sep. 8-12, 2017, 5 pages.
Hubner R, et al., "Time Course of Selected Treatment-Emergent Adverse Events in NAPOLI-1: A Phase 3 Study of Liposomal Irinotecan (nal-IRI; MM-398) ± 5-Fluorouracil and Leucovorin (5-FU/LV) vs 5-FU/LV in Metastatic Pancreatic Cancer Previously Treated With Gemcitabine-Based Therapy." Poster presented at the European Society for Medical Oncology (ESMO) Annual Congress, Copenhagen, Denmark, Oct. 7-11, 2016, 8 pages.
Hubner R, et al., Abstract 242P. "Effects of nal-IRI (MM-398) ± 5-Fluorouracil on Quality of Life (QoL) of Patients With Metastatic Pancreatic Ductal Adenocarcinoma (mPDAC) Previously Treated With Gemcitabine Based Therapy: Results From NAPOLI-1 ," Ann Oncol. 27(Supp_9):ix76 doi:10.1093/annonc/mdw582 (2016).
Hubner R, et al., Abstract 3832. "Time Course of Selected Treatment Emergent Adverse Events (TEAES) in NAPOLI-1: A Phase 3 Study of nal-IRI (MM-398) ± 5-Fluorouracil and Leucovorin (5-FU/LV) vs 5-FU/LV in Metastatic Pancreatic Cancer (mPAC) Previously Treated With Gemcitabine-Based Therapy," Ann Oncol. 27(6):207-242 10.1093/annonc/mdw371 (2016), 4 printed pages.
Hubner R, et al., Abstract 741P. "Prognostic Value of Baseline Neutrophil-to-Lymphocyte Ratio (NLR) for Predicting Clinical Outcome in Metastatic Pancreatic Ductal Adenocarcinoma (mPDAC) Patients Treated With Liposomal Irinotecan (nal-IRI) + 5-Fluorouracil and Leucovorin (5-FU/LV) vs 5-FU/LV Alone," Ann Oncol. 28(Suppl_5):253 doi:10.1093/annonc/mdx369 (2017).
Hubner R, et al., Abstract O-004. "Effects of nal-IRI (MM-398) ± 5-fluorouracil on Quality of Life (QoL) in NAPOLI-1: A Phase 3 Study in Patients with Metastatic Pancreatic Ductal Adenocarcinoma (mPDAC) Previously Treated with Gemcitabine." Annals of Oncology. 27(Suppl 2):ii118-ii128 (2016), 1 page.
Hwang J, et al., Abstract 4618. "A Randomized Phase II Study of FOLFOX or FOLFIRI.3 as Second-Line Therapy in Patients With Advanced Pancreatic Cancer Previously Treated With Gemcitabine-Based Chemotherapy," J Clin Oncol. 27(15_Suppl):4618 (2009), 2 printed pages.
Hwang J, et. al., "Improving the Toxicity of Irinotecan/5-FU/Leucovorin: A 21-Day Schedule, " Oncology. 17(9):37-43 (2003). Available at cancernetwork.com/view/improving-toxicity-irinotecan5-fu-leucovorin-21-day-schedule, 13 printed pages.
HYCAMTIN (topotecan hydrochloride) for injection package insert, revision Feb. 28, 2014, retrieved from https://www.accessdata.fda.gov/drugsatfda_docs/label/2014/020671s020lbl.pdf, 23 pages.
HYCAMTIN (topotecan) for injection package insert, revision Jun. 2, 2015, retrieved from https://www.accessdata.fda.gov/drugsatfda_docs/label/2015/020671s021lbl.pdf, 21 pages.
Ignatiadis M, et. al., "A Multicenter Phase II Study of Docetaxel in Combination with Gefitinib in Gemcitabine-Pretreated Patients with Advanced/Metastatic Pancreatic Cancer," Oncology. 71(3-4):159-63 (2006).
Ignatius R, et al., "Presentation of Proteins Encapsulated in Sterically Stabilized Liposomes by Dendritic Cells Initiates CD8+ T-cell Responses in Vivo," Blood. 96(10):3505-13 (2000).
Ilson D, "Nanolipoosomal Irinotecan Effective for Pancreatic Cancer," NEJM journal Watch, available at jwatch.org/na39795/2015/12/08/nanoliposomal-irinotecan-effective-pancreatic-cancer, (2015), 7 printed pages.
Immordino M, et al., "Stealth Liposomes: Review of the Basic Science, Rationale, and Clinical Applications, Existing and Potential," Int J Nanomedicine. 1(3):297-315 (2006).
Infante J, et al., "Phase I and Pharmacokinetic Study of IHL-305 (PEGylated Liposomal Irinotecan) in Patients with Advanced Solid Tumors," Cancer Chemother Pharmacol. 70(5):699-705 (2012).
Ioka T, et al., "Liposomal Irinotecan (nal-IRI) Plus 5-Fluorouracil/Levoleucovorin (5-FU/LV) vs 5-FU/LV in Japanese Patients (pts) With Gemcitabine-Refractory Metastatic Pancreatic Cancer (mPAC)." Poster presented at the European Society for Medical Oncology (ESMO) Asia 2019 Congress, Singapore, Nov. 22-24, 2019, 9 pages.
Ioka T, et al., Abstract 132P. "Liposomal Irinotecan (nal-IRI) Plus 5-Fluorouracil/Levoleucovorin (5-FU/LV) vs 5-FU/LV in Japanese Patients (pts) With Gemcitabine-Refractory Metastatic Pancreatic Cancer (mPAC)," Ann Oncol. 30(Suppl_9):ix47-ix48 doi:10.1093/annonc/mdz422 (2019).
Ioka T, et al., Abstract 274TiP. "A Randomized Phase 2 Study of Nanoliposomal Irinotecan (nal-IRI, BAX2398)-Containing Regimen in Japanese Patients With Metastatic Pancreatic Adenocarcinoma (mPAC)," Ann Oncol. 27(Supp_9):ix84-ix85 doi:10.1093/annonc/mdw582 (2016).
Jacobs A, et al., "A Randomized Phase III Study of Rubitecan (ORA) vs. Best Choice (BC) in 409 Patients with Refractory Pancreatic Cancer Report from a North-American Multi-Center Study," J Clin Oncol., 2004 ASCO Annual Meeting Proceedings 22(14S):4013 (2004).
Jameson G, et al., "Adverse Events in Patients with Metastatic Pancreatic Cancer Receiving Liposomal Irinotecan: Understanding the Occurrence and How Management Affects Patient Outcomes." Poster presented at the Oncology Nursing Society (ONS) Annual Conference, Washington, DC, May 17-20, 2018, 7 pages.
Jameson G, et al., Abstract 1. "Adverse Events in Patients with Metastatic Pancreatic Cancer Receiving Liposomal Irinotecan: Under-

(56) References Cited

OTHER PUBLICATIONS standing the Occurrence and How Management Affects Patient Outcomes," Oncology Nursing Society (ONS) 43rd Annual Congress, available at ons.confex.com/ons/2018/meetingapp.cgi/Paper/2970, (2018), 2 pages.
Jones S, et. al., Abstract 2547. "Phase I and Pharmacokinetic (PK) Study of IHL-305 (Pegylated Liposomal Irinotecan) in Patients With Advanced Solid Tumors," J Clin Oncol. 27(15_suppl):2547 and Table 1 (2009), 6 printed pages.
Kalra A, et al., "Evaluating Determinants for Enhanced Activity of MM-398/PEP02; A Novel Nanotherapeutic Encapsulation of Irinotecan (CPT-11)." Poster for abstract 5696 presented at American Association for Cancer Research 103rd Annual Meeting 2012, Mar. 31-Apr. 4, 2012, Chicago, IL, 11 pages.
Kalra A, et al., "Preclinical Activity of Nanoliposomal Irinotecan Is Governed by Tumor Deposition and Intratumor Pro-Drug Conversion," Cancer Res. Author Manuscript Published OnlineFirst Oct. 1, 2014, 31 pages.
Kalra A, et al., "Preclinical Activity of Nanoliposomal Irinotecan Is Governed by Tumor Deposition and Intratumor Prodrug Conversion," Cancer Res. 74(23):7003-13 (2014).
Kalra A, et al., "Preclinical Activity of Nanoliposomal Irinotecan Is Governed by Tumor Deposition and Intratumor Prodrug Conversion," Cancer Res. Author queries on manuscript, pp. 1-11 (2014), 13 total pages.
Kalra A, et al., "Preclinical Activity of Nanoliposomal Irinotecan Is Governed by Tumor Deposition and Intratumor Prodrug Conversion," Cancer Res. 74(23):7003-13 (2014), published OnlineFirst, OF1-OF11, Oct. 1, 2014, 12 pages.
Kalra A, et al., "The Tumor Microenvironment Modulates the Delivery and Activation of Liposomal Encapsulated Irinotecan, MM-398," Poster for abstract 5622 presented at the 104th Annual Meeting of the American Association of Cancer Research, Apr. 6-10, 2013, Washington DC, 10 pages.
Kalra A, et al., Abstract 2065. "Magnetic Resonance Imaging with an Iron Oxide Nanoparticle Demonstrates the Preclinical Feasibility of Predicting Intratumoral Uptake and Activity of MM-398, a Nanoliposomal Irinotecan (nal-IRI)." In Proceedings of the 105th Annual Meeting of the American Association for Cancer Research; Apr. 5-9, 2014. Cancer Res 2014;74(19 Suppl):Abstract nr 2065, doi:10.1158/1538-7445.AM2014-2065, 1 printed page.
Kalra A, et al., Abstract 2065: "Magnetic Resonance Imaging with an Iron Oxide Nanoparticle Demonstrates Preclinically the Feasibility of Predicting Intratumoral Uptake and Activity of MM-398, a Nanoliposomal Irinotecan (nal-IRI)." Poster presented at American Association for Cancer Research annual meeting 2014, San Diego, CA, 5 pages.
Kalra A, et al., Abstract 5622. "The Tumor Microenvironment Modulates the Delivery and Activation of Liposomal Encapsulated Irinotecan, MM-398." In Proceedings of the 104th Annual Meeting of the American Association of Cancer Research; Apr. 6-10, 2013. Cancer Res 2013;73(8 Suppl):Abstract nr 5622, doi:10.1158/1538-7445.AM2013-5622, 2 printed pages.
Kalra A, et al., Abstract 5696. "Evaluating Determinants for Enhanced Activity of MM-398/PEP02; A Novel Nanotherapeutic Encapsulation of Irinotecan (CPT-11)." In Proceedings of the 103rd Annual Meeting of the American Association for Cancer Research; Mar. 31-Apr. 4, 2012; Chicago, IL. Cancer Res 2012; 72(8 Suppl):Abstract nr 5696. doi:1538-7445.AM2012-5696, 3 printed pages.
Kalra A., "Magnetic Resonance Imaging (MRI) to Predict Tumor Drug Delivery and Response to Nanoliposomal Therapy." Presentation presented at Tumor Models Boston 2014, 32 pages.
Kambe M, et al., "Phase I Study of Irinotecan by 24-h Intravenous Infusion in Combination with 5-Fluorouracil in Metastatic Colorectal Cancer," Int J Clin Oncol. 17(2):150-4 (2012).
Kang M, et al., "Activity of MM-398, Nanoliposomal Irinotecan (nal-IRI), in Ewing's Family Tumor Xenografts Is Associated with High Exposure of Tumor to Drug and High SLFN11 Expression," Clin Cancer Res. 21(5):1139-50 (2015).
Kang S and Saif M, "Optimal Second Line Treatment Options for Gemcitabine Refractory Advanced Pancreatic Cancer Patients. Can We Establish Standard of Care with Available Data?," JOP. J Pancreas (Online) 9(2):83-90 (2008).
Katopodis O, et. al., "Second-Line Chemotherapy With Capecitabine (Xeloda) and Docetaxel (Taxotere) in Previously Treated, Unresectable Adenocarcinoma of Pancreas: The Final Results of a Phase II Trial," Cancer Chemother Pharmacol. 67(2):361-8 (2011). Epub 2010.
Katsu T, et al., "Ion-Selective Electrode for Transmembrane pH Difference Measurements," Anal. Chem. 73(8):1849-54 (2001).
Clinical Trials Identifier NCT00940758: Apr. 6, 2017 update, first posted Jul. 16, 2009, "Phase I and Pharmacokinetic Study of Biweekly PEP02 (Liposome Irinotecan) in Patients With Metastatic Colorectal Cancer Refractory to First-line Oxaliplatin-based Chemotherapy." Retrieved from ClinicalTrials.gov archive, 5 printed pages.
Clinical Trials Identifier NCT01359007: May 23, 2011 update, "A Phase II Study Evaluating the Rate of RO Resection (Microscopically Negative Margins) After Induction Therapy With 5-Fluorouracil, Leucovorin, Oxaliplatin, Irinotecan (FOLFIRINOX) in Patients With Borderline Resectable or Locally Advanced Inoperable Pancreatic Cancer." Retrieved from ClinicalTrials.gov archive, 3 printed pages.
Clinical Trials Identifier NCT01359007: May 28, 2015 update, "A Phase II Study Evaluating the Rate of R0 Resection (Microscopically Negative Margins) After Induction Therapy With 5-Fluorouracil, Leucovorin, Oxaliplatin, Irinotecan (FOLFIRINOX) in Patients With Borderline Resectable or Locally Advanced Inoperable Pancreatic Cancer." Retrieved from ClinicalTrials.gov archive, 3 printed pages.
Clinical Trials Identifier NCT01375816: Jun. 16, 2011 update, "A Randomized Phase II Study of PEP02 or Irinotecan in Combination With Leucovorin and 5-Flourouracil in Second Line Therapy of Metastatic Colorectal Cancer." Retrieved from ClinicalTrials.gov archive, 5 printed pages.
Clinical Trials Identifier NCT01375816: Jun. 4, 2015 update, first posted Jun. 17, 2011, "A Randomized Phase II Study of PEP02 or Irinotecan in Combination With Leucovorin and 5-Fluorouracil in Second Line Therapy of Metastatic Colorectal Cancer." Retrieved from ClinicalTrials.gov archive, 10 printed pages.
Clinical Trials Identifier NCT01446458: Oct. 4, 2011 update, "Phase I Study of Stereotactic Body Radiation Therapy and 5-Fluorouracil, Oxaliplatin and Irinotecan (FOLFIRINOX) in the Neoadjuvant Therapy of Pancreatic Cancer." Retrieved from ClinicalTrials.gov archive, 5 printed pages.
Clinical Trials Identifier NCT01494506: Dec. 16, 2011 update, "A Randomized, Open Label Phase 3 Study of MM-398 Versus 5-Flourouracil and Leucovorin in Patients With Metastatic Pancreatic Cancer." Retrieved from ClinicalTrials.gov archive, 3 printed pages.
Clinical Trials Identifier NCT01494506: Aug. 9, 2012 update, "A Randomized, Open Label Phase 3 Study of MM-398, With or Without 5-Fluorouracil and Leucovorin, Versus 5-Fluorouracil and Leucovorin in Patients With Metastatic Pancreatic Cancer Who Have Failed Prior Gemcitabine-based Therapy." Retrieved from ClinicalTrials.gov archive, 3 printed pages.
Clinical Trials Identifier NCT01494506: Aug. 1, 2013 update, "A Randomized, Open Label Phase 3 Study of MM-398, With or Without S~Fluorouracil and Leucovorin, Versus 5 Fluorouracil and Leucovorin in Patients with Metastatic Pancreatic Cancer Who Have Failed Prior Gemcitabine-based Therapy." Retrieved from ClinicalTrials.gov archive, 3 printed pages.
Clinical Trials Identifier NCT01494506: Jun. 16, 2016 update, "A Randomized, Open Label Phase 3 Study of MM-398, With or Without 5-Fluorouracil and Leucovorin, Versus 5 Fluorouracil and Leucovorin in Patients with Metastatic Pancreatic Cancer Who Have Failed Prior Gemcitabine-based Therapy." Retrieved from ClinicalTrials.gov archive, 5 printed pages.
Clinical Trials Identifier NCT01523457: Jan. 31, 2012 update, "Phase II Study of Modified FOLFIRINOX in Advanced Pancreatic Cancer." Retrieved from ClinicalTrials.gov archive, 4 printed pages.

(56) References Cited

OTHER PUBLICATIONS

Clinical Trials Identifier NCT01643499: Jul. 17, 2012 update, "A Genotype-guided Dosing Study of mFOLFIRINOX in Previously Untreated Patients with Advanced Gastrointestinal Malignancies." Retrieved from ClinicalTrials.gov archive, 5 printed pages.

Clinical Trials Identifier NCT01688336: Sep. 18, 2012 update, "Phase II Single Arm Clinical Trial of FOLFIRINOX for Unresectable Locally Advanced and Borderline Resectable Pancreatic Cancer." Retrieved from ClinicalTrials.gov archive, 5 printed pages.

Clinical Trials Identifier NCT01770353: Aug. 9, 2013 update, "A Pilot Study in Patients Treated with MM-398 to Determine Tumor Drug Levels and to Evaluate the Feasibility of Ferumoxytol Magnetic Resonance Imaging to Measure Tumor Associated Macrophages." Retrieved from ClinicalTrials.gov archive, 3 printed pages.

Clinical Trials Identifier NCT01770353: Apr. 26, 2015 update, "A Pilot Study in Patients Treated with MM-398 to Determine Tumor Drug Levels and to Evaluate the Feasibility of Ferumoxytol Magnetic Resonance Imaging to Measure Tumor Associated Macrophages." Retrieved from ClinicalTrials.gov archive, 4 printed pages.

Clinical Trials Identifier NCT01770353: May 6, 2015 update, "A Pilot Study in Patients Treated with MM-398 to Determine Tumor Drug Levels and to Evaluate the Feasibility of Ferumoxytol Magnetic Resonance Imaging to Measure Tumor Associated Macrophages." Retrieved from ClinicalTrials.gov archive, 4 printed pages.

Clinical Trials Identifier NCT01770353: Mar. 22, 2016 update, "A Pilot Study in Patients Treated with MM-398 to Determine Tumor Drug Levels and to Evaluate the Feasibility of Ferumoxytol Magnetic Resonance Imaging to Measure Tumor Associated Macrophages and to Predict Patient Response to Treatment." Retrieved from ClinicalTrials.gov archive, 4 printed pages.

Clinical Trials Identifier NCT01770353: Jul. 7, 2016 update, "A Pilot Study in Patients Treated with MM-398 to Determine Tumor Drug Levels and to Evaluate the Feasibility of Ferumoxytol Magnetic Resonance Imaging to Measure Tumor Associated Macrophages and to Predict Patient Response to Treatment." Retrieved from ClinicalTrials.gov archive, 4 printed pages.

Clinical Trials Identifier NCT01771146: Jan. 17, 2013 update, "A Prospective Evaluation of Neoadjuvant FOLFIRINOX Regimen in Patients with Non-metastatic Pancreas Cancer (Baylor University Medical Center and Texas Oncology Experience)." Retrieved from ClinicalTrials.gov archive, 3 printed pages.

Clinical Trials Identifier NCT01926197: Aug. 19, 2013 update, "A Randomized Phase III Study Evaluating Modified FOLFIRINOX (mFFX) With or Without Stereotactic Body Radiotherapy (SBRT) in the Treatment of Locally Advanced Pancreatic Cancer." Retrieved from ClinicalTrials.gov archive, 3 printed pages.

Clinical Trials Identifier NCT01992705: Nov. 22, 2013 update, "Neoadjuvant FOLFIRINOX and Stereotactic Body Radiotherapy (SBRT) Followed by Definitive Surgery for Patients with Borderline Resectable Pancreatic Adenocarcinoma: A Single-Arm Pilot Study." Retrieved from ClinicalTrials.gov archive, 5 printed pages.

Clinical Trials Identifier NCT02013336: Feb. 6, 2017 update, first posted Dec. 17, 2013, "Phase 1 Dose-escalating Study of MM-398 (Irinotecan Sucrosofate Liposome Injection) Plus Intravenous Cyclophosphamide in Recurrent or Refractory Pediatric Solid Tumors." Retrieved from ClinicalTrials.gov archive, 6 printed pages.

Clinical Trials Identifier NCT02022644: May 8, 2017 update, first posted Dec. 30, 2013, "A Phase I Study of Convection-Enhanced Delivery of Liposomal-Irinotecan Using Real-Time Imaging With Gadolinium in Patients With Recurrent High Grade Glioma." Retrieved from ClinicalTrials.gov archive, 9 printed pages.

Clinical Trials Identifier NCT02028806: Jan. 6, 2014 update, "Phase II Trial to Investigate the Efficacy and Safety of mFOLFIRINOX in Patients with Metastatic Pancreatic Cancer in China." Retrieved from ClinicalTrials.gov archive, 4 printed pages.

Clinical Trials Identifier NCT02047474: Jan. 27, 2014 update, "Phase II Study of Peri-Operative Modified Folfirinox in Localized Pancreatic Cancer." Retrieved from ClinicalTrials.gov archive, 5 printed pages.

Clinical Trials Identifier NCT02109341: Apr. 8, 2014 update, "Phase I/II Study to Evaluate Nab-paclitaxel in Substitution of CPT11 or Oxaliplatin in FOLFIRINOX Schedule as First Line Treatment on Metastatic Pancreatic Cancer." Retrieved from ClinicalTrials.gov archive, 5 printed pages.

Clinical Trials Identifier NCT02143219: May 20, 2014 update, "Phase-2 Study Evaluating Overall Response Rate (Efficacy) and Autonomy Daily Living Preservation (Tolerance) of 'FOLFIRINOX' Pharmacogenic Dose Adjusted, in Elderly Patients (70 yo. or Older) With a Metastatic Pancreatic Adenocarcinoma." Retrieved from ClinicalTrials.gov archive, 5 printed pages.

Clinical Trials Identifier NCT02148549: May 27, 2014 update, "The Pilot Study of Neoadjuvant Chemotherapy of FIRINOX for Patients With Borderline Resectable Pancreatic Cancer." Retrieved from ClinicalTrials.gov archive, 4 printed pages.

Clinical Trials Identifier NCT02551991: Sep. 30, 2019 update, first posted Sep. 16, 2015, "A Randomized, Open-label, Phase 2 Study of Nanoliposomal Irinotecan (Nal-IRI)-Containing Regimens Versus Nab-Paclitaxel Plus Gemcitabine in Patients With Previously Untreated, Metastatic Pancreatic Adenocarcinoma." Retrieved from ClinicalTrials gov archive, 5 printed pages.

Clinical Trials Identifier NCT02631733: Dec. 15, 2015 update, "A Phase I Study of a Combination of MM-398 and Veliparib in Solid Tumors." Retrieved from ClinicalTrials.gov archive, 6 printed pages.

Clinical Trials Identifier NCT02631733: Feb. 16, 2016 update, "A Phase I Study of a Combination of MM-398 and Veliparib in Solid Tumors." Retrieved from ClinicalTrials.gov archive, 6 printed pages.

Clinical Trials Identifier NCT02631733: Jun. 20, 2016 update, "A Phase I Study of a Combination of MM-398 and Veliparib in Solid Tumors." Retrieved from ClinicalTrials.gov archive, 6 printed pages.

Clinical Trials Identifier NCT02631733: Jun. 21, 2016 update, "A Phase I Study of a Combination of MM-398 and Veliparib in Stolid Tumors." Retrieved from ClinicalTrials.gov archive, 6 printed pages.

Clinical Trials Identifier NCT02631733: Jul. 6, 2016 update, "A Phase I Study of a Combination of MM-398 and Veliparib in Solid Tumors." Retrieved from ClinicalTrials.gov archive, 6 printed pages.

Clinical Trials Identifier NCT02631733: Jul. 11, 2016 update, "A Phase I Study of a Combination of MM-398 and Veliparib in Solid Tumors." Retrieved from ClinicalTrials.gov archive, 6 printed pages.

Clinical Trials Identifier NCT02631733: Jul. 19, 2016 update, "A Phase I Study of a Combination of MM-398 and Veliparib in Solid Tumors." Retrieved from ClinicalTrials.gov archive, 6 printed pages.

Clinical Trials Identifier NCT02631733: Aug. 7, 2016 update, "A Phase I Study of a Combination of MM-398 and Veliparib in Solid Tumors." Retrieved from ClinicalTrials.gov archive, 6 printed pages.

Clinical Trials Identifier NCT02631733: Sep. 21, 2016 update, "A Phase I Study of a Combination of MM-398 and Veliparib in Solid Tumors." Retrieved from ClinicalTrials.gov archive, 6 printed pages.

Clinical Trials Identifier NCT02631733: Oct. 4, 2017 update, first posted Dec. 16, 2015, "A Phase I Study of a Combination of MM-398 and Veliparib in Solid Tumors." Retrieved from ClinicalTrials.gov archive, 10 printed pages.

Clinical Trials Identifier NCT02884128: Aug. 25, 2016 update, "A Study of PEP02 in Combination With 5-fluorouracil (5-FU) and Leucovorin (LV) in Advanced Solid Tumors." Retrieved from ClinicalTrials.gov archive, 3 printed pages.

Clinical Trials Identifier NCT02884128: Aug. 30, 2016 update, first posted Aug. 30, 2016, "A Multi-Center, Open-Label Phase I Dose-Escalation Study of PEP02 in Combination With 5-fluorouracil (5-FU) and Leucovorin (LV) in Advanced Solid Tumors." Retrieved from ClinicalTrials.gov archive, 5 printed pages.

Clinical Trials Identifier NCT02896803: Sep. 11, 2016 update, "A Phase II Trial of Bolus Fluorouracil and Oxaliplatin (mFLOX) as First-line Regimen for Patients With Unresectable or Metastatic Pancreatic Cancer Not Eligible for nfusional Fluorouracil, Irinotecan and Oxaliplatin." Retrieved from ClinicalTrials.gov archive, 4 printed pages.

Clinical Trials Identifier NCT02896907: Sep. 11, 2016 update, "A Pilot Study of Intravenous Ascorbic Acid and Folfirinox in the Treatment of Advanced Pancreatic Cancer." Retrieved from ClinicalTrials.gov archive, 4 printed pages.

Clinical Trials Identifier NCT03088813: Sep. 30, 2019 update, first posted Mar. 23, 2017, "Study of Irinotecan Liposome Injection

(56) References Cited

OTHER PUBLICATIONS (ONIVYDE®) in Patients With Small Cell Lung Cancer." Retrieved from ClinicalTrials.gov archive, 8 printed pages.
ClinicalTrials.gov search results for ONIVYDE, retrieved from clinicaltrials.gov website on Jan. 27, 2021, 27 pages.
Cockrum P, et al., "Impact of Dose Reductions on Clinical Outcomes Among Patients With Metastatic Pancreatic Cancer Treated With Liposomal Irinotecan in Oncology Clinics in the US." Poster presented at the American Society of Clinical Oncology Gastrointestinal Cancers Symposium (ASCO GI), San Francisco, CA, Jan. 23-25, 2020, 8 pages.
Cockrum P, et al., Abstract 665. "Impact of Dose Reductions on Clinical Outcomes Among Patients (pts) With Metastatic Pancreatic Cancer (mPC) Treated With Liposomal Irinotecan (nal-IRI) in Oncology Clinics in the United States," J Clin Oncol. 38(4_Suppl):665 DOI: 10.1200/JCO.2020.38.4_suppl.665 (2020), 2 printed pages.
Cockrum P, et al., Abstract e16739. "National Comprehensive Cancer Network (NCCN) Category I/FDA-Approved Metastatic Pancreatic Adenocarcinoma (mPDAC) Treatments in Commercially Insured Patients: An Analysis of Inpatient (IP) and Emergency Room (ER) Admissions," J Clin Oncol. 38(15_Suppl):e16739 DOI: 10.1200/JCO.2020.38.15_suppl.e16739 (2020), 2 printed pages.
Cockrum P, et al., Abstract PCN134. "An Examination of Quality Metrics: Inpatient and Emergency Department Burden of Commercially Insured Treated Metastatic Pancreatic Cancer (mPC) Patients in the United States (US)," Value in Health. 23(Suppl 1):S46 (2020).
Cockrum P, et al., Abstract PCN167. "An Integrated Delivery Network Focus on Cost Drivers in Chemotherapy: The Economic Burden of Neutropenia and Inpatient Admissions Among Commercially Insured Metastatic Pancreatic Cancer Patients (mPC)," Value in Health. 23(Suppl 1):S52 (2020).
EP3337467: Sandoz 2nd written submission in preparation for oral proceedings, dated Apr. 6, 2023, D11a (Koshkaryev A, et al., "Differential Tissue Clearance Results in Improved Therapeutic Index for Nanoliposomal rinotecan (nal-IRI; Onivyde) when Combined with the PARP Inhibitor Veliparib." Poster presented at AACR Meeting on Apr. 16-20, 2016, 5 pages); D11b (Corresponding poster session details, 3 pages); D11c (Corresponding abstract 2075, 1 page).
AVANTI Polar Lipids, Inc., Information Sheet for 1,2-distearoyl-sn-glycero-3-phosphoethanolamine-N-[methoxy(polyethylene glycol)-2000] (ammonium salt) (PEG-DSPE), retrieved from https://avantilipids.com/product/880120, 3 printed pages (2023).
AVANTI Polar Lipids, Inc., Product Sheet for 1,2-distearoyl-sn-glycero-3-phosphoethanolamine-N-[methoxy(polyethylene glycol)-2000] (ammonium salt) (PEG-DSPE), retrieved from https://avantilipids.com/product/880120, 3 printed pages (2023).
AVANTI Polar Lipids, Inc., Safety Data Sheet for 1,2-distearoyl-sn-glycero-3-phosphocholine (DSPC), 8 pages (2018).
Barbier S, et al., "Liposomal Irinotecan Shows a Larger Therapeutic Index than Non-liposomal Irinotecan in Patient-Derived Xenograft Models of Pancreatic Cancer," Oncol Ther. 11(1):111-128 (2023).
Choi M, et al., A Multicenter Phase 1 Trial Evaluating Nanoliposomal Irinotecan for Heated Intraperitoneal Chemotherapy Combined with Cytoreductive Surgery for Patients with Peritoneal Surface Disease, Ann Surg Oncol. 30(2):804-813 (2023); doi: 10.1245/s10434-022-12723-6, ePub 2022, 10 pages.
Clinical Trials Identifier NCT01770353: Nov. 27, 2019 update, first posted Jan. 17, 2013, "A Pilot Study in Patients Treated with MM-398 to Determine Tumor Drug Levels and to Evaluate the Feasibility of Ferumoxytol Magnetic Resonance Imaging to Measure Tumor Associated Macrophages and to Predict Patient Response to Treatment." Study results retrieved from ClinicalTrials.gov, 23 printed pages.
Clinical Trials Identifier NCT02551991: Oct. 10, 2022 update, first posted Sep. 16, 2015, "A Randomized, Open-label, Phase 2 Study of Nanoliposomal Irinotecan (Nal-IRI)-Containing Regimens Versus Nab-Paclitaxel Plus Gemcitabine in Patients With Previously Untreated, Metastatic Pancreatic Adenocarcinoma." Study results retrieved from clinicaltrials.gov, 15 printed pages.
Cockrum P, et al., Abstract EP14.05-011. "Real-World Impact of Platinum Sensitivity and Disease Stage on Survival Among Medicare Patients with Small Cell Lung Cancer," Poster presented at IASLC 2022 World Conference on Lung Cancer, Vienna, Austria, Aug. 6-9, 2022, 5 pages.
Cockrum P, et al., Abstract EP14.05-012. "Comparing Costs for Medicare FFS Patients Treated with Etoposide-based or Irinotecan-based Regimens for Extensive Stage Small Cell Lung Cancer," Poster presented at IASLC 2022 World Conference on Lung Cancer, Vienna, Austria, Aug. 6-9, 2022, 5 pages.
Cockrum P, et al., Abstract EP14.05-013. "Real-World Resource Use and Costs by Stage and Platinum Sensitivity among Medicare Patients with Small Cell Lung Cancer," Poster presented at IASLC 2022 World Conference on Lung Cancer, Vienna, Austria, Aug. 6-9, 2022, 5 pages.
Cockrum P, et al., Abstract EP14.05-013. "Real-World Resource Use and Costs by Stage and Platinum Sensitivity among Medicare Patients with Small Cell Lung Cancer," J Thorac Oncol. 17(9S):S548-S549 (2022).
Cockrum P, et al., Abstract EP14.05-014. "Trends in Population Survival Among Adults Diagnosed with Small Cell Lung Cancer in the U.S. from 2013-2021," J Thorac Oncol. 17(9S):S549 (2022).
Cockrum P, et al., Abstract EP14.05-014. "Trends in Population Survival Among Adults Diagnosed with Small Cell Lung Cancer in the U.S. from 2013-2021," Poster presented at IASLC 2022 World Conference on Lung Cancer, Vienna, Austria, Aug. 6-9, 2022, 4 pages.
Cockrum P, et al., Abstract EP14.05-015. "Quantifying Recent Trends in Real-World Treatment Patterns Among Adults Diagnosed with Small Cell Lung Cancer in the U.S. from 2013-2021," Poster presented at IASLC 2022 World Conference on Lung Cancer, Vienna, Austria, Aug. 6-9, 2022, 4 pages.
Cockrum P, et al., Abstract EP14.05-015. "Quantifying Recent Trends in Real-World Treatment Patterns Among Adults Diagnosed with Small Cell Lung Cancer in the U.S. from 2013-2021," J Thorac Oncol. 17(9S):S549-S550 (2022).
Craig Z, et al., "Health-Related Quality of Life (HRQOL) in Patients (pts) with Progressive Poorly Differentiated Extra-Pulmonary Neuroendocrine Carcinoma (PD-EP-NEC) Enrolled in NET-02: A Phase II Trial of Liposomal Irinotecan (nal-IRI)/5-Fluorouracil (5-FU)/Folinic Acid or Docetaxel as Second-Line Therapy." Poster presented at ASCO Quality Care Meeting, Sep. 30-Oct. 1, 2022, Chicago, Illinois, 4 pages.
Craig Z, et al., Abstract 293. "Health-Related Quality of Life (HRQOL) in Patients (pts) with Progressive, Poorly Differentiated, Extra-Pulmonary Neuroendocrine Carcinoma (PD-EP-NEC) Enrolled in NET-02: A Phase II Trial of Liposomal Irinotecan (nal-IRI)/5-Fluorouracil (5-FU)/Folinic Acid or Docetaxel as Second-Line Therapy," J Clin Oncol. 40(28_Suppl):293 (2022).
Dayyani F, et al., "Second-Line Treatment Options for Patients with Metastatic Pancreatic Ductal Adenocarcinoma: A Systematic Literature Review," Cancer Treat Rev. 113:102502; doi: 10.1016/j.ctrv.2022.102502, 10 pages (2023), 10 pages; Epub 2022.
De Gramont A, et al., "A Review of GERCOD Trials of Bimonthly Leucovorin Plus 5-Fluorouracil 48-h Continuous Infusion in Advanced Colorectal Cancer: Evolution of a Regimen," Eur J Cancer. 34(5):619-26 (1998).
DeLap R, et al., "The Effect of Leucovorin on the Therapeutic Index of Fluorouracil in Cancer Patients, " Yale J Biol Med. 61(1):23-34 (1988).
Dieguez G, et al., Abstract EP14.05-011. "Real-World Impact of Platinum Sensitivity and Disease Stage on Survival Among Medicare Patients with Small Cell Lung Cancer," J Thorac Oncol. 17(9S):S547-S548 (2022).
Gong J, et al., "Phase I Trial of Bermekimab with Nanoliposomal Irinotecan and 5-Fluorouracil/Folinic Acid in Advanced Pancreatic Ductal Adenocarcinoma," Sci Rep. 12(1):15013, doi: 10.1038/s41598-022-19401-3, (2022), 11 pages.
Gustavsson B, et al., "A Review of the Evolution of Systemic Chemotherapy in the Management of Colorectal Cancer," Clin Colorectal Cancer. 14(1):1-10 (2015), Epub 2014.

(56) References Cited

OTHER PUBLICATIONS

Hageman M. and Morozowich W., Chapter 5.12, "Case Study: Irinotecan (CPT-11), A Water-soluble Prodrug of SN-38," In: Prodrugs. Biotechnology: Pharmaceutical Aspects, vol. V. Stella, V.J., Borchardt, R.T., Hageman, M.J., Oliyai, R., Maag, H., Tilley, J.W. (eds). Springer, New York, NY. https://doi.org/10.1007/978-0-387-49785-3_44, pp. 570-579 (2007).
Hall J, et al., "Novel Patient-Derived Xenograft Mouse Model for Pancreatic Acinar Cell Carcinoma Demonstrates Single Agent Activity of Oxaliplatin," J Transl Med. 14(1):129 doi: 10.1186/s12967-016-0875-z, pp. 1-14 (2016).
Hoch U, et al., "Activity of NKTR-102 in Nonclinical Models of Gastrointestinal Cancers." Abstract P-0025. Poster presented at the European Society for Medical Oncology (ESMO) Conference: 12th World Congress on Gastrointestinal Cancer, Barcelona, Spain, Jun. 30-Jul. 3, 2010, 5 pages.
Imaoka H, et al., "A Phase 1/2 Study of Nanoliposomal Irinotecan Plus S-1 in Metastatic Pancreatic Cancer After First-Line Gemcitabine-Based Chemotherapy," Poster presented at the ESMO Asia Congress, Singapore, Dec. 2-4, 2022, 5 pages.
Imaoka H, et al., Abstract 124TiP. "A Phase I/II Study of Nanoliposomal Irinotecan Plus S-1 in Metastatic Pancreatic Cancer After First-Line Gemcitabine Based Chemotherapy," Annals of Oncology. 33(S9):S1484 (2022).
Ipsen, "Ipsen Announces Results from Phase III Resilient Trial Evaluating Onivyde® in Second-Line Monotherapy for Small Cell Lung Cancer," Aug. 3, 2022. Retrieved from https://www.ipsen.com/websites/Ipsen_Online/wp-content/uploads/2022/08/02231134/Ipsen-Onivyde-Press-Release-August-2022.pdf, 4 pages.
Ipsen, "Ipsen Presents Phase III NAPOLI 3 Trial of Onivyde® Regimen Demonstrating Positive Survival Results in Previously Untreated Metastatic Pancreatic Ductal Adenocarcinoma at ASCO GI," Jan. 20, 2023. Retrieved from https://www.ipsen.com/websites/Ipsen_Online/wp-content/uploads/2023/01/20140534/Ipsen-NAPOLI-3-Phase-III-Press-Release-01-2023.pdf, 5 pages.
Jolivet J, "Role of Leucovorin Dosing and Administration Schedule," Eur J Cancer. 31A(7-8):1311-1315 (1995).
Kanterman J, et al., "Adverse Immunoregulatory Effects of 5FU and CPT11 Chemotherapy on Myeloid-Derived Suppressor Cells and Colorectal Cancer Outcomes," Cancer Res. 74(21):6022-35 (2014).
Karthaus M, et al., Abstract 721. "Prediction of Early Treatment Failure of Second-Line nal-iri/5-FU/FA in Patients with Advanced Pancreatic Adenocarcinoma (AIO-PAK-0216)," J Clin Oncol. 41(4_Suppl):721 (2023), 4 printed pages.
Klein-Brill A, et al., "Comparison of FOLFIRINOX vs Gemcitabine Plus Nab-Paclitaxel as First-Line Chemotherapy for Metastatic Pancreatic Ductal Adenocarcinoma," JAMA Netw Open. 5(6):e2216199, doi: 10.1001/jamanetworkopen.2022.16199, pp. 1-12 (2022).
Lee J, et al., "Phase II Trial of Irinotecan Plus Oxaliplatin and 5-Fluorouracil/Leucovorin in Patients With Untreated Metastatic Gastric Adenocarcinoma," Ann Oncol. 18(1):88-92 (2007), Epub 2006.
Leonard S, et al., "Nanoliposomal Irinotecan (nal-IRI, MM-398) Has Greater Anti-Tumor Activity Than Topotecan and Irinotecan in Mouse Models of Small Cell Lung Cancer," Cancer Res. 77(13_Suppl):Abstract 5151 (2017), 4 printed pages.
Maiello E, et al., "FOLFIRI Regimen in Advanced Colorectal Cancer: The Experience of the Gruppo Oncologico dell'italia Meridionale (GOIM)," Ann Oncol. 16 (Suppl 4):iv56-iv60 (2005).
Mashkovsky MD, excerpts from "Medicaments," 16th ed., reprint, corr. and supp. New Wave (2012), pp. 8, 12, and 13, including English translation of p. 8, left column, lines 39-44; p. 12, right column, lines 26-32; and p. 13, left column, lines 26-27.
Mcnamara M, et al., Abstract 646. "NET-02 Final Results: A Randomised, Phase II Trial of Liposomal Irinotecan (nal-IRI)/5-Fluorouracil(5-FU)/Folinic Acid or Docetaxel as Second-Line (2L) Therapy in Patients (pts) with Progressive Poorly Differentiated Extrapulmonary Neuroendocrine Carcinoma (PD-EP-NEC)," J Clin Oncol. 41(4_Suppl):646 (2023), 5 printed pages.
Melisi D, et al., Abstract 701. "nITRO: A Phase 2 Study of Perioperative Liposomal Irinotecan+ 5-Fluorouracil/Leucovorin + Oxaliplatin (NALIRIFOX) in Patients with Resectable Pancreatic Ductal Adenocarcinoma (rPDAC)," J Clin Oncol. 41(4_Suppl):701 (2023), 4 printed pages.
Philip P, et al., "Phase 3, Multicenter, Randomized Study of Devimistat® (CPI-613) with Modified FOLFIRINOX (mFFX) Versus Folfirinox (FFX) as First-Line Therapy for Patients With Metastatic Adenocarcinoma of the Pancreas (AVENGER500®)." Poster presented at the American Society of Clinical Oncology (ASCO) Annual Meeting, Jun. 3-7, 2022, Chicago, Illinois, 8 printed pages.
Philip P, et al., Abstract 4023. "Phase 3, Multicenter, Randomized Study of CPI-613 with Modified FOLFIRINOX (mFFX) Versus Folfirinox (FFX) as First-Line Therapy for Patients With Metastatic Adenocarcinoma of the Pancreas (AVENGER500)," J Clin Oncol. 40(16_Suppl):4023 DOI:10.1200/JCO.2022.40.16_suppl.4023 (2022), 4 printed pages.
Raghunathan K, et al., "Impact of Schedule on Leucovorin Potentiation of Fluorouracil Antitumor Activity in Dietary Folic Acid Deplete Mice," Biochem Pharmacol. 53(8): 1197-1202 (1997).
Ramirez R, et al., Abstract EP14.05-019. "Contemporary Real-World Adverse Events Associated with Small Cell Lung Cancer Diagnosed in a U.S. Population from 2013-2021," J Thorac Oncol. 17(9S):S551-S552 (2022).
Ramirez R, et al., Abstract EP14.05-019. "Contemporary Real-World Adverse Events Associated with Small Cell Lung Cancer Diagnosed in a U.S. Population from 2013-2021," Poster presented at IASLC 2022 World Conference on Lung Cancer, Vienna, Austria, Aug. 6-9, 2022, 4 pages.
Ravi H, et al., "Pretherapy Ferumoxytol-enhanced MRI to Predict Response to Liposomal Irinotecan in Metastatic Breast Cancer," Radiol Imaging Cancer. 5(2):e220022; doi: 10.1148/rycan.220022, (2023), 14 pages.
Rogers S, et al., "An Exploratory Analysis of the Intestinal Microbiome in Neoadjuvant Chemotherapy for Pancreatic Cancer," Poster presented at the AACR Special Conference on Pancreatic Cancer, Boston, MA, Sep. 13-16, 2022, 4 pages.
Rogers S, et al., Abstract B037. "An Exploratory Analysis of the Intestinal Microbiome in Neoadjuvant Chemotherapy for Pancreatic Cancer," Cancer Res. 82(22_Suppl):B037 (2022), 4 printed pages.
Rogers S, et al., Abstract TPS619. "A Phase II, Open-Label Pilot Study Evaluating the Safety and Activity of Liposomal Irinotecan (Nal-IRI) in Combination with 5-FU and Oxaliplatin (NALIRIFOX) in Preoperative Treatment of Pancreatic Adenocarcinoma: NEO-Nal-IRI Study," J Clin Oncol. 41(4_Suppl):TPS619 (2023), 4 printed pages.
Rustum Y, "Biochemical Rationale for the 5-Flurouracil Leucovorin Combination and Update of Clinical Experience," J Chemother. 2 (Suppl 1):5-11 (1990).
Drummond D, et al., "Optimizing Liposomes for Delivery of Chemotherapeutic Agents to Solid Tumors," Pharmacol Rev. 51(4):691-743 (1999).
Drummond D, et al., "Pharmacokinetics and In Vivo Drug Release Rates in Liposomal Nanocarrier Development," J Pharm Sci. 97(11):4696-740 (2008).
Drummond D, et al., Chapter 8, "Intraliposomal Trapping Agents for Improving In Vivo Liposomal Drug Formulation Stability," In Liposome Technology, Third Edition, vol. 2, Ed. G. Gregoriadis, pp. 149-168 (2006).
Drummond D, et al., Chapter 9, "Liposomal Drug Delivery Systems for Cancer Therapy," In Drug Discovery Systems in Cancer Therapy, Ed. D Brown, Humana Press, Totowa, NJ, pp. 191-213 (2004).
Ducreux M, et al., "Randomized Phase II Study Evaluating Oxaliplatin Alone, Oxaliplatin Combined with Infusional 5-FU, and Infusional 5-FU Alone in Advanced Pancreatic Carcinoma Patients," Ann Oncol. 15(3): 467-73 (2004).
Duffour J, et al., "Efficacy of Prophylactic Anti-Diarrhoeal Treatment in Patients Receiving Campto for Advanced Colorectal Cancer," Anticancer Res. 22(6B): 3727-31 (2002).
Eckardt J, et al., "Phase III Study of Oral Compared With Intravenous Topotecan as Second-Line Therapy in Small-Cell Lung Cancer," J Clin Oncol. 25(15):2086-92 (2007).

(56) References Cited

OTHER PUBLICATIONS

Eisenhauer E, et al., "New Response Evaluation Criteria in Solid Tumours: Revised RECIST Guideline (version 1.1)," Eur J Cancer. 45(2):228-47 (2009).
Elinzano H, et al., "Nanoliposomal Irinotecan and Metronomic Temozolomide for Patients With Recurrent Glioblastoma BrUOG329, A Phase I Brown University Oncology Research Group Trial," Am J Clin Oncol. 44(2):49-52 (2021). Epub 2020 version, pp. 1-4.
Elinzano H, et al., Abstract e14548. "Nanoliposomal Irinotecan and Metronomic Temozolomide for Patients With Recurrent Glioblastoma: BrUOG329, A Phase IB/IIA Brown University Oncology Research Group (BrUOG) Trial," J Clin Oncol. 38(15_Suppl):e14548 DOI: 10.1200/JCO.2020.38.15_suppl.e14548 (2020), 2 printed pages.
ELOXATIN package insert, revision Dec. 28, 2011, retrieved from https://www.accessdata.fda.gov/drugsatfda_docs/label/2011/021492s012lbl.pdf, 51 pages.
Emerson D, et al., "Antitumor Efficacy, Pharmacokinetics, and Biodistribution of NX 211: A Low-Clearance Liposomal Formulation of Lurtotecan," Clin Cancer Res. 6(7):2903-12 (2000).
English translation of title and abstract for Hasegawa, Y, "Biomarker as Predictive Safety Testing in Oncology", Igaku No Ayumi (Journal of Clinical and Experimental Medicine), 224(13):1171-4 (2008) (original in Japanese).
EP Patent Application No. 05745505.7: European Search Report dated Sep. 1, 2010, 6 pages.
Ettrich T, et al., "Liposomal Irinotecan (nal-IRI) Plus 5-Fluorouracil (5-FU) and Leucovorin (LV) or Gemcitabine Plus Cisplatin in Advanced Cholangiocarcinoma: The AIO-NIFE-Trial, an Open Label, Randomized, Multicenter Phase II Trial," Poster presented at the American Society of Clinical Oncology (ASCO) Annual Meeting, Chicago, Illinois, Jun. 1-5, 2018, 5 pages.
Ettrich T, et al., Abstract TPS4145. "Liposomal Irinotecan (nal-IRI) Plus 5-Fluorouracil (5-FU) and Leucovorin (LV) or Gemcitabine Plus Cisplatin in Advanced Cholangiocarcinoma: The AIO-NIFE-Trial, an Open Label, Randomized, Multicenter Phase II Trial," J Clin Oncol. 36(15_Suppl): TPS4145 Doi: 10. 1200/JCO.2018.36. 15_suppl.TPS4145 (2018), 2 printed pages.
European Medicines Agency Assessment Report for Onivyde, Committee for Medicinal Products for Human Use (CHMP), Jul. 21, 2016, 107 pages.
Extra J, et al., "Phase I Study of Oxaliplatin in Patients with Advanced Cancer," Cancer Chemother Pharmacol. 25(4):299-303 (1990).
Falcone A, et al., "Sequence Effect of Irinotecan and Fluorouracil Treatment on Pharmacokinetics and Toxicity in Chemotherapy-Naive Metastatic Colorectal Cancer Patients," J Clin Oncol. 19(15):3456-62 (2001).
Fannon M, et al., "Sucrose Octasulfate Regulates Fibroblast Growth Factor-2 Binding, Transport, and Activity: Potential for Regulation of Tumor Growth," J Cell Physiol. 215(2):434-41 (2008), NIH public access author manuscript version, 19 pages.
Farncombe M, "Management of Bleeding in a Patient with Colorectal Cancer: A Case Study," Support Care Cancer. 1(3):159-160 (1993).
FDA News Release, "FDA Approves New Treatment for Advanced Pancreatic Cancer." Retrieved from http://ww.fda.gov/NewsEvents/Newsroom/PressAnnouncements/ucm468654.htm, Oct. 22, 2015, 3 printed pages.
FDA, "Draft Guidance on Daunorubicin Citrate," Jul. 2014, 6 pages.
FDA, "Draft Guidance on Doxorubicin Hydrochloride," Recommended Feb. 2010, Revised Nov. 2013, Dec. 2014, 6 pages.
Figer A, et. al., "A Comparison of Two Dose Regimens in Pancreatic Cancer," J Chemother. 12(5):442-5 (2000).
Fioravanti A, et. al., "Metronomic 5-Fluorouracil, Oxaliplatin and Irinotecan in Colorectal Cancer," Eur J Pharmacol. 619(1-3): 8-14 (2009).
Fischel J, et al., "Ternary Combination of Irinotecan, Fluorouracil-Folinic Acid and Oxaliplatin: Results on Human Colon Cancer Cell Lines," Br J Cancer. 84(4):579-85 (2001).
Fitzgerald J, et al., "Systems Pharmacology Identification of Tumour Nanoparticle Permeability as Predictor of Clinical Anti-Cancer Activity of MM-398, Nanoliposomal Irinotecan, nal-IRI." Poster presented at 15th International Conference on Systems Biology. Sep. 14-18, 2014, 10 pages.
Fleming D. "Importance of sequence in chemotherapy administration," retrieved from http://www.oncologynurseadvisor.com/advisor-forum/importance-of-sequence-in-chemotherapy-administration/article/378072/ (2014).
Fleming G, et. al., "Phase I and Pharmacokinetic Study of 24-Hour Infusion 5-Fluorouracil and Leucovorin in Patients With Organ Dysfunction," Ann Oncol. 14(7):1142-7 (2003).
Freise C, et al., "Characterization of a Cyclosporine-Containing Liposome," Transplant Proc. 23(1 Pt 1):473-4 (1991).
Freise C, et al., "Increased Efficacy of Cyclosporin Liposomes in a Rat Orthotopic Liver Transplant Model," Surgical Forum. 43:395-7 (1992).
Freise C, et al., "The Increased Efficacy and Decreased Nephrotoxicity of a Cyclosporine Liposome," Transplantation. 57(6):928-932 (1994).
Fuchs C, et al., "Phase III Comparison of Two Irinotecan Dosing Regimens in Second-Line Therapy of Metastatic Colorectal Cancer," J Clin Oncol. 21(5):807-14 (2003).
Fugit K, et al., "The Role of pH and Ring-opening Hydrolysis Kinetics on Liposomal Release of Topotecan," J Control Release. 174:88-97 (2014), Epub Nov. 12, 2013, Author manuscript, pp. 1-27.
Gaber M, et al., "Thermosensitive Liposomes: Extravasation and Release of Contents in Tumor Microvascular Networks," Int J Radiat Oncol Biol Phys. 36(5):1177-87 (1996).
Gaber M, et al., "Thermosensitive Sterically Stabilized Liposomes: Formulation and in Vitro Studies on the Mechanism of Doxorubicin Release by Bovine Serum and Human Plasma," Pharm Res. 12(10):1407-16 (1995).
Gaddy D, "Preclinical Anti-tumor Activity of Nanoliposomal Irinotecan (Nal-IRI, MM-398) + 5-FU + Oxaliplatin in Pancreatic Cancer." Abstract presented at AACR 2016, 1 page.
Gaddy D, et al., "A Systematic Literature Review to Identify and Compare Clinical Trials Evaluating Novel Therapeutic Agents in Post-Gemcitabine Advanced Pancreatic Cancer Patients." Poster presented at the International Society for Pharmacoeconomics and Outcomes Research (ISPOR) 18th Annual European Congress, Milan, Italy, Nov. 7-11, 2015, 6 pages.
Gaddy D, et al., "Preclinical Anti-tumor Activity of Nanoliposomal Irinotecan (Nal-IRI, MM-398) Supports Utilization as a Foundation of Front-Line Pancreatic Cancer Regimens." Poster presented at the American Society of Clinical Oncology Gastrointestinal Cancers Symposium (ASCO GI), San Francisco, CA, Jan. 19-21, 2017, 5 pages.
Gaddy D, et al., "Preclinical Anti-tumor Activity of Nanoliposomal Irinotecan (nal-IRI, MM-398) + 5-FU + Oxaliplatin in Pancreatic Cancer." Poster presented at AACR 2016, 5 pages.
Gaddy D, et al., Abstract 336. "Preclinical Antitumor Activity of Nanoliposomal Irinotecan (Nal-IRI, MM-398) and Utilization as a Foundation of Front-Line Pancreatic Cancer Regimens," J Clin Oncol. 35(4_Suppl):336 DOI: 10.1200/JCO.2017.35.4_suppl.336 (2017), 2 printed pages.
Gaddy D, et al., Abstract PCN29. "A Systematic Literature Review to Identify and Compare Clinical Trials Evaluating Novel Therapeutic Agents in Post-Gemcitabine Advanced Pancreatic Cancer," Value in Health. 18(7):A434 (2015).
Gahramanov S, et al., "Pseudoprogression of Glioblastoma After Chemo- and Radiation Therapy: Diagnosis by Using Dynamic Susceptibility-Weighted Contrast-Enhanced Perfusion MR Imaging with Ferumoxytol versus Gadoteridol and Correlation with Survival," Radiology. 266(3):842-52 (2013). doi: 10.1148/radiol. 12111472. Epub Nov. 30, 2012.
Garcia-Alfonso P, et. al., "Capecitabine in Combination with Irinotecan (XELIRI), Administered as a 2-Weekly Schedule, as First-Line Chemotherapy for Patients With Metastatic Colorectal Cancer: A Phase II Study of the Spanish GOTI Group," Br J Cancer. 101(7):1039-43 (2009).

(56) References Cited

OTHER PUBLICATIONS

Garcia-Carbonero R and Supko J, "Current Perspectives on the Clinical Experience, Pharmacology, and Continued Development of the Camptothecins," Clin Cancer Res. 8(3):641-61 (2002).
Garufi C, et al., "A Phase II Study of Irinotecan Plus Chronomodulated Oxaliplatin, 5-Fluorouracil and Folinic Acid in Advanced Colorectal Cancer Patients," Br J Cancer. 89(10):1870-5 (2003).
Gebbia V, et al., "Irinotecan Plus Bolus/Infusional 5-Fluorouracil and Leucovorin in Patients With Pretreated Advanced Pancreatic Carcinoma: A Multicenter Experience of the Gruppo Oncologico Italia Meridionale," Am J Clin Oncol. 33(5):461-64 (2010).
Gebbia V, et al., "Second-Line Chemotherapy in Advanced Pancreatic Carcinoma: A Multicenter Survey of the Gruppo Oncologico Italia Meridionale on the Activity and Safety of the FOLFOX4 Regimen in Clinical Practice," Ann Oncol. 18(Suppl 6):vi124-7 (2007).
Geddie M, et al., "Improving the Developability of an Anti-EphA2 Single-Chain Variable Fragment for Nanoparticle Targeting," MAbs. 9(1):58-67 (2017). Epub 2016.
Gelmon K, et. al., "A Phase 1 Study of OSI-211 Given as an Intravenous Infusion Days 1, 2, and 3 Every Three Weeks in Patients With Solid Cancers," Invest New Drugs. 22(3):263-75 (2004).
GEMZAR (gemcitabine HCl) package insert, revision Apr. 1998, 24 pages.
GEMZAR package insert, revision Feb. 4, 2011, retrieved from https://www.accessdata.fda.gov/drugsatfda_docs/label/2011/020509s069lbl.pdf, 21 pages.
GEMZAR package insert, revision May 8, 2014, retrieved from https://www.accessdata.fda.gov/drugsatfda_docs/label/2014/020509s077lbl.pdf, 18 pages.
Genther Williams S, et al., "Treatment with the PARP Inhibitor, Niraparib, Sensitizes Colorectal Cancer Cell Lines to Irinotecan Regardless of MSI/MSS Status," Cancer Cell Int. 15(1):14, doi: 10.1186/s12935-015-0162-8 (2015), pp. 1-11.
Gilbert D, et al., "Topoisomerase I Inhibition in Coloreclal Cancer: Biomarkers and Therapeutic Targets," Br J Cancer. 106(1):18-24 (2012), doi: 10.1038/bjc.2011.498, Epub Nov. 22, 2011.
Giles F, et. al., "Phase I and Pharmacokinetic Study of a Low-Clearance, Unilamellar Liposomal Formulation of Lurtotecan, a Topoisomerase 1 Inhibitor, in Patients with Advanced Leukemia," Cancer. 100(7):1449-58 (2004).
Gill S, et al., "PANCREOX: A Randomized Phase III Study of Fluorouracil/Leucovorin With or Without Oxaliplatin for Second-Line Advanced Pancreatic Cancer in Patients Who Have Received Gemcitabine-Based Chemotherapy," J Clin Oncol. 34(32):3914-20 and Appendix (2016).
Glassman D, et al., "Nanoliposomal Irinotecan With Flurouracil for the Treatment of Advanced Pancreatic Cancer." Poster presented at the American Society of Clinical Oncology Gastrointestinal Cancers Symposium (ASCO GI), San Francisco, CA, Jan. 18-20, 2018, 7 pages.
Glassman D, et al., Abstract 471. "Nano-Liposomal Irinotecan and 5-FU/LV (N+F) for the Treatment of Advanced PDAC: Memorial Sloan Kettering (MSK) Single Cancer Center Evaluation," J Clin Oncol. 36(4_Suppl):471 DOI: 10.1200/JCO.2018.36.4_suppl.471 (2018), 2 printed pages.
Glimelius B, et. al., "A Randomized Phase III Multicenter Trial Comparing Irinotecan in Combination With the Nordic Bolus 5-FU and Folinic Acid Schedule or the Bolus/Infused de Gramont Schedule (Lv5FU2) in Patients With Metastatic Colorectal Cancer," Ann Oncol. 19(5):909-14 (2008).
Glimelius B, et al., "Prediction of Irinotecan and 5-Fluorouracil Toxicity and Response in Patients With Advanced Colorectal Cancer," Pharmacogenomics J. 11(1):61-71 (2011). Epub 2010.
GLOBOCAN Cancer Facts Sheets: All Cancers 2012. Available from: http://globocan.iarc.fr/old/FactSheets/cancers/all-new.asp, accessed on Oct. 3, 2016, 9 printed pages.
Goldberg R, et. al., "A Randomized Controlled Trial of Fluorouracil Plus Leucovorin, Irinotecan, and Oxaliplatin Combinations in Patients With Previously Untreated Metastatic Colorectal Cancer," J Clin Oncol. 22(1):23-30 (2004). Epub 2003.
Goldstein D, et al., "nab-Paclitaxel Plus Gemcitabine for Metastatic Pancreatic Cancer: Long-Term Survival From a Phase III Trial," J Natl Cancer Inst. 107(2): dju413, pp. 1-10 (2015).
Gounaris I, et. al., "Options for the Treatment of Gemcitabine-Resistant Advanced Pancreatic Cancer," JOP. J Pancreas (Online) 11(2):113-23 (2010).
Gourzoulidis G, et al., "The Cost-Effectiveness of Nanoliposomal Irinotecan and 5-Fluorouracil (5-FU)/ Leucovorin (LV) for the Treatment of Patients With Metastatic Adenocarcinoma of Pancreas Who Have Progressed Following the Use of Gemcitabine-Related Therapies in Greece." Poster presented at the Virtual International Society for Pharmacoeconomics and Outcomes Research (ISPOR) European Congress, Milan, Italy, Nov. 16-19, 2020, 9 pages.
Gourzoulidis G, et al., Abstract PCN57. "The Cost-Effectiveness of Nanoliposomal Irinotecan and 5-Fluorouracil 5-FU)/ Leucovorin (LV) for the Treatment of Patients With Metastatic Adenocarcinoma of Pancreas Who Have Progressed Following the Use of Gemcitabine-Related Therapies in Greece," Virtual International Society for Pharmacoeconomics and Outcomes Research (ISPOR) European Congress, Milan, Italy, Nov. 16-19, 2020, available at ispor.org/heor-resources/presentations-database/presentation/euro2020-3282/105175, 2 printed pages.
Grant S, et al., "Dose-Ranging Evaluation of the Substituted Benzamide Dazopride When Used as an Antiemetic in Patients Receiving Anticancer Chemotherapy," Cancer Chemother Pharmacol. 31(6):442-44 (1993).
Greiner P, et. al., "Pharmacokinetics of (-)-Folinic Acid After Oral and Intravenous Administration of the Racemate," Br J Clin Pharmacol. 28(3):289-95 (1989).
Guichard S, et al., "Combination of Oxaliplatin and Irinotecan on Human Colon Cancer Cell Lines: Activity In Vitro and In Vivo," Anticancer Drugs. 12(9):741-51 (2001).
Guichard S, et. al., "Cellular Interactions of 5-Fluorouracil and the Camptothecin Analogue CPT-11 (Irinotecan) in a Human Colorectal Carcinoma Cell Line," Biochem Pharmacol. 55(5):667-76 (1998).
Guichard S, et al., "Sequence-Dependent Activity of the Irinotecan-5FU Combination in Human Colon-Cancer Model HT-29 In Vitro and In Vivo," Int J Cancer. 73(5):729-34 (1997).
Haller D, "Chemotherapy for Advanced Pancreatic Cancer," Int J Radiat Oncol Biol Phys. 56(4 Suppl):16-23 (2003).
Han S, et al., Abstract ACTR-33. "A Phase I Study of Convection-Enhanced Delivery of Liposomal-Irinotecan Using Real-Time Imaging With Gadolinium in Patients With Recurrent High Grade Glioma," Neuro-Oncology. 18(Suppl_6):vi9 doi.org/10.1093/neuonc/now212.031 (2016).
Hann B, et. al., Abstract 5648. "Lipidic Nanoparticle CPT-11 in a Bioluminescent Orthotopic Pancreas Cancer Model," Cancer Res. 67(9 Suppl):5648 (2007), 4 printed pages.
Janna N, et al., "Randomized Phase III Trial Comparing Irinotecan/Cisplatin with Etoposide/Cisplatin in Patients with Previously Untreated Extensive-Stage Disease Small-Cell Lung Cancer," J Clin Oncol. 24(13):2038-43 (2006).
Hare J, "Utilization of Liposomes in Combination Cancer Chemotherapy," PHD thesis, University of Alberta, Department of Pharmacology, 2011, 367 pages.
Hare J, et al., "Treatment of Colorectal Cancer Using a Combination of Liposomal Irinotecan (Irinophore C(TM)) and 5-Fluorouracil," PLoS One. 8(4):e62349, doi: 10.1371/journal.pone.0062359, 12 pages (2013).
Harker-Murray P, et al., Abstract CT146. "Plasma Pharmacokinetics of Liposomal Irinotecan (nal-iri) in Pediatric Oncology Patients with Recurrent or Refractory Solid Tumors: South Plains Oncology Consortium Study 2012-001," In Proceedings of the American Association for Cancer Research Annual Meeting 2017; Apr. 1-5, 2017. Washington, DC. Cancer Res. 2017;77(13 Suppl):Abstract nr CT146, doi:10.1158/1538-7445.AM2017-CT146, 4 printed pages.
Hashimoto S, et al., "Depletion of Alveolar Macrophages Decreases Neutrophil Chemotaxis to Pseudomonas Airspace Infections," Am J Physiol. 270(5 Pt 1):L819-28 (1996).

(56) References Cited

OTHER PUBLICATIONS

Hattori Y, et al., "Novel Irinotecan-Loaded Liposome Using Phytic Acid with High Therapeutic Efficacy for Colon Tumors," J Control Release. 136(1):30-7 (2009).
Hay M, et. al., "Clinical Development Success Rates for Investigational Drugs," Nature Biotechnol. 32(1):40-51 (2014).
Hayashi H, et al., "Phase II Study of Bi-Weekly Irinotecan for Patients with Previously Treated HER2-Negative Metastatic Breast Cancer: KMBOG0610B," Breast Cancer. 20(2):131-6 (2013); doi: 10.1007/s12282-011-0316-z. Epub Nov. 29, 2011.
Hayes M, et al., "Assembly of Nucleic Acid-Lipid Nanoparticles from Aqueous-Organic Monophases," Biochim Biophys Acta. 1758(4):429-42 (2006).
Hayes M, et al., "Genospheres: Self-Assembling Nucleic Acid-Lipid Nanoparticles Suitable for Targeted Gene Delivery," Gene Ther. 13(7):646-51 (2006).
Hayes M, et al., "Increased Target Specificity of Anti-HER2 Genospheres by Modification of Surface Charge and Degree of PEGylation," Mol Pharm. 3(6):726-36 (2006).
Heinemann V, et. al., "Randomized Phase III Trial of Gemcitabine Plus Cisplatin Compared With Gemcitabine Alone in Advanced Pancreatic Cancer," J Clin Oncol. 24(24):3946-52 (2006).
Herrera-Restrepo O, et al., "Budget Impact in the USA of Liposomal Irinotecan as a Post-Gemcitabine Treatment Option for Patients With Metastatic Pancreatic Adenocarcinoma (mPC)." Poster presented at the International Society for Pharmacoeconomics and Outcomes Research (ISPOR) Annual Meeting, New Orleans, LA, May 18-22, 2019, 12 pages.
Herrera-Restrepo O, et al., Abstract PCN80. "Budget Impact in the USA of Liposomal Irinotecan as a Post-Gemcitabine Treatment Option for Patients With Metastatic Pancreatic Adenocarcinoma (mPC)," Value in Health. 22(Suppl 2):S70 (2019).
Hidalgo M, "Pancreatic Cancer," N Engl J Med. 362(17):1605-17 (2010).
Hirsch J, et al., "Comparing Total Cost of Care for Medicare Fee-For-Service Patients With Pancreatic Cancer, by Chemotherapy Regimen." Poster presented at the American Society of Clinical Oncology Gastrointestinal Cancers Symposium (ASCO GI), San Francisco, CA, Jan. 23-25, 2020, 5 pages.
Hirsch J, et al., "Comparing Total Costs of Care for Medicare Fee-For-Service (FFS) Patients With Metastatic Pancreatic Cancer by Chemotherapy Regimen," Poster presented at the Academy of Managed Care Pharmacy, Nexus (AMCP, Nexus): virtual meeting, week of Oct. 19, 2020, 8 pages.
Hirsch J, et al., "The Cost of Adverse Events for FDA-Approved/NCCN Category 1 Treatments for Medicare Fee-For-Service (FFS) Patients With Metastatic Pancreatic Cancer." Poster presented at the Hematology Oncology Pharmacy Association (HOPA) Annual Conference, Tampa, FL, Mar. 11-14, 2020, 6 pages.
Hirsch J, et al., "The Cost of Adverse Events for FDA-Approved/NCCN Category 1 Treatments for Medicare Fee-For-Service Patients With Metastatic Pancreatic Cancer." Poster presented at the American Society of Health-System Pharmacists (ASHP) Midyear 2019 Clinical Meeting and Exhibition, Las Vegas, NV, Dec. 8-12, 2019, 6 pages.
Hirsch J, et al., Abstract 4-138. "The Cost of Adverse Events for FDA-Approved/NCCN Category 1 Treatments for Medicare Fee-For-Service Patients With Metastatic Pancreatic Cancer," American Society of Health-System Pharmacists (ASHP) Midyear Clinical Meeting Professional Poster Abstracts, (2019), 2 pages.
Hirsch J, et al., Abstract 721. "Comparing Total Cost of Care For Medicare FFS Patients With Pancreatic Cancer by Chemotherapy Regimen," J Clin Oncol. 38(4_Suppl):721 DOI: 10.1200/JCO.2020.38.4_suppl.721 (2020), 4 printed pages.
Hirsch J, et al., Abstract e19394. "Comparing Total Cost of Care for Medicare FFS Patients With Pancreatic Cancer by Chemotherapy Regimen," J Clin Oncol. 38(15_Suppl):e19394 DOI: 10.1200/JCO.2020.38.15_suppl.e19394 (2020), 2 printed pages.
Hong K, et al., "Anti-HER2 Immunoliposomes for Targeted Drug Delivery," Ann N Y Acad Sci. 886:293-6 (1999).
Honig A, et al., "Brain Metastases in Breast Cancer—an In Vitro Study to Evaluate New Systemic Chemotherapeutic Options," Anticancer Res. 25(3A):1531-7 (2005).
Becker C, et al., Abstract PCN58. "Budget Impact Analysis of Nanoliposomal Irinotecan for Treatment of Pancreatic Cancer Following Progression on Gemcitabine—A US Payer Perspective," Value in Health. 19(7):A718-A719 (2016).
Bendell J, et al., "Treatment Patterns and Clinical Outcomes in Patients With Metastatic Colorectal Cancer Initially Treated with FOLFOX-Bevacizumab or FOLFIRI-Bevacizumab: Results From ARIES, a Bevacizumab Observational Cohort Study," Oncologist. 17(12):1486-95 (2012).
Bernards N, et al., "Liposomal Irinotecan Achieves Significant Survival and Tumor Burden Control in a Triple Negative Breast Cancer Model of Spontaneous Metastasis," Mol Pharm. 15(9):4132-8 (2018).
Bernards N, et al., "Liposomal Irinotecan Injection (nal-IRI) Achieves Significant Survival and Tumor Burden Control in a Triple Negative Breast Cancer Model of Spontaneous Metastasis," Poster presented at the World Molecular Imaging Congress Sep. 13-16, 2017, Philadelphia, Pennsylvania, 5 pages.
Blanc J, et al., "Subgroup Analysis by Prior Non-Liposomal Irinotecan Therapy in NAPOLI-1: A Phase 3 Study of hal-IRI ± 5-Fluorouracil/Leucovorin in Patients With Metastatic Pancreatic Ductal Adenocarcinoma Previously Treated with Gemcitabine-Based Therapy." Poster presented at the European Society for Medical Oncology Asia 2017 Congress, Singapore, Nov. 17-19, 2017, 8 pages.
Blanc J, et al., Abstract 228P. "Subgroup Analysis by Prior Non-Liposomal Irinotecan Therapy in NAPOLI-1: A Phase 3 Study of nal-IRI ± 5-Fluorouracil/Leucovorin in Patients With Metastatic Pancreatic Ductal Adenocarcinoma Previously Treated with Gemcitabine-Based Therapy," Ann Oncol. 28(Suppl_10):x67-x68 doi:10.1093/annonc/mdx660 (2017).
Blanc J, et al., Abstract PD-18. "Subgroup Analysis by Prior Non-Liposomal Irinotecan Therapy in NAPOLI-1: A Phase 3 Study of nal-IRI ± 5-Fluorouracil/Leucovorin in Patients With Metastatic Pancreatic Ductal Adenocarcinoma Previously Treated With Gemcitabine-Based Therapy," Ann Oncol. 28(Suppl_3):7 doi: 10.1093/annonc/mdx263 (2017).
BlueCross Blue Shield of North Carolina Corporate Medical Policy, Bevacizumab in Advanced Adenocarcinoma of the Pancreas, File Name: bevacizumab_in_advanced_adenocarcinoma_of_the_pancreas, Origination: Mar. 2010, Last review: Feb. 2019, 5 pages.
Boeck S and Heinemann V, "Second-Line Therapy in Gemcitabine-Pretreated Patients With Advanced Pancreatic Cancer," J Clin Oncol. 26(7):1178-9 (2008).
Boeck S, et al., "Capecitabine Plus Oxaliplatin (CapOx) versus Capecitabine Plus Gemcitabine (CapGem) versus Gemcitabine Plus Oxaliplatin (mGemOx): Final Results of a Multicenter Randomized Phase II Trial in Advanced Pancreatic Cancer," Ann Oncol. 19(2):340-7 (2008), Epub Oct. 24, 2007.
Boman N, et al., "Optimization of the Retention Properties of Vincristine in Liposomal Systems," Biochim Biophys Acta. 1152(2):253-58 (1993).
Borner M, et. al., "A Randomized Phase II Trial of Capecitabine and Two Different Schedules of Irinotecan in First-Line Treatment of Metastatic Colorectal Cancer. Efficacy, Quality-of-Life and Toxicity," Ann Oncol. 16(2): 282-8 (2005).
Bouché O, et al. "Randomized Multicenter Phase II Trial of a Biweekly Regimen of Fluorouracil and Leucovorin LV5FU2), LV5FU2 Plus Cisplatin, or LV5FU2 Plus Irinotecan in Patients With Previously Untreated Metastatic Gastric Cancer: A Fédération Francophone De Cancérologie Digestive Group Study—FFCD 9803," J Clin Oncol. 22(21):4319-28 (2004).
Boulikas T, "Clinical Overview on Lipoplatin: A Successful Liposomal Formulation of Cisplatin," Expert Opin Investig Drugs. 18(8):1197-218 (2009), author manuscript version, 22 pages.
Bozzuto G and Molinari A, "Liposomes as Nanomedical Devices," Int J Nanomedicine. 10:975-99 (2015).
Brixi-Benmansour H, et al., "Phase II Study of First-line FOLFIRI for Progressive Metastatic Well-differentiated Pancreatic Endocrine Carcinoma," Dig Liver Dis. 43(11):912-6 (2011).

(56) References Cited

OTHER PUBLICATIONS

Brus C and Saif M, "Second Line Therapy for Advanced Pancreatic Adenocarcinoma: Where Are We and Where Are We Going?," J Pancreas (Online) 11(4):321-3 (2010).
Bulbake U, et al., "Liposomal Formulations in Clinical Use: An Updated Review," Pharmaceutics. 9(2):12 doi: 10.3390/pharmaceutics9020012 (2017), 33 pages.
Burris H and Rocha-Lima C, "New Therapeutic Directions for Advanced Pancreatic Cancer: Targeting the Epidermal Growth Factor and Vascular Endothelial Growth Factor Pathways," Oncologist. 13(3):289-98 (2008).
Burris H, et al., "Phase II Trial of Oral Rubitecan in Previously Treated Pancreatic Cancer Patients," Oncologist. 10(3):183-90 (2005).
Butowski N, et al., "A Phase I Study of CED of Nanoliposomal-Irinotecan Using Real-Time Imaging With Gadolinium in Patients With Recurrent High Grade Glioma." Poster presented at the American Society of Clinical Oncology (ASCO) Annual Conference, Chicago, IL, May 29-Jun. 2, 2015, 4 pages.
Butowski N, et al., Abstract TPS2081. "A Phase I Study of Convection-Enhanced Delivery of Nanoliposomal Irinotecan Using Real-Time Imaging in Patients With Recurrent High Grade Glioma," J Clin Oncol. 33(15_Suppl):2081 DOI: 10.1200/jco.2015.33.15_suppl.tps2081 (2015), 2 printed pages.
Butt R, et al., "Postfractionation for Enhanced Proteomic Analyses: Routine Electrophoretic Methods Increase the Resolution of Standard 2D-PAGE," J Proteome Res. 4(3):982-91 (2005).
Caelyx (doxorubicin), MedBroadcast, accessed Jan. 26, 2021 from medbroadcast.com/drug/getdrug/caelyx, 11 printed pages.
CAMPTOSAR package insert, revised May 16, 2002, 37 pages.
CAMPTOSAR package insert, revision Dec. 19, 2014, retrieved from https://www.accessdata.fda.gov/drugsatfda_docs/label/2014/020571s048lbl.pdf, initial U.S. approval 1996, 40 printed pages.
CAMPTOSAR package insert, revision May 14, 2010, retrieved from https://www.accessdata.fda.gov/drugsatfda_docs/label/2010/020571s031s032s033s036s037lbl.pdf, 37 pages.
Cantore M, et al., "Combined Irinotecan and Oxaliplatin in Patients with Advanced Pre-Treated Pancreatic Cancer," Oncology 67(2):93-7 (2004).
Cao S, et al., "Synergistic Antitumor Activity of Capecitabine in Combination with Irinotecan," Clin Colorectal Cancer. 4(5):336-43 (2005).
Cao Y, et al., "A Gold Nanoparticle Bouquet Held on Plasma Membrane: An Ultrasensitive Dark-Field Imaging Approach for Cancer Cell Analysis," Nanotheranostics. 4(4):201-209 (2020).
Carter K, et. al., "Sphingomyelin Liposomes Containing Porphyrin—Phospholipid for Irinotecan Chemophototherapy," Theranostics. 6(13):2329-36 (2016).
CAS Registry Record for 23214-92-8 (doxorubicin), entered STN Nov. 16, 1984, 2 pages.
CAS Registry Record for 97682-44-5 (irinotecan), entered STN Aug. 18, 1985, 1 page.
Cascinu S, et al., "Pancreatic Cancer: ESMO Clinical Practice Guidelines for Diagnosis, Treatment and Follow-up," Ann Oncol. 21(Suppl 5):v55-v58 (2010).
Cassileth P, et al., "Antiemetic Efficacy of Dexamethasone Therapy in Patients Receiving Cancer Chemotherapy," Arch Intem Med. 143(7):1347-9 (1983).
Cereda S, et al., "XELIRI or FOLFIRI as Salvage Therapy in Advanced Pancreatic Cancer," Anticancer Res. 30(11):4785-90 (2010).
Cerenzia W, et al., Abstract e16233. "Identifying Continuing Educational Needs Among Oncologists in Managing Patients With Pancreatic Cancer," J Clin Oncol. 36(15_Suppl):e16233 DOI: 10.1200/JCO.2018.36.15_suppl.e16233 (2018), 2 printed pages.
Chabot G, "Clinical Pharmacokinetics of Irinotecan," Clin. Pharmacokinet. 33(4):245-59 (1997).
Chan D, et al., "Evaluating the Pharmacodynamics and Pharmacokinetic Effects of MM-398, a Nanoliposomal Irinotecan (nal-IRI) in Subcutaneous Xenograft Tumor Models of Human Squamous Cell Carcinoma and Small Cell Lung Cancers," Poster presented at AACR Annual Meeting Apr. 5-9, 2014, 6 pages.
Chan D, et al., "Evaluating the Pharmacodynamics and Pharmacokinetic Effects of MM-398, a Nanoliposomal Irinotecan (nal-IRI) in Subcutaneous Xenograft Tumor Models of Human Squamous Cell Carcinoma and Small Cell Lung Cancers," Cancer Res.74(19 Suppl): Abstract 4626 (2014), 2 printed pages.
Chan D, et al., "PEP02 (Liposome Irinotecan) Effectively Inhibits Human Lung Squamous Cell Carcinoma and Small Cell Lung Cancers in Subcutaneous and Orthotopic Xenograft Tumor Models," J Thoracic Oncology. 6(6)(Suppl 2):S420-1 (2011).
Chan D, et al., "PEP02 (Liposome Irinotecan) Effectively Inhibits Human Squamous Cell Carcinoma and Small Cell Lung Cancers in Subcutaneous and Orthotopic Xenograft Tumor Models." Presentation at Santa Monica Lung Cancer Meeting, 2012, 9 pages.
Chan D, et al., "PEP02 (Liposome Irinotecan) Effectively Inhibits Human Squamous Cell Carcinoma and Small Cell Lung Cancers in Subcutaneous and Orthotopic Xenograft Tumor Models." Presentation at the 14th World Conference on Lung Cancer, 2011, 11 pages.
Chan E, et al., "A Phase 1/2 Study Combining MM-151 + nal-IRI + 5-FU + Leucovorin in RAS/RAF Wild-Type Metastatic Colorectal Cancer." Poster presented at the American Society of Clinical Oncology (ASCO) Annual Meeting, Chicago, Illinois, Jun. 3-7, 2016, 7 pages.
Chan E, et al., Abstract TPS3633. "A Phase 1b/2 Study Combining MM-151 + nal-IRI + 5-FU + Leucovorin in RAS-Wildtype Metastatic Colorectal Cancer (mCRC)," J Clin Oncol. 34(15_Suppl):TPS3633 10.1200/JCO.2016.34.15_suppl.TPS3633 (2016), 4 printed pages.
Chang T, et al., "Phase I Study of Nanoliposomal Irinotecan (PEP02) in Advanced Solid Tumor Patients," Cancer Chemother Pharmacol. 75(3):579-86 (2015).
Chauhan V, et. al., "Normalization of Tumour Blood Vessels Improves the Delivery of Nanomedicines in a Size-Dependent Manner," Nat Nanotechnol. 7(6):383-8 (2012), author manuscript version, 15 pages.
Chen J, et al., "Improved Pharmacokinetics and Reduced Toxicity of Brucine After Encapsulation into Stealth Liposomes: Role of Phosphatidylcholine," Int J Nanomedicine. 7:3567-77 (2012).
Chen L, et al., "Effect of Baseline Carbohydrate Antigen 19-9 (CA19-9) Level on Overall Survival (OS) in NAPOLI-1 Trial: a Phase 3 Study of MM-398 (nal-IRI), with or without 5-Fluorouracil and Leucovorin (5-FU/LV), versus 5-FU/LV in Metastatic Pancreatic Cancer (mPAC) Previously Treated with Gemcitabine-based Therapy." Poster handout at the Gastrointestinal Cancers Symposium of the ASCO meeting of Jan. 21-23, 2016, San Francisco, Califomia, 2 pages.
Chen L, et al., "Effect of Baseline Carbohydrate Antigen 19-9 (CA19-9) Level on Overall Survival (OS) in NAPOLI-1 Trial: a Phase 3 Study of MM-398 (nal-IRI), with or without 5-Fluorouracil and Leucovorin (5-FU/LV), versus 5-FU/LV in Metastatic Pancreatic Cancer (mPAC) Previously Treated with Gemcitabine-based Therapy." Poster presented at the Gastrointestinal Cancers Symposium of the ASCO meeting of Jan. 21-23, 2016, San Francisco, Califomia, 16 pages.
EP2861210: Proprietor's response to opponent's reply to proprietor's grounds of appeal following opposition, dated Jun. 30, 2021, 23 pages.
EP2861210: Proprietor's response to opponent's reply to proprietor's grounds of appeal following opposition, dated Jun. 30, 2021, D37 (Declaration of Carla Schoonderbeek) including D37A (Directive 2001/20/EC of the European Parliament and of the Counsel of Apr. 4, 2001 ("the Clinical Trials Directive" or CTD)), 26 total pages.
EP2861210: Proprietor's response to opponent's reply to proprietor's grounds of appeal following opposition, dated Jun. 30, 2021, D38 (Declaration of Grant H. Castle, Ph.D.) including D38A (European Commission: "Communication from the Commission—Detailed guidance on the request to the competent authorities for authorisation of a clinical trial on a medicinal product for human use, the notification of substantial amendments and the declaration of the end of the trial (CT-1)"), 23 total pages.

(56) References Cited

OTHER PUBLICATIONS

EP2861210: Communication of the Board of Appeals, Preliminary Opinion, dated Aug. 9, 2021, 21 pages.
EP2861210: Proprietor Response to the Board of Appeals' Preliminary Opinion, dated Dec. 21, 2021, 12 pages.
EP2861210: Minutes of the oral proceedings before the Opposition Board of Appeal, held Mar. 18, 2022, 4 pages.
EP2861210: Boards of Appeal of the European Patent Office decision dismissing appeal to decision of the Opposition Division revoking European Patent No. 2861210, decision dated Mar. 18, 2022, 35 pages.
EP3266456: EPO Notice of Sandoz AG Opposition dated Feb. 1, 2022, 6 pages.
EP3266456: Sandoz AG Opposition dated Feb. 1, 2022, 23 pages.
EP3266456: EPO Notice of Teva Pharmaceuticals Industries Ltd. Opposition dated Feb. 2, 2022, 6 pages.
EP3266456: Teva Pharmaceutical Industries Ltd. Opposition dated Feb. 2, 2022, 12 pages.
EP3266456: EPO Notice of Generics [UK] Limited Opposition dated Feb. 4, 2022, 5 pages.
EP3266456: Generics [UK] Ltd. Opposition dated Feb. 4, 2022, 13 pages.
EP3266456: EPO Opposition Consolidated List of Citations, Feb. 4, 2022, 2 pages.
EP3266456: Consolidated Opposition dated Feb. 2022, D1 (Chen L, et al., "Phase I Study of Liposome Irinotecan (PEP02) in Combination with Weekly Infusion of 5-FU/LV in Advanced Solid Tumors," J Clin Oncol. 28(15_suppl):abstract e13024 (2010), 2 pages).
EP3266456: Consolidated Opposition dated Feb. 2022, D2 (Chen L, et al., "Phase I Study of Biweekly Liposome Irinotecan (PEP02, MM-398) in Metastatic Colorectal Cancer Failed on First-line Oxaliplatin-based Chemotherapy," J Clin Oncol. 30(4_suppl):Abstract 613 (2012), 2 pages).
EP3266456: Consolidated Opposition dated Feb. 2022, D3 (Ko A, et al., "A Multinational Phase II Study of Liposome Irinotecan (PEP02) for Patients with Gemcitabine-Refractory Metastatic Pancreatic Cancer," J Clin Oncol. 29(4_suppl):Abstract 237 (2011), 2 pages).
EP3266456: Consolidated Opposition dated Feb. 2022, D4 (Chen L, et al., "Phase I Study of Liposome Encapsulated Irinotecan (PEP02) in Advanced Solid Tumor Patients," J Clin Oncol., 26(15_suppl):abstract 2565 (2008), 2 pages).
EP3266456: Consolidated Opposition dated Feb. 2022, D5 ((Clinical Trials Identifier NCT01494506: May 29, 2012 version submitted, "A Randomized, Open Label Phase 3 Study of MM-398 Versus 5-Fluorouracil and Leucovorin in Patients With Metastatic Pancreatic Cancer." 6 pages).
EP3266456: Consolidated Opposition dated Feb. 2022, D5a ((Clinical Trials Identifier NCT01494506: Aug. 8, 2012 submitted, "A Randomized, Open Label Phase 3 Study of MM-398, With or Without 5-Fluorouracil and Leucovorin, Versus 5-Fluorouracil and Leucovorin in Patients with Metastatic Pancreatic Cancer Who Have Failed Prior Gemcitabine-based Therapy." 7 pages).
EP3266456: Consolidated Opposition dated Feb. 2022, D6 ((Clinical Trials Identifier NCT01375816: Jun. 16, 2011 version submitted, "A Randomized Phase II Study of PEP02 or Irinotecan in Combination with Leucovorin and 5-Fluorouracil in Second Line Therapy of Metastatic Colorectal Cancer." 6 pages).
EP3266456: Consolidated Opposition dated Feb. 2022, D7 (Tsai C, et al., "Nanovector-Based Therapies in Advanced Pancreatic Cancer," J Gastroint Oncol 2(3):185-94 (2011)).
EP3266456: Consolidated Opposition dated Feb. 2022, D8 (CAMPTOSAR package insert, 2009, 37 pages).
EP3266456: Consolidated Opposition dated Feb. 2022, D9 (FUSILEV package insert, 2008, 7 pages).
EP3266456: Consolidated Opposition dated Feb. 2022, D10 (Yoo C, et al., "A Randomised Phase II Study of Modified FOLFIRI.3 vs Modified FOLFOX as Second-Line Therapy in Patients with Gemcitabine-Refractory Advanced Pancreatic Cancer," Br J Cancer. 101(10):1658-63 (2009).
EP3266456: Consolidated Opposition dated Feb. 2022, D11 (Drummond D, et al., "Development of a Highly Active Nanoliposomal Irinotecan Using a Novel Intraliposomal Stabilization Strategy," Cancer Res. 66(6):3271-77 (2006)).
EP3266456: Consolidated Opposition dated Feb. 2022, D12 (Baker J, et al., "Irinophore C, a Novel Nanoformulation of Irinotecan, Alters Tumor Vascular Function and Enhances the Distribution of 5-Fluorouracil and Doxorubicin," Clin Cancer Res. 14(22):7260-71 (2008)).
EP3266456: Consolidated Opposition dated Feb. 2022, D13 (Venditto V, et al., "Cancer Therapies Utilizing the Camptothecins: A Review of the in Vivo Literature," Mol Pharm. 7(2):307-349 (2010)).
EP3266456: Consolidated Opposition dated Feb. 2022, D14 (Tardi P, et. al., "Coencapsulation of Irinotecan and Floxuridine Into Low Cholesterol-Containing Liposomes That Coordinate Drug Release In Vivo," Biochim Biophys Acta. 1768(3):678-87 (2007). Epub 2006).
EP3266456: Consolidated Opposition dated Feb. 2022, D15 (Opposition Division's decision to revoke EP2861210, dated Aug. 28, 2019, 24 pages).
EP3266456: Consolidated Opposition dated Feb. 2022, D16 (EP2861210: Communication of the Board of Appeals, Preliminary Opinion, dated Aug. 9, 2021, 21 pages).
EP3266456: Consolidated Opposition dated Feb. 2022, D17 (Clinical Trials Identifier NCT01494506: Dec. 16, 2011 version, "A Randomized, Open Label Phase 3 Study of MM-398 Versus 5-Fluorouracil and Leucovorin in Patients With Metastatic Pancreatic Cancer." 2 pages).
EP3266456: Consolidated Opposition dated Feb. 2022, D18 (Hoskins J, et al., "UGT1A1*28 Genotype and Irinotecan-Induced Neutropenia: Dose Matters," J Natl Cancer Inst. 99(17):1290-95 (2007)).
EP3266456: Consolidated Opposition dated Feb. 2022, D19 (Brixi-Benmansour H, et al., "Phase II Study of First-line FOLFIRI for Progressive Metastatic Well-differentiated Pancreatic Endocrine Carcinoma," Dig Liver Dis. 43(11):912-6 (2011)).
EP3266456: Consolidated Opposition dated Feb. 2022, D20 (Infante J, et al., "Phase I and Pharmacokinetic Study of IHL-305 (PEGylated Liposomal Irinotecan) in Patients with Advanced Solid Tumors," Cancer Chemother Pharmacol. 70(5):699-705 (2012)).
EP3266456: Consolidated Opposition dated Feb. 2022, D23 (European Commission Implementing Decision granting marketing authorisation for Onivyde, Oct. 14, 2016, 39 pages).
EP3266456: Consolidated Opposition dated Feb. 2022, D24 (Wang-Gillam A, et al., "Nanoliposomal Irinotecan with Flourouracil and Folinic Acid in Metastatic Pancreatic Cancer After Previous Gemcitabine-Based Therapy (NAPOLI-1): A Global, Randomised, Open-Label, Phase 3 Trial," Lancet, 387(10018):545-57 (2016). Epub doi: 10.1016/S0140-6736(15)00986-1, pp. 1-13 (2015)).
EP3266456: Consolidated Opposition dated Feb. 2022, D25 (FDA News Release, "FDA Approves New Treatment for Advanced Pancreatic Cancer." http://ww.fda.gov/NewsEvents/Newsroom/PressAnnouncements/ucm468654.htm, Oct. 22, 2015, 3 pages).
EP3266456: Consolidated Opposition dated Feb. 2022, D26 (MHRA Public Assessment Report for 5-Fluorouracil, 2006, 60 pages).
EP3266456: Consolidated Opposition dated Feb. 2022, D27 (Gebbia V, et al., "Irinotecan Plus Bolus/Infusional 5-Fluorouracil and Leucovorin in Patients With Pretreated Advanced Pancreatic Carcinoma: A Multicenter Experience of the Gruppo Oncologico Italia Meridionale," Am J Clin Oncol. 33(5):461-64 (2010).
EP3266456: Consolidated Opposition dated Feb. 2022, D28 (Chen P, et al., "Comparing Routes of Delivery for Nanoliposomal Irinotecan Shows Superior Anti-Tumor Activity of Local Administration in Treating Intracranial Glioblastoma Xenografts," Neuro Oncol. 15(2):189-97 (2013), Epub Dec. 21, 2012).
EP3266456: Proprietor's Submission in Response to Oppositions, dated Sep. 5, 2022, including auxiliary requests 1-3, 52 pages.
EP3266456: Proprietor's Submission in Response to Oppositions dated Sep. 5, 2022, D29 (Summary of Product Characteristics for Calcium Folinate 15 mg Tablets), 7 pages.
EP3266456: Sandoz AG (Opponent 1) Response to Proprietor's Reply to the Notice of Opposition dated Oct. 14, 2022, 10 pages.

(56) References Cited

OTHER PUBLICATIONS

EP3266456: Generics [UK] Limited (Opponent 3) Response to Proprietor's Reply to the Notice of Opposition dated Nov. 15, 2022, 9 pages.
EP3266456: Teva (Opponent 2) Response to Proprietor's Reply to the Notice of Opposition dated Nov. 16, 2022, 6 pages.
EP3266456: Teva (Opponent 2) Response to Proprietor's Reply to the Notice of Opposition dated Nov. 16, 2022, D30 (Boards of Appeal of the European Patent Office decision dismissing appeal to decision of the Opposition Division revoking European Patent No. 2861210, decision dated Mar. 18, 2022, 35 pages).
EP3266456: Teva (Opponent 2) Response to Proprietor's Reply to the Notice of Opposition dated Nov. 16, 2022, D31 (Noble C, et al., "Novel Nanoliposomal CPT-11 Infused by Convection-Enhanced Delivery in Intracranial Tumors: Pharmacology and Efficacy," Cancer Res. 66(5):2801-6 (2006)).
EP3266456: Teva (Opponent 2) Response to Proprietor's Reply to the Notice of Opposition dated Nov. 16, 2022, D32 (Krauze M, et al., "Convection-Enhanced Delivery of Nanoliposomal CPT-11 (Irinotecan) and PEGylated Liposomal Doxorubicin (Doxil) in Rodent Intracranial Brain Tumor Xenografts," Neuro Oncol. 9(4):393-403 (2007)).
EP3266456: Teva (Opponent 2) Response to Proprietor's Reply to the Notice of Opposition dated Nov. 16, 2022, D34 (Chen L, et al., "Phase I Study of Biweekly Liposome Irinotecan (PEP02, MM-398) in Metastatic Colorectal Cancer Failed on First-line Oxaliplatin-based Chemotherapy," J Clin Oncol. 30(4_suppl):Abstract 613 (2012), 5 printed pages).
Pan-Canadian Oncology Drug Review (pCODR) Expert Review Committee (pERC) Final Recommendation for Irinotecan Liposome (Onivyde) for Metastaic Pancreatic Cancer, pERC Meeting: Oct. 19, 2017, pERC Reconsideration Meeting: Dec. 17, 2017, pp. 1-14.
Papadatos-Pastos D, et.al., "FOLFIRINOX—A New Paradigm in the Treatment of Pancreatic Cancer," Expert Rev Anticancer Ther. 14(10):1115-25 (2014).
Papahadjopoulos D, et al., "Targeting of Drugs to Solid Tumors Using Anti-HER2 Immunoliposomes," J Liposome Res. 8(4):425-42 (1998).
Papahadjopoulos D, et. al., "Sterically Stabilized Liposomes: Improvements in Pharmacokinetics and Antitumor Therapeutic Efficacy," Proc Natl Acad Sci USA. 88(24):11460-4 (1991).
Papi M, et. al., "Clinically Approved PEGylated Nanoparticles Are Covered by a Protein Corona That Boosts the Uptake by Cancer Cells," Nanoscale. 9(29):10327-34 (2017).
Parekh H, et al., "A Phase II, Open-Label Pilot Study Evaluating the Safety and Activity of Nal-IRI in Combination With 5-FU and Oxaliplatin in Preoperative Treatment of Pancreatic Adenocarcinoma (NEO-Nal-IRI Study)." Poster presented at the American Society of Clinical Oncology Gastrointestinal Cancers Symposium (ASCO GI), San Francisco, CA, Jan. 23-25, 2020, 3 pages.
Parekh H, et al., Abstract TPS790. "A Phase II, Open-Label Pilot Study Evaluating the Safety and Activity of Nal-IRI in Combination With 5-FU and Oxaliplatin in Preoperative Treatment of Pancreatic Adenocarcinoma (NEO-Nal-IRI Study) (NCT03483038)," J Clin Oncol. 38(4_Suppl):TPS790 (2020), 2 printed pages.
Park J, English abstract and Table 1 and Figure 1 of "Second Line Chemotherapy for Pancreatic Cancer," Korean J Gastroenterol. 57(4):207-12 (2011).
Park J, et al., "Anti-HER2 Immunoliposomes for Targeted Therapy of Human Tumors," Cancer Lett. 118(2):153-60 (1997).
Park J, et al., "Anti-HER2 Immunoliposomes: Enhanced Efficacy Attributable to Targeted Delivery," Clin Cancer Res. 8(4):1172-81 (2002).
Park J, et al., "Development of Anti-p185HER2 Immunoliposomes for Cancer Therapy," Proc Natl Acad Sci U S A. 92(5):1327-31 (1995).
Park J, et al., "Immunoliposomes for Cancer Treatment," Adv Pharmacol. 40:399-435 (1997).
Park J, et al., "Sterically Stabilized Immunoliposomes: Formulations for Delivery of Drugs and Genes to Tumor Cells In Vivo," In Targeting of Drugs 6: Strategies for Stealth Therapeutic Systems, Gregoriadis G, et al., eds., Plenum Press, New York, pp. 41-47 (1998).
Park J, et al., "Tumor Targeting Using Anti-HER2 Immunoliposomes," J Control Release. 74(1-3):95-113 (2001).
Park J, et. al., "Anti-HER2 Immunoliposomes for Targeted Drug Delivery," Med Chem Res. 8(7/8):383-91 (1998).
Patankar N, et. al., "Topophore C: A Liposomal Nanoparticle Formulation of Topotecan for Treatment of Ovarian Cancer," Invest New Drugs. 31(1):46-58 (2013). Epub 2012.
Patel M, et. al., "Effects of Oxaliplatin and CPT-11 on Cytotoxicity and Nucleic Acid Incorporation of the Fluoropyrimidines," J Cancer Res Clin Oncol. 130(8):453-9 (2004).
Patton W, "Detection Technologies in Proteome Analysis," J Chromatogr B. 771(1-2):3-31 (2002).
Pavai S and Yap S, "The Clinical Significance of Elevated Levels of Serum CA19-9," Med J Malaysia. 58(5):667-72 (2003).
Pavillard V, et al., "Combination of Irinotecan (CPT11) and 5-Fluorouracil with an Analysis of Cellular Determinants of Drug Activity," Biochem Pharmacol. 56(10):1315-22 (1998).
Pavillard V, et al., "Determinants of the Cytotoxicity of Irinotecan in Two Human Colorectal Tumor Cell Lines," Cancer Chemother Pharmacol. 49(4):329-35 (2002).
Paz N, et al., "MM-398/PEP02, A Novel Liposomal Formulation of Irinotecan Demonstrates Stromal-Modifying Anti-Cancer Properties," Poster for abstract A63 presented at the AACR Special Conference on Pancreatic Cancer: Progress and Challenges; Jun. 18-21, 2012; Lake Tahoe, NV, 9 pages.
Paz N, et al., Abstract A63. "MM-398/PEP02, A Novel Liposomal Formulation of Irinotecan, Demonstrates Stromal-Modifying Anti-cancer Properties," In Proceedings of the AACR Special Conference on Pancreatic Cancer: Progress and Challenges; Jun. 18-21, 2012; Lake Tahoe, NV. Cancer Res. 2012;72(12 Suppl):Abstract nr A63, 3 printed pages.
Paz-Ares L, et al., "Efficacy and Safety of Irinotecan Liposome Injection (nal-IRI) in Patients with Small Cell Lung Cancer (SCLC)," Presentation presented at 2019 World Conference on Lung Cancer; Sep. 7-10, 2019; Barcelona, Spain; 9 pages.
Paz-Ares L, et al., "Liposomal Irinotecan vs Topotecan in Patients with Small Cell Lung Cancer Who Have Progressed On/After Platinum-Based Therapy." Poster presented Sep. 23-26, 2018 at 19th World Conference on Lung Cancer meeting, 9 pages.
Paz-Ares L, et al., "RESILIENT part 2: An Open-Label, Randomized, Phase 3 Study of Liposomal Irinotecan Injection in Patients With Small Cell Lung Cancer Who Have Progressed With Platinum-Based First-Line Therapy." Poster presented at the American Society of Clinical Oncology (ASCO) Annual Conference, virtual format, May 29-Jun. 2, 2020, 7 pages.
Paz-Ares L, et al., "RESILIENT: Study of Irinotecan Liposome Injection (nal-IRI) in Patients with Small Cell Lung Cancer—Preliminary Findings from Part 1 Dose-Defining Phase," Abstract No. 8562, J Clin Oncol. 37(15)(Suppl):8562 (2019), 3 pages.
Paz-Ares L, et al., "RESILIENT: Study of Irinotecan Liposome Injection (nal-IRI) in Patients with Small Cell Lung Cancer—Preliminary Findings from Part 1 Dose-Defining Phase," Poster presented at ASCO in Chicago, IL May 31-Jun. 4, 2019, 6 pages.
Paz-Ares L, et al., Abstract TPS9081. "RESILIENT part II: An Open-Label, Randomized, Phase III Study of Liposomal Irinotecan Injection in Patients With Small-Cell Lung Cancer Who Have Progressed With Platinum-Based First-Line Therapy," J Clin Oncol. 38(15_Suppl):TPS9081 DOI: 10.1200/JCO.2020.38.15_suppl.TPS9081 (2020), 2 printed pages.
Paz-Ares Rodriguez L, et al., Abstract OA03.03. "Initial Efficacy and Safety Results of Irinotecan Liposome Injection (NAL-IRI) in Patients With Small Cell Lung Cancer," 2019 World Conference on Lung Cancer Abstracts; Sep. 7-10, 2019; Barcelona, Spain; pp. 220-221.
Peddi P, et al., "Multi-Institutional Experience with FOLFIRINOX in Pancreatic Adenocarcinoma," Journal of the Pancreas (JOP). 13(5):497-501 (2012), online access, 11 printed pages.

(56) References Cited

OTHER PUBLICATIONS

Peikov V, et al., "pH-Dependent Association of SN-38 with Lipid Bilayers of a Novel Liposomal Formulation," Int J Pharm. 299(1-2):92-9 (2005).
Peinert S, et al., "Safety and Efficacy of Weekly 5-Fluorouracil/Folinic Acid/Oxaliplatin/Irinotecan in the First-Line Treatment of Gastrointestinal Cancer," Ther Adv Med Oncol. 2(3):161-74 (2010).
Pellino A, et al., "Observational Retrospective Evaluation of Treatment With Liposomal Irinotecan Plus Fluorouracil/Leucovorin for Metastatic Pancreatic Cancer Patients: An Italian Large Real-World Analysis." Poster presented at the American Society of Clinical Oncology Gastrointestinal Cancers Symposium (ASCO GI), San Francisco, CA, Jan. 23-25, 2020, 5 pages.
Pellino A, et al., Abstract 660. "Observational Retrospective Evaluation of Treatment With Liposomal Irinotecan Plus Fluorouracil/Leucovorin for Metastatic Pancreatic Cancer Patients: An Italian Large Real-World Analysis," J Clin Oncol. 38(4_Suppl):660 DOI: 10.1200/JCO.2020.38.4_suppl.660 (2020), 2 printed pages.
Pelzer U, et al., "A Randomized Trial in Patients With Gemcitabine Refractory Pancreatic Cancer. Final Results of the CONKO 003 Study," J Clin Oncol. 2008 ASCO Annual Meeting Proceedings. 26(15S):4508 (2008), 2 printed pages.
Pelzer U, et al., "A Randomized Trial in Patients With Gemcitabine Refractory Pancreatic Cancer. Final Results of the CONKO-003 Study." Presentation presented at the American Society of Clinical Oncology (ASCO) Annual Meeting, Chicago, Illinois, May 30-Jun. 3, 2008, 18 pages.
Pelzer U, et al., "Best Supportive Care (BSC) Versus Oxaliplatin, Folinic Acid and 5-Fluorouracil (OFF) Plus BSC in Patients for Second-Line Advanced Pancreatic Cancer: A Phase III-Study from the German CONKO-Study Group," Eur J Cancer. 47(11):1676-81 (2011).
Pelzer U, et al., "Second-Line Therapy in Refractory Pancreatic Cancer. Results of a Phase II Study," Onkologie. 32(3):99-102 (2009).
Pelzer U, et al., Abstract P865. "Quality-Adjusted Time Without Symptoms or Toxicity (Q-TWiST) of Nanoliposomal Irinotecan (nal-IRI;MM-398) Plus 5-Fluorouracil and Leucovorin (5-FU/LV) vs 5-FU/LV alone in patients (pts) With Metastatic Pancreatic Adenocarcinoma (mPAC) Previously Treated With Gemcitabine-Based Therapy," Oncol Res Treat. 39(Suppl 3):260 (2016).
Petrelli F, et al., "What Else in Gemcitabine-Pretreated Advanced Pancreatic Cancer? An Update of Second Line Therapies," Rev Recent Clin Trials. 5(1):43-56 (2010).
Petrioli R, et al., "Gemcitabine, Oxaliplatin, and Capecitabine (GEMOXEL) Compared with Gemcitabine Alone in Metastatic Pancreatic Cancer: A Randomized Phase II Study," Cancer Chemother Pharmacol. 75(4):683-90 (2015).
Pfizer Background Document on the UGT1A1 Polymorphisms and Irinotecan Toxicity: ACPS Nov. 3, 2004 Advisory Committee Meeting, 19 pages.
PharmaEngine, www.pharmaengine.com/pep02.html Webpage titled "PEP02". Aug. 4, 2011, 4 printed pages.
Philip P, et al., "Consensus Report of the National Cancer Institute Clinical Trials Planning Meeting on Pancreas Cancer Treatment," J Clin Oncol. 27(33):5660-9 (2009).
Picozzi V, et al., "An Assessment of the Total Cost of Pancreatic Cancer Using Real-World Evidence." Poster presented at the American Society of Clinical Oncology Gastrointestinal Cancers Symposium (ASCO GI), San Francisco, CA, Jan. 23-25, 2020, 6 pages.
Picozzi V, et al., Abstract 773. "An Assessment of the Total Cost of Pancreatic Cancer Using Real-World Evidence," J Clin Oncol. 38(4_Suppl):773 DOI: 10.1200/JCO.2020.38.4_suppl.773 (2020), 2 printed pages.
Pillai G, "Nanomedicines for Cancer Therapy: An Update of FDA Approved and Those under Various Stages of Development," SOJ Pharm Pharm Sci. 1(2):13 (2014), 13 pages.
Pino M, et. al., "Capecitabine and Celecoxib as Second-Line Treatment of Advanced Pancreatic and Biliary Tract Cancers," Oncology. 76(4):254-61 (2009).
Pliarchopoulou K, et al., "Pancreatic Cancer: Current and Future Treatment Strategies," Cancer Treat Rev. 35(5):431-6 (2009).
Ponce S, et al., "RESILIENT Part 1: Pharmacokinetics of Second-Line (2L) Liposomal Irinotecan in Patients with Small Cell Lung Cancer (SCLC)," Poster presented at the European Society for Medical Oncology (ESMO) Virtual Congress 2020, virtual format, Sep. 19-21, 2020, 8 pages.
Ponce S, et al., Abstract 1793P. "RESILIENT Part 1: Pharmacokinetics of Second-Line (2L) Liposomal Irinotecan in Patients with Small Cell Lung Cancer (SCLC)," Ann Oncol. 31(S4):S1038-S1039 (2020).
Poplin E, et. al., "Phase III Southwest Oncology Group 9415/Intergroup 0153 Randomized Trial of Fluorouracil, Leucovorin, and Levamisole Versus Fluorouracil Continuous Infusion and Levamisole for Adjuvant Treatment of Stage III and High-Risk Stage II Colon Cancer," J Clin Oncol. 23(9):1819-25 (2005).
Qin B, et al., "In-vitro Schedule-Dependent Interaction Between Oxaliplatin and 5-Fluorouracil in Human Gastric Cancer Cell Lines," Anti-Cancer Drugs. 17(4):445-53 (2006).
Rahib L, et al., "Projecting Cancer Incidence and Deaths to 2030: The Unexpected Burden of Thyroid, Liver, and Pancreas Cancers in the United States," Cancer Res. 74(11):2913-21 (2014).
Rahib L, et. al., "Evaluation of Pancreatic Cancer Clinical Trials and Benchmarks for Clinically Meaningful Future Trials: A Systematic Review," JAMA Oncol. 2(9):1209-16 (2016).
Rahma O, et al., "Second-Line Treatment in Advanced Pancreatic Cancer: A Comprehensive Analysis of Published Clinical Trials," Ann Oncol. 24(8):1972-9 (2013), epub doi:10.1093/annonc/mdt166, May 12, 2013, pp. 1-8.
Ramanathan R, et al., "Correlation between Ferumoxytol Uptake in Tumor Lesions by MRI and Response to Nanoliposomal Irinotecan in Patients with Advanced Solid Tumors: A Pilot Study," Clin Cancer Res. 23(14):3638-48 (2017).
Ramanathan R, et al., "Lesion Characterization with Ferumoxytol MRI in Patients with Advanced Solid Tumors and Correlation with Treatment Response to MM-398, Nanoliposomal Irinotecan (nal-IRI)." Poster presented at EORTC-NCI-AACR International Conference on Molecular Targets and Cancer Therapeutics on Nov. 20, 2014, 7 pages.
Ramanathan R, et al., "Lesion Characterization with Ferumoxytol MRI in Patients with Advanced Solid Tumors and Correlation with Treatment Response to MM-398, Nanoliposomal Irinotecan (nal-IRI)," Abstract No. 261. Eur. J. Cancer, 50:87 (2014).
Ramanathan R, et al., "Pilot Study in Patients with Advanced Solid Tumors to Evaluate Feasibility of Ferumoxytol FMX) as a Tumor Imaging Agent Prior to MM-398, a Nanoliposomal Irinotecan (nal-IRI)." Poster presented at AACR Annual Meeting 2014, San Diego, CA, 9 pages.
Ramnani K, et al., Abstract CT13. "Impact of Treatment Sequence on Overall Survival in Metastatic Pancreatic Cancer Patients Treated with Liposomal Irinotecan in the Real-World Setting," Hematology Oncology Pharmacy Association (HOPA) Annual Conference, Mar. 11-14, 2020, available at eventscribe.com/2020/posters/HOPAahead/SplitViewer.asp?PID=Njg0NzMyODlyNzY, (2020), 2 pages.
Ramsay E, et. al., "Irinophore C: A Liposome Formulation of Irinotecan With Substantially Improved Therapeutic Efficacy Against a Panel of Human Xenograft Tumors," Clin Cancer Res. 14(4):1208-17 (2008).
Raymond E, et al., "Multicentre Phase II Study and Pharmacokinetic Analysis of Irinotecan in Chemotherapy-Naive Patients with Glioblastoma," Ann Oncol. 14(4):603-14 (2003).
Rea D, et al., "A Phase I/II and Pharmacokinetic Study of Irinotecan in Combination with Capecitabine as First-Line Therapy for Advanced Colorectal Cancer," Ann Oncol. 16(7):1123-32 (2005).
Reni M, et al., "Salvage Chemotherapy with Mitomycin, Docetaxel, and Irinotecan (MDI Regimen) in Metastatic Pancreatic Adenocarcinoma: A Phase I and II Trial," Cancer Invest. 22(5):688-96 (2004).
Reni M, et. al., "Raltitrexed-Eloxatin Salvage Chemotherapy in Gemcitabine-Resistant Metastatic Pancreatic Cancer," Br J Cancer. 94(6):785-91 (2006).

(56) References Cited

OTHER PUBLICATIONS

Renouf D, et. al., "A Phase II Study of Erlotinib in Gemcitabine Refractory Advanced Pancreatic Cancer," Eur J Cancer. 50(11):1909-15 (2014).
Reynolds J, et al., "HER2-Targeted Liposomal Doxorubicin Displays Enhanced Anti-Tumorigenic Effects Without Associated Cardiotoxicity," Toxicol Appl Pharmacol. 262(1):1-10 (2012).
Riviere K, et al., "Anti-Tumor Activity of Liposome Encapsulated Fluoroorotic Acid as a Single Agent and in Combination with Liposome Irinotecan," J Control Release. 153(3):288-96 (2011), Author manuscript, pp. 1-19.
Rivory L, et al., "Pharmacokinetic Interrelationships of Irinotecan (CPT-11) and Its Three Major Plasma Metabolites in Patients Enrolled in Phase I/II Trials," Clin Cancer Res. 3(8):1261-6 (1997).
Rocha Lima C, et al., "Irinotecan Plus Gemcitabine Results in No Survival Advantage Compared With Gemcitabine Monotherapy in Patients With Locally Advanced or Metastatic Pancreatic Cancer Despite Increased Tumor Response Rate," J Clin Oncol. 22(18):3776-83 (2004).
Rombouts S, et al., "FOLFIRINOX in Locally Advanced and Metastatic Pancreatic Cancer: A Single Centre Cohort Study," J Cancer. 7(13):1861-6 (2016).
Rosenecker J, et al., "Increased Liposome Extravasation in Selected Tissues: Effect of Substance P." Proc Natl Acad Sci U S A. 93(14):7236-41 (1996).
Roth A, et al., "Anti-CD166 Single Chain Antibody-Mediated Intracellular Delivery of Liposomal Drugs to Prostate Cancer Cells," Mol Cancer Ther. 6(10):2737-46 (2007).
Rothenberg M, et al., "Phase I and Pharmacokinetic Trial of Weekly CPT-11," J Clin Oncol. 11(11):2194-204 (1993).
Rothenberg M, et. al., "Allemative Dosing Schedules for Irinotecan, " Oncology. 12(8 Suppl 6):68-71 (1998). Available at cancernetwork.com/view/alternative-dosing-schedules-irinotecan, 16 printed pages.
Roy A, et al., "A Randomized Phase II Study of PEP02 (MM-398), Irinotecan or Docetaxel as a Second-Line Therapy in Patients With Locally Advanced or Metastatic Gastric or Gastro-Oesophageal Junction Adenocarcinoma," Ann Oncol. 24(6):1567-73 (2013).
Rubesova E, et al., "Gd-Labeled Liposomes for Monitoring Liposome-Encapsulated Chemotherapy: Quantification of Regional Uptake in Tumor and Effect on Drug Delivery," Acad Radiol. 9(Suppl 2):S525-7 (2002).
Sachdev J, et al., "A Phase 1 Study in Patients with Metastatic Breast Cancer to Evaluate the Feasibility of Magnetic Resonance Imaging with Ferumoxytol as a Potential Biomarker for Response to Treatment with Irinotecan Liposome Injection (nal-IRI, MM-398)." Poster presented at 38th Annual San Antonio Breast Cancer Symposium on Dec. 8, 2015, 10 pages.
Sachdev J, et al., "Characterization of Metastatic Breast Cancer Lesions with Ferumoxytol MRI and Clinical Response to MM-398, Nanoliposomal Irinotecan (nal-IRI), in 3 Subjects." Poster presented at San Antonio Breast Cancer Symposium 2014, 8 pages.
Sachdev J, et al., "Characterization of Metastatic Breast Cancer Lesions with Ferumoxytol MRI and Treatment Response to MM-398, Nanoliposomal Irinotecan (nal-IRI)," Cancer Res.75(9 Suppl): Abstract P5-01-06 (2015), 3 printed pages.
Sachdev J, et al., "Phase I Expansion Study of Irinotecan Liposome Injection (nal-IRI) in Patients with Metastatic Breast Cancer (mBC)." Poster presented at the American Association for Cancer Research Annual Meeting 2019; Mar. 29-Apr. 3, 2019; Atlanta, GA, 9 printed pages.
Sachdev J, et al., Abstract CT048. "Phase I Expansion Study of Irinotecan Liposome Injection (nal-IRI) in Patients with Metastatic Breast Cancer (mBC)," Cancer Res. In Proceedings of the American Association for Cancer Research Annual Meeting 2019; Mar. 29-Apr. 3, 2019; Atlanta, GA. Cancer Res. 2019; 79(13 Suppl):Abstract nr CT048, 4 printed pages.
Sadzuka Y, et al. "Effect of Liposomalization on the Antitumor Activity, Side-Effects and Tissue Distribution of CPT-11," Cancer Lett. 127(1-2): 99-106 (1998).
Sadzuka Y, et al., "Effective Irinotecan (CPT-11)-containing Liposomes: Intraliposomal Conversion to the Active Metabolite SN-38." Jpn J Cancer Res. 90(2):226-32 (1999).
Saif M, et. al., "Pharmacokinetically Guided Dose Adjustment of 5-Fluorouracil: A Rational Approach to Improving Therapeutic Outcomes," J Natl Cancer Inst. 101(22):1543-52 (2009).
Saito R, et al., "Distribution of Liposomes into Brain and Rat Brain Tumor Models by Convection-Enhanced Delivery Monitored with Magnetic Resonance Imaging," Cancer Res. 64(7):2572-9 (2004).
Saito R, et al., "Gadolinium-loaded Liposomes Allow for Real-Time Magnetic Resonance Imaging of Convection-Enhanced Delivery in the Primate Brain," Exp Neurol. 196(2):381-9 (2005).
Saito R, et al., "Tissue Affinity of the Infusate Affects the Distribution Volume During Convection-Enhanced Delivery Into Rodent Brains: Implications for Local Drug Delivery," J Neurosci Methods. 154(1-2):225-32 (2006).
Saltz L, "Clincial Use of Irinotecan: Current Status and Future Considerations," Oncologist. 2(6):402-9 (1997).
Saltz L, et al., "Irinotecan Plus Fluorouracil and Leucovorin for Metastatic Colorectal Cancer. Irinotecan Study Group," N Engl J Med. 343(13):905-14 (2000).
Saltz LB, et. al., "Phase I Clinical and Pharmacokinetic Study of Irinotecan, Fluorouracil, and Leucovorin in Patients With Advanced Solid Tumors," J Clin Oncol. 14(11):2959-67 (1996).
Sancho A, et. al., Abstract 15625. "Oxaliplatin and Capecitabine After Gemcitabine Failure in Patients With Advanced Pancreatic, Biliary, and Gallbladder Adenocarcinoma (APBC)," J Clin Oncol. 26(15_suppl):15625 (2008), 5 printed pages.
Satoh T, et. al., "Pharmacokinetic Assessment of Irinotecan, SN-38, and SN-38-Glucuronide: A Substudy of the FIRIS Study," Anticancer Res. 33(9):3845-53 (2013).
Scheithauer W, et. al., "Fluorouracil Plus Racemic Leucovorin Versus Fluorouracil Combined With the Pure I-Isomer of Leucovorin for the Treatment of Advanced Colorectal Cancer: A Randomized Phase III Study," J Clin Oncol. 15(3):908-14 (1997).
Schroen A, et. al., "Challenges to Accrual Predictions to Phase III Cancer Clinical Trials: A Survey of Study Chairs and Lead Statisticians of 248 NCI Sponsored Trials," Clin Trials. 8(5):591-600 (2011), author manuscript version, 14 pages.
Serwer L, et al., "Investigation of Intravenous Delivery of Nanoliposomal Topotecan for Activity Against Orthotopic Glioblastoma Xenografts," Neuro Oncol. 13(12):1288-95 (2011).
Shi S, et al., "Combinational Therapy: New Hope for Pancreatic Cancer?" Cancer Lett. 317(2):127-35 (2012). Epub 2011.
Shimada S, et al., "Irinotecan Plus Low-Dose Cisplatin for α-Fetoprotein-Producing Gastric Carcinoma with Multiple Liver Metastases: Report of Two Cases," Surg Today. 32(12):1075-80 (2002).
Sachdev J, et al., "Phase I Study of Liposomal Irinotecan in Patients With Metastatic Breast Cancer: Findings from the Expansion Phase," Breast Cancer Res Treat.. 185(3):759-71 (2021), Epub 2020 with supplementary materials pp. 1-8, retrieved from https://static-content.springer.com/esm/art%3A10.1007%2Fs10549-020-05995-7/MediaObjects/10549_2020_5995_MOESM1_ESM.docx.
Sanders C, et al., "Efficacy and Safety of Liposomal Irinotecan with Fluorouracil and Leucovorin Among Asian Patients with Metastatic Pancreatic Adenocarcinoma Previously Treated with Gemcitabine-Based Therapy: A Systematic Review and Meta-Analysis." Poster presented at Academy of Managed Care Pharmacy NEXUS 2022, National Harbor, Maryland, Oct. 11-14, 2022, 4 pages.
Savel H, et al., "On the Choice of Longitudinal Models for the Analysis of Antitumor Efficacy in Mouse Clinical Trials of Patient-derived Xenograft Models," Cancer Res Commun. 3(1):140-147 (2023).
Smith R, et al., Abstract EP14.05-012. "Comparing Costs for Medicare FFS Patients Treated with Etoposide or Irinotecan for Extensive Stage Small Cell Lung Cancer," J Thorac Oncol. 17(9S):S548 (2022).
Tomicki S, et al., "Costs by Site of Service for Commercially-Insured Patients with Metastatic Pancreatic Cancer Receiving Guideline-Recommended Chemotherapy: Comparing Community Oncology and Hospital Outpatient Settings," Clinicoecon Outcomes Res. 14:653-663 (2022).

(56) References Cited

OTHER PUBLICATIONS

Tsujimoto H, et al., "Effect of Leucovorin on the Antitumor Efficacy of the 5-FU Prodrug, Tegafur-Uracil, in Human Colorectal Cancer Xenografts with Various Expression Levels of Thymidylate Synthase," Oncol Lett. 1(6):973-980 (2010).
Van Der Wilt C, et al., "Modulation of Both Endogenous Folates and Thymidine Enhance the Therapeutic Efficacy of Thymidylate Synthase Inhibitors," Cancer Res. 61(9):3675-81 (2001).
Vogel A, et al., "Nal-IRI and 5-FU/LV Compared to 5-FU/LV in Patients with Cholangio- and Gallbladder Carcinoma Previously Treated with Gemcitabine-Based Therapies (NALIRICC e AIO-HEP-0116)." Presentation at ESMO Congress 2022, Sep. 9-13, 2022, Paris, France, 4 pages.
Vogel A, et al., Abstract 53MO. "Nal-IRI and 5-FU/LV Compared to 5-FU/LV in Patients with Cholangio- and Gallbladder Carcinoma Previously Treated with Gemcitabine-Based Therapies (NALIRICC e AIO-HEP-0116)," Annals of Oncology. 33(S7):S563-S564 (2022).
Wainberg Z, et al., "NAPOLI-3: A Randomized, Open-Label Phase 3 Study of Liposomal Irinotecan + 5-Fluorouracil/Leucovorin + Oxaliplatin (NALIRIFOX) Versus nab-Paclitaxel + Gemcitabine in Treatment-Naïve Patients with Metastatic Pancreatic Ductal Adenocarcinoma," Presentation presented at the American Society of Clinical Oncology Gastrointestinal Cancers Symposium (ASCO GI), Jan. 19-21, 2023, 8 pages.
Wainberg Z, et al., Abstract LBA661. "NAPOLI-3: A Randomized, Open-Label Phase 3 Study of Liposomal Irinotecan + 5-Fluorouracil/ Leucovorin + Oxaliplatin (NALIRIFOX) Versus nab-Paclitaxel + Gemcitabine in Treatment-Naïve Patients with Metastatic Pancreatic Ductal Adenocarcinoma (mPDAC)," J Clin Oncol. 41(4_ Suppl):LBA661 DOI: 10.1200/JCO.2023.41.4_suppl.LBA661 (2023), 5 printed pages.
Xi J, et al., Abstract SYST-13. "Phase II Study of the Combination of Liposomal Irinotecan and Pembrolizumab for Triple-Negative Breast Cancer (TNBC) with Brain Metastases (BM)," Neuro-Oncology Advances. 4(Supp_1):124 (2022).
Yoo C, et al., "Final Analysis Results From the NIFTY Trial, a Phase IIb, Randomized, Open-Label Study of Liposomal Irinotecan Plus Fluorouracil and Leucovorin in Patients With Previously Treated Metastatic Biliary Tract Cancer." Poster presented at ESMO Congress 2022, Sep. 9-13, 2022, Paris, France, 7 pages.
Yoo C, et al., Abstract 55P. "Final Results From the NIFTY Trial, a Phase IIb, Randomized, Open-Label Study of Liposomal Irinotecan (nal-IRI) Plus Fluorouracil (5-FU)/Leucovorin (LV) in Patients (pts) With Previously Treated Metastatic Biliary Tract Cancer (BTC)," Annals of Oncology. 33(S7):S565 (2022).
Yu K, et al., "Prior Irinotecan Exposure Does Not Preclude Benefit to Liposomal Irinotecan in Patients with Metastatic Pancreatic Ductal Adenocarcinoma," Cancer Med. 12(8):9496-9505 (2023).
Zhang B, et al., "The Role of FOLFIRINOX in Metastatic Pancreatic Cancer: A Meta-Analysis," World J Surg Oncol. 19(1):182, doi: 10.1186/s12957-021-02291-6, pp. 1-9 (2021).
Zhang H, "Onivyde for the Therapy of Multiple Solid Tumors," Onco Targets Ther. 9:3001-3007 (2016).
U.S. Appl. No. 15/664,930: Dec. 20, 2017 Nonfinal Office Action, 7 pages.
U.S. Appl. No. 15/664,976: Sep. 11, 2018 Nonfinal Office Action, 23 pages.
U.S. Appl. No. 15/664,976: May 21, 2019 Nonfinal Office Action, 11 pages.
U.S. Appl. No. 15/664,976: Nov. 4, 2019 Nonfinal Office Action, 9 pages.
U.S. Appl. No. 15/664,976: May 18, 2020 Final Office Action, 11 pages.
U.S. Appl. No. 15/664,976: Oct. 13, 2020 Notice of Allowance including Examiner's Reasons for Allowance, 13 pages.
U.S. Appl. No. 15/768,352: Feb. 14, 2019 Non-Final Office Action, 15 pages.
U.S. Appl. No. 15/768,352: Jun. 3, 2019 Examiner Interview Summary, 5 pages.
U.S. Appl. No. 15/768,352: Jun. 12, 2019 Notice of Allowance including Examiner's Reasons for Allowance and Examiner Interview Summary, 21 pages.
U.S. Appl. No. 15/768,352: Jul. 12, 2019 Examiner Interview Summary, 4 pages.
U.S. Appl. No. 15/768,352: Aug. 28, 2019 Notice of Allowance including Examiner's Reasons for Allowance and Examiner Interview Summary, 16 pages.
U.S. Appl. No. 15/809,815: Mar. 6, 2018 Nonfinal Office Action, 12 pages.
U.S. Appl. No. 15/809,815: Sep. 11, 2018 Final Office Action, 14 pages.
U.S. Appl. No. 15/809,815: Jul. 8, 2019 Non-Final Office Action, 13 pages.
U.S. Appl. No. 15/809,815: Feb. 27, 2020 Final Office Action, 16 pages.
U.S. Appl. No. 15/852,551: Jan. 11, 2019 Nonfinal Office Action, 5 pages.
U.S. Appl. No. 15/896,389: Jul. 18, 2019 Nonfinal Office Action, 24 pages.
U.S. Appl. No. 15/896,389: Jan. 31, 2020 Final Office Action, 28 pages.
U.S. Appl. No. 15/896,389: Mar. 26, 2020 Examiner Interview Summary and Applicant slides, 22 pages.
U.S. Appl. No. 15/896,389: Apr. 9, 2020 Advisory Action, 3 pages.
U.S. Appl. No. 15/896,389: Jun. 5, 2020 Notice of Allowance including Examiner's Reasons for Allowance and Examiner Interview Summary, 13 pages.
U.S. Appl. No. 15/896,436: Jul. 5, 2019 Nonfinal Office Action, 18 pages.
U.S. Appl. No. 15/967,638: Jan. 14, 2019 Nonfinal Office Action, 14 pages.
U.S. Appl. No. 16/012,351: Mar. 8, 2019 Non-Final Office Action, 13 pages.
U.S. Appl. No. 16/012,351: Jan. 7, 2020 Final Office Action, 9 pages.
U.S. Appl. No. 16/012,372: Mar. 8, 2019 Non-Final Office Action, 8 pages.
U.S. Appl. No. 16/012,372: Jan. 7, 2020 Final Office Action, 9 pages.
U.S. Appl. No. 16/012,372: Jul. 27, 2020 Non-Final Office Action, 8 pages.
U.S. Appl. No. 16/036,885: Sep. 3, 2019 Non-Final Office Action, 15 pages.
U.S. Appl. No. 16/302,050: Jan. 17, 2020 Non-Final Office Action, 17 pages.
U.S. Appl. No. 16/510,394: Mar. 6, 2020 Non-Final Office Action, 15 pages.
U.S. Appl. No. 16/567,902: Apr. 27, 2020 Non-Final Office Action, 20 pages.
U.S. Appl. No. 16/567,902: Aug. 10, 2020 Final Office Action, 21 pages.
U.S. Appl. No. 16/586,609: Oct. 5, 2020 Non-Final Office Action, 5 pages.
Ramirez R, et al., Abstract e20614. "Patient Characteristics and Outcomes Associated with Small Cell Lung Cancer by Treatment Status in a U.S. Medicare Population," J Clin Oncol. 40(16_ suppl):e20614 (2022), 4 printed pages.
Ramnaraign B, et al., "A Phase II, Open-Label Pilot Study Evaluating the Safety and Activity of Liposomal Irinotecan (Nal-IRI) in Combination With 5-FU and Oxaliplatin (NALIRIFOX) in Preoperative Treatment of Pancreatic Adenocarcinoma (NEO-Nal-IRI study)," J Clin Oncol. 39(3_suppl):TPS446, (2021), 4 printed pages.
Ramnaraign B, et al., "A Phase II, Open-Label Pilot Study Evaluating the Safety and Activity of Nal-IRI in Combination With 5-FU and Oxaliplatin (NALIRIFOX) in Preoperative Treatment of Pancreatic Adenocarcinoma (NEO-Nal-IRI study)," Poster presented at the American Society of Clinical Oncology Gastrointestinal Cancer Symposium (Asco Gi) 2021, Jan. 15-17, 2021, Virtual Congress, 4 pages.
Ravi H, et al., "Pre-Therapy Ferumoxytol-Enhanced Magnetic Resonance Imaging (MRI) Predicts Response of Metastatic Breast

(56) References Cited

OTHER PUBLICATIONS

Cancer to Liposomal Irinotecan," Presentation presented at the International Society for Magnetic Resonance in Medicine Meeting, May 7-12, 2022, 7 pages.
Ravi H, et al., "R1 and R2 Mismatch on Ferumoxytol-Enhanced MRI Predicts Response of Breast Cancer Brain Metastases to Liposomal Irinotecan," Presentation presented at the International Society for Magnetic Resonance in Medicine Meeting, May 7-12, 2022, 6 pages.
Ravi H, et al., Abstract 3418. "Pre-Therapy Ferumoxytol-Enhanced Magnetic Resonance Imaging (MRI) Predicts Response of Metastatic Breast Cancer to Liposomal Irinotecan." International Society for Magnetic Resonance in Medicine Meeting, May 7-12, 2022, 6 printed pages.
Ravi H, et al., Abstract 3419. "R1 and R2 Mismatch on Ferumoxytol-Enhanced MRI Predicts Response of Breast Cancer Brain Metastases to Liposomal Irinotecan." International Society for Magnetic Resonance in Medicine Meeting, May 7-12, 2022, 6 printed pages.
Rogers S, et al., "A Phase II, Open-Label Pilot Study Evaluating the Safety and Activity of Liposomal Irinotecan (Nal-IRI) in Combination With 5-FU and Oxaliplatin (NALIRIFOX) in Preoperative Treatment of Pancreatic Adenocarcinoma (NEO-Nal-IRI study) (NCT03483038)," J Clin Oncol. 39(15_suppl):TPS4170, (2021), 4 printed pages.
Rogers S, et al., "A Phase II, Open-label Pilot Study Evaluating the Safety and Activity of Nal-IRI in Combination with 5-FU and Oxaliplatin in Preoperative Treatment of Pancreatic Adenocarcinoma (NEO-Nal-IRI Study)," Poster presented at the American Society of Clinical Oncology Gastrointestinal Cancer Symposium (ASCO GI), Jan. 20-22, 2022, San Francisco, 3 pages.
Rogers S, et al., Abstract TPS4196. "A Phase II, Open-Label, Pilot Study Evaluating the Safety and Activity of Liposomal Irinotecan (Nal-IRI) in Combination with 5-FU and Oxaliplatin (NALIRIFOX) in Preoperative Treatment of Pancreatic Adenocarcinoma: NEO-Nal-IRI Study," J Clin Oncol. 40(16_suppl):TPS4196 (2022), 4 printed pages.
Rogers S, et al., Abstract TPS619. "A Phase II, Open-Label Pilot Study Evaluating the Safety and Activity of Liposomal Irinotecan (Nal-IRI) in Combination with 5-FU and Oxaliplatin (NALIRIFOX) in Preoperative Treatment of Pancreatic Adenocarcinoma: NEO-Nal-IRI study," J Clin Oncol. 40(4_suppl):TPS619 (2022), 4 printed pages.
Sachdev J, et al., "Phase I Study of Liposomal Irinotecan in Patients With Metastatic Breast Cancer: Findings from the Expansion Phase," Breast Cancer Res Treat. 185(3):759-71 (2021), Epub 2020.
Sahai V, et al., "A Single Arm, Multicenter Phase Ib/II Study of Nivolumab in Combination with Liposomal Irinotecan, 5-Fluorouracil and Leucovorin as Second-Line Therapy for Patients with Advanced Biliary Tract Cancer: BilT-03," Poster presented at the American Society of Clinical Oncology Gastrointestinal Cancer Symposium (ASCO GI), Jan. 20-22, 2022, San Francisco, 6 pages.
Sahai V, et al., Abstract 438. "A Multicenter Phase Ib/II Study of Liposomal-Irinotecan, 5-Fluorouracil (5-FU), and Leucovorin (LV) with Nivolumab as Second-Line Therapy for Patients with Advanced Biliary Tract Cancer (BilT-03)," J Clin Oncol. 40(4_suppl):438 (2022), 4 printed pages.
Savel H., et al., Abstract P9. "Longitudinal Modeling of Treatment Response in Patient-Derived Mouse Models (PDX) for Translational Oncology Research," Journal of Epidemiology and Public Health. 70(Suppl 2):S91 (2022); 4 total pages (Abstract in French (pp. 1-2) and English (pp. 3-4).
Taieb J, et al., "Real-World Study of Treatment Patterns and Outcomes Among Patients With Metastatic Pancreatic Ductal Adenocarcinoma (PDAC) in Europe," Poster presented at the American Society of Clinical Oncology Gastrointestinal Cancer Symposium (ASCO GI) 2021, Jan. 15-17, 2021, Virtual Congress, 6 pages.
Taieb J, et al., "Real-World Study of Treatment Patterns and Outcomes Among Patients With Metastatic Pancreatic Ductal Adenocarcinoma (PDAC) in Europe," J Clin Oncol. 39(3_suppl):391-391, DOI: 10.1200/JCO.2021.39.3_suppl.391 (2021), 4 printed pages.
Taieb J, et al., "Treatment Sequences and Prognostic Factors in Metastatic Pancreatic Ductal Adenocarcinoma: Univariate and Multivariate Analyses of a Real-World Study in Europe," Abstract SO-3, doi.org/10.1016/j.annonc.2021.05.027, Annals Oncol. 32(S3):S203 (2021).
Tomicki S, et al., "Real-World Cost of Care for Commercially Insured Versus Medicare Patients With Metastatic Pancreatic Cancer Who Received Guideline-Recommended Therapies," Am Health Drug Benefits. 14(2):70-78 (2021).
Tomicki S, et al., "Total Cost of Care and Utilization Among Medicare Fee-For-Service (FFS) Patients With Metastatic Pancreatic Cancer Treated With FDA-Approved/NCCN® Category 1 Regimens at 340B vs. Non-340B Hospitals," Abstract PDB17, Value in Health. 24(Suppl 1):S80-S81 (2021).
Tomicki S, et al., "Total Cost of Care and Utilization Among Medicare Fee-For-Service (FFS) Patients With Metastatic Pancreatic Cancer Treated With FDA-Approved/NCCN® Category 1 Regimens at 340B vs. Non-340B Hospitals," Presented at International Society for Pharmacoeconomics and Outcomes, May 17-19, 2021, Virtual poster, 11 pages.
Wang-Gillam A, et al., "Nanoliposomal Irinotecan with Flourouracil and Folinic Acid in Metastatic Pancreatic Cancer After Previous Gemcitabine-Based Therapy (NAPOLI-1): A Global, Randomised, Open-Label, Phase 3 Trial," Lancet, 387(10018):545-57 (2016).
Yoo C, et al., "Liposomal Irinotecan (nal-IRI) in Combination With Fluorouracil (5-FU) and Leucovorin (LV) for Patients (pts) With Metastatic Biliary Tract Cancer (BTC) After Progression on Gemcitabine Plus Cisplatin (GemCis): Multicenter Comparative Randomized Phase 2B Study (NIFTY)," Presented at the American Society of Clinical Oncology 2021 Meeting, Jun. 4-8, 2021, 18 pages.
Yoo C, et al., "Liposomal Irinotecan (nal-IRI) in Combination With Fluorouracil (5-FU) and Leucovorin (LV) for Patients With Metastatic Biliary Tract Cancer (BTC) After Progression on Gemcitabine Plus Cisplatin (GemCis): Multicenter Comparative Randomized Phase 2b Study (NIFTY)," J Clin Oncol. 39(15_suppl):4006-4006, DOI: 10.1200/JCO.2021.39.15_suppl.4006 (2021), 4 printed pages.
Yoo C, et al., "Liposomal Irinotecan Plus Fluorouracil and Leucovorin Versus Fluorouracil and Leucovorin for Metastatic Biliary Tract Cancer After Progression on Gemcitabine Plus Cisplatin (NIFTY): A Multicentre, Open-Label, Randomized, Phase 2b Study," Lancet Oncol. 22(11):1560-1572, doi: 10.1016/S1470-2045(21)00486-1, pp. 1-13 (2021).
Yu H, et al., "Real-World Clinical Outcomes of Patients With Metastatic Pancreatic Ductal Adenocarcinoma (mPDAC) Treated With Liposomal Irinotecan-Based Regimens: Impact of Prior Irinotecan (IRI) Exposure," Poster presented at the American Society of Clinical Oncology Gastrointestinal Cancer Symposium (ASCO GI), virtual format, Jan. 20-22, 2022, San Francisco, 6 pages.
Yu K, et al., "Clinical Outcomes Among Patients With Metastatic Pancreatic Ductal Adenocarcinoma Treated With Liposomal Irinotecan," Front Oncol. 11:678070. doi: 10.3389/fonc.2021.678070, pp. 1-9 (2021).
Yu K, et al., "Population-Based, Real-World Prognostic Factors Related to Survival Among Patients With Metastatic Pancreatic Ductal Adenocarcinoma (mPDAC)," J Clin Oncol. 39(3_suppl):389-389, DOI: 10.1200/JCO.2021.39.3_suppl.389, (2021), 4 printed pages.
Yu K, et al., "Population-Based, Real-World Prognostic Factors Related to Survival Among Patients With Metastatic Pancreatic Ductal Adenocarcinoma (mPDAC)," Poster presented at the American Society of Clinical Oncology Gastrointestinal Cancer Symposium (ASCO GI) 2021, Jan. 15-17, 2021, Virtual Congress, 7 pages.
Yu K, et al., "Real-World Prognostic Factors for Survival Among Treated Patients With Metastatic Pancreatic Ductal Adenocarcinoma," Cancer Med. 10(24):8934-43 (2021).
Yu K, et al., Abstract 580. "Real-World Clinical Outcomes of Patients with Metastatic Pancreatic Ductal Adenocarcinoma (mPDAC) Treated with Liposomal Irinotecan-Based Regimens: Impact of Prior Irinotecan (IRI) Exposure," J Clin Oncol. 40(4_suppl):580 (2022), 4 printed pages.

(56) References Cited

OTHER PUBLICATIONS

Zhu Z, et al., "Assessing Real-World Survival Outcomes of Patients (pts) With Metastatic Pancreatic Ductal Adenocarcinoma (mPDAC) Treated With First-Line FOLFIRINOX Compared to Patients From a Phase 1/2 Trial Treated With NALIRIFOX," J Clin Oncol. 39(15_suppl):e16252, DOI: 10.1200/JCO.2021.39.15_suppl.e16252 (2021), 4 printed pages.
U.S. Appl. No. 15/664,976: Apr. 21, 2021 Notice of Allowance including Examiner's Reasons for Allowance, 14 pages.
U.S. Appl. No. 15/809,815: Aug. 26, 2021 Non-Final Office Action, 14 pages.
U.S. Appl. No. 15/852,551: Jun. 28, 2019 Notice of Allowance including Examiner's Reasons for Allowance, 8 pages.
U.S. Appl. No. 16/012,351: Mar. 8, 2021 Notice of Allowance including Examiner's Reasons for Allowance, 9 pages.
U.S. Appl. No. 16/012,372: Feb. 11, 2021 Notice of Allowance including Examiner's Reasons for Allowance, 9 pages.
U.S. Appl. No. 16/302,050: Aug. 11, 2021 Non-Final Office Action, 17 pages.
U.S. Appl. No. 16/302,050: Mar. 8, 2022 Notice of Allowance including Examiner's Reasons for Allowance, 7 pages.
U.S. Appl. No. 16/346,436: Jun. 24, 2020 Notice of Allowance including Examiner's Reasons for Allowance, 8 pages.
U.S. Appl. No. 16/567,902: Mar. 8, 2021 Notice of Allowance including Examiner's Reasons for Allowance and Examiner Interview Summary, 22 pages.
U.S. Appl. No. 16/586,609: Apr. 15, 2021 Notice of Allowance including Examiner's Reasons for Allowance, 7 pages.
U.S. Appl. No. 16/711,072: Dec. 10, 2021 Non-Final Office Action, 19 pages.
U.S. Appl. No. 16/711,072: Oct. 3, 2022 Final Office Action, 19 pages.
U.S. Appl. No. 16/906,601: Jan. 7, 2022 Non-Final Office Action, 21 pages.
U.S. Appl. No. 16/906,601: Jun. 17, 2022 Final Office Action, 17 pages.
U.S. Appl. No. 17/011,617: Mar. 10, 2022 Non-Final Office Action, 16 pages.
EP3337467: Sandoz written submission in preparation for oral proceedings, dated Mar. 9, 2023, 11 pages.
EP3337467: Sandoz written submission in preparation for oral proceedings, dated Mar. 9, 2023, D21 (Irimie A, et al., "Multiple Primary Malignancies—Epidemiological Analysis at a Single Tertiary Institution," J Gastrointestin Liver Dis. 19(1):69-73 (2010)).
EP3337467: Sandoz written submission in preparation for oral proceedings, dated Mar. 9, 2023, D22 (Li F, et al., "Multiple Primary Malignancies Involving Lung Cancer," BMC Cancer. 15:696; doi: 10.1186/s12885-015-1733-8 (2015), 8 pages).
EP3337467: Proprietor written submission in preparation for oral proceedings, dated Mar. 9, 2023, 9 pages.
EP3337467: Sandoz 2nd written submission in preparation for oral proceedings, dated Apr. 6, 2023, 5 pages.
EP3337467: Sandoz 2nd written submission in preparation for oral proceedings, dated Apr. 6, 2023, D11a Koshkaryev A, et al., "Differential Tissue Clearance Results in Improved Therapeutic Index for Nanoliposomal Irinotecan (nal-IRI; Onivyde) when Combined with the PARP Inhibitor Veliparib." Poster presented at AACR Meeting on Apr. 16-20, 2016, 5 pages); D11b (Corresponding poster session details, 3 pages); D11c (Corresponding abstract 2075, 1 page).
EP3337467: Proprietor's withdrawal of approval of the granted text, dated Apr. 24, 2023, 1 page.
EP3337467: Decision revoking patent, dated Apr. 24, 2023, 2 pages.
EP3266456: Summons to attend oral proceedings including preliminary opinion of the Opposition Division dated Feb. 28, 2023, 19 pages.
EP3337478: Opposition Division's decision to maintain patent as amended with minutes of the oral proceedings before the Opposition Division, dated Mar. 9, 2023, 103 pages.
EP3337478: Generics [UK] Limited statement of grounds of appeal to opposition decision, dated May 16, 2023, 14 pages.
EP3337478: Proprietor request for correction of minutes of oral proceeding, dated May 11, 2023, 2 pages.
EP3337478: Opposition Division's corrected minutes of the oral proceedings, dated Jun. 6, 2023, 21 pages.
EP3337478: Sandoz statement of grounds of appeal to opposition decision, dated Jul. 11, 2023, 39 pages.
EP3337478: Sandoz statement of grounds of appeal to opposition decision, dated Jul. 11, 2023, D35 (Dean A, et al., "A Randomized, Open-label, Phase 2 Study of Nanoliposomal Irinotecan (nal-IRI)-containing Regimens versus nab-Paclitaxel Plus Gemcitabine in Patients with Previously Untreated, Metastatic Pancreatic Adenocarcinoma (mPAC)." Poster presented at the Gastrointestinal Cancers Symposium ASCO 2016, 11 pages).
U.S. Appl. No. 16/711,072: Jul. 12, 2023 Non-Final Office Action, 26 pages.
U.S. Appl. No. 17/208,042: Jan. 13, 2023 Non-Final Office Action, 17 pages.
U.S. Appl. No. 17/208,042: Mar. 7, 2023 Examiner Interview Summary, 4 pages.
U.S. Appl. No. 17/208,042: May 24, 2023 Examiner Interview Summary, 4 pages.
U.S. Appl. No. 17/703,312: Jan. 19, 2023 Non-Final Office Action, 5 pages.
Alese O, et al., "A Phase I Trial of Trifluridine/Tipiracil in Combination With Nanoliposomal Irinotecan in Advanced GI Cancers," Abstract PD-4, doi.org/10.1016/j.annonc.2021.05.022, Annals Oncol. 32(S3):S200 (2021).
Awasthi N, et al., "Augmenting Experimental Gastric Cancer Activity of Irinotecan through Liposomal Formulation and Antiangiogenic Combination Therapy," Mol Cancer Ther. 21(7):1149-1159 (2022).
Bai L, et al., "A Phase 2 Study of Liposomal Irinotecan With 5-Fluorouracil and Leucovorin in Squamous Cell Carcinoma of Head and Neck or Esophagus After Prior Platinum-Based Chemotherapy or Chemoradiotherapy," J Clin Oncol. 39(15_suppl):6025-6025, DOI: 10.1200/JCO.2021.39.15_suppl.6025 (2021), 4 printed pages.
Bai L, et al., "A Phase 2 Study of Liposomal Irinotecan With 5-Fluorouracil and Leucovorin in Squamous Cell Carcinoma of Head and Neck or Esophagus After Prior Platinum-Based Chemotherapy or Chemoradiotherapy," Poster presented at American Society of Clinical Oncology 2021 Meeting, Jun. 4-8, 2021, 6 pages.
Bai L, et al., "Phase 1 Study of Nanoliposomal Irinotecan in Combination with Trifluridine / Tipiracil in Refractory Solid Tumors—Data from Dose-Finding Portion," Poster presented at the American Society of Clinical Oncology Gastrointestinal Cancer Symposium (ASCO GI), Jan. 20-22, 2022, San Francisco, 6 pages.
Bai L, et al., Abstract 660. "Phase 1 Study of Nanoliposomal Irinotecan in Combination with Trifluridine/Tipiracil in Refractory Solid Tumors," J Clin Oncol. 40(4_suppl):660 (2022), 4 printed pages.
Brendel K, et al., "Population Pharmacokinetics of Liposomal Irinotecan in Patients With Cancer and Exposure—Safety Analyses in Patients With Metastatic Pancreatic Cancer," CPT Pharmacometrics Syst Pharmacol. 10(12):1550-63, doi: 10.1002/psp4.12725 (2021).
Bulusu K, et al., "Modelling of Compound Combination Effects and Applications to Efficacy and Toxicity: State-of-the-Art, Challenges and Perspectives," Drug Discov Today. 21(2):225-38 (2016), Epub 2015.
Butowski N, et al., Abstract F-2722. "A Phase I Study of Convection-Enhanced Delivery (CED) of Liposomal-Irinotecan Using Real-Time Imaging with Gadolinium in Patients with Recurrent High Grade Glioma," Brain Tumor Res Treat. 10:S326 (2022).
Chang E, et al. "The Role of Tumor Size in the Radiosurgical Management of Patients with Ambiguous Brain Metastases," Neurosurgery. 53(2):272-280; discussion at 280-281 (2003).
Choi G, et al., "Safety and Effectiveness of Prospective Observational Postmarketing Surveillance Study for Pancreatic Adenocarcinoma Treated by Liposomal Irinotecan Plus 5-Flurouracil/Leucovorin in Korea," Abstract P196, 2nd American Association for Cancer Research—Korean Cancer Association Joint Conference on Precision Medicine In Solid Tumors, Nov. 10-11, 2021 (EST), 1 page.

(56) References Cited

OTHER PUBLICATIONS

Chotzagiannoglou V, et al., Abstract PCN154. "Budget Impact Analysis of Liposomal Irinotecan for Treatment of Metastatic Adenocarcinoma of Pancreas Following Progression on Gemcitabine-Based Therapies from Greek Payer's Perspective," Value in Health. 23(S2):S450 (2020).
Cockrum P, et al., "Treatment Patterns and Costs Associated with Small Cell Lung Cancer in a U.S. Medicare Population," Poster presented at International Society for Pharmacoeconomics and Outcomes Research 2022, National Harbor, MD, May 15-18, 2022, 5 pages.
Cockrum P, et al., Abstract CO87. "Treatment Patterns and Costs Associated with Small Cell Lung Cancer in a U.S. Medicare Population," Value in Health. 25(7 Supp):S320 (2022).
Cockrum P, et al., Abstract e20601. "Characterizing Platinum Sensitivity Among Medicare FFS Patients with Limited Versus Extensive-Stage Small Cell Lung Cancer Receiving NCCN Category 1 Preferred Regimens," J Clin Oncol. 40(16_suppl):e20601 (2022), 4 printed pages.
Cockrum P, et al., Abstract e20617. "Treatment Patterns and Outcomes Associated with Small Cell Lung Cancer by Platinum Sensitivity Status in a U.S. Medicare Population," J Clin Oncol. 40(16_suppl):e20617 (2022), 4 printed pages.
De Forni M, et al., "Phase I and Pharmacokinetic Study of the Camptothecin Derivative Irinotecan, Administered on a Weekly Schedule in Cancer Patients," Cancer Res. 54(16):4347-4354 (1994).
Dieguez G et al., "Risk Adjustment and Total Cost of Care Per Month of Overall Survival Among Medicare Fee-for-Service (FFS) Patients Receiving NCCN Category-1 Treatments for Metastatic Pancreatic Cancer," Abstract, doi.org/10.1093/ajhp/zxab362, Found at American Journal of Health-System Pharmacy, 78(20):1831-1918 (2021), 2 printed pages.
Dieguez G et al., "Risk Adjustment and Total Cost of Care per Month of Overall Survival Among Medicare Fee-for-Service (FFS) Beneficiaries Receiving Treatment for Metastatic Pancreatic Cancer," Poster presented at American Society of Health-System Pharmacists (ASHP) Midyear Clinical Meeting & Exhibition, Dec. 6-7, 2021, 6 pages.
Dieguez G, et al., "Resource Utilization and Total Cost of Care Among Medicare Advantage Patients With Metastatic Pancreatic Cancer Receiving NCCN® Category 1 Preferred Regimens," Poster presented at the American Society of Clinical Oncology Gastrointestinal Cancer Symposium (ASCO GI), virtual format, Jan. 20-22, 2022, San Francisco, 6 pages.
Dieguez G, et al., "Total Cost of Care Among Commercially Insured Patients With Metastatic Pancreatic Cancer Receiving NCCN® Category 1 Preferred Regimens in Hospital Outpatient vs Community Oncology Settings," Poster presented at the Academy of Managed Care Pharmacy (AMCP), Chicago, Illinois, Mar. 31, 2022, 5 pages.
Dieguez G, et al., "Trends in Treatment Patterns Among Medicare Fee-For-Service (FFS) Patients Receiving Treatment for Metastatic Pancreatic Cancer," Poster presented at European Society for Medical Oncology (ESMO) Congress 2021, Sep. 16-21, 2021, 5 pages.
Dieguez G, et al., "Trends in Treatment Patterns Among Medicare Fee-For-Service (FFS) Patients Receiving Treatment for Metastatic Pancreatic Cancer," Abstract 1478P, doi.org/10.1016/j.annonc.2021.08.805, Annals Oncol. 32(S5):S1091-S1092 (2021).
Dieguez G, et al., "Trends in Use of One, Two, and Three-Line NCCN Category 1 Regimens Among Medicare Fee-For-Service (FFS) Patients Receiving Treatment for Metastatic Pancreatic Cancer," J Clin Oncol. 39(28_suppl):297-297, DOI:10.1200/JCO.2020.39.28_suppl.297 (2021), 4 printed pages.
Dieguez G, et al., "Trends in Use of One, Two, and Three-Line NCCN Category 1 Regimens Among Medicare Fee-For-Service (FFS) Patients Receiving Treatment for Metastatic Pancreatic Cancer," Poster presented at ASCO Quality Care Symposium 2021, Sep. 24-25, 2021, 5 pages.
Dieguez G, et al., Abstract 531. "Resource Utilization and Total Cost of Care Among Medicare Advantage Patients with Metastatic Pancreatic Cancer Receiving NCCN Category 1 Preferred Regimens," J Clin Oncol. 40(4_suppl):531 (2022), 4 printed pages.
Dieguez G, et al., Abstract C2. "Total Cost of Care Among Commercially Insured Patients with Metastatic Pancreatic Cancer Receiving National Comprehensive Cancer Network Category 1 Preferred Regimens in Hospital Outpatient vs Community Oncology Settings," J Manag Care Spec Pharm. 28(3-a Suppl):S13 (2022).
Dotan E, et al., "A Randomized Phase II Study of Gemcitabine and Nab-Paclitaxel Compared with 5-Fluorouracil, Leucovorin, and Liposomal Irinotecan in Older Patients with Treatment Naïve Metastatic Pancreatic Cancer (GIANT): ECOG-ACRIN EA2186. Trial in Progress," Poster presented at 2022 American Society for Clinical Oncology (ASCO) Annual Meeting, Chicago, IL, Jun. 3-7, 2022, 1 page.
Dotan E, et al., Abstract TPS4185. "A Randomized Phase II Study of Gemcitabine and Nab-Paclitaxel Compared with 5-Fluorouracil, Leucovorin, and Liposomal Irinotecan in Older Patients with Treatment-Naïve Metastatic Pancreatic Cancer (GIANT): ECOG-ACRIN EA2186—Trials in Progress," J Clin Oncol. 40(16_suppl):TPS4185 (2022), 4 printed pages.
Elias R, et al., "Comparison of First-Line (1L) Treatment (Tx) Patterns and Overall Survival by Age at Diagnosis Among Patients With Metastatic Pancreatic Ductal Adenocarcinoma (mPDAC)," Poster Presented at the American Society of Clinical Oncology Gastrointestinal Cancer Symposium (ASCO GI) 2021, Jan. 15-17, 2021, Virtual Congress, 6 pages.
Elias R, et al., "Comparison of First-Line (1L) Treatment (Tx) Patterns and Overall Survival by Age at Diagnosis Among Patients With Metastatic Pancreatic Ductal Adenocarcinoma (mPDAC)," J Clin Oncol. 39(3_suppl):388-388, DOI: 10.1200/JCO.2021.39.3_suppl.388, (2021), 5 printed pages.
Elias R, et al., "Real-World Impact of Age at Diagnosis on Treatment Patterns and Survival Outcomes of Patients with Metastatic Pancreatic Ductal Adenocarcinoma," Oncologist. 27(6):469-475 (2022).
Gebauer F, et al., "Study Protocol of an Open-Label, Single Arm Phase II Trial Investigating the Efficacy, Safety and Quality of Life of Neoadjuvant Chemotherapy With Liposomal Irinotecan Combined With Oxaliplatin and 5-Fluorouracil/ Folinic Acid Followed by Curative Surgical Resection in Patients With Hepatic Oligometastatic Adenocarcinoma of the Pancreas (HOLIPANC)," BMC Cancer. 21(1):1239, doi: 10.1186/s12885-021-08966-3, pp. 1-11 (2021).
George B, et al., "Real-World Impact of Prior Surgery on Outcomes of Patients With Metastatic Ductal Adenocarcinoma (mPDAC) Treated With Liposomal Irinotecan-Based Regimens," Abstract PCN17, Value in Health. 24(Suppl 1):S21 (2021).
George B, et al., "Real-World Impact of Prior Surgery on Outcomes of Patients With Metastatic Ductal Adenocarcinoma (mPDAC) Treated With Liposomal Irinotecan-Based Regimens," Presented at International Society for Pharmacoeconomics and Outcomes, May 17-19, 2021, Virtual poster, 10 pages.
George B, et al., "Real-World Serum CA19-9 Level Monitoring Patterns and Its Association With Clinical Outcomes Among Patients With Metastatic Pancreatic Ductal Adenocarcinoma (mPDAC)," Poster presented at the American Association for Cancer Research (AACR) 2021 Virtual Congress, Apr. 10-15, 2021, 8 pages.
George B, et al., "Real-World Serum CA19-9 Level Monitoring Patterns and Its Association With Clinical Outcomes Among Patients With Metastatic Pancreatic Ductal Adenocarcinoma (mPDAC)," https://doi.org/10.1158/1538-7445.AM2021-765, Cancer Res. 81(13_Suppl):765 (2021), 4 printed pages.
George B, et al., "The Association Between Real-World CA19-9 Level Monitoring Pattems and With Clinical Outcomes Among Patients With Metastatic Pancreatic Ductal Adenocarcinoma (mPDAC) in the Second- and Third-Line of Therapy," J Clin Oncol. 39(15_suppl):e16251, DOI: 10.1200/JCO.2021.39.15_suppl.e16251 (2021), 4 printed pages.
George B, et al., "The Association of Real-World CA 19-9 Level Monitoring Patterns and Clinical Outcomes Among Patients With Metastatic Pancreatic Ductal Adenocarcinoma," Front Oncol. 11:754687, doi: 10.3389/fonc.2021.754687, pp. 1-8 (2021).
Gourzoulidis G, et al., Abstract PCN108. "The Cost-Effectiveness of Liposomal Irinotecan and 5-Fluorouracil (5-FU)/ Leucovorin

(56) References Cited

OTHER PUBLICATIONS (LV) for the Treatment of Patients With Metastatic Adenocarcinoma of Pancreas Who Have Progressed Following the Use of Gemcitabine-Related Therapies in Greece," Value in Health. 23(S2):S442 (2020).
Grierson P, et al., "Liposomal irinotecan plus 5-FU/LV combined with paricalcitol in patients with advanced pancreatic cancer progressed on gemcitabine-based therapy," Poster presented at the American Society of Clinical Oncology Gastrointestinal Cancer Symposium (ASCO GI), Jan. 20-22, 2022, San Francisco, 5 pages.
Grierson P, et al., Abstract 566. "A Pilot Study of Liposomal Irinotecan Plus 5-FU/LV Combined with Paricalcitol in Patients with Advanced Pancreatic Cancer Which Progressed on Gemcitabine-Based Therapy," J Clin Oncol. 40(4_suppl):566 (2022), 4 printed pages.
UPAC. Compendium of Chemical Terminology, 2nd ed. (the "Gold Book"). Compiled by A. D. McNaught and A. Wilkinson. Blackwell Scientific Publications, Oxford (1997). Online version 2014. Created by S. J. Chalk. ISBN 0-9678550-9-8. DOI: 10.1351/goldbook.D01513, 1 page.
Kim G, et al, "Real-World Characteristics and Outcomes of Patients With Metastatic Ductal Adenocarcinoma (mPDAC) Treated With Liposomal Irinotecan-Based Regimens by Race," Abstract PCN27, Value in Health. 24(Suppl 1):S23 (2021).
Kim G, et al, "Real-World Characteristics and Outcomes of Patients With Metastatic Ductal Adenocarcinoma (mPDAC) Treated With Liposomal Irinotecan-Based Regimens by Race," Presented at International Society for Pharmacoeconomics and Outcomes, May 17-19, 2021, Virtual poster, 9 pages.
Kim G, et al., Real-World 30-day Readmission Patterns Among Commercially Insured Patients with Metastatic Pancreatic Ductal Adenocarcinoma (mPDAC), Poster presented at the International Society for Pharmacoeconomics and Outcomes Research (ISPOR) 2022, Washington, DC, Virtual Congress, May 15-18, 2022, 5 pages.
Kim G, et al., "Real-World One-Year Overall Survival Among Patients With Metastatic Pancreatic Ductal Adenocarcinoma (mPDAC) Treated With Liposomal Irinotecan in the NAPOLI-1 Based Regimen," Poster presented at the American Society of Clinical Oncology Gastrointestinal Cancer Symposium (ASCO GI) 2021, Jan. 15-17, 2021, Virtual Congress, 6 printed pages.
Kim G, et al., "Real-World One-Year Overall Survival Among Patients With Metastatic Pancreatic Ductal Adenocarcinoma (mPDAC) Treated With Liposomal Irinotecan in the NAPOLI-1 Based Regimen," J Clin Oncol. 39(3_suppl):392-392, DOI: 10.1200/JCO.2021.39.3_suppl.392, (2021), 4 printed pages.
Kim G, et al., "Real-World Progression Outcomes Among Patients (pts) With Metastatic Pancreatic Ductal Adenocarcinoma (mPDAC) Treated With Liposomal Irinotecan-Based Regimens in the United States," Abstract 1480P, doi.org/10.1016/j.annonc.2021.08.807, Annals Oncol. 32(S5):S1092-S1093 (2021).
Kim G, et al., "Real-World Progression Outcomes Among Patients (pts) With Metastatic Pancreatic Ductal Adenocarcinoma (mPDAC) Treated With Liposomal Irinotecan-Based Regimens in the United States," Poster presented at European Society for Medical Oncology (ESMO) Congress, Virtual Congress, Sep. 16-21, 2021, 5 pages.
Kim G, et al., "Real-World Safety and Medication Use of Second-Line (2L) 5-Fluorouracil (5-FU)-Based Regimens Among Patients (pts) With Metastatic Pancreatic Ductal Adenocarcinoma (mPDAC)," J Clin Oncol. 39(15_suppl):e16248, DOI: 10.1200/JCO.2021.39.15_suppl.e16248 (2021), 5 printed pages.
Kim G, et al., "Real-World Safety and Supportive Care Use of Second-Line 5-Fluorouracil-Based Regimens Among Patients With Metastatic Pancreatic Ductal Adenocarcinoma," Curr Med Res Opin. 38(8):1295-1303 (2022).
Kim G, et al., "Real-World Safety Data and Differentiation of Second-Line (2L) 5-Fluorouracil (5-FU) Based Regimens Among Patients With Metastatic Pancreatic Ductal Adenocarcinoma (mPDAC)," J Clin Oncol. 39(3_suppl):390-390, DOI: 10.1200/JCO.2021.39.3_suppl.390, (2021), 5 printed pages.
Kim G, et al., "Real-World Safety Data and Differentiation of Second-Line (2L) 5-Fluorouracil (5-FU) Based Regimens Among Patients With Metastatic Pancreatic Ductal Adenocarcinoma (mPDAC)," Poster presented at the American Society of Clinical Oncology Gastrointestinal Cancer Symposium (ASCO GI) 2021, Jan. 15-17, 2021, Virtual Congress, 7 pages.
Kim G, et al., "Real-World Treatment Discontinuation Patterns Among Patients (pts) With Metastatic Pancreatic Ductal Adenocarcinoma (mPDAC) Treated With Liposomal Irinotecan-Based Regimens in the United States," Presented at European Society for Medical Oncology (ESMO) Congress, Virtual Congress, Sep. 16-21, 2021, 5 pages.
Kim G, et al., "Real-World Treatment Discontinuation Patterns Among Patients (pts) With Metastatic Pancreatic Ductal Adenocarcinoma (mPDAC) Treated With Liposomal Irinotecan-Based Regimens in the United States," Abstract 1513P, doi.org/10.1016/j.annonc.2021.08.842, Annals Oncol. 32(S5):S1107-S1108 (2021).
Kim G, et al., Abstract CO37. "Real-World 30-Day Readmission Patterns Among Commercially Insured Patients with Metastatic Pancreatic Ductal Adenocarcinoma (MPDAC)," Value in Health. 25(7 Supp):S310-S311 (2022).
Kokhreidze J, et al., "Psychometric Properties of Patient Reported Outcome (PRO) Instruments in Patients With Small Cell Lung Cancer (SCLC) in RESILIENT Part 1," J Clin Oncol. 39(15_suppl):e24027, DOI: 10.1200/JCO.2021.39.15_suppl.e24027, (2021), 4 printed pages.
Latimer H, et al., "Dispersion in Total Cost of Care for Medicare Fee-For-Service (FFS) Patients With Metastatic Pancreatic Cancer Receiving FDA-Approved/NCCN Category 1 Regimens at 340B Versus Non-340B Institutions," J Clin Oncol. 39(15_suppl):e18843, DOI: 10.1200/JCO.2021.39.15_suppl.e18843 (2021), 4 printed pages.
Latimer H, et al., "Dispersion in Total Cost of Care for Medicare Fee-For-Service (FFS) Patients With Metastatic Pancreatic Cancer Receiving FDA-Approved/NCCN Category 1 Regimens at Teaching Versus Non-Teaching Institutions," J Clin Oncol. 39(15_suppl):e16244, DOI: 10.1200/JCO.2021.39.15_supple16244 (2021), 4 printed pages.
Latimer H, et al., "Total Cost of Care and Utilization Among Medicare Fee-For-Service (FFS) Patients With Metastatic Pancreatic Cancer Treated With FDA-Approved/NCCN® Category 1 Regimens at Teaching vs. Non-Teaching Hospitals," Abstract PDB2, Value in Health. 24(Suppl 1):S78 (2021).
Latimer H, et al., "Total Cost of Care and Utilization Among Medicare Fee-For-Service (FFS) Patients With Metastatic Pancreatic Cancer Treated With FDA-Approved/NCCN® Category 1 Regimens at Teaching vs. Non-Teaching Hospitals," Presented at International Society for Pharmacoeconomics and Outcomes, May 17-19, 2021, Virtual poster, 11 pages.
Laursen A, et al., "Real World Patterns of Pain Medication Use Among Patients With Metastatic Pancreatic Ductal Adenocarcinoma (mPDAC)," Poster presented at ASCO Quality Care Symposium 2021. Boston, MA, Online, Sep. 24-25, 2021, 4 pages.
Laursen A, et al., "Real-World Patterns of Pain Medication Use Among Patients With Metastatic Pancreatic Ductal Adenocarcinoma (mPDAC)," J Clin Oncol. 39(28_suppl):302-302, DOI: 10.1200/JCO.2020.39.28_suppl.302 (2021), 4 printed pages.
Ma W, et al, "A Phase I Study of Pharmacokinetic (PK)-Driven Sequential Dosing of Rucaparib (RUB) with Irinotecan Liposome (nal-IRI) and Fluorouracil (5FU) in Metastatic Gastrointestinal (mGI) and Pancreas (PANC) Cancers," Poster presented at the American Society of Clinical Oncology Gastrointestinal Cancer Symposium (ASCO GI), Jan. 20-22, 2022, San Francisco, 5 pages.
Ma W, et al., Abstract 563. "A Phase I Study of Pharmacokinetic (PK)-Driven Sequential Dosing of Rucaparib (RUB) with Irinotecan Liposome (nal-IRI) and Fluorouracil (5FU) in Metastatic Gastrointestinal (mGI) and Pancreatic (PANC) Cancers," J Clin Oncol. 40(4_suppl):563 (2022), 4 printed pages.
MacEwan J, et al., "Real-World 'Chair Time' Burden Associated With Intravenous Treatment Regimens for Patients with Metastatic Pancreatic Ductal Adenocarcinoma," Poster presented at International Society for Pharmacoeconomics and Outcomes Research 2022, National Harbor, Maryland, May 15-18, 2022, 4 pages.

(56) References Cited

OTHER PUBLICATIONS

MacEwan J, et al., Abstract CO119. "Real-World 'Chair-Time' Burden Associated with Intravenous Treatment Regimens for Patients with Metastatic Pancreatic Ductal Adenocarcinoma," Value in Health. 25(7 Supp):S326 (2022).
Marsh R, et al., "Pancreatic Cancer and Folfirinox: A New Era and New Questions," Cancer Med. 4(6):853-63 (2015).
McNamara M, et al., "NET-02: A Multi-Centre, Randomised, Phase II Trial of Liposomal Irinotecan (nal-IRI) and 5-Fluorouracil (5-FU)/Folinic Acid or Docetaxel as Second-Line Therapy in Patients (pts) with Progressive Poorly Differentiated Extra-Pulmonary Neuroendocrine Carcinoma (PD-EP-NEC)," Presentation presented at the American Society of Clinical Oncology (ASCO) Annual Meeting, Chicago, Illinois, Jun. 3-7, 2022, 26 pages.
McNamara M, et al., Abstract 4005. "NET-02: A Multicenter, Randomized, Phase II Trial of Liposomal Irinotecan (nal-IRI) and 5-Fluorouracil (5-FU)/Folinic Acid or Docetaxel as Second-Line Therapy in Patients (pts) with Progressive Poorly Differentiated Extra-Pulmonary Neuroendocrine Carcinoma (PD-EP-NEC)," J Clin Oncol. 40(16_suppl):4005 (2022), 5 printed pages.
Milano G, et al., "Liposomal Irinotecan (Onivyde): Exemplifying the Benefits of Nanotherapeutic Drugs," Cancer Sci. 113(7):2224-2231 (2022).
Mokrzecky C, et al., "Understanding Extended Duration of Therapy (DOT) Among Patients with Metastatic Pancreatic Ductal Adenocarcinoma (mPDAC) Treated with Liposomal Irinotecan-Based Regimens," Poster presented at the American Society of Clinical Oncology Gastrointestinal Cancer Symposium (ASCO GI), virtual format, Jan. 20-22, 2022, San Francisco, 6 pages.
Mokrzecky C, et al., Abstract 579. "Understanding Extended Duration of Therapy (DOT) Among Patients with Metastatic Pancreatic Ductal Adenocarcinoma (mPDAC) Treated with Liposomal Irinotecan-Based Regimens," J Clin Oncol. 40(4_suppl):579 (2022), 4 printed pages.
Muñoz C, et al., "Phase II, Multicenter, Open-Label, Non-Randomized Study of Neoadjuvant Chemotherapy NALIRINOX (5-FU/LV + Oxaliplatin + Nal-IRI) Followed by Chemoradiotherapy in Patients with Rectal Cancer in a Watch-and-Wait Program," Poster presented at 2022 American Society for Clinical Oncology (ASCO) Annual Meeting, Chicago, IL, Jun. 3-7, 2022, 4 pages.
Muñoz C, et al., Abstract 3612. "Phase II, Multicenter, Open-Label, Non-Randomized Study of Neoadjuvant Chemotherapy NALIRINOX (5-FU/LV + Oxaliplatin + Nal-IRI) Followed by Chemoradiotherapy in Patients with Rectal Cancer in a Watch-and-Wait Program," J Clin Oncol. 40(16_suppl):3612 (2022), 4 printed pages.
Oh D, et al., "Randomized Phase II Study of Nalicap (nal-IRI/Capecitabine) Compared to NAPOLI (nal-IRI/5-FU/LV) in Gemcitabine-Pretreated Advanced Pancreatic Cancer: Trial-in-Progress," Poster presented at the American Society of Clinical Oncology Gastrointestinal Cancer Symposium (ASCO GI), Jan. 20-22, 2022, San Francisco, 4 pages.
Oh D, et al., Abstract TPS621. "Randomized Phase II Study of NALICAP (nal-IRI/Capecitabine) Compared to NAPOLI (nal-IRI/5-FU/LV) in Gemcitabine-Pretreated Advanced Pancreatic Cancer: Trial-in-progress," J Clin Oncol. 40(4_suppl):TPS621 (2022), 4 printed pages.
Okusaka T, et al., "Nal-IRI+5-FU/LV vs 5-FU/LV in Metastatic Pancreatic Cancer: Additional Safety Report of Randomized Japanese Phase 2 Trial," Poster presented at the American Society for Oncology Gastrointestinal (ASCO GI) Cancers Symposium 2022, Jan. 20-22, 2022, 6 pages.
Okusaka T, et al., Abstract 549. "Nal-IRI+5-FU/LV vs 5-FU/LV in Metastatic Pancreatic Cancer: Additional Safety Report of Randomized Japanese Phase 2 Trial," J Clin Oncol. 40(4_suppl):549 (2022), 4 printed pages.
O'Reilly E, et al., "Real-World Overall Survival of Patients Diagnosed With Recurrent Versus de novo Metastatic Pancreatic Ductal Adenocarcinoma (PDAC)," J Clin Oncol. 39(15_suppl):e16250, DOI: 10.1200/JCO.2021.39.15_suppl.e16250 (2021), 4 printed pages.
Paluri R, et al., "Impact of the COVID-19 Pandemic on Care Delivery and Outcomes for Patients With Metastatic Pancreatic Ductal Adenocarcinoma (mPDAC)," J Clin Oncol. 39(15_suppl):4137-4137, DOI: 10.1200/JCO.2021.39.15_suppl.4137 (2021), 4 printed pages.
Paluri R, et al., "Impact of the COVID-19 Pandemic on Management of Patients with Metastatic Pancreatic Ductal Adenocarcinoma in the United States," Oncologist. 27(6):e518-e523 (2022).
Paluri R, et al., "Impact of the COVID-19 Pandemic on Metastatic Pancreatic Ductal Adenocarcinoma (mPDAC) Care Delivery," Presented at the American Society for Clinical Oncology (ASCO) Annual Meeting: Jun. 4-8, 2021; Virtual, 6 pages.
Park J, et al., "Trial in Progress: Phase 1b Study of Vactosertib in Combination with nal-IRI plus 5FU/LV in Patients with Metastatic Pancreatic Ductal Adenocarcinoma who have Failed First-Line Gemcitabine/nab-Paclitaxel," Poster presented at the American Society of Clinical Oncology Gastrointestinal Cancer Symposium (ASCO GI), Jan. 20-22, 2022, San Francisco, 4 pages.
Park J, et al., Abstract TPS632. "Phase 1b Study of Vactosertib in Combination with nal-IRI Plus 5FU/LV in Patients with Metastatic Pancreatic Ductal Adenocarcinoma Who Have Failed First-Line Gemcitabine/nab-paclitaxel," J Clin Oncol. 40(4_suppl):TPS632 (2022), 4 printed pages.
Paz-Ares L, et al., "RESILIENT Part 1: A Phase 2 Dose-Exploration and Dose-Expansion Study of Second-Line Liposomal Irinotecan in Adults With Small Cell Lung Cancer," Cancer. 128(9):1801-1811 (2022).
Paz-Ares L, et al., "RESILIENT Part 1: A Phase 2 Dose-Exploration and Dose-Expansion Study of Second-Line Liposomal Irinotecan in Adults With Small Cell Lung Cancer," Cancer. doi: 10.1002/cncr.34123, online ahead of print, pp. 1-11 (2022).
Paz-Ares L, et al., "RESILIENT Part 1: A Phase II Dose-Exploration and Dose-Expansion Study of Second-Line Liposomal Irinotecan Monotherapy in Adults With Small Cell Lung Cancer," Presented at World Conference on Lung Cancer, Jan. 28-31, 2021, Virtual event, 12 pages.
Paz-Ares L, et al., "RESILIENT Part 1: Safety and Efficacy of Second-Line Liposomal Irinotecan in Patients With Small Cell Lung Cancer," Abstract FP10.04, J Thoracic Oncol. 16(3S):S216 (2021).
Paz-Ares L, et al., "RESILIENT Part 2: A Phase 3 Study of Liposomal Irinotecan in Patients With Small-Cell Lung Cancer in the Second-Line Setting," Abstract P48.14, J Thoracic Oncol. 16(3S):S505 (2021).
Paz-Ares L, et al., "RESILIENT Part 2: A Phase III Study of Liposomal Irinotecan in Patients With Small-Cell Lung Cancer in the Second-Line Setting," Presented at World Conference on Lung Cancer, Jan. 28-31, 2021, Virtual event, 9 pages.
Perkhofer L, et al., "Nal-IRI With 5-Fluorouracil (5-FU) and Leucovorin or Gemcitabine Plus Cisplatin in Advanced Biliary Tract Cancer. Final Results of the NIFE-trial (AIO-YMO HEP-0315), A Randomized Phase II Study of the AIO Biliary Tract Cancer Group," Abstract LBA10, doi.org/10.1016/j.annonc.2021.08.2082, Annals Oncol. 32(S5):S1282 (2021).
Perkhofer L, et al., "Nal-IRI With 5-FU and Leucovorin or Gemcitabine Plus Cisplatin in Advanced Biliary Tract Cancer: Final Results of the Randomized Phase 2 NIFE Trial (AIO-YMO HEP-0315)," Presentation at the European Society for Medical Oncology (ESMO) Congress, Virtual Congressl Sep. 16-21, 2021, 9 pages.
Poplin E, et. al., "Phase III, Randomized Study of Gemcitabine and Oxaliplatin Versus Gemcitabine (Fixed-Dose Rate Infusion) Compared With Gemcitabine (30-Minute Infusion) in Patients With Pancreatic Carcinoma E6201: A Trial of the Eastern Cooperative Oncology Group," J Clin Oncol. 27(23):3778-85 (2009).
Poplin E, et al., "Phase III, Randomized Study of Gemcitabine and Oxaliplatin Versus Gemcitabine (Fixed-Dose Rate Infusion) Compared With Gemcitabine (30-Minute Infusion) in Patients With Pancreatic Carcinoma E6201: A Trial of the Eastern Cooperative Oncology Group," J Clin Oncol. 27(23):3778-85 (2009) and author correction J Clin Oncol. 27(34):5859 (2009).
Prager G, et al., "Long-Term Survival in Patients with Pancreatic Cancer (PAC) Treated with Liposomal Irinotecan in Combination with 5-Fluorouracil and Leucovorin (nal-IRI+5-FU/LV)," Poster

(56) References Cited

OTHER PUBLICATIONS presented at the European Society for Medical Oncology (ESMO) World Congress on Gastrointestinal Cancer, Jun. 29-Jul. 2, 2022, Barcelona, Spain, 6 pages.
Prager G, et al., Abstract P-8. "Long-Term Survival in Patients with Pancreatic Cancer (PAC) Treated with Liposomal Irinotecan in Combination with 5-Fluorouracil and Leucovorin (nal-IRI+5-FU/LV)," Ann Oncol. 33(S4):S248-S249 (2022).
Ramirez R, et al., "Trends in Treatment Patterns Associated with Small Cell Lung Cancer in a U.S. Medicare Population," Poster presented at 2022 American Society for Clinical Oncology (ASCO) Annual Meeting, Chicago, IL, Jun. 3-7, 2022, 5 pages.
Ramirez R, et al., Abstract 8584. "Trends in Treatment Patterns Associated with Small Cell Lung Cancer in a U.S. Medicare Population," J Clin Oncol. 40(16_suppl):8584 (2022), 4 printed pages.
Umemura A, et al., "Modified FOLFIRINOX for Locally Advanced and Metastatic Pancreatic Cancer Patients Resistant to Gemcitabine and S-1 in Japan: A Single Institutional Experience," Hepato-Gastroenterology. 61:00-00 doi10.5754/hge14111, pp. 6-12 (2013).
Vaage J, et. al., "Therapy of a Xenografted Human Colonic Carcinoma Using Cisplatin or Doxorubicin Encapsulated in Long-Circulating Pegylated Stealth Liposomes," Int J Cancer. 80(1):134-7 (1999).
Van Cutsem E et. al., "Phase III Trial of Bevacizumab in Combination With Gemcitabine and Erlotinib in Patients With Metastatic Pancreatic Cancer," J Clin Oncol. 27(13):2231-7 (2009).
Van Cutsem E, et al., "A Phase Ib Dose-Escalation Study of Erlotinib, Capecitabine and Oxaliplatin in Metastatic Colorectal Cancer Patients," Ann Oncol. 19(2):332-9 (2008), Epub Nov. 6, 2007.
Van Rijswijk R, et. al., "Weekly High-Dose 5-Fluorouracil and Folinic Acid in Metastatic Pancreatic Carcinoma: A Phase II Study of the EORTC Gastrointestinal Tract Cancer Cooperative Group," Eur J Cancer. 40(14):2077-81 (2004).
Veal G, et al., "A Phase I Study in Paediatric Patients to Evaluate the Safety and Pharmacokinetics of SPI-77, A Liposome Encapsulated Formulation of Cisplatin," Br J Cancer. 84(8):1029-35 (2001).
Venook A, "Critical Evaluation of Current Treatments in Metastatic Colorectal Cancer," Oncologist. 10(4):250-61 (2005).
Ventura M, et al., "Efficacy of nal-IRI and Hypoxia Modulation in Orthotopic Patient-Derived Pancreatic Tumor Models of High (OCIP51) and Low (OCIP19) Hypoxia," Presentation presented at the World Molecular Imaging Congress 2017, Philadelphia, Pennsylvania, Sep. 13-16, 2017, 15 pages.
Ventura M, et al., "Ferumoxytol as an MR Imaging Surrogate Marker of Liposomal Drug Deposition and Longitudinal Efficacy in a Preclinical Model of Breast Cancer." Poster presented at World Molecular Imaging Congress, Sep. 13-16, 2017, Philadelphia, Pennsylvania, 6 pages.
Ventura M, et al., "Imaging-Based Assessment of the Treatment Efficacy of Nanoliposomal Irinotecan (nal-IRI) in a Triple Negative Breast Cancer Model of Spontaneous Metastasis." Poster presented at Annual World Molecular Imaging Congress, Sep. 7-10, 2016, 8 pages.
Ventura M, et al., Abstract. "Efficacy of nal-IRI and Hypoxia Modulation in Orthotopic Patient-Derived Pancreatic Tumor Models of High (OCIP51) and Low (OCIP19) Hypoxia," The World Molecular Imaging Congress 2017, Philadelphia, Pennsylvania, Sep. 13-16, 2017, 1 page.
Verreault M, et al., "Vascular Normalization in Orthotopic Glioblastoma Following Intravenous Treatment with Lipid-Based Nanoparticulate Formulations of Irinotecan (Irinophore C™), Doxorubicin (Caelyx®) or Vincristine," BMC Cancer. 11:124, pp. 1-18 (2011).
Vickers M, et. al., "Comorbidity, Age and Overall Survival in Patients With Advanced Pancreatic Cancer—Results from NCIC CTG PA.3: A Phase III Trial of Gemcitabine Plus Erlotinib or Placebo," Eur J Cancer. 48(10):1434-42 (2012). Epub 2011.
Villalona-Calero M, et. al., "Phase I Study of Low-Dose Suramin as a Chemosensitizer in Patients With Advanced Non-Small Cell Lung Cancer," Clin Cancer Res. 9(9):3303-11 (2003).
Von Hoff D, et. al., "NAPOLI 1: Randomized Phase 3 Study of MM-398 (nal-IRI), With or Without 5-Fluorouracil and Leucovorin, Versus 5-Fluorouracil and Leucovorin, in Metastatic Pancreatic Cancer Progressed on or following Gemcitabine-Based Therapy." Poster presented at the ESMO World Congress on Gastrointestinal Cancer 2014, 11 pages.
Von Hoff D, et. al., "Gemcitabine Plus nab-Paclitaxel Is an Active Regimen in Patients With Advanced Pancreatic Cancer: A PhaseI/II Trial," J Clin Oncol. 29(34):4548-54 (2011).
Von Hoff D, et. al., "Increased Survival in Pancreatic Cancer with nab-Paclitaxel plus Gemcitabine," N Engl J Med. 369(18):1691-703 (2013).
Von Pawel J, et al., "Randomized Phase III Trial of Amrubicin Versus Topotecan as Second-Line Treatment for Patients with Small-Cell Lung Cancer," J Clin Oncol. 32(35):4012-9 and appendix (1 page) (2014).
Von Pawel J, et al., "Topotecan Versus Cyclophosphamide, Doxorubicin, and Vincristine for the Treatment of Recurrent Small-Cell Lung Cancer," J Clin Oncol. 17(2):658-67 (1999).
Wagener D, et al., "Phase II Trial of CPT-11 in Patients with Advanced Pancreatic Cancer: An EORTC Early Clinical Trials Group Study," Ann Oncol. 6(2):129-32 (1995).
Wählby C, et al., "Sequential Immunofluorescence Staining and Image Analysis for Detection of Large Numbers of Antigens in Individual Cell Nuclei," Cytometry. 47(1):32-41 (2002).
Wainberg Z, et al., "A phase 1/2, open-label, dose-expansion study of liposomal irinotecan (nal-IRI) plus 5-Fluorouracil/leucovorin (5-FU/LV) and oxaliplatin (OX) in patients with previously untreated metastatic pancreatic cancer (mPAC)." Presentation presented at the ESMO 21st World Congress on Gastrointestinal Cancer, Barcelona, Spain, Jul. 3-6, 2019, 13 pages.
Wainberg Z, et al., "First-line liposomal irinotecan + 5-fluorouracil/leucovorin + oxaliplatin in patients with pancreatic ductal adenocarcinoma: long-term follow-up results from a phase 1/2 study." Presentation presented at the ESMO World Congress on Gastrointestinal Cancer, Jul. 1-4, 2020, 13 pages.
Wainberg Z, et al., "First-Line Liposomal Irinotecan + 5-Fluorouracil/Leucovorin + Oxaliplatin in Patients With Pancreatic Ductal Adenocarcinoma: Long-Term Follow-Up Results From a Phase 1/2 Study." Poster presented at the European Society for Medical Oncology (ESMO) World Congress on Gastrointestinal Cancer, virtual format, Jul. 1-4, 2020, 7 pages.
Wainberg Z, et al., "First-line Liposomal Irinotecan With Oxaliplatin, 5-Fluorouracil and Leucovorin (NALIRIFOX) in Pancreatic Ductal Adenocarcinoma: A Phase I/II Study," Eur J Cancer. 151:14-24 (2021).
Wainberg Z, et al., "NAPOLI-3: An Open-Label, Randomized, Phase 3 Study of First-Line Liposomal Irinotecan + 5 Fluorouracil/Leucovorin + Oxaliplatin Versus Nab-Paclitaxel + Gemcitabine in Patients With Metastatic Pancreatic Ductal Adenocarcinoma." Poster presented at the American Society of Clinical Oncology (ASCO) Annual Conference, virtual format, May 29-Jun. 2, 2020, 6 pages.
Wainberg Z, et al., Abstract LBA-1. "First-line liposomal irinotecan + 5 fluorouracil/leucovorin + oxaliplatin in patients with pancreatic ductal adenocarcinoma: Long-term follow-up results from a phase 1/2 study," Ann Oncol. 31(Suppl 3):S241 doi.org/10.1016/j.annonc.2020.04.076 (2020).
Wainberg Z, et al., Abstract SO-005: "A Phase 1/2, Open-Label, Dose-Expansion Study of Liposomal Irinotecan (Nal-IRI) Plus 5-Fluorouracil/Leucovorin (5-FU/LV) and Oxaliplatin (OX) in Patients with Previously Untreated Metastatic Pancreatic Cancer," Ann Oncol. 30(Suppl 4): doi: 10.1093/annonc/mdz157 | iv123 (Jul. 2019), 1 page.
Wainberg Z, et al., Abstract TPS4661. "NAPOLI-3: An Open-Label, Randomized, Phase III Study of First-Line iposomal Irinotecan + 5 Fluorouracil/Leucovorin + Oxaliplatin Versus Nab-Paclitaxel + Gemcitabine in Patients With Metastatic Pancreatic Ductal Adenocarcinoma," J Clin Oncol. 38(15_Suppl):TPS4461 Doi: 10.1200/JCO.2020.38.15_suppl.TPS4661 (2020), 2 printed pages.

(56) References Cited

OTHER PUBLICATIONS

Walker E and Ko A, "Beyond First-Line Chemotherapy for Advanced Pancreatic Cancer: An Expanding Array of Therapeutic Options?" World J Gastroenterol. 20(9):2224-36 (2014).
Walker S, et. al., "Simulation of Y-Site Compatibility of Irinotecan and Leucovorin at Room Temperature in 5% Dextrose in Water in 3 Different Containers," Can J Hosp Pharm. 58(4):212-22 (2005).
Wang W, et. al., "Weekly 24-Hour Infusion of High-dose 5-Fluorouracil and Leucovorin in Patients with Advanced Colorectal Cancer: Taiwan Experience," Jpn J Clin Oncol. 28(1):16-19 (1998).
Wang-Gillam A, et al., "Characteristics of Long-Term Survivors in a Randomized Phase 3 Trial (NAPOLI-1) of Patients With Metastatic Pancreatic Ductal Adenocarcinoma (mDPAC) Treated With Liposomal Irinotecan (nal-IRI; MM-398) + 5-FU/LV." Poster presented at the American Society of Clinical Oncology Gastrointestinal Cancers Symposium (ASCO GI), San Francisco, CA, Jan. 19-21, 2017, 9 pages.
Wang-Gillam A, et al., "Dose Modifications of Liposomal Irinotecan (nal-IRI) + 5-Fluorouracil/Leucovorin (5-FU/LV) in NAPOLI-1: Impact on Efficacy." Poster presented at the American Society of Clinical Oncology Gastrointestinal Cancers Symposium (ASCO GI), San Francisco, CA, Jan. 18-20, 2018, 8 pages.
Wang-Gillam A, et al., "Nanoliposomal Irinotecan with Flourouracil and Folinic Acid in Metastatic Pancreatic Cancer After Previous Gemcitabine-Based Therapy (NAPOLI-1): A Global, Randomised, Open-Label, Phase 3 Trial," Lancet, 387(10018):545-57 (2016). Epub doi: 10.1016/S0140-6736(15)00986-1, pp. 1-13 (2015).
Wang-Gillam A, et al., "Nomogram for Predicting Overall Survival in Patients Treated With Liposomal Irinotecan (nal-IRI) ± 5-Fluorouracil/Leucovorin (5-FU/LV) in Metastatic Pancreatic Ductal Adenocarcinoma (mPDAC) Previously Treated With Gemcitabine-Based Therapy in NAPOLI-1." Poster presented at the American Society of Clinical Oncology Gastrointestinal Cancers Symposium (ASCO GI), San Francisco, CA, Jan. 18-20, 2018, 9 pages.
Wang-Gillam A, et al., "Updated Overall Survival Analysis of NAPOLI-1: Phase 3 Study of Nanoliposomal Irinotecan (nal-IRI, MM-398), With or Without 5-Fluorouracil and Leucovorin (5-FU/LV), Versus 5-FU/LV in Metastatic Pancreatic Cancer (mPAC) Previously Treated With Gemcitabine-Based Therapy." Poster presented at the American Society of Clinical Oncology Gastrointestinal Cancers Symposium (ASCO GI), San Francisco, CA, Jan. 21-23, 2016, 11 pages.
Wang-Gillam A, et al., "Updated Overall Survival Analysis of NAPOLI-1: Phase 3 Study of Nanoliposomal Irinotecan (nal-IRI, MM-398), With or Without 5-Fluorouracil and Leucovorin, vs 5-Fluorouracil and Leucovorin in Metastatic Pancreatic Ductal Adenocarcinoma Previously Treated With Gemcitabine." Poster presented at the American Society of Clinical Oncology (ASCO) Annual Meeting, Chicago, Illinois, Jun. 3-7, 2016, 8 pages.
Wang-Gillam A, et al., Abstract 293. "Characteristics of Long-Term Survivors in a Randomized Phase III Trial (NAPOLI-1) of Patients With Metastatic Pancreatic Ductal Adenocarcinoma (mPDAC) Treated With Liposomal Irinotecan (nal-IRI; MM-398) + 5-FU/LV," J Clin Oncol. 35(4_Suppl):293 DOI: 10.1200/JCO.2017.35.4_suppl.293 (2017), 2 printed pages.
Wang-Gillam A, et al., Abstract 388. "Dose Modifications of Liposomal Irinotecan (nal-IRI) + 5-Fluorouracil/ Leucovorin (5-FU/LV) in NAPOLI-1: Impact on Efficacy," J Clin Oncol. 36(4_Suppl):388 DOI: 10.1200/JCO.2018.36.4_suppl.388 (2018), 2 printed pages.
Wang-Gillam A, et al., Abstract 4126. "Updated Overall Survival (OS) Analysis of NAPOLI-1: Phase 3 Study of Nanoliposomal Irinotecan (nal-IRI, MM-398), With or Without 5-Fluorouracil and Leucovorin (5-FU/LV), vs 5-FU/LV in Metastatic Pancreatic Cancer (mPAC) Previously Treated With Gemcitabine (Gem)-Based Therapy," J Clin Oncol. 34(15_Suppl):4126 DOI: 10.1200/JCO.2016.34.15_suppl.4126 (2016), 5 printed pages.
Wang-Gillam A, et al., Abstract 417. "Updated Overall Survival Analysis of NAPOLI-1: Phase III Study of Nanoliposomal Irinotecan (nal-IRI, MM-398), With or Without 5-Fluorouracil and Leucovorin (5-FU/LV), Versus 5-FU/LV in Metastatic Pancreatic Cancer (mPAC) Previously Rreated With Gemcitabine-Based Therapy," J Clin Oncol. 34(4_Suppl):417 DOI: 10.1200/jco.2016.34.4_suppl.417 (2016), 2 printed pages.
Wang-Gillam A, et al., Abstract 459. "Nomogram for Predicting Overall Survival (OS) in Patients (pts) Treated With Liposomal Irinotecan (nal-IRI) ± 5-Fluorouracil/Leucovorin (5-FU/LV) in Metastatic Pancreatic Ductal Adenocarcinoma (mPDAC) Previously Treated With Gemcitabine-Based Therapy in NAPOLI-1," J Clin Oncol. 36(4_Suppl):459 DOI: 10.1200/JCO.2018.36.4_suppl.459 (2018), 2 printed pages.
Wang-Gillam A, et al., Abstract e15795. "The Prognostic Value of Baseline Neutrophil-to-Lymphocyte Ratio (NLR) and Platelet-to-Lymphocyte ratio (PLR) for Predicting Clinical Outcome in Patients with Metastatic Pancreatic Ductal Adenocarcinoma (mPDAC) Treated With Liposomal Irinotecan (nalIRI; MM398) + 5-Fluorouracil and Leucovorin (5-FU/LV) vs 5-FU/LV," J Clin Oncol. 35(15_Suppl):e15795 DOI: 10.1200/JCO.2017.35.15_suppl.e15795 (2017), 3 printed pages.
Wang-Gillam A, et al., Abstract e16204. "A Survival Prediction Nomogram for Liposomal Irinotecan (nal-IRI)+5-Fluorouracil/Leucovorin (5-FU/LV) in Patients (pts) With Metastatic Pancreatic Ductal Adenocarcinoma (mPDAC) Previously Treated With Gemcitabine-Based Therapy," J Clin Oncol. 36(15_Suppl):e16204 DOI: 10.1200/JCO.2018.36.15_suppl.e16204 (2018), 2 printed pages.
Wang-Gillam A, et. al., letter to editor, "Nanoliposomal Irinotecan in the Clinical Practice Guideline for Metastatic Pancreatic Cancer: Applicability to Clinical Situations," J Clin Oncol. 35(6):689-90 (2017). Epub 2016.
Wasserman E, et al., "Combination of Oxaliplatin Plus Irinotecan in Patients With Gastrointestinal Tumors: Results of Two Independent Phase I Studies with Pharmacokinetics," J Clin Oncol. 17(6):1751-9 (1999).
Waterhouse D, et al., "Lipid-Based Nanoformulation of Irinotecan: Dual Mechanism of Action Allows for Combination Chemo/Angiogenic Therapy," Nanomedicine 6(9):1645-54 (2011).
Wei H, et al, "Active Loading Liposomal Irinotecan Hydrochloride: Preparation, In Vitro and In Vivo Evaluation," Asian J Pharm Sci. 8(5):303-11 (2013).
Weng K, et al., "Convection-Enhanced Delivery of Targeted Quantum Dot-Immunoliposome Hybrid Nanoparticles to Intracranial Brain Tumor Models," Nanomedicine (Lond). 8(12):1913-25. 2013.
Lakatos G, et al., Abstract P-51. "Prognostic Value of Baseline Biliary Stents on Outcomes in Patients With Metastatic Pancreatic Ductal Adenocarcinoma (mPDAC) in the NAPOLI-1 Trial," Ann Oncol. 29(Suppl_5):v42 doi:10.1093/annonc/mdy151 (2018).
Lamichhane N, et. al., "Liposomes: Clinical Applications and Potential for Image-Guided Drug Delivery," Molecules. 23(2):288 doi: 10.3390/molecules2302028 (2018), 17 pages.
Landry R, et al., "Pharmacokinetic Study of Ferumoxytol: A New Iron Repalcement Therapy in Normal Subjects and Hemodialysis Patients," Am J Nephrol. 25(4):400-10 (2005).
Larsen A, et al., "Influence of Liposomal Irinotecan (nal-IRI) and Non-Liposomal Irinotecan, Alone and in Combination, on Tumor Growth and Angiogenesis in Colorectal Cancer (CRC) Models." Poster presented at the American Society of Clinical Oncology Gastrointestinal Cancers Symposium (ASCO GI), San Francisco, CA, Jan. 18-20, 2018, 9 pages.
Larsen A, et al., Abstract 711. "Influence of Liposomal Irinotecan (nal-IRI) and Non-Liposomal Irinotecan, Alone and in Combination, on Tumor Growth and Angiogenesis in Colorectal Cancer (CRC) Models," J Clin Oncol. 36(4_Suppl):711 DOI: 10.1200/JCO.2018.36.4_suppl.711 (2018), 2 printed pages.
Latimer H, et al., Abstract C5. "Utilization of Hospital Inpatient Services Among Patients With Metastatic Pancreatic Cancer With Commercial and Medicare Insurance Treated With FDA-Approved/NCCN Category 1 Regimens," J Manag Care Spec Pharm. 26(10-a):S20 (2020).
Le A, et. al., "Conceptual Framework for Cutting the Pancreatic Cancer Fuel Supply," Clin Cancer Res. 18(16):4285-90 (2012).

(56) References Cited

OTHER PUBLICATIONS

Lee C, et al., "Novel Chondroitin Sulfate-binding Cationic Liposomes Loaded with Cisplatin Efficiently Suppress the Local Growth and Liver Metastasis of Tumor Cells in Vivo," Cancer Res. 62(15):4282-8 (2002).

Lee H, et al., "(64)Cu-MM-302 Positron Emission Tomography Quantifies Variability of Enhanced Permeability and Retention of Nanoparticles in Relation to Treatment Response in Patients with Metastatic Breast Cancer," Clin Cancer Res. 23(15):4190-4202 (2017).

Lee H, et al., "A Gradient-Loadable (64)Cu-Chelator for Quantifying Tumor Deposition Kinetics of Nanoliposomal Therapeutics by Positron Emission Tomography," Nanomedicine. 11(1):155-65 (2015). Epub 2014.

Lee H, et al., A Novel 64Cu-Liposome PET Agent (MM-DX-929) Predicts Response to Liposomal Chemotherapeutics in Preclinical Breast Cancer Models, Poster presented at San Antonio Breast Cancer Symposium, Dec. 4-8, 2012, 13 pages.

Lee H, et al., A Novel 64Cu-Liposome PET Agent (MM-DX-929) Predicts Response to Liposomal Chemotherapeutics in Preclinical Breast Cancer Models, Cancer Res. 72(24 Suppl): Abstract nrP4-02-05 (2012), San Antonio Breast Cancer Symposium, Dec. 4-8, 2012, 2 printed pages.

Lee H, et al., "Delivery and Anti-Tumor Activity of Nanoliposomal Irinotecan (Nal-IRI, MM-398) in Metastatic Xenograft Models of Triple Negative Breast Cancer." Poster presented at 39th Annual San Antonio Breast Cancer Symposium, Dec. 6-10, 2016, 8 pages.

Lee K, et al., Abstract P-153. "Decreased Appetite (DA) at Baseline Impacts Prognosis in the NAPOLI-1 Phase 3 Study in Metastatic Pancreatic Ductal Adenocarcinoma (mPDAC)," Ann Oncol. 29(Suppl_5):v42-v43 doi:10.1093/annonc/mdy151 (2018).

Lee K-H, et al., "Decreased Appetite (DA) at Baseline Impacts Prognosis in the NAPOLI-1 Phase 3 Study in Metastatic Pancreatic Ductal Adenocarcinoma (mPDAC)." Poster presented at the European Society for Medical Oncology 20th World Congress on Gastrointestinal Cancer, Barcelona, Spain, Jun. 20-23, 2018, 9 pages.

Lee M, et al., "5-Fluorouracil/Leucovorin Combined wtih Irinotecan and Oxaliplatin (FOLFIRINOX) as Second-Line Chemotherapy in Patients with Advanced Pancreatic Cancer Who Have Progressed on Gemcitabine-Based Therapy," Chemotherapy. 59(4):273-9 (2013).

Leonard S, et al., "Deposition Characteristics and Resulting DNA Damage Patterns of Liposomal Irinotecan (nal-IRI) in Pancreatic Cancer Xenografts." Poster presented at the American Society of Clinical Oncology Gastrointestinal Cancers Symposium (ASCO GI), San Francisco, CA, Jan. 18-20, 2018, 9 pages.

Leonard S, et al., "Extended Topoisomerase 1 Inhibition Through Liposomal Irinotecan Results in Improved Efficacy over Topotecan and Irinotecan in Models of Small-Cell Lung Cancer," Anti-Cancer Drugs. 28(10):1086-96 (2017).

Leonard S, et al., "Irinotecan Liposome Injection has Greater Anti-Tumor Activity than Topotecan and Irinotecan in Mouse Models of Small Cell Lung Cancer," Poster presented at AACR 110th Annual World Congress 2017, Washington, DC, Apr. 1-5, 2017, 6 pages.

Leonard S, et al., "Preclinical Support for Evaluation of Irinotecan Liposome Injection (nal-IRI, MM-398) in Small Cell Lung Cancer," Abstracts from the IASLC 17th World Conference on Lung Cancer held Dec. 4-7, 2016, J Thoracic Oncology. 12(1)(Suppl):S699 (2016), 1 page.

Leonard S, et al., "Preclinical Support for Evaluation of Irinotecan Liposome Injection (nal-IRI, MM-398) in Small Cell Lung Cancer," Poster presented at 17th World Conference on Lung Cancer, Vienna, Austria, Dec. 4-7, 2016, 5 pages.

Leonard S, et al., Abstract 335. "Deposition Characteristics and Resulting DNA Damage Patterns of Liposomal Irinotecan (nal-IRI) in Pancreatic Cancer Xenografts," J Clin Oncol. 36(4_Suppl):335 DOI: 10.1200/JCO.2018.36.4_suppl.335 (2018), 2 printed pages.

Leucovorin Calcium package insert, Teva, revised Oct. 2009, 6 pages.

Li J and Saif M, "Any Progress in the Management of Advanced Pancreatic Cancer? Highlights from the 45th ASCO Annual Meeting." JOP. J Pancreas (Online) 10(4):361-5 (2009).

Li J, et. al., "Any Second-Line Therapy for Advanced Pancreatic Cancer? Highlights from the 2010 ASCO Gastrointestinal Cancers Symposium." JOP. J Pancreas (Online). 11(2):151-3 (2010).

Liu B, et al., "Mapping Tumor Epitope Space by Direct Selection of Single-Chain Fv Antibody Libraries on Prostate Cancer Cells," Cancer Res. 64(2):704-10 (2004).

Liu B, et al., "Recombinant Full-Length Human IgG1s Targeting Hormone-Refractory Prostate Cancer," J Mol Med Berl). 85(10):1113-23 (2007).

Liu J-J, et al., "Simple and Efficient Liposomal Encapsulation of Topotecan by Ammonium Sulfate Gradient: Stability, Pharmacokinetic and Therapeutic Evaluation," Anticancer Drugs. 13(7):709-17 (2002).

Löhr J, et. al., "Cationic Liposomal Paclitaxel Plus Gemcitabine or Gemcitabine Alone in Patients With Advanced Pancreatic Cancer. A Randomized Controlled Phase II Trial," Ann Oncology. 23(5):1214-22 (2012). Epub 2011.

Lordick F, et al., "Phase II Study of Weekly Oxaliplatin Plus Infusional Fluorouracil and Folinic Acid (FUFOX Regiment) as First-Line Treatment in Metastatic Gastric Cancer," Br J Cancer. 93(2):190-4 (2005).

Lorusso P, et al., "Abstract CT325: Combination of the PARP Inhibitor Veliparib (ABT888) with Irinotecan in Patients with Triple Negative Breast Cancer. Preliminary Activity and Signature of Response." Proceedings: AACR 106th Annual Meeting, Apr. 18-22, 2015, Philadelphia, PA (2015), 3 printed pages.

Lorusso P, et al., "Phase I Safety, Pharmacokinetic, and Pharmacodynamic Study of the Poly(ADP-ribose) Polymerase (PARP) Inhibitor Veliparib (ABT-888) in Combination with Irinotecan in Patients with Advanced Solid Tumors," Clin Cancer Res. 22(13):3227-37 (2016), Epub Feb. 3, 2016.

Lorusso P, et al., "Phase I Study of the Safety, Pharmacokinetics (PK), and Pharmacodynamics (PD) of the Poly (ADP-ribose) Polymerase (PARP) Inhibitor Veliparib (ABT-888; V) in Combination with Irinotecan (CPT-11; Ir) in Patients (pts) with Advanced Solid Tumors," Journal of Clinical Oncology 29.15_suppl: Abstract 3000 (2011), 3 printed pages.

Lorusso P, et al., "Phase I Study of the Safety, Pharmacokinetics (PK), and Pharmacodynamics (PD) of the Poly ADP-ribose) Polymerase (PARP) Inhibitor Veliparib (ABT-888; V) in Combination with Irinotecan (CPT-11; Ir) in Patients (pts) with Advanced Solid Tumors," Supplement ASCO Meeting Library, Jun. 5, 2011, 1 page.

Lorusso P, et al., "Phase I Study of the Safety, Pharmacokinetics, and Pharmacodynamics of the Poly(ADP-ribose) Polymerase (PARP) Inhibitor Veliparib (ABT-888) in Combination with Irinotecan (CPT-11) in Patients with Advanced Solid Tumors," Presentation presented at American Society of Clinical Oncology 2011 Meeting, 37 pages.

Louvet C, et al., "Gemcitabine in Combination With Oxaliplatin Compared With Gemcitabine Alone in Locally Advanced or Metastatic Pancreatic Cancer: Results of a GERCOR and GISCAD Phase III Trial," J Clin Oncol. 23(15):3509-16 (2005).

Lundberg B, et al., "Conjugation of Apolipoprotein B with Liposomes and Targeting to Cells in Culture," Biochim Biophys Acta. 1149(2):305-12 (1993).

LYNPARZA™ (olaparib) capsules package insert, ©AstraZeneca. 2014, Revised: Dec. 2014, 6 pages.

Ma W, et al., "Nanoliposomal Irinotecan (nal-IRI, nal-IRI) Population Pharmacokinetics (PK) and Its Association with Efficacy and Safety in Patients with Solid Tumors." Poster presented at 2015 European Cancer Congress, Vienna, Austria, Sep. 25, 2015, 7 pages.

Ma W, et al., Abstract 2365. "Nanoliposomal Irinotecan (MM-398, nal-IRI) Population Pharmacokinetics (PK) and its Association With Efficacy and Safety in Patients With Solid Tumors Based on the Phase 3 Study NAPOLI-1 and Five Phase 1 and 2 Studies," Eur J Cancer. 51(3):S458 10.1016/S0959-8049(16)31281-3 (2015).

Ma W, et al., Abstract e13588. "Population Pharmacokinetics and Exposure-Safety Relationship of Nanoliposomal Irinotecan (MM-398, nal-IRI) in Patients With Solid Tumors," J Clin Oncol. 33(15_Suppl):e13588 DOI: 10.1200/jco.2015.33.15_suppl.e13588 (2015), 2 printed pages.

(56) References Cited

OTHER PUBLICATIONS

Mabro M, et. al., "A Phase II Study of FOLFIRI-3 (Double Infusion of Irinotecan Combined With LV5FU) After FOLFOX in Advanced Colorectal Cancer Patients," Br J Cancer. 94(9):1287-92 (2006).
Mabro M, et. al., "Bimonthly Leucovorin, Infusion 5-Fluorouracil, Hydroxyurea, and Irinotecan (FOLFIRI-2) for Pretreated Metastatic Colorectal Cancer," Am J Clin Oncol. 26(3):254-8 (2003).
Macarulla Mercadé T, et al., "NAPOLI-1 Phase 3 Trial Outcomes by Prior Surgery, and Disease Stage, in Patients With Metastatic Pancreatic Ductal Adenocarcinoma (mPDAC)." Poster presented at the European Society for Medical Oncology Annual Congress, Munich, Germany, Oct. 19-23, 2018, 7 pages.
Macarulla Mercadé T, et al., "Prognostic Effect of Primary Tumour Location in the NAPOLI-1 Phase 3 Study in Metastatic Pancreatic Ductal Adenocarcinoma (mPDAC)." Poster presented at the European Society for Medical Oncology 19th World Congress on Gastrointestinal Cancer, Barcelona, Spain, Jun. 20-23, 2018, 10 pages.
Macarulla Mercadé T, et al., "Selected Subgroup Analyses of Liposomal Irinotecan in Patients With Metastatic Pancreatic Ductal Adenocarcinoma in the Global NAPOLI-1 Phase III Trial." Presentation presented at the European Society for Medical Oncology (ESMO) 20th World Congress on Gastrointestinal Cancer, Barcelona, Spain, Jun. 20-23, 2018, 16 pages.
Macarulla Mercade T, et al., "Subgroup Analysis by Baseline Pain Intensity (BPI) and Baseline Analgesic Use (BAU) in NAPOLI-1, A phase 3 Study of Liposomal Irinotecan (nal IRI)±5-Fluorouracil/Leucovorin (5-FU/LV) in Patients With Metastatic Pancreatic Ductal Adenocarcinoma Previously Treated With Gemcitabine-Based Therapy." Poster presented at the American Society of Clinical Oncology Gastrointestinal Cancers Symposium (ASCO GI), San Francisco, CA, Jan. 18-20, 2018, 8 pages.
Macarulla Mercadé T, et al., "Subgroup Analysis by Baseline Weight-Associated Parameters: A phase 3 Study of Liposomal Irinotecan (nal-IRI)±5-Fluorouracil/Leucovorin (5-FU/LV) in Patients With Metastatic Pancreatic Ductal Adenocarcinoma Previously Treated With Gemcitabine-Based Therapy." Poster presented at the American Society of Clinical Oncology Gastrointestinal Cancers Symposium (ASCO GI), San Francisco, CA, Jan. 18-20, 2018, 7 pages.
Macarulla Mercadé T, et al., "The Effect of Best Response to Prior Anticancer Therapy on Efficacy Outcomes in the NAPOLI-1 Trial of Patients With Metastatic Pancreatic Ductal Adenocarcinoma (mPDAC) Previously Treated with Gemcitabine-Based Therapy." Poster presented at the European Society for Medical Oncology 20th World Congress on Gastrointestinal Cancer, Barcelona, Spain, Jun. 20-23, 2018, 10 pages.
Macarulla Mercadé T, et al., Abstract 379. "Subgroup Analysis by Baseline Pain Intensity (BPI) and Analgesic Use (BAU) in NAPOLI-1: A phase III Study of Liposomal Irinotecan (nal IRI)+5-Fluorouracil/ Leucovorin (5-FU/LV) in Patients (pts) With Metastatic Pancreatic Ductal Adenocarcinoma (mPDAC) Previously Treated With Gemcitabine-Based Therapy," J Clin Oncol. 36(4_Suppl):379 DOI: 10.1200/JCO.2018.36.4_suppl.379 (2018), 4 printed pages.
Chen L, et al., "Expanded Analyses of NAPOLI-1: Phase 3 Study of MM-398 (nal-IRI), with or without 5-Fluorouracil and Leucovorin, versus 5-Fluorouracil and Leucovorin, in Metastatic Pancreatic Cancer (mPAC) Previously Treated with Gemcitabine-based Therapy." Presented Jan. 15, 2015, ASCO GI, 17 pages.
Chen L, et al., "Expanded Analyses of NAPOLI-1: Phase 3 Study of MM-398 (nal-IRI), With or Without 5-Fluorouracil and Leucovorin, Versus 5-Fluorouracil and Leucovorin, in Metastatic Pancreatic Cancer (mPAC) Previously Treated with Gemcitabine-Based Therapy." Poster presented at the ASCO meeting of May 29-Jun. 2, 2015, Chicago, Illinois, 7 pages.
Chen L, et al., "Phase I Study of Biweekly Liposome Irinotecan (PEP02, MM-398) in Metastatic Colorectal Cancer Failed on First-line Oxaliplatin-based Chemotherapy," J Clin Oncol. 30(4_suppl):Abstract 613 (2012), 6 printed pages.
Chen L, et al., "Phase I Study of Liposome Encapsulated Irinotecan (PEP02) in Advanced Solid Tumor Patients," J Clin Oncol., 2008 ASCO Annual Meeting Proceedings (Post-Meeting Edition), 26(15S) (May 20 Suppl):2565 (2008), 1 page.
Chen L, et al., "Phase I Study of Liposome Encapsulated Irinotecan (PEP02) in Advanced Solid Tumor Patients," Poster presented at the ASCO meeting of May 30-Jun. 3, 2008, Chicago, Illinois, 9 pages.
Chen L, et al., "Phase I Study of Liposome Irinotecan (PEP02) in Combination with Weekly Infusion of 5-FU/LV in Advanced Solid Tumors," J Clin Oncol., 2010 ASCO Annual Meeting Abstracts, 28(15_suppl) (May 20 Suppl):e13024 (2010), 1 page.
Chen L, et al., "Safety Across Subgroups in NAPOLI-1:A Phase 3 Study of nal-IRI (MM-398) ± 5-Fluorouracil and Leucovorin (5-FU/LV) Versus 5-FU/LV in Metastatic Pancreatic Cancer (mPAC) Previously Treated with Gemcitabine-Based Therapy." Poster presented at the 18th European Society of Medical Oncology World Congress on Gastrointestinal Cancer; Barcelona, Spain; Jun. 29-Jul. 2, 2016, 10 pages.
Chen L, et al., Abstract PD-023. "Safety Across Subgroups in NAPOLI-1:A Phase 3 Study of nal-IRI (MM-398) ± 5-Fluorouracil and Leucovorin (5-FU/LV) Versus 5-FU/LV in Metastatic Pancreatic Cancer (mPAC) Previously Treated with Gemcitabine-Based Therapy." Annals of Oncology. 27(Suppl 2):ii102-ii117 (2016), 1 page.
Chen L-T, et al., "CA19-9 Decrease and Overall Survival (OS) in the NAPOLI-1 Trial of Liposomal Irinotecan (nal-IRI) ± 5-Fluorouracil and Leucovorin (5-FU/LV) in Metastatic Pancreatic Ductal Adenocarcinoma (mPDAC) Previously Treated With Gemcitabine-Based Therapy." Poster presented at the European Society for Medical Oncology (ESMO) World Congress on Gastrointestinal Cancer, Barcelona, Spain, Jun. 28-Jul. 1, 2017, 5 pages.
Chen L-T, et al., "CA19-9 Decrease and Overall Survival in the NAPOLI-1 Trial of Liposomal Irinotecan (nal-IRI) ± 5-Fluorouracil and Leucovorin (5-FU/LV) in Metastatic Pancreatic Ductal Adenocarcinoma Previously Treated With Gemcitabine-Based Therapy." Poster presented at the European Society for Medical Oncology Asia 2017 Congress, Singapore, Nov. 17-19, 2017, 8 pages.
Chen L-T, et al., "Early Dose Reduction/Delay and the Efficacy of Liposomal Irinotecan With Fluorouracil and Leucovorin in Metastatic Pancreatic Ductal Adenocarcinoma (mPDAC): A Post Hoc Analysis of NAPOLI-1," Pancreatology. 21(1):192-9 (2021). Epub 2020.
Chen L-T, et al., "Efficacy and Safety of Liposomal Irinotecan (nal-IRI) + 5-Fluorouracil and Leucovorin in Patients With Metastatic Pancreatic Ductal Adenocarcinoma Who Previously Received Gemcitabine-Based Therapy: Post Hoc Analysis of the NAPOLI-1 Trial." Poster presented at the American Society of Clinical Oncology Gastrointestinal Cancers Symposium (ASCO GI), San Francisco, CA, Jan. 19-21, 2017, 9 pages.
Chen L-T, et al., "Final Results of NAPOLI-1: A Phase 3 Study of nal-IRI (MM-398) ± 5-Fluorouracil and Leucovorin (5-FU/LV) vs 5-FU/LV in Metastatic Pancreatic Ductal Adenocarcinoma (mPDAC) Previously Treated With Gemcitabine-Based Therapy." Poster presented at the European Society for Medical Oncology (ESMO) Annual Congress, Copenhagen, Denmark, Oct. 7-11, 2016, 8 pages.
Chen L-T, et al., "Impact of Dose Reduction or Dose Delay on the Efficacy of Liposomal Irinotecan (nal-IRI)+5-Fluorouracil/Leucovorin (5-FU/LV): Survival Analysis From NAPOLI-1." Poster presented at the European Society for Medical Oncology (ESMO) Annual Congress, Munich, Germany, Oct. 19-23, 2018, 9 pages.
Chen L-T, et al., "The Prognostic Value of the Modified Glasgow Prognostic Score (mGPS) in Predicting Overall Survival (OS) in Patients With Metastatic Pancreatic Ductal Adenocarcinoma (mPDAC) Receiving Liposomal Irinotecan (nal-IRI)+5-Fluorouracil and Leucovorin (5-FU/LV)." Poster presented at the European Society for Medical Oncology (ESMO) Annual Congress, Munich, Germany, Oct. 19-23, 2018, 9 pages.
Chen L-T, et al., Abstract 221PD. "Efficacy and Safety of Nanoliposomal Irinotecan (nal-IRI, MM-398, PEP02, BAX-2398) in Patients With Metastatic Pancreatic Cancer in Asia: A Subgroup Analysis of the Phase 3 NAPOLI-1 Study," Ann Oncol. 27(Supp_9):ix69-ix70 doi:10.1093/annonc/mdw582 (2016).

(56) References Cited

OTHER PUBLICATIONS

Chen L-T, et al., Abstract 227P. "CA19-9 Decrease and Overall Survival (OS) in the NAPOLI-1 Trial of Liposomal Irinotecan (nal-IRI) ± 5-Fluorouracil and Leucovorin (5-FU/LV) in Metastatic Pancreatic Ductal Adenocarcinoma (mPDAC) Previously Treated With Gemcitabine-Based Therapy," Ann Oncol. 28(Suppl_10):x66-x67 doi: 10.1093/annonc/mdx660 (2017).
Chen L-T, et al., Abstract 303. "Efficacy and Safety of Liposomal Irinotecan (nal-IRI) + 5-Fluorouracil and Leucovorin (5-FU/LV) in Patients (pts) With Metastatic Pancreatic Ductal Adenocarcinoma (mPDAC) Who Previously Received Gemcitabine (Gem)-Based Therapy: Post Hoc Analysis of the NAPOLI-1 Trial," J Clin Oncol. 35(4_Suppl):303 DOI: 10.1200/JCO.2017.35.4_suppl.303 (2017), 2 printed pages.
Chen L-T, et al., Abstract 3707. "Final Results of NAPOLI-1: A Phase 3 Study of nal-IRI (MM-398) ± 5-Fluorouracil and Leucovorin (5-FU/LV) vs 5-FU/LV in Metastatic Pancreatic Cancer (mPAC) Previously Treated With Gemcitabine-Based Therapy," Ann Oncol. 27(6):207-242 10.1093/annonc/mdw371 (2016), 4 printed pages.
Chen L-T, et al., Abstract 734P. "Impact of Dose Reduction or Dose Delay on the Efficacy of Liposomal Irinotecan (nal-IRI)+5-Fluorouracil/Leucovorin (5-FU/LV): Survival Analysis From NAPOLI-1," Ann Oncol. 29(Suppl_8):viii250-viii251 doi:10.1093/annonc/mdy282 (2018).
Chen L-T, et al., Abstract 749P. "The Prognostic Value of the Modified Glasgow Prognostic Score (mGPS) in Predicting Overall Survival (OS) in Patients With Metastatic Pancreatic Ductal Adenocarcinoma (mPDAC) Receiving Liposomal Irinotecan (nal-IRI)+5-Fluorouracil and Leucovorin (5-FU/LV)," Ann Oncol. 29(Suppl_8):viii255-viii256 doi:10.1093/annonc/mdy282 (2018).
Chen L-T, et al., Abstract PD-017. "CA19-9 Decrease and Overall Survival (OS) in the NAPOLI-1 Trial of Liposomal Irinotecan (nal-IRI) ± 5-Fluorouracil and Leucovorin (5-FU/LV) in Metastatic Pancreatic Ductal Adenocarcinoma (mPDAC) Previously Treated With Gemcitabine-Based Therapy," Ann Oncol. 28(Supp_3):6-7 doi:10.1093/annonc/mdx263 (2017).
Chen P, et al., "Comparing Routes of Delivery for Nanoliposomal Irinotecan Shows Superior Anti-Tumor Activity of Local Administration in Treating Intracranial Glioblastoma Xenografts," Neuro Oncol. 15(2):189-97 (2013), Epub Dec. 21, 2012.
Chiang N-J, et al., "A Phase I Dose-Escalation Study of PEP02 (Irinotecan Liposome Injection) in Combination with 5-Fluorouracil and Leucovorin in Advanced Solid Tumors," BMC Cancer. 16(1):907 (2016). doi: 10.1186/s12885-016-2933-6, pp. 1-8.
Chiang, N-J, et al., "Development of Nanoliposomal Irinotecan (nal-IRI, MM-398, PEP02) in the Management of Metastatic Pancreatic Cancer," Expert Opin Pharmacother. 17(10):1413-20 (2016).
Chibaudel B, et al., "PEPCOL: a GERCOR Randomized Phase II Study of Nanoliposomal Irinotecan PEP02 (MM-398) or Irinotecan with Leucovorin/5-Fluorouracil as Second-Line Therapy in Metastatic Colorectal Cancer", Cancer Med. 5(4):676-83 (2016).
Chibaudel B, et al., "PEPCOL: A Randomized Non-Comparative Phase II Study to Evaluate the Efficacy and Safety of PEP02 (MM-398) or Irinotecan in Combination with Leucovorin and 5-Fluorouracil as Second-Line Treatment for Patients with Unresectable Metastatic Colorectal Cancer. A GERCOR Study." Poster presented at ASCO 2015, 6 pages.
Chiesa M, et al., "A Pilot Phase II Study of Chemotherapy with Oxaliplatin, Folinic Acid, 5-Fluorouracil and Irinotecan in Metastatic Gastric Cancer," Tumori. 93(3):244-7 (2007).
Chiesa MD, et al., "Sequential Chemotherapy with Dose-Dense Docetaxel, Cisplatin, Folinic Acid and 5-Fluorouracil (TCF-dd) Followed by Combination of Oxaliplatin, Folinic acid, 5-Fluorouracil and Irinotecan (COFFI) in Metastatic Gastric Cancer. Results of a Phase II Trial," Cancer Chemother Pharmacol. 67(1):41-8 (2011), epub 2010.
Chin V, et. al., "Chemotherapy and Radiotherapy for Advanced Pancreatic Cancer (Review)," Cochrane Database Syst Rev. 3(3):CD011044 doi: 10.1002/14651858.CD011044.pub2 (2018), 143 pages.
Choi C, et al., "Effects of 5-Fluorouracil and Leucovorin in the Treatment of Pancreatic-Biliary Tract Adenocarcinomas," Am J Clin Oncol. CCT 23(4): 425-8 (2000), 7 printed pages.
Chou T, et al., "Effect of Composition on the Stability of Liposomal Irinotecan Prepared by a pH Gradient Method," J Biosci Bioeng. 95(4):405-8 (2003).
Chu C-J, et al., "Efficiency of Cytoplasmic Delivery by pI I-Sensitive Liposomes to Cells in Culture," Pharm Res. 7(8):824-34 (1990).
Chuang V and M. Suno, "Levoleucovorin as Replacement for Leucovorin in Cancer Treatment," Ann Pharmacother. 46(10):1349-57 (2012).
Clarke J, et al., "A Phase 1 Trial of Intravenous Liposomal Irinotecan in Patients with Recurrent High-Grade Glioma," Cancer Chemother Pharmacol. 79(3):603-10 (2017).
Clarke J, et al., "A Phase I Trial of Intravenous Liposomal Irinotecan in Patients With Recurrent High-Grade Gliomas." Poster presented at the American Society of Clinical Oncology (ASCO) Annual Conference, Chicago, IL, May 29-Jun. 2, 2015, 7 pages.
Clarke J, et al., Abstract 2029. "A Phase I Trial of Intravenous Liposomal Irinotecan in Patients With Recurrent High-Grade Gliomas," J Clin Oncol. 33(15_Suppl):2029 DOI: 10.1200/jco.2015.33.15_suppl.2029 (2015), 2 printed pages.
Clinical Trials Identifier NCT00104754: Jul. 20, 2016 update, first posted Mar. 4, 2005, "Phase II Trial of Liposome Encapsulated SN38 (LE-SN38) in the Treatment of Small Cell Lung Cancer." Retrieved from ClinicalTrials.gov archive, 8 printed pages.
Clinical Trials Identifier NCT00311610: Jun. 29, 2016 update, first posted Apr. 6, 2006, "Phase II Trial of Le SN38 in Patients with Metastatic Colorectal Cancer After Progression on Oxaliplatin." Retrieved from ClinicalTrials.gov archive, 8 printed pages.
Clinical Trials Identifier NCT00364143: Jan. 26, 2012 update, first posted Aug. 15, 2006, "A Phase I Study of IHL-305 (Irinotecan Liposome Injection) in Patients With Advanced Solid Tumors." Retrieved from ClinicalTrials.gov archive, 6 printed pages.
Clinical Trials Identifier NCT00426127: Dec. 29, 2017 update, first posted Jan. 24, 2007, "Docetaxel and Liposomal Doxorubicin Chemotherapy With Enoxaparin in Patients With Advanced Pancreatic Cancer," Retrieved from ClinicalTrials.gov archive, 8 printed pages.
Clinical Trials Identifier NCT00734682: Jan. 7, 2015 update, first posted Aug. 14, 2008, "A Phase I Trial of Nanoliposomal CPT-11 (NL CPT-11) in Patients With Recurrent High-Grade Gliomas." Retrieved from ClinicalTrials.gov archive, 6 printed pages.
Clinical Trials Identifier NCT00813072: Mar. 2, 2012 update, first posted Dec. 22, 2008, "A Randomized Phase II Study of PEP02, Irinotecan or Docetaxel as a Second Line Therapy in Patients With Locally Advanced or Metastatic Gastric or Gastroesophageal Junction Adenocarcinoma." Retrieved from ClinicalTrials.gov archive, 9 printed pages.
Clinical Trials Identifier NCT00813163: Jan. 11, 2011 update, "A Phase II Study of PEP02 as a Second Line Therapy for Patients With Metastatic Pancreatic Cancer." Retrieved from ClinicalTrials.gov archive, 3 printed pages.
Clinical Trials Identifier NCT00813163: Mar. 1, 2012 update, "A Phase II Study of PEP02 as a Second Line Therapy for Patients With Metastatic Pancreatic Cancer." Retrieved from ClinicalTrials.gov archive, 3 printed pages.
Clinical Trials Identifier NCT00813163: Jan. 12, 2015 update, "A Phase II Study of PEP02 as a Second Line Therapy for Patients with Metastatic Pancreatic Cancer." Retrieved from ClinicalTrials.gov archive, 3 printed pages.
Clinical Trials Identifier NCT00813163: Apr. 6, 2017 update, first posted Dec. 22, 2008, "A Phase II Study of PEP02 as a Second Line Therapy for Patients With Metastatic Pancreatic Cancer." Retrieved from ClinicalTrials.gov archive, 6 printed pages.
Clinical Trials Identifier NCT00940758: Jul. 16, 2009 update, "Pharmacokinetic Study of Biweekly PEP02 (Liposome Irinotecan) in Patients With Metastatic Colorectal Cancer Refractory to First-line Oxaliplatin-based Chemotherapy." Retrieved from ClinicalTrials.gov archive, 3 printed pages.
Clinical Trials Identifier NCT00940758: Feb. 3, 2010 update, "Phase I and Pharmacokinetic Study of Biweekly PEP02 (Liposome Irinotecan)

(56) References Cited

OTHER PUBLICATIONS in Patients With Metastatic Colorectal Cancer Refractory to First-line Oxaliplatin-based Chemotherapy." Retrieved from ClinicalTrials.gov archive, 3 printed pages.
Clinical Trials Identifier NCT00940758: Mar. 1, 2012 update, "Phase I and Pharmacokinetic Study of Biweekly PEP02 (Liposome Irinotecan) in Patients With Metastatic Colorectal Cancer Refractory to First-line Oxaliplatin-based Chemotherapy." Retrieved from ClinicalTrials.gov archive, 3 printed pages.
Weng K, et al., "Targeted Tumor Cell Internalization and Imaging of Multifunctional Quantum Dot-Conjugated Immunoliposomes in Vitro and in Vivo," Nano Lett. 8(9):2851-7 (2008).
Willett C, et. al., "Direct Evidence That the VEGF-Specific Antibody Bevacizumab Has Antivascular Effects in Human Rectal Cancer," Nat Med. 10(2):145-7 (2004), author manuscript version, 7 pages.
Wilson W, et al., "Targeting Hypoxia in Cancer Therapy," Nat Rev Cancer. 11(6):393-410 (2011).
Wulaningsih W, et. al., "Irinotecan Chemotherapy Combined With Fluoropyrimidines Versus Irinotecan Alone for Overall Survival and Progression-Free Survival in Patients With Advanced and/or Metastatic Colorectal Cancer," Cochrane Database Syst Rev. 2.CD008593 doi: 10.1002/14651858.CD008593.pub3. (2016), 36 pages.
Xeloda (capecitabine) package insert, Roche, revised Nov. 2000, 19 pages.
Xiong H, et. al., "Phase 2 Trial of Oxaliplatin Plus Capecitabine (XELOX) as Second-line Therapy for Patients With Advanced Pancreatic Cancer," Cancer. 113(8):2046-52 (2008).
Yamashita Y, et al., "Convection-Enhanced Delivery of a Topoisomerase I Inhibitor (Nanoliposomal Topotecan) and a Topoisomerase II Inhibitor (Pegylated Liposomal Doxorubicin) in Intracranial Brain Tumor Xenografts," Neuro Oncol. 9(1):20-8 (2007). Epub 2006.
Yamashita Y, et. al., "Convection-Enhanced Delivery of Liposomal Doxorubicin in Intracranial Brain Tumor Xenografts," Targ Oncol. 1:79-85 (2006).
Yang W, et. al. "Development of a Method to Quantify Total and Free Irinotecan and 7-ethyl-10-hydroxycamptothecin (SN-38) for Pharmacokinetic and Bio-Distribution Studies After Administration of Irinotecan Liposomal Formulation," Asian J Pharm Sci. 14(6):687-97 (2019). Epub 2018.
Yang W, et. al., "The Influence of Trapping Agents on the Antitumor Efficacy of Irinotecan Liposomes: Head-to-Head Comparison of Ammonium Sulfate, Sulfobutylether-β-Cyclodextrin and Sucrose Octasulfate," Biomater Sci., 7(1):419-28 (2019).
Yang, et. al., "Oxaliplatin Long-Circulating Liposomes Improved Therapeutic Index of Colorectal Carcinoma," BMC Biotechnology. 11:21 doi: 10.1186/1472-6750-11-21 (2011), 8 pages.
Ychou, M, et al., "An Open Phase I Study Assessing the Feasibility of the Triple Combination: Oxaliplatin Plus Irinotecan Plus Leucovorin/5-Fluorouracil Every 2 Weeks in Patients With Advanced Solid Tumors," Ann Oncol. 14(3):481-9 (2003).
Yeh B, et al., "Structural Basis for Activation of Fibroblast Growth Factor Signaling by Sucrose Octasulfate," Mol Cell Biol. 22(20):7184-92 (2002).
Yi S, et al., "Irinotecan Monotherapy as Second-Line Treatment in Advanced Pancreatic Cancer," Cancer Chemother Pharmacol. 63(6):1141-5 (2009), Epub Oct. 7, 2008.
Yoo C, et al., "A Randomised Phase II Study of Modified FOLFIRI.3 vs Modified FOLFOX as Second-Line Therapy in Patients with Gemcitabine-Refractory Advanced Pancreatic Cancer," Br J Cancer. 101(10):1658-63 (2009).
Yoo C, et al., "Multicenter Randomized Phase II Trial of 5-Fluorouracil/Leucovorin (5-FU/LV) With or Without Liposomal Irinotecan (nal-IRI) in Metastatic Biliary Tract Cancer (BTC) as Second-Line Therapy After Progression on Gemcitabine Plus Cisplatin (GemCis): NIFTY Trial." Poster presented at the European Society for Medical Oncology (ESMO) 2019 Congress, Barcelona, Spain, Sep. 27-Oct. 1, 2019, 6 pages.
Yoo C, et al., Abstract 829TiP. "Multicenter Randomized Phase II Trial of 5-Fluorouracil/Leucovorin (5-FU/LV) With or Without Liposomal Irinotecan (nal-IRI) in Metastatic Biliary Tract Cancer (BTC) as Second-Line Therapy After Progression on Gemcitabine Plus Cisplatin (GemCis): NIFTY Trial," Ann Oncol. 30(Supp_5):v318 /doi.org/10.1093/annonc/mdz247.155 (2019).
Younis I, et al., "Enterohepatic Recirculation Model of Irinotecan (CPT-11) and Metabolite Pharmacokinetics in Patients With Glioma," Cancer Chemother Pharmacol. 63(3):517-24 (2009), author manuscript version, 16 pages.
Yu K, et al., "Hospitalizations and Real-World Clinical Outcomes of Liposomal Irinotecan in a NAPOLI1-Based Regimen Among Patients With Metastatic Pancreatic Ductal Adenocarcinoma (mPDAC): A Multi-Center Chart Review," Poster presented at the Academy of Managed Care Pharmacy, Nexus (AMCP, Nexus): virtual meeting, week of Oct. 19, 2020, 9 pages.
Yu K, et al., Abstract C3. "Hospitalizations and Real-World Clinical Outcomes of Liposomal Irinotecan in a NAPOLI1-Based Regimen Among Patients With Metastatic Pancreatic Ductal Adenocarcinoma (mPDAC): A Multi-Center Chart Review," J Manag Care Spec Pharm. 26(10-a):S19 (2020).
Yu K, et al., "A US Multicenter Chart Review Study of Patients With Metastatic Pancreatic Ductal Adenocarcinoma Receiving Liposomal Irinotecan after Gemcitabine-Based Therapy." Poster presented at the International Conference on Pharmacoepidemiology & Therapeutic Risk Management (ICPE) All Access, Sep. 16-17, 2020, 8 pages.
Yu K, et al., "Real-World Treatment Patterns and Effectiveness of Liposomal Irinotecan in a NAPOLI1-Based Regimen Among Patients With Metastatic Pancreatic Ductal Adenocarcinoma (mPDAC): A Multi-Academic Center Chart Review." Poster presented at the European Society for Medical Oncology (ESMO) Virtual Congress 2020, Sep. 19-21, 2020, 9 pages.
Yu K, et al., Abstract 1555P. "Real-World Treatment Patterns and Effectiveness of Liposomal Irinotecan in a NAPOLI1-Based Regimen Among Patients With Metastatic Pancreatic Ductal Adenocarcinoma (mPDAC): A Multi-Academic Center Chart Review," Ann Oncol. 31(Suppl_4):S950-S951 doi.org/10.1016/j.annonc.2020.08.2038 (2020), 2 printed pages.
Yu K, et al., Abstract e16733. "A Multicenter Chart Review Study of Patients with Metastatic Pancreatic Ductal Adenocarcinoma Receiving Liposomal Irinotecan after Gemcitabine-Based Therapy," J Clin Oncol. 38(15_Suppl):e16733 DOI: 10.1200/JCO.2020.38.15_suppl.e16733 (2020), 4 printed pages.
Yu K, et al., Abstract PO-3727. "A US Multicenter Chart Review Study of Patients With Metastatic Pancreatic Ductal Adenocarcinoma Receiving Liposomal Irinotecan after Gemcitabine-Based Therapy," International Conference on Pharmacoepidemiology & Therapeutic Risk Management (ICPE), Sep. 14, 2020, available at eventscribe.com/2020/ICPEAllAccess/PosterTitles.asp?pfp=PosterTitles, 1 page.
Yu X, et. al., "Targeted Drug Delivery in Pancreatic Cancer," Biochim Biophys Acta. 21805(1):97-104 (2010). Epub 2009, author manuscript version, 16 pages.
Zamboni W, et. al., "Phase I and Pharmacokinetic Study of Pegylated Liposomal CKD-602 in Patients with Advanced Malignancies," Clin Cancer Res. 15(4):1466-72 (2009) and correction found at Clin Cancer Res. 15(8):2949-50 (2009).
Zander S, et al., "EZN-2208 (PEG-SN38) Overcomes ABCG2-Mediated Topotecan Resistance in BRCA1-Deficient Mouse Mammary Tumors," PLoS One. 7(9):345248 (2012), pp. 1-9.
Zaniboni A, et al., "FOLFIRI as Second-Line Chemotherapy for Advanced Pancreatic Cancer: A GISCAD Multicenter Phase II Study," Cancer Chemother Pharmacol 69(6):1641-5 (2012).
Zeghari-Squalli, N et al., "Cellular Pharmacology of the Combination of the DNA Topoisomerase I Inhibitor SN-38 and the Deaminocyclohexane Platinum Derivative Oxaliplatin," Clin Cancer Res. 5(5):1189-96 (1999).
Zhang K, et al., "Comprehensive Optimization of a Single-Chain Variable Domain Antibody Fragment as a Targeting Ligand for a Cytotoxic Nanoparticle," MAbs. 7(1):42-52 (2015).
Chang L, et al., PEG-Coated Irinitecan Cationic Liposomes Improve the Therapeutic Efficacy of Breast Cancer in Animals, Eur Rev Med Pharmacol Sci. 17(24):3347-61 (2013).

(56) References Cited

OTHER PUBLICATIONS

Zhang Y, et al., "Poly(ADP-ribose) Polymerase and XPF-ERCC1 Participate in Distinct Pathways for the Repair of Topoisomerase I-Induced DNA Damage in Mammalian Cells," Nucleic Acids Res. 39(9):3607-20 (2011).
Zhao M, et al., "Clinical Observation of Irinotecan or Topotecan as Second-Line Chemotherapy on Treating 43 Patients with Small-Cell Lung Cancer," Chin Oncol. 21(2):156-8 (2011), text in Chinese with Tables 1-3 and Figure 1 in English.
Zheng J, et al., "[18F]FAZA-PET Detection of Hypoxia Changes following Anti-cancer Therapy." Poster presented at Annual World Molecular Imaging Congress, Sep. 18-21, 2013, 7 pages.
Zheng J, et al., "Longitudinal Tumor Hypoxia Imaging with [18F[FAZA-PET Provides Early Prediction of Nanoliposomal Irinotecan (nal-IRI) Treatment Activity," EJNMMI Res 5(1):57, 10 pages (2015).
Zhou X, et al., "Clinical Analysis of Bevacizumab Plus FOLFIRI Regimen as Front-Line Therapy for Chinese Patients with Advanced Colorectal Cancer," J Cancer Ther. 2(4):470-4 (2011).
Znojek P, et al., "Preferential Potentiation of Topoisomerase I Poison Cytotoxicity by PARP Inhibition in S Phase," Br J Cancer. 111(7):1319-26 (2014).
Muldoon L, et al., "Comparing Service Utilization and Costs for Medicare FFS Patients With Metastatic Pancreatic Cancer by Chemotherapy Regimen and Line of Therapy." Poster presented at the International Society for Pharmacoeconomics and Outcomes Research (ISPOR) Annual Meeting, New Orleans, LA, May 18-22, 2019, 6 pages.
Muldoon L, et al., Abstract e18357. "Treatment Patterns, Survival Rate, and Parts A and B Costs by Line of Therapy for FDA-Approved/NCCNCategory 1 Treatments for Patients With Metastatic Pancreatic Cancer," J Clin Oncol. 37(15_Suppl):e18357 DOI: 10.1200/JCO.2019.37.15_suppl.e18357 (2019), 2 printed pages.
Muldoon L, et al., Abstract PCN302. "Comparing Service Utilization and Costs for Medicare FFS Patients With Metastatic Pancreatic Cancer by Chemotherapy Regimen and Line of Therapy," Value in Health. 22(Suppl 2):S113-S114 (2019).
Mullany S, et al., "Effect of Adding the Topoisomerase I Poison 7-ethyl-10-hydroxy-camptothecin (SN-38) to 5-Fluorouracil and Folinic Acid in HCT-8 Cells: Elevated dTTP Pools and Enhanced Cytotoxicity," Cancer Chemother Pharmacol. 42(5):391-9 (1998).
Münstedt K, et al., "Role of Dexamethasone Dosage in Combination with 5-HT3 Antagonists for Prophylaxis of Acute Chemotherapy-Induced Nausea and Vomiting," Br J Cancer. 79(3-4):637-9 (1999).
Munzone E, "Adverse Side Effects Associated to Metronomic Chemotherapy," Presentation presented at Aiom Cancer Metronomic Therapy, Feb. 26, 2016, Milan, 32 pages.
Murai J, et al., "Identification of Novel PARP Inhibitors Using a Cell-Based TDP1 Inhibitory Assay in a Quantitative High-Throughput Screening Platform," Author manuscript; Published in final edited form as: DNA Repair (Amst). 21:177-82 (2014), 13 pages.
Murai J, et al., "Rationale for Poly(ADP-ribose) Ploymerase (PARP) Inhibitors in Combination Therapy with Campothecins or Temozolomide Based on PARP Trapping versus Catalytic Inhibition," J Pharmacol Exp Ther. 349(3):408-16 (2014).
Myocet liposomal, Summary of product characteristics and labelling and package leaflet, European Medicines Agency, available at ema.europa.eu/en/documents/product-information/myocet-liposomal-previously-myocet-epar-product-information_en.pdf, Date of first authorisation: Jul. 13, 2000, Date of latest renewal: Jul. 2, 2010, 37 pages.
Nakai Y, et al., "Inhibition of Renin-Angiotensin System Affects Prognosis of Advanced Pancreatic Cancer Receiving Gemcitabine," Br J Cancer. 103(11):1644-8 (2010).
Nakajima T, et. al., "Synergistic Antitumor Activity of the Novel SN-38-Incorporating Polymeric Micelles, NK012, Combined With 5-Fluorouracil in a Mouse Model of Colorectal Cancer, as Compared With That of Irinotecan Plus 5-Fluorouracil," Int J Cancer. 122(9):2148-53 (2008).
Nardi M, et. al., Abstract 14520. "Metronomic Irinotecan and Standard FOLFIRI Regimen as First-Line Chemotherapy in Metastatic Colorectal Cancer (MCRC). Final Results of Phase II Study," J Clin Oncol. 25(18_suppl):14520 (2007), 1 printed page.
National Cancer Institute, "Irinotecan Hydrochloride Liposome, "Posted: Oct. 27, 2015, Updated:Mar. 28, 2019, available at cancer.gov/about-cancer/treatment/drugs/irinotecan-hydrochloride-liposome, 2 pages.
National Comprehensive Cancer Network Clinical Practice Guidelines In Oncology (NCCN Guidelines). "Pancreatic Adenocarcinoma." Version I.2016. Mar. 22, 2016 (PANC-9), 133 pages.
Neesse A, et al., "Stromal Biology and Therapy in Pancreatic Cancer," Gut. 60(6):861-8 (2011). Epub 2010.
Nelson R, "Lipsomal Irinotecan Boosts Survival in Pancreatic Cancer," Medscape, available at medscape.com/viewarticle/838501, 2015, 2 printed pages.
Nentwich, F., "Doxorubicin Hydrochloride," In Intravenous Therapy: A Comprehensive Application of Intravenous Therapy and Medication Administration at p. 310. Published by Jones & Bartlett Learning, 1990.
Neuzillet C, et al., "FOLFIRI Regimen in Metastatic Pancreatic Adenocarcinoma Resistant to Gemcitabine and Platinum-Salts," World J Gastroenterol. 18(33):4533-41 (2012).
Neuzillet C., et al., "FOLFIRI Regimen as Second-/Third-line Chemotherapy in Patients with Advanced Pancreatic Adenocarcinoma Refradory to Gemcitabine and Platinum Salts: A Retrospective Series of 70 Patients." J Clin Oncol. 29: 2011 (Suppl 4; Abstract 272). 2011 Gastrointestinal Cancers Symposium (2011), 2 printed pages.
Nieto J, et. al., "Metastatic Pancreatic Cancer 2008: Is the Glass Less Empty?," Oncologist. 13(5):562-76 (2008) and erratum found at Oncologist 13(6):738 (2008).
NIH National Cancer Institute, "FDA Approves Irinotecan Liposome to Treat Pancreatic Cancer," Nov. 24, 2015 by NCI Staff, 2 printed pages.
No authors listed. "5HT3-receptor Antagonists as Antiemetics in Cancer," Drug Ther Bull. 43(8):57-62 (2005).
Noble C, et al, "Development of Ligand-Targeted Liposomes for Cancer Therapy," Expert Opin Ther Targets. 8(4):335-53 (2004).
Noble C, et al., "Novel Nanoliposomal CPT-11 Infused by Convection-Enhanced Delivery in Intracranial Tumors: Pharmacology and Efficacy," Cancer Res. 66(5):2801-6 (2006).
Noble C, et al., "Pharmacokinetics, Tumor Accumulation and Antitumor Activity of Nanoliposomal Irinotecan Following Systemic Treatment of Intracranial Tumors," Nanomedicine. 9(14):2099-108 (2014).
Noordhuis P, et. al., "5-Fluorouracil Incorporation into RNA and DNA in Relation to Thymidylate Synthase Inhibition of Human Colorectal Cancers," Ann Oncol. 15(7):1025-32 (2004).
Novarino A, et. al., "Oxaliplatin, 5-Fluorouracil, and Leucovorin as Second-Line Treatment for Advanced Pancreatic Cancer," Am J Clin Oncol. 32(1):44-8 (2009).
Oberstein P and Olive K, "Pancreatic Cancer: Why Is It So Hard to Treat?" Ther Adv Gastroenterol. 6(4):321-37 (2013).
O'Brien M, et al., "Phase III Trial Comparing Supportive Care Alone With Supportive Care With Oral Topotecan in Patients With Relapsed Small-Cell Lung Cancer," J Clin Oncol. 24(34):5441-7 (2006).
O'Dwyer P, et al., "Uridine Diphosphate Glucuronosyltransferase (UGT) 1A1 and Irinotecan: Practical Pharmacogenomics Arrives in Cancer Therapy," J Clin Oncol. 24(28):4534-8 (2006).
Oettle H and Lehmann T, "Gemcitabine-Resistant Pancreatic Cancer: A Second-Line Option," Lancet. 387(10018):507-8 (2016). Epub 2015.
Oettle H, et al., "Second-Line Oxaliplatin, Folinic Acid, and Fluorouracil Versus Folinic Acid and Fluorouracil Alone for Gemcitabine-Refractory Pancreatic Cancer: Outcomes From the CONKO-003 Trial," J Clin Oncol. 32(23):2423-9 (2014).
Ogata Y, et. al., "Dosage Escalation Study of S-1 and Irinotecan in Metronomic Chemotherapy against Advanced Colorectal Cancer," Kurume Med J. 56(1-2):1-7 (2009).
Oh S, et al., "Pilot Study of Irinotecan/Oxaliplatin (IROX) Combination Chemotherapy for Patients with Gemcitabine- and

(56) References Cited

OTHER PUBLICATIONS

5-Fluorouracil-Refractory Pancreatic Cancer," Invest New Drugs. 28(3):343-9 (2010), Epub May 15, 2009.
Ohkawa S, et al., "Randomised Phase II Trial of S-1 Plus Oxaliplatin vs S-1 in Patients with Gemcitabine-Refractory Pancreatic Cancer," Br J Cancer. 112(9):1428-34 (2015).
Okusaka T, et al., "Phase II Study of FOLFIRINOX for Chemotherapy-NaÏve Japanese Patients with Metastatic Pancreatic Cancer," Cancer Sci. 105(10):1321-6 (2014).
Olszewski A, et. al., "Phase I Study of Oxaliplatin in Combination with Gemcitabine, Irinotecan, and 5-Fluorouracil/Leucovorin(G-FLIE) in Patients with Metastatic Solid Tumors Including Adenocarcinoma of the Pancreas," J Gastrointest Cancer. 44(2):182-9 (2013).
Oncology NEWS International, "Experts Debate Bolus vs Continuous Infusion 5-FU." Feb. 1, 2003, vol. 12, Issue 2, 3 printed pages.
Onivyde [MM-398] package insert, revision Oct. 22, 2015, retrieved from http://www.accessdata.fda.gov/drugsatfda_docs/label/2015/207793lbl.pdf, 18 pages.
O'Reilly E, et al., "Impact of Prior Irinotecan Exposure on Outcomes of Metastatic Pancreatic Cancer Patients." Poster presented at the American Society of Clinical Oncology Gastrointestinal Cancers Symposium (ASCO GI), San Francisco, CA, Jan. 23-25, 2020, 6 pages.
O'Reilly E, et al., "Real-World Patterns of Care Among Patients With Metastatic Pancreatic Cancer." Poster presented at the American Society of Clinical Oncology Gastrointestinal Cancers Symposium (ASCO GI), San Francisco, CA, Jan. 23-25, 2020, 6 pages.
O'Reilly E, et al., Abstract 666. "Real-World Patterns of Care Among Patients With Metastatic Pancreatic Cancer (mPC)," J Clin Oncol. 38(4_Suppl):666 DOI: 10.1200/JCO.2020.38.4_suppl.666 (2020), 2 printed pages.
O'Reilly E, et al., Abstract 667. "Impact of Prior Irinotecan Exposure on Outcomes of Metastatic Pancreatic Cancer (mPC) Patients," J Clin Oncol. 38(4_Suppl):667 DOI: 10.1200/JCO.2020.38.4_suppl.667 (2020), 2 printed pages.
O'Reilly E, et. al., "A Cancer and Leukemia Group B Phase II Study of Sunitinib Malate in Patients with Previously Treated Metastatic Pancreatic Adenocarcinoma (CALGB 80603)," Oncologist. 15(12):1310-9 (2010).
O'Reilly S, "Topotecan: What Dose, What Schedule, What Route?" Clin Cancer Res. 5(1):3-5 (1999).
Owonikoko T, et al., "A Systematic Analysis of Efficacy of Second-Line Chemotherapy in Sensitive and Refractory Small-Cell Lung Cancer," J Thorac Oncol. 7(5):866-72 (2012).
OXALIPLATIN package insert, revision Nov. 2013, retrieved from https://www.accessdata.fda.gov/drugsatfda_docs/label/2013/022160s009lbl.pdf, 43 pages.
Pal A, et. al., "Preclinical Safety, Pharmacokinetics and Antitumor Efficacy Profile of Liposome-Entrapped SN-38 Formulation," Anticancer Res. 25(1A):331-41 (2005).
Pallis A, et al., "A Multicenter Randomized Phase II Study of the Irinotecan/Gemcitabine Doublet Versus Irinotecan Monotherapy in Previously Treated Patients with Extensive Stage Small-Cell Lung Cancer," Lung Cancer. 65(2):187-91 (2009), Epub Dec. 18, 2008.
Palomaki G, et al., "Can UGT1A1 Genotyping Reduce Morbidity and Mortality in Patients with Metastatic Colorectal Cancer Treated with Irinotecan? An Evidence-Based Review," Genet Med. 11(1):21-34 (2009).
PCT/US2016/047814: PCT International Preliminary Report on Patentability dated Feb. 20, 2018, 6 pages.
PCT/US2016/047814: PCT International Search Report dated Nov. 17, 2016, 3 pages.
PCT/US2016/047827: PCT International Preliminary Report on Patentability dated Feb. 20, 2018, 6 pages.
PCT/US2016/047827: PCT International Search Report dated Nov. 17, 2016, 3 pages.
PCT/GB2017/053293: PCT International Preliminary Report on Patentability dated May 7, 2019, 7 pages.
PCT/GB2017/053293: PCT International Search Report and Written Opinion dated Feb. 2, 2018, 12 pages.
PCT/IB2017/000681: PCT International Preliminary Report on Patentability dated Nov. 20, 2018, 6 pages.
PCT/IB2017/000681: PCT International Search Report and Written Opinion dated Aug. 25, 2017, 8 pages.
PCT/US2005/015349: PCT International Search Report and Written Opinion dated Aug. 18, 2005, 14 pages.
PCT/US2013/045495: PCT International Preliminary Report on Patentability dated Dec. 16, 2014, 8 pages.
PCT/US2013/045495: PCT International Search Report and Written Opinion dated Aug. 22, 2013, 11 pages.
PCT/US2013/046914: PCT International Preliminary Report on Patentability dated Dec. 23, 2014, 7 pages.
PCT/US2013/046914: PCT International Search Report dated Sep. 2, 2013, 3 pages.
PCT/US2013/075513: PCT International Preliminary Report on Patentability dated Jun. 16, 2015, 7 pages.
PCT/US2013/075513: PCT International Search Report dated Jun. 6, 2014, 2 pages.
PCT/US2014/062007: PCT International Preliminary Report on Patentability dated Apr. 26, 2016, 10 pages.
PCT/US2014/062007: PCT International Search Report dated Jan. 9, 2015, 3 pages.
PCT/US2015/064491: PCT International Preliminary Report on Patentability dated Jun. 13, 2017, 7 pages.
PCT/US2015/064491: PCT International Search Report dated Feb. 19, 2016, 4 pages.
PCT/US2016/027515: PCT International Preliminary Report on Patentability dated Oct. 17, 2017, 8 pages.
PCT/US2016/027515: PCT International Search Report dated Jun. 27, 2016, 4 pages.
PCT/US2016/047727: PCT International Preliminary Report on Patentability dated Feb. 27, 2018, 6 pages.
PCT/US2016/047727: PCT International Search Report and Written Opinion dated Nov. 16, 2016, 8 pages.
PCT/US2016/057247: PCT International Preliminary Report on Patentability dated Apr. 17, 2018, 8 pages.
PCT/US2016/057247: PCT International Search Report dated Dec. 23, 2016, 4 pages.
U.S. Appl. No. 11/121,294: Aug. 17, 2009 Nonfinal Office Action, 33 pages.
U.S. Appl. No. 11/121,294: Mar. 12, 2010 Final Office Action, 15 pages.
U.S. Appl. No. 11/121,294: May 19, 2010 Advisory Action, 3 pages.
U.S. Appl. No. 11/121,294: Aug. 4, 2010 Nonfinal Office Action, 14 pages.
U.S. Appl. No. 11/121,294: Dec. 6, 2010 Final Office Action, 17 pages.
U.S. Appl. No. 11/121,294: Apr. 13, 2011 Nonfinal Office Action, 10 pages.
U.S. Appl. No. 11/121,294: Jul. 12, 2011 Examiner Interview Summary, 3 pages.
U.S. Appl. No. 11/121,294: Nov. 23, 2011 Final Office Action, 20 pages.
U.S. Appl. No. 11/601,451: Jan. 11, 2010 Nonfinal Office Action, 14 pages.
U.S. Appl. No. 11/601,451: Aug. 27, 2010 Final Office Action, 17 pages.
U.S. Appl. No. 11/601,451: Jul. 12, 2011 Examiner Interview Summary, 4 pages.
U.S. Appl. No. 13/416,204: May 8, 2012 Pre-Interview Communication, 4 pages.
U.S. Appl. No. 13/416,204: Jun. 29, 2012 Interview Summary and First Action Interview Office Action, 6 pages.
U.S. Appl. No. 13/654,373: Aug. 12, 2013 Nonfinal Office Action and Interview Summary, 10 pages.
U.S. Appl. No. 14/151,632: Apr. 18, 2016 Nonfinal Office Action, 9 pages.
U.S. Appl. No. 14/175,365: Jun. 26, 2014 Nonfinal Office Action, 20 pages.
U.S. Appl. No. 14/406,776: Feb. 26, 2016 Nonfinal Office Action, 9 pages.

(56) References Cited

OTHER PUBLICATIONS

U.S. Appl. No. 14/632,422: Jan. 10, 2017 Nonfinal Office Action, 18 pages.
U.S. Appl. No. 14/812,950: Oct. 2, 2015 Pre-Interview Communication, 3 pages.
U.S. Appl. No. 14/844,500: Dec. 16, 2015 Nonfinal Office Action, 25 pages.
U.S. Appl. No. 14/851,111: Feb. 25, 2016 Nonfinal Office Action, 13 pages.
U.S. Appl. No. 14/879,302: Aug. 15, 2016 Nonfinal Office Action, 30 pages.
U.S. Appl. No. 14/879,302: Dec. 15, 2016 Nonfinal Office Action, 14 pages.
U.S. Appl. No. 14/879,358: Dec. 28, 2015 Nonfinal Office Action, 20 pages.
U.S. Appl. No. 14/879,358: Jul. 12, 2016 Nonfinal Office Action, 14 pages.

* cited by examiner

MS-751 cells viability (1000cells/well in 384-well plate) treated with SN-38 and with different PARP inhibitors (0.33 ug/ml) for 24hrs, washed and incubated for additional 72hrs with fresh media BT20 cell survival treated with SN-38 and Talazoparib

HCC38 cell survival treated with SN-38 and Talazoparib

Days 2,3,4

Days 3,4,5

Days 4,5,6

—○— MM-398 15 mg/kg qw + veliparib 50 mg/kg qd x 3 days

--▽-- MM-398 28 mg/kg qw + veliparib 50 mg/kg qd x 3 days

—□— MM-398 50 mg/kg qw + veliparib 50 mg/kg qd x 3 days

| Dose Escalation Cohorts | | | |
|---|---|---|---|
| Dose Level | Veliparib Dose (mg BID) | Veliparib Start Day | nal-IRI Dose (salt) ($mg/m^2$ q2w) |
| 1 | 100 | Day 5 | 80 |
| 2 | 200 | Day 5 | 80 |
| 3 | 200 | Day 3 | 80 |
| 4 | 300 | Day 3 | 80 |
| 5 | 400 | Day 3 | 80 |

COMBINATION THERAPY FOR CANCER TREATMENT

CROSS REFERENCE TO RELATED APPLICATIONS

This application is a continuation of U.S. application Ser. No. 16/586,609, filed on Sep. 27, 2019, which is a continuation of U.S. application Ser. No. 15/852,551, filed on Dec. 22, 2017, now U.S. Pat. No. 10,478,428, which is a continuation of U.S. application Ser. No. 15/337,274, filed on Oct. 28, 2016, now U.S. Pat. No. 9,895,365, which is a continuation of PCT Application No. PCT/US2016/047827, filed on Aug. 19, 2016, which claims the benefit of priority under 35 U.S.C. § 119 to U.S. Provisional Application Ser. No. 62/323,422, filed on Apr. 15, 2016, 62/308,924, filed on Mar. 16, 2016, 62/269,511, filed on Dec. 18, 2015, 62/269,756, filed on Dec. 18, 2015, 62/207,709, filed on Aug. 20, 2015, and 62/207,760, filed on Aug. 20, 2015. The contents of each of the foregoing applications are incorporated herein by reference in their entirety.

TECHNICAL FIELD

This invention relates to the treatment of cancer with a Poly(ADP-ribose) polymerase (PARP) inhibitor and a topoisomerase inhibitor.

BACKGROUND

Liposomal irinotecan and PARP inhibitors are therapies useful in the treatment of cancer. Liposome encapsulated irinotecan formulations of the topoisomerase inhibitor irinotecan provide sustained exposure of irinotecan and the metabolite SN-38 in a tumor. ONIVYDE (irinotecan liposome injection) is an example of liposomal irinotecan recently approved in the United States for the treatment of patients with metastatic adenocarcinoma of the pancreas after disease progression following gemcitabine-based therapy. Poly(ADP-ribose) polymerases are a family of enzymes involved in DNA repair believed to act via two mechanisms: catalytic inhibition and trapping of PARP-DNA complexes, and inhibition of this repair pathway can result in cell death following DNA damage. PARP inhibitors are a new class of chemotherapeutic agents currently in development for the treatment of various cancer types.

While certain combinations of PARP and topoisomerase inhibitors have shown to be synergistic in in vitro assays, the clinical development of PARP inhibitor and topoisomerase inhibitor combinations has been limited due to increased toxicities and resultant dose reductions, thereby limiting the potential clinical utility of the combination. For example, significant myelosuppression was seen in a dose-escalation study of veliparib and topotecan, wherein the maximum tolerated dose was exceeded at the first planned dose level. Most PARP inhibitors are being developed to date solely as monotherapies. As a result, there is a need for methods to safely and effectively combine a PARP inhibitor with a Top1 inhibitor to treat cancer.

SUMMARY

The present disclosure provides methods of treating cancer by administering a topoisomerase inhibitor and a PARP inhibitor with reduced peripheral toxicity. This can be accomplished by administering the topoisomerase inhibitor in a form (e.g., liposomal irinotecan) that prolongs accumulation of the topoisomerase inhibitor in a tumor relative to sites outside the tumor, and then subsequently administering the PARP inhibitor(s) to the patient after an interval between the administration of the topoisomerase inhibitor and the PARP inhibitor. The interval can be selected to provide enough time for the topoisomerase inhibitor (e.g., irinotecan and/or its metabolite SN-38) to clear plasma or tissue outside of the tumor to a greater extent than inside the tumor. Preferably, the interval is an effective topoisomerase-1 inhibitor plasma clearing interval. As used herein, the term "effective topoisomerase-1 inhibitor plasma clearing interval" (e.g., irinotecan plasma clearing interval) is that interval between concluding the administration of a topoisomerase-1 inhibitor formulation (e.g., liposomal irinotecan) and initiating the administration of one or more PARP inhibitors, where the time interval is selected to allow sufficient clearance of the topoisomerase-1 inhibitor (e.g., irinotecan or its active metabolite SN-38) from the blood plasma (or peripheral tissue) but allows an effective quantity of the topoisomerase-1 inhibitor (e.g., irinotecan and/or SN38) to remain in one or more tumors within the patient during the subsequent administration of the PARP inhibitor in an amount effective to provide a desired effect on the tumor (e.g., heightened combined toxicity localized within the tumor). Preferably, the PARP inhibitor is administered after an irinotecan plasma clearing interval of 3-5 days (e.g., 3, 4 or 5 days) after completing the administration of liposomal irinotecan on days 1 and 15 during each of one or more 28-day treatment cycles.

Methods of treating cancer disclosed herein include the treatment of solid tumors. In certain examples, the cancer treated can be selected from the group consisting of cervical cancer, ovarian cancer, triple negative breast cancer, non-small cell lung cancer, small cell lung cancer, gastrointestinal stromal tumors gastric cancer, pancreatic cancer, colorectal cancer, and a neuroendocrine cancer. Preferably, the cancer is cervical cancer.

The topoisomerase inhibitor can be provided as a liposome formulation. Preferably, the topoisomerase inhibitor is a liposomal irinotecan. The liposomal irinotecan can provide an irinotecan terminal elimination half-life of 26.8 hours and a maximal irinotecan plasma concentration of 38.0 micrograms/ml. In some examples, the liposomal irinotecan can include irinotecan sucrose octasulfate encapsulated within phospholipid vesicles having a size of about 110 nm. For example, the liposomal irinotecan can be the product ONIVYDE® (irinotecan liposome injection) (Merrimack Pharmaceuticals, Inc, Cambridge, Mass.), previously designated "MM-398." The PARP inhibitor can include one or more compounds selected from the group consisting of niraparib, olaparib, veliparib, and rucaparib, preferably veliparib or olaparib.

The topoisomerase-1 inhibitor is preferably a liposomal irinotecan (e.g., MM-398), which can be administered at dose of 80 mg/$m^2$ (salt) irinotecan once every 2 weeks in combination with a PARP inhibitor (e.g., veliparib, olaparib, niraparib or rucaparib) administered daily during each two week cycle starting 3-5 days after administration of liposomal irinotecan without administering the PARP inhibitor on days when the liposomal irinotecan is administered (e.g., without administering the PARP inhibitor 1, 2 or 3 days before the next liposomal irinotecan administration). Preferably, the PARP inhibitor is not administered within 3 days of (i.e., neither 3 days after nor 3 days before) the administration of liposomal irinotecan.

Specific methods of treating a cancer provided herein include administering an antineoplastic therapy consisting of the administration of liposomal irinotecan every 2 weeks (e.g., on days 1 and 15 of a 28-day treatment cycle), and the administration of a PARP inhibitor one or more times per day (e.g., twice per day) for one or more days (e.g., 7-9 days) starting at least 3 days (e.g., 3, 4 or 5 days) after each administration of the liposomal irinotecan, without administering other antineoplastic agents during the antineoplastic therapy. For example, one antineoplastic therapy is a 28-day treatment cycle consisting of: administering 70 mg/m$^2$ MM-398 liposomal irinotecan (free base) on days 1 and 15, and administering a therapeutically effective amount of the PARP inhibitor (e.g., 50-400 mg twice per day for veliparib) on each of days 5-12 and days 19-25 of the treatment cycle, where no other antineoplastic agent is administered during the treatment cycle. Another antineoplastic therapy is a 28-day treatment cycle consisting of: administering 70 mg/m$^2$ MM-398 liposomal irinotecan (free base) on days 1 and 15, and administering a therapeutically effective amount of the PARP inhibitor (e.g., 50-400 mg twice per day for veliparib) on each of days 3-12 and days 17-25 of the treatment cycle, where no other antineoplastic agent is administered during the treatment cycle.

In some examples, liposomal irinotecan and a PARP inhibitor can be combined in an antineoplastic therapy for the treatment of a solid tumor, comprising a 28-day antineoplastic therapy treatment cycle consisting of: administering the liposomal irinotecan on days 1 and 15 of the treatment cycle, and administering the PARP inhibitor on one or more days starting at least 3 days after the liposomal irinotecan and ending at least 1 day prior to administration of additional liposomal irinotecan. In some examples, the PARP inhibitor is not administered for at least 3 days after the administration of liposomal irinotecan. For example, the PARP inhibitor can be administered on one or more of days 5-12 of the antineoplastic therapy treatment cycle, and administered on one or more of days 19-25 of the antineoplastic therapy treatment cycle. In some examples, the PARP inhibitor is administered on one or more of days 3-12 of the antineoplastic therapy treatment cycle, and administered on one or more of days 17-25 of the antineoplastic therapy treatment cycle. In some examples, the PARP inhibitor is not administered within 3 days before or after the administration of the liposomal irinotecan. In addition, therapeutically effective doses of the topoisomerase inhibitor and PARP inhibitor compounds are provided herein. In some examples, each administration of liposomal irinotecan is administered at a dose of 80 mg/m$^2$ (salt) of MM-398. In some examples, each administration of the PARP inhibitor is administered at a dose of from about 20 mg/day to about 800 mg/day. Each administration of the PARP inhibitor can be administered once or twice daily at a dose of from about 20 mg/day to about 400 mg/day.

DETAILED DESCRIPTION

Figure 1A:
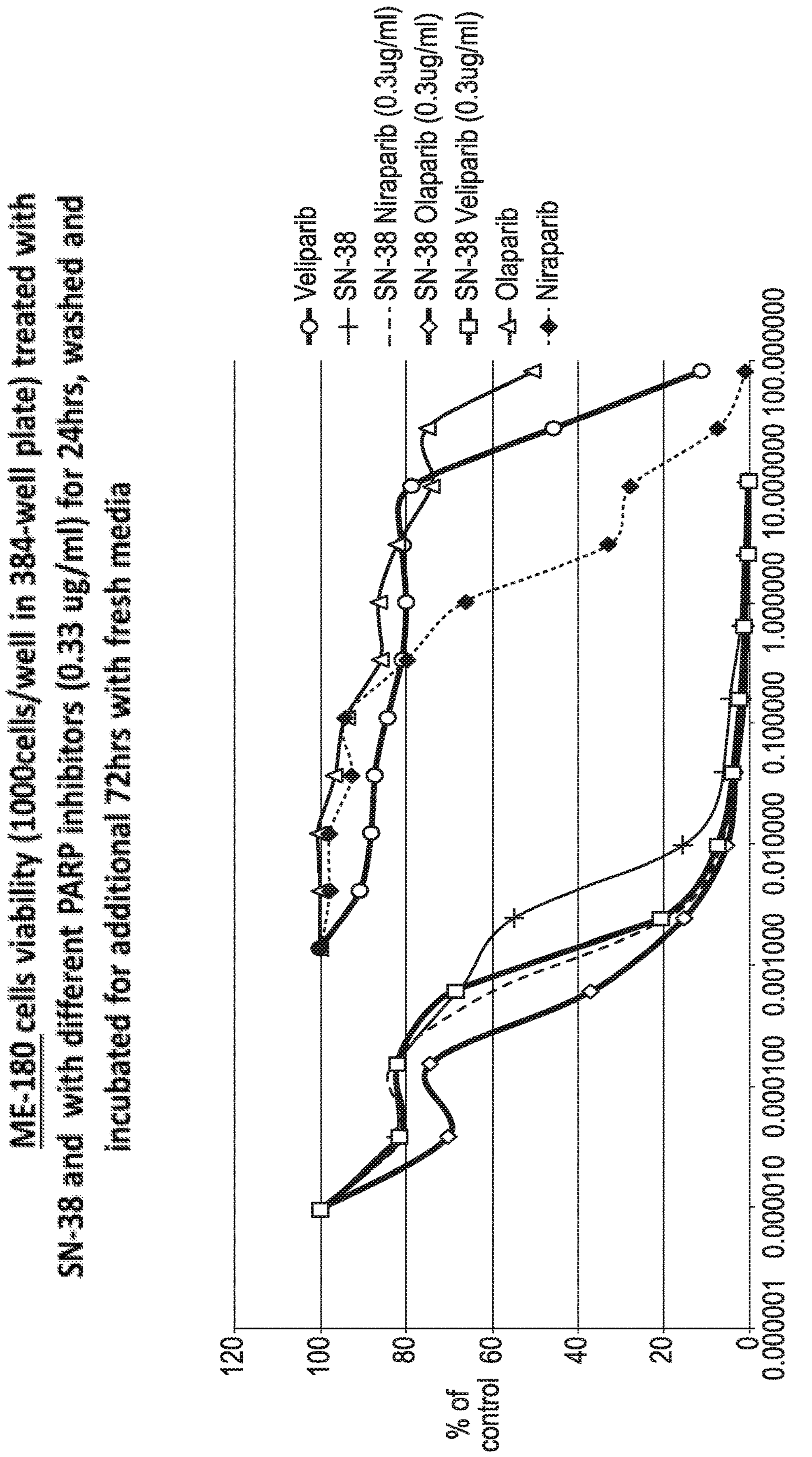
FIG. 1A is a graph showing the results of a cell viability in vitro measurement of ME-180 human cervical cancer cells treated with the topoisomerase 1 inhibitor SN-38 and various PARP inhibitors.
Figure 1B:
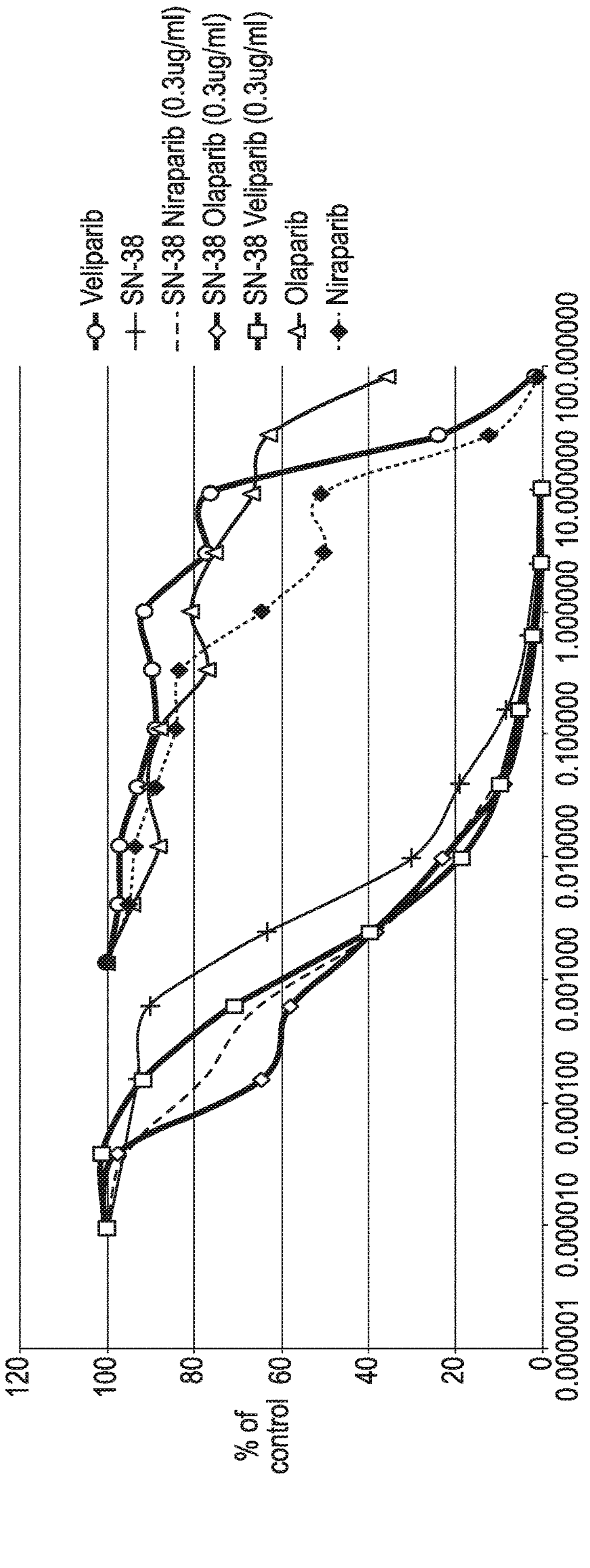
FIG. 1B is a graph showing the results of a cell viability in vitro measurement of MS-751 human cervical cancer cells treated with the topoisomerase 1 inhibitor SN-38 and various PARP inhibitors.
Figure 1C:
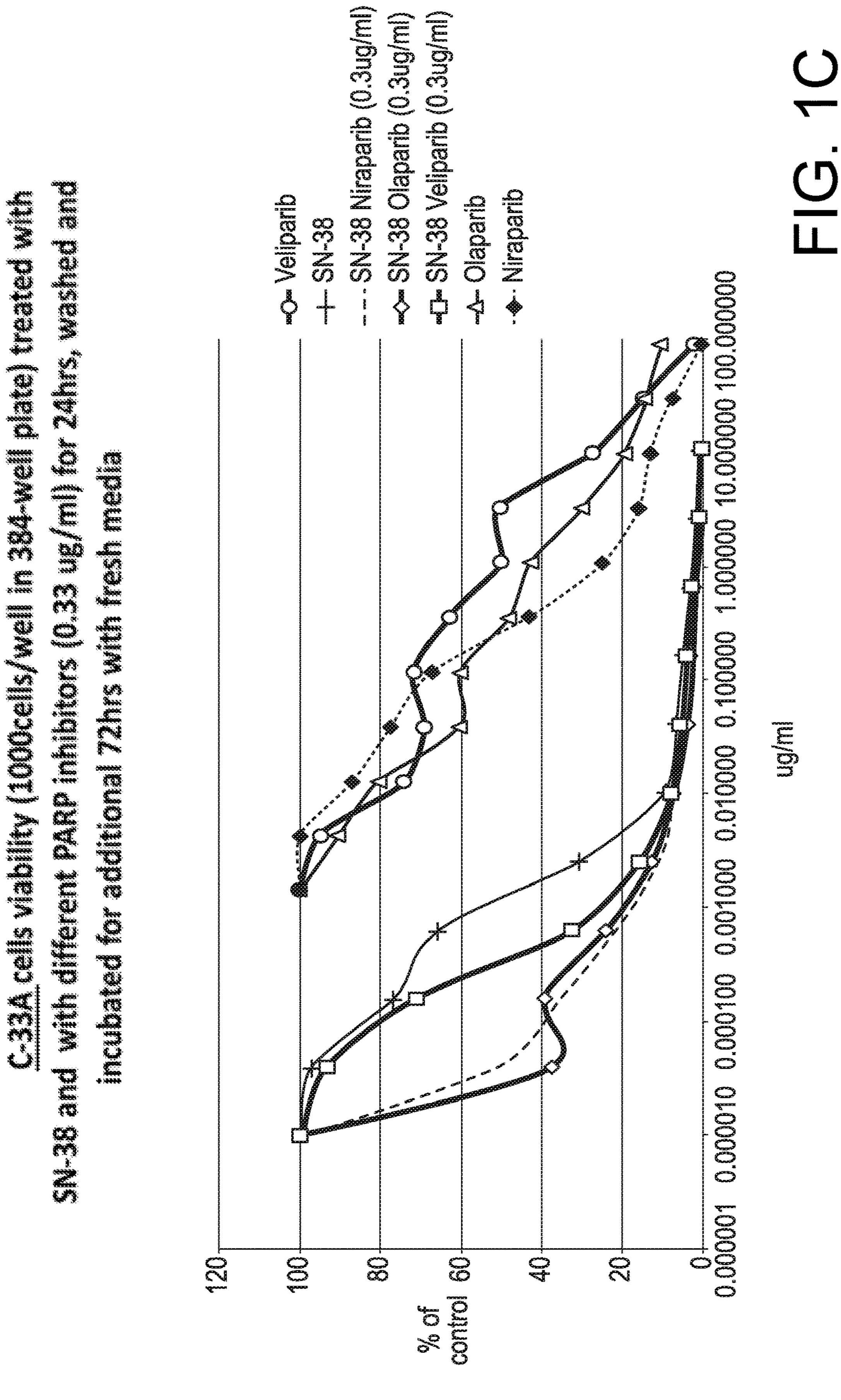
FIG. 1C is a graph showing the results of a cell viability in vitro measurement of C-33A human cervical cancer cells treated with the topoisomerase 1 inhibitor SN-38 and various PARP inhibitors.
Figure 1D:
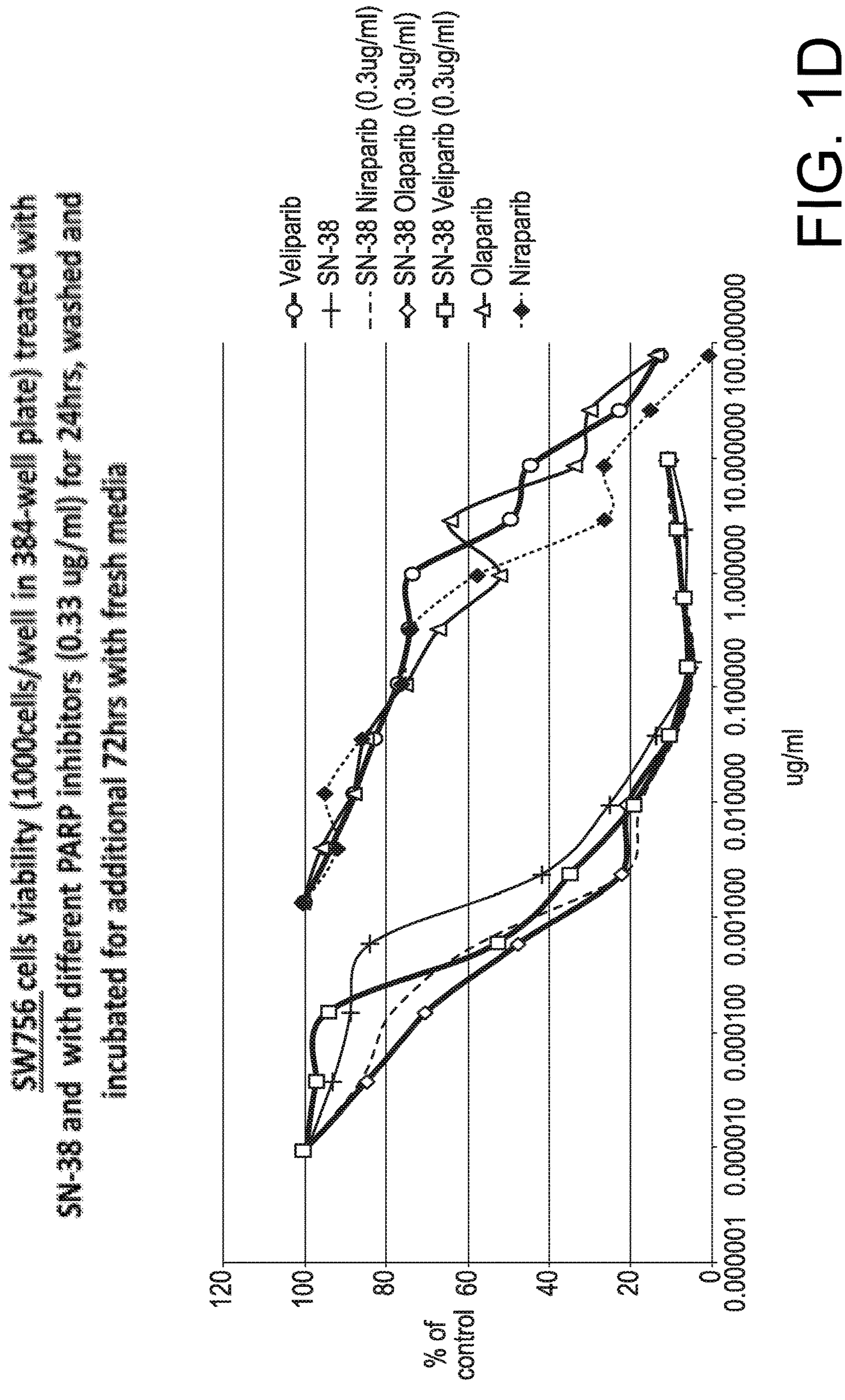
FIG. 1D is a graph showing the results of a cell viability in vitro measurement of SW756 human cervical cancer cells treated with the topoisomerase 1 inhibitor SN-38 and various PARP inhibitors.
Figure 1E:
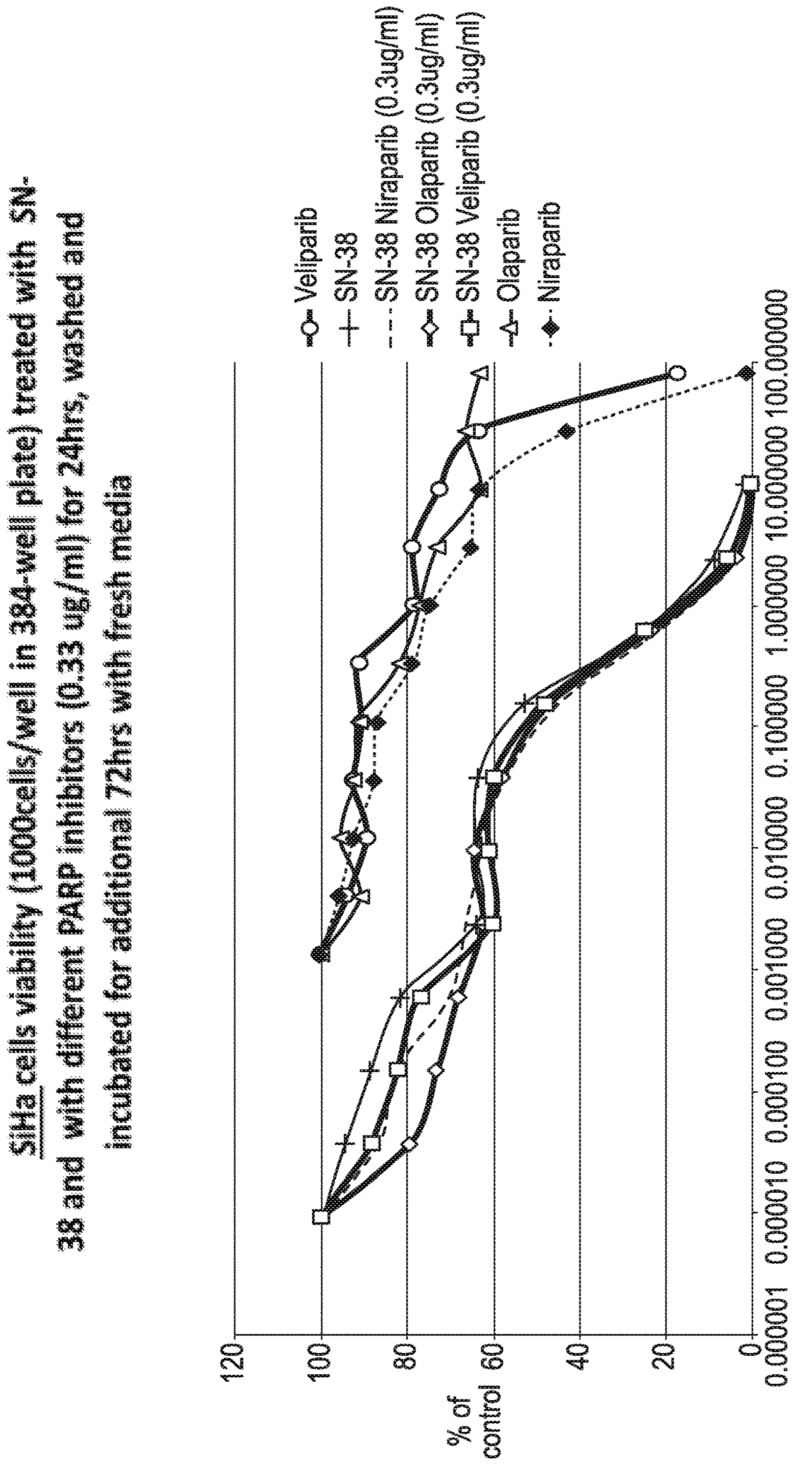
FIG. 1E is a graph showing the results of a cell viability in vitro measurement of SiHa human cervical cancer cells treated with the topoisomerase 1 inhibitor SN-38 and various PARP inhibitors.

The present disclosure provides for methods of administering a combination of a topoisomerase-1 (Top1) inhibitor (e.g., irinotecan and/or its metabolite SN-38) and a PARP inhibitor to a tumor with reduced peripheral toxicity. The Top1 inhibitor can be administered in a liposome formulation resulting in the prolonged accumulation of the Top1 inhibitor in a solid tumor compared to peripheral plasma and/or healthy organs. Subsequently, a PARP inhibitor can be administered after a period of time permitting a reduction in the amount of the Top1 inhibitor outside the tumor relative to the amount of Top1 inhibitor within the tumor. Preferably, the Top1 inhibitor is administered as a liposomal irinotecan that provides SN-38 to a solid tumor.

Methods of treating a cancer are provided, as well as therapeutic uses of PARP inhibitor compounds in combination with liposomal irinotecan formulations for the treatment of cancer, particularly cancer comprising solid tumors. These uses and methods can provide a treatment regimen comprising: (a) administering to a patient in need thereof an effective amount of an irinotecan liposomal formulation; and (b) after completion of the administration of the Top1 inhibitor, administering to the patient an effective amount of a PARP inhibitor, wherein the PARP inhibitor is administered to the patient following an interval that allows for a reduction in peripheral toxicity as compared to simultaneous administration of the Top1 inhibitor and the PARP inhibitor. The interval can be selected to provide time for sufficient clearance of the Top1 inhibitor (e.g., either or both of irinotecan and SN-38) from the blood plasma to avoid peripheral toxicity due to the synergistic toxic effects of the combination of Top1 inhibitor and PARP inhibitor, while allowing an effective quantity of Top1 inhibitor to remain in one or more tumors within the patient for the subsequent administration of the PARP inhibitor to have a desired synergistic therapeutic effect. This treatment regimen can preferably provide one or more attributes, which may include increased efficacy of the combination as compared to single agent treatment; reduced side effects, dosing the drugs at a higher dose compared with administration of the combination of a PARP inhibitor and a non-liposomal Top1 inhibitor.

The uses and methods disclosed herein are based in part on experiments evaluating the combination of a topoisomerase 1 inhibitor (e.g., liposomal irinotecan or SN-38) and a PARP inhibitor in both pre-clinical and human clinical studies. The topoisomerase 1 inhibitor was administered in certain in vitro animal models using a formulation delivering a more prolonged exposure of the topoisomerase 1 inhibitor (e.g., irinotecan and/or the irinotecan active metabolite designated SN-38) within solid tumors than in peripheral tissue and plasma outside the tumor. Combinations of the topoisomerase 1 inhibitor SN38 and/or irinotecan and PARP inhibitor compounds were tested in various in vitro experiments. As detailed in Example 1, the in vitro testing of multiple combinations of a topoisomerase 1 inhibitor (SN38) and various PARP inhibitors in more than 20 different cancer cell lines (including cervical, breast, ovarian, colorectal, pancreatic, and small cell lung cancer cell lines) all demonstrated decreased cancer cell line viability (FIGS. 1A, 1B, 1C, 1D, 1E, 2A, 2B, 2C, 2D, 2E, and 13A). The liposomal irinotecan (MM398) demonstrated greater tumor volume reduction than non-liposomal (free) irinotecan (CPT11) in mouse xenograft studies across multiple types of cancer cell lines (including breast, ovarian, colorectal and pancreatic cancer cell lines).

As detailed in Example 2, the tolerability of a topoisomerase 1 inhibitor (liposomal irinotecan) administered in combination with various PARP inhibitors was evaluated by measuring the change in animal (mouse) body weight in multiple murine models by comparing various dosing schedules. In some experiments, both liposomal irinotecan and a PARP inhibitor were administered together on the same day (day 1). In other experiments, the PARP inhibitor was first administered daily starting 2, 3 or 4 days after each administration of the liposomal irinotecan. The PARP inhibitor was administered for multiple consecutive days (e.g., 3 consecutive days), and not administered on the same day as the topoisomerase 1 inhibitor. As detailed in multiple experiments herein, administration of the PARP inhibitor at least one day after the liposomal irinotecan resulted in improved tolerability of comparable combined doses of the PARP inhibitor and liposomal irinotecan (MM-398) as measured by change in percent bodyweight in the animal (e.g., FIGS. 6A, 6B, 6C, 6D, 8A, and 8B). Delaying the administration of the PARP inhibitor 2, 3 or 4 days after administration of the liposomal irinotecan led to greater overall tolerability of a combined administration of the liposomal irinotecan and the PARP inhibitor, compared to the administration of the liposomal irinotecan and the PARP inhibitor on the same day. For example, administration of veliparib on days 2, 3 and 4 after administration of liposomal irinotecan on day 1 resulted in successively increased tolerability (measured as higher percent mouse bodyweight) of the combination of these two drugs (observed at 15 mg/kg liposomal irinotecan dose on day 1 followed by veliparib dosing on days 2, 3 and 4 (FIG. 5A); at 28 mg/kg liposomal irinotecan dosage on day 1 followed by veliparib dosing on days 3, 4, and 5 (FIGS. 5B and 8B), or followed by veliparib dosing on days 2, 3 and 4 (FIG. 8B); and at 50 mg/kg liposomal irinotecan dose on day 1 followed by veliparib dosing on days 4, 5 and 6 (FIG. 5C), or followed by veliparib dosing on days 2, 3 and 4 or followed by veliparib dosing on days 3, 4, and 5 (FIG. 8A)). Similarly, administering olaparib starting on days 2 or 3 after MM398 resulted in comparable or improved tolerability compared to administration of both agents on day 1. For example, administering a 200 mg/kg dose of olaparib to mice on days 2, 3, 4 and 5 after administration of 10 mg/kg MM398 liposomal irinotecan on day 1 resulted in a lower reduction in bodyweight than administering the same doses of both MM398 and olaparib on days 1, 2, 3 and 4.

Combinations of a topoisomerase 1 inhibitor (SN38 and/or irinotecan) and PARP inhibitor compounds were tested in various preclinical in vivo experiments to evaluate the effectiveness of the administration of various PARP inhibitors starting 3 or 4 days after administration of the liposomal topoisomerase 1 inhibitor MM398. As detailed in Example 3, the administration of liposomal irinotecan (MM398) on day 1 followed by the PARP inhibitor veliparib on either days 3, 4 and 5 or days 4, 5, and 6, resulted in decreased tumor volume and extended percent survival in mouse xenograft models of cervical cancer using two different cell lines (MS751 and C33A) (FIGS. 7A, 7B, 9A, 9B, 10 and 11).

Based in part on these experiments, methods of treating human cancer include the administration of a PARP inhibitor one or more days (preferably 2, 3, 4, 5 or 6 days) after the administration of liposomal topoisomerase inhibitor such as liposomal irinotecan. Preferably, the PARP inhibitor and the liposomal irinotecan are not administered on the same day. Example 5 provides preferred embodiments for the use of liposomal irinotecan and one or more PARP inhibitors for the treatment of human cancer, such as cervical cancer, while other embodiments (e.g., Table 3) are also provided.

Topoisomerase Inhibitors, Including Liposomal Irinotecan and Camptothecin Conjugates The topoisomerase inhibitor can be administered in any form that provides for the prolonged retention of a topoisomerase-1 inhibitor activity within a tumor compared to outside the tumor, after administration of the topoisomerase inhibitor. For example, the topoisomerase inhibitor can be a formulation that delivers SN-38 to a tumor cell in vivo, administered in an amount and manner providing a higher concentration of the SN-38 within the tumor than outside the tumor for a period of time after administration of the topoisomerase inhibitor. Suitable formulations of topoisomerase inhibitors include conjugate molecules of a topoisomerase inhibitor (e.g., camptothecin conjugated to a polymer or antibody), liposomes containing a topoisomerase inhibitor or other targeted release formulation technologies. The Top1 inhibitor is preferably formulated to provide prolonged accumulation in a tumor site, compared to accumulation in healthy (non-cancer) tissue outside the tumor site (e.g., in the plasma and/or healthy organs such as colon, duodenum, kidney, liver, lung and spleen). Various Top1 inhibitor liposomal formulations are described in U.S. Pat. No. 8,147,867 and U.S. Patent Application Publication No. 2015/0005354, both of which are incorporated herein by reference.

In one embodiment, the topoisomerase inhibitor is SN-38, camptothecin or a compound that is converted to SN-38 within the body, such as irinotecan. Irinotecan and SN-38 are examples of Top1 inhibitors. Irinotecan is converted by esterase enzymes into the more active metabolite, SN-38. The chemical name of irinotecan is (S)-4,11-diethyl-3,4,12,14-tetrahydro-4-hydroxy-3,14-dioxo1H-pyrano[3',4':6,7]-indolizino[1,2-b]quinolin-9-yl-[1,4'bipiperidine]-1'-carboxylate. Irinotecan hydrochloride trihydrate is also referred to by the name CPT-11 and by the trade name CAMPTOSAR®.

The topoisomerase inhibitor can be camptothecin conjugated to a biocompatible polymer such as a cyclodextrin or cyclodextrin analog (e.g., sulfonated cyclodextrins). For example, the topoisomerase inhibitor can be a cyclodextrin-containing polymer chemically bound to a camptothecin, irinotecan, SN-38 or other topoisomerase 1 inhibitor compound. A cyclodextrin-camptothecin conjugated topoisomerase 1 inhibitor can be administered at a pharmaceutically acceptable dose including 6, 12, or 18 mg/m2 weekly administration, or 12, 15 or 18 mg/m2 biweeekly administration. Examples of camptothecin-cyclodextrin conjugate topoisomerase 1 inhibitors (e.g., the cyclodextrin-containing polymer conjugate with camptothecin designated "CRLX101"), and related intermediates for preparing the same, are disclosed, for example, in Greenwald et al., Bioorg. Med. Chem., 1998, 6, 551-562, as well as United States Patent Application 2010/0247668, United States Patent Application 2011/0160159 and United States Patent Application 2011/0189092

The topoisomerase inhibitor can also be a liposomal formulation of a topoisomerase inhibitor such as irinotecan, camptothecin or topotecan. Liposomal irinotecan (e.g., MM-398, also called "nal-IRI") is a highly stabilized liposomal formulation of irinotecan that provides for sustained exposure of irinotecan, and the active metabolite SN-38 in the tumor to a higher proportion of cells during the more sensitive S-phase of the cell cycle. MM-398 is a liposomal irinotecan that has shown promising preclinical and clinical activity in a range of cancer types, and was recently approved in the United States in combination with 5-FU/LV for patients with metastatic adenocarcinoma of the pancreas after disease progression following gemcitabine-based therapy. Compared with free irinotecan, nal-IRI has an extended PK profile with prolonged local tumor exposure of MM-398 and SN-38. Since SN-38 is cleared more quickly from normal tissues than from tumor, it is hypothesized that delayed dosing of veliparib relative to MM-398 will allow for the expected window of maximum irinotecan-induced toxicity to pass in the absence of concurrent veliparib toxicity. However, the tumor levels of SN-38 are predicted to be sustained upon subsequent veliparib dosing, therefore maintaining the ability of both drugs to act on tumor tissue simultaneously and maintain synergy.

One suitable liposomal Top1 inhibitor formulation is liposomal irinotecan available under the brand name ONIVYDE® (irinotecan liposome injection) (Merrimack Pharmaceuticals, Inc, Cambridge, Mass.), previously designated "MM-398" prior to FDA approval, and liposomal irinotecan products that are bioequivalent to ONIVYDE. The ONIVYDE/MM-398 (irinotecan liposome injection) includes irinotecan as an irinotecan sucrosofate salt encapsulated in liposomes for intravenous use. The drug product liposome is a small unilamellar lipid bilayer vesicle, approximately 110 nm in diameter, which encapsulates an aqueous space which contains irinotecan in a gelated or precipitated state, as the sucrosofate salt. The liposome carriers are composed of 1,2-distearoyl-sn-glycero-3-phosphocholine (DSPC), 6.81 mg/mL; cholesterol, 2.22 mg/mL; and methoxy-terminated polyethylene glycol (MW 2000)-distearoylphosphatidylethanolamine (MPEG-2000-DSPE), 0.12 mg/mL. Each mL also contains 2-[4-(2-hydroxyethyl) piperazin-1-yl]ethanesulfonic acid (HEPES) as a buffer, 4.05 mg/mL; sodium chloride as isotonicity reagent, 8.42 mg/mL. ONIVYDE/MM-398 is believed to include about 80,000 molecules of irinotecan in a gelated or precipitated state as a sucrosofate salt encapsulated in a liposome of about 100 nm in diameter.

As used herein, unless otherwise indicated, the dose of irinotecan in ONIVYDE/MM-398 refers to the dose of irinotecan based on the molecular weight of irinotecan hydrochloride trihydrate (i.e., "(salt)" dose), unless clearly indicated otherwise. Alternatively, the irinotecan dose in ONIVYDE/MM-398 may also be expressed as the irinotecan free base (i.e., "(base)" dose). Converting a dose based on irinotecan (salt) dose to an irinotecan (base) dose based on irinotecan free base is accomplished by multiplying the dose based on irinotecan hydrochloride trihydrate with the ratio of the molecular weight of irinotecan free base (586.68 g/mol) and the molecular weight of irinotecan hydrochloride trihydrate (677.19 g/mol). This ratio is 0.87 which can be used as a conversion factor. For example, the 80 $mg/m^2$ irinotecan (salt) dose of ONIVYDE/MM-398 refers to the amount of irinotecan based on irinotecan hydrochloride trihydrate, and is equivalent to a 69.60 $mg/m^2$ irinotecan (base) dose of ONIVYDE/MM-398 based on irinotecan free base (80×0.87). In the clinic this is rounded to 70 $mg/m^2$ to minimize any potential dosing errors. Similarly, a clinical dose of 120 $mg/m^2$ (salt) dose of ONIVYDE/MM-398 (based on the corresponding amount of irinotecan hydrochloride trihydrate providing the same amount of irinotecan free base) is equivalent to 100 $mg/m^2$ (base) dose of ONIVYDE/MM-398 (based on the actual amount of irinotecan free base administered in the liposomal irinotecan).

ONIVYDE/MM-398 has been shown to improve the pharmacokinetic and safety profile of the free irinotecan, through high retention of the irinotecan molecules within the liposome, by extending the half-life of irinotecan in the plasma, and increased exposure of tumor cells to irinotecan compared with other organs. Table 1 below provides a summary of median (% IQR)*total irinotecan and SN-38 pharmacokinetic parameters observed in patients with solid tumors after administration of ONIVYDE/MM-398 at a dose of 80 $mg/m^2$ irinotecan (salt) dose administered once every 2 weeks.

TABLE 1

| | Total Irinotecan | | | | | SN-38 | | |
|---|---|---|---|---|---|---|---|---|
| Dose ($mg/m^2$) | $C_{max}$ [μg/ml] | $t_{1/2}$ [h]$^\dagger$ | $AUC_{0-\infty}$ [h·μg/ml]$^\dagger$ | $V_d$ [$L/m^2$]$^\dagger$ | CL [L $h/m^2$]$^\dagger$ | $C_{max}$ [ng/ml] | $t_{1/2}$ [h]$^\dagger$ | $AUC_{0-\infty}$ [h·ng/ml]$^\dagger$ |
| 80 (n = 25) | 38.0 (36%) | 26.8 (110%) | 1030 (169%) | 2.2 (55%) | 0.077 (143%) | 4.7 (89%) | 49.3 (103%) | 587 (69%) |

$$*\%IQR\text{: \% Interquartile Ratio} = \frac{\text{Interquartile-range}}{\text{Median}} \cdot 100\%$$

$^\dagger t_{1/2}$, $AUC_{0-\infty}$ and $V_d$ were only calculated for a subset of patients with sufficient number of samples in the terminal phase: n = 23 for total irinotecan; n = 13 for SN-38.

$C_{max}$: Maximum plasma concentration $t_{1/2}$: Terminal elimination half-life $AUC_{0-\infty}$: Area under the plasma concentration curve extrapolated to time infinity $V_d$: Volume of distribution For ONIVYDE/MM-398, over the dose range of 60 to 180 $mg/m^2$, the maximum concentrations of both total irinotecan and SN-38 increase linearly with dose. The AUCs of total irinotecan increase linearly with dose; the AUCs of SN-38 increase less than proportionally with dose. The half-lives of both total irinotecan and SN-38 do not change with dose. In a pooled analysis from 353 patients, higher plasma SN-38 $C_{max}$ was associated with increased likelihood of experiencing neutropenia, and higher plasma total irinotecan $C_{max}$ was associated with increased likelihood of experiencing diarrhea. Direct measurement of liposomal irinotecan shows that 95% of irinotecan remains liposome-encapsulated during circulation. The volume of distribution of MM-398 80 $mg/m^2$ is 2.2 $L/m^2$. The volume of distribution of Irinotecan HCl is between 110 $L/m^2$ (dose=125 $mg/m^2$) and 234 $L/m^2$ (dose=340 $mg/m^2$). The plasma protein binding of MM-398 is <0.44% of the total irinotecan in MM-398. The plasma protein binding of irinotecan HCl is 30% to 68% and approximately 95% of SN-38 is bound to human plasma proteins. The plasma clearance of total irinotecan from MM-398 80 $mg/m^2$ is 0.077 $L/h/m^2$ with a terminal half live of 26.8 h. Following administration of irinotecan HCl 125 $mg/m^2$, the plasma clearance of irinotecan is 13.3 $L/h/m^2$ with a terminal half live of 10.4 h.

Examples of an effective amount of liposomal irinotecan provided as MM-398 include doses (salt) from about 60 $mg/m^2$ to about 120 $mg/m^2$, including doses of 70, 80, 90, 100, 110 or 120 $mg/m^2$ (based on the weight of irinotecan hydrochloride trihydrate salt) and doses of 50, 60, 70, 80, 95, and 100 $mg/m^2$ (based on the weight of irinotecan free base), each given once every two (2) weeks (e.g., on days 1 and 15 of a 28 day antineoplastic treatment cycle). In some embodiments, the effective amount of MM-398 is about 80 $mg/m^2$ (salt), optionally administered in combination with 400 $mg/m^2$ of leucovorin over 30 minutes, followed by intravenous administration of 2400 $mg/m^2$ of 5-fluorouracil as an infusion over 46 hours. In some embodiments, the effective amount of MM-398 is about 90 $mg/m^2$ (free base).

Figure 16A:
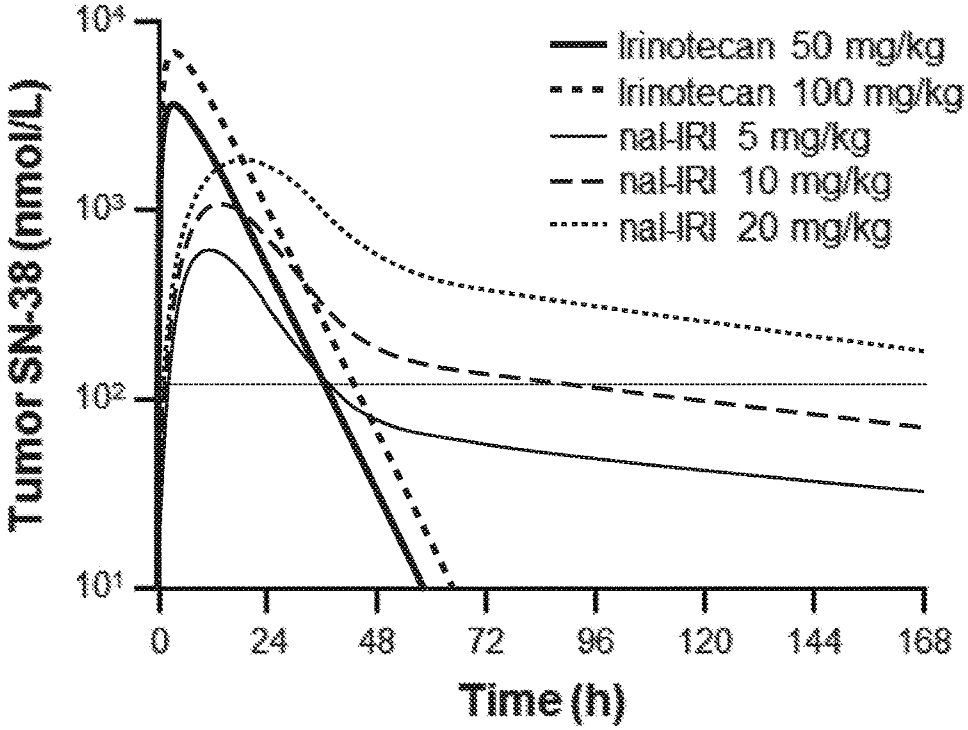
FIG. 16A is a graph showing the tumor SN-38 (nmol/L) measured in tumors after administration of free (non-liposomal) irinotecan (CPT-11) at 50 mg/kg or 100 mg/kg, compared to the administration of MM-398 (5 mg/kg, 10 mg/kg or 20 mg/kg).
Figure 16B:
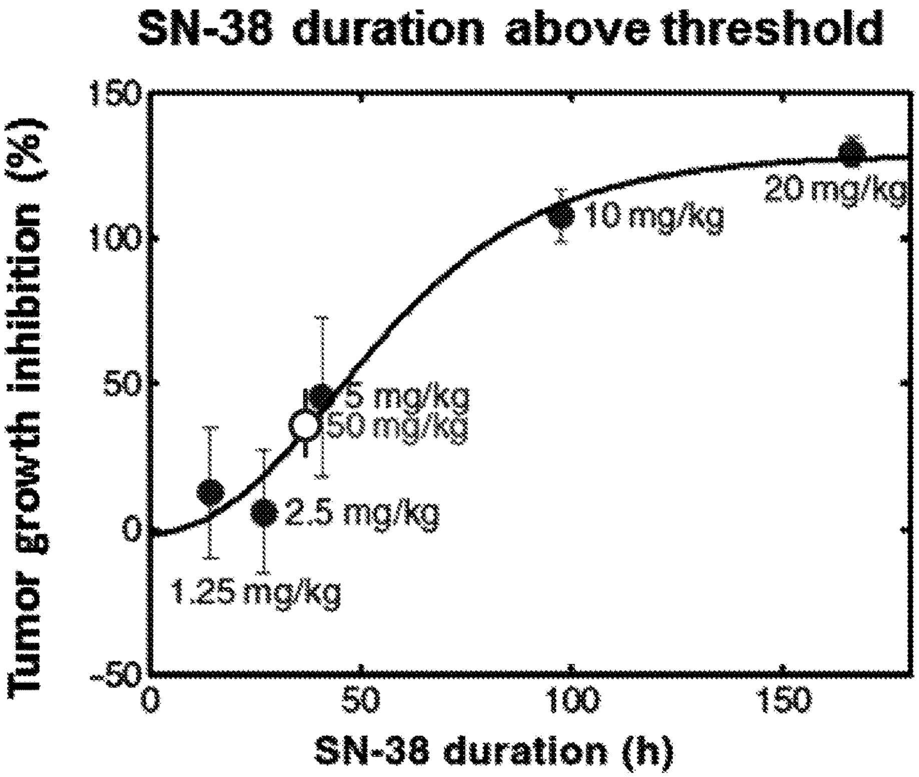
FIG. 16B is a graph showing levels of tumor growth inhibition as a function of time of SN-38 concentration required to yield tumor response.

Liposomal irinotecan MM-398 extends the tumor exposure of the topoisomerase 1 inhibitor SN-38. MM-398 liposomal irinotecan was found to be more active than irinotecan in multiple murine xenograph models. The duration of tumor exposure to the topoisomerase 1 inhibitor SN-38 above a threshold minimum concentration (e.g., 120 nM) correlated with antitumor activity of the liposomal irinotecan. In addition, MM-398 liposomal irinotecan can provide prolonged SN-38 tumor durations that exceed those provided by non-liposomal irinotecan. For example, FIG. 13B depicts tumor content of SN-38 in multiple murine cervical cancer models. Nude mice bearing cervical tumors were injected with a single dose of MM-398 at 10 mg/kg and tumor content of CPT-11 and SN-38 were measured by LC-MS. FIG. 16A is a graph showing the tumor SN-38 (nmol/L) measured in tumors after administration of free (non-liposomal) irinotecan (CPT-11) at 50 mg/kg or 100 mg/kg, compared to the administration of MM-398 (5 mg/kg, 10 mg/kg or 20 mg/kg). The graph depicts the prolonged accumulation of SN-38 (concentration) measured in a tumor after liposomal irinotecan (MM-398) administration compared to other organs, obtained using a using HT-29 colorectal cancer (CRC) tumor xenograft-bearing mice. FIG. 16B is a graph showing levels of tumor growth inhibition as a function of time of SN-38 concentration required to yield tumor response. Levels of SN-38 of 120 nM were identified as the SN-38 tumor concentration required to yield tumor response. The in vitro IC50 for SN-38 effect on cell line can be used as an in vivo threshold (GI50 for HT-29 was observed to be about 60 nM). MM-398 liposomal irinotecan was observed to prolong the duration of SN-38 exposure at doses of 10 mg/kg and 20 mg/kg.

PARP Inhibitors

PARPs are a family of enzymes involved in DNA repair that act via two mechanisms: catalytic inhibition and trapping of PARP-DNA complexes, and inhibition of this repair pathway can result in cell death following DNA damage. In preferred embodiments, combining PARP inhibitors with Top1 inhibitors results in increased efficacy in the clinic compared to either agent alone. While it has been demonstrated that synergism between PARP inhibitors and Top1 inhibitors is due to PARP catalytic inhibition, and does not involve PARP trapping, this promising preclinical activity has given rise to unacceptable toxicity in the clinic for these combinations.

The PARP inhibitor can be selected from compounds that inhibit Poly(ADP-ribose) polymerase (PARP), a family of enzymes involved in DNA repair. Preferably, the PARP inhibitor is a compound that acts via two mechanisms: catalytic inhibition and trapping of PARP-DNA complexes. The PARP inhibitor can be one or more clinically available PARP inhibitor compounds (e.g. talazoparib, niraparib, olaparib, and veliparib, among others), including compounds that can act via both mechanisms, although to different degrees. For example, niraparib is much more potent at PARP trapping than veliparib, whereas they both exhibit similar PARP catalytic activity. The PARP inhibitor can be selected from one or more compounds selected from the group consisting of talazoparib, niraparib, olaparib, veliparib, iniparib, rucaparib, CEP 9722 or BGB-290. In a further embodiment, the PARP inhibitor is veliparib, olaparib, rucaparib or niraparib. In another embodiment, the PARP inhibitor is veliparib, or olaparib. The PARP inhibitor can be veliparib administered after liposomal irinotecan. The PARP inhibitor can be olaparib administered after liposomal irinotecan Olaparib is indicated as monotherapy in patients with deleterious or suspected deleterious germline BRCA mutated (as detected by an FDA-approved test) advanced ovarian cancer who have been treated with three or more prior lines of chemotherapy. The recommended dose of olaparib for this indication is 400 mg (eight 50 mg capsules) taken twice daily, for a total daily dose of 800 mg. Patients taking olaparib are instructed to avoid concomitant use of strong and moderate CYP3A inhibitors and consider alternative agents with less CYP3A inhibition. If the inhibitor cannot be avoided, reduce the Lynparza dose to 150 mg (three 50 mg capsules) taken twice daily for a strong CYP3A inhibitor or 200 mg (four 50 mg capsules) taken twice daily for a moderate CYP3A inhibitor.

The PARP inhibitor can inhibit PARP 1 and/or PARP 2. For example, the PARP inhibitor can be a PARP ½ inhibitor with IC50 of 5 nM/1 nM in cell-free assays and 300-times less effective against tankyrase-1 (e.g., olaparib). The PARP inhibitor can be an inhibitor of PARP 1 and PARP2 with Ki of 5.2 nM and 2.9 nM respectively in cell-free assays, and inactive to SIRT2 (e.g., veliparib). The PARP inhibitor can be an inhibitor of PARP1 with a Ki of 1.4 nM in a cell-free assay, and can also show binding affinity for other PARP domains (e.g., rucaparib). The PARP inhibitor can be effective against triple negative breast cancer (TNBC) alone or in combination with other agents. The PARP inhibitor can be a PARP1 inhibitor with an IC50 of 0.58 nM in a cell free assay that does not inhibit PARG and is sensitive to a PTEN mutation (e.g., talazoparib). The PARP inhibitor can be a potent and selective tankyrase inhibitor with an IC50 of 46 nM and 25 nM for TNKS 1/2, respectively (e.g., G007-LK). The PARP inhibitor can be a potent inhibitor of PARP 1 with a Ki of less than about 5 nM in a cell free assay (e.g., AG-14361). The PARP inhibitor can be a selective inhibitor of PARP 2 with an IC50 of 0.3 micromolar, and can be about 27-fold selective against PARP 1 (e.g., UPF-1069). The PARP inhibitor can be a potent and selective inhibitor with an IC50 for PARP 3 of about 0.89 micromolar, and about 7-fold selectivity over PARP 1 (e.g., ME0328). The PARP inhibitor can be an inhibitor of PARP 1 and PARP2 with Ki values of 1 nM and 1.5 nM, respectively.

Preferred examples of PARP inhibitors are provided in the table 2A below, as well as pharmaceutically acceptable prodrugs, salts (e.g., tosylates) and esters thereof.

TABLE 2A

| Examples of PARP inhibitors | |
|---|---|
| Olaparib (AZD-2281) | 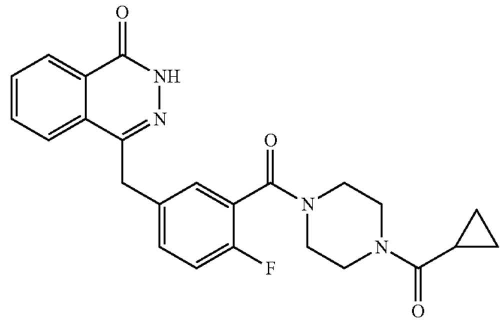 [SMILES: O=C(c1cc(Cc2n[nH]c(=O)c3ccccc23)ccc1F)N1CCN(C(=O)C2CC2)CC1] |
| Veliparib (ABT-888) | 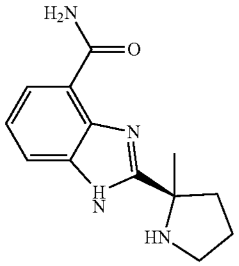 [SMILES: C[C@]1(c2nc3c(C(N)=O)cccc3[nH]2)CCCN1] |
| Niraparib (MK04827) | 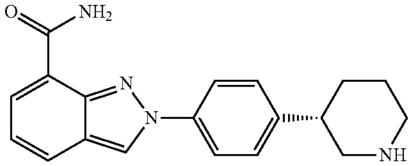 [SMILES: NC(=O)c1cccc2cn(-c3ccc([C@@H]4CCCNC4)cc3)nc12] |
| Rucaparib (AG 014699) | 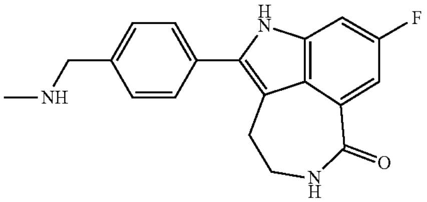 [SMILES: CNCc1ccc(-c2[nH]c3cc(F)cc4c3c2CCNC4=O)cc1] |
| Talazoparib (BMN-673) | 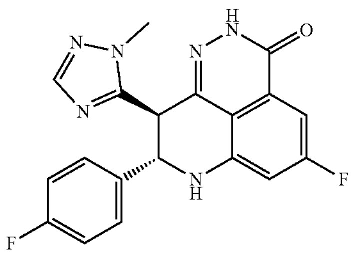 [SMILES: Cn1ncnc1[C@H]1c2n[nH]c(=O)c3cc(F)cc(c23)N[C@@H]1c1ccc(F)cc1] |

TABLE 2A-continued

| Examples of PARP inhibitors | |
|---|---|
| Iniparib (BSI-201 | 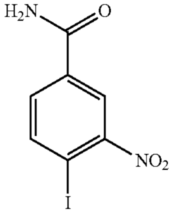 [SMILES: NC(=O)c1ccc(I)c([N+](=O)[O-])c1] |

The dose of the PARP inhibitor and the frequency of dosing can be selected based on various characteristics of the PARP inhibitor, including the pharmacokinetic properties of the compound (e.g., half-life), prior dosing regimens and patient characteristics. Parameters that can be used in selecting the PARP inhibitor dose include those listed in Table 2B below.

In addition, patients can be selected to receive treatment combining a topoisomerase inhibitor and a PARP inhibitor. For example, patients can be selected based on their status in BRCA (e.g. BRCA1, BRCA2), Homologous Recombination Deficiency (HRD), BROCA-HR or other genetic risk panel analysis of a patient.

TABLE 2B

Characteristics of Some PARP inhibitors

| Characteristic | Veliparib | Olaparib | Rucaparib | Niraparib | Talazoparib |
|---|---|---|---|---|---|
| Molecular Weight | 244.3 | 434.5 | 323.4 | 320.4 | 380.4 |
| PARP1 IC50 | 4.73-5.2 | 1.94-5 | 1.4-1.98 | 2.1-3.8 | 0.57-1.2 |
| PAR EC50 | 5.9 | 3.6 | 4.7 | | 2.5 |
| Monotherapy dosing | 200-400 mg BID | 300 mg BID | 240-600 mg BID | 300 mg QD | 1 mg QD |
| CDx | BRCA | BRCA, HRD | HRD | BRCA, HR | HRD, HR |

In the methods of this disclosure, the PARP inhibitor is administered at a therapeutically effective dose (e.g., a dose selected for the PARP inhibitor monotherapy, such as from about 200 mg/day to about 800 mg/day for veliparib). In a further embodiment, the PARP inhibitor is administered twice daily at a dose of from about 100 to about 400 mg for veliparib, rucaparib or olaparib. In some embodiments, 200 mg BID dose of veliparib is administered to patients after (e.g., 3-5 days after) each administration of liposomal irinotecan.

Uses in the Treatment of Cancer

In the methods of this disclosure, the PARP inhibitor is preferably administered after an "effective irinotecan plasma clearing interval," as defined above. The effective plasma clearing interval in the methods of this disclosure is from about 24 to about 168 hours, including 48 hours to about 168 hours. In a further embodiment, the effective plasma clearing interval is from about 48 to about 96 hours. In a further embodiment, the effective plasma clearing interval is 24 hours or 2, 3, 4 or 5 days.

In certain embodiments, the MM-398 and the PARP inhibitor are administered in at least one cycle. A cycle comprises the administration of a first agent (e.g., a first prophylactic or therapeutic agents) for a period of time, followed by the administration of a second agent (e.g., a second prophylactic or therapeutic agents) for a period of time, optionally followed by the administration of a third agent (e.g., a third prophylactic or therapeutic agents) for a period of time and so forth, and repeating this sequential administration, i.e., the cycle. In one embodiment, the combination of MM-398 and a PARP inhibitor is administered for at least one cycle. In one embodiment the cycle is a 2 week cycle. In another embodiment, the cycle is a 3 week cycle. In another embodiment, the cycle is a 4 week cycle. In one embodiment MM-398 is administered at the beginning of the cycle and administration of a PARP inhibitor (e.g., veliparib) is delayed until at least about 24, 48, 72, 96, or 120 hours, after the administration of MM-398. In one embodiment, MM-398 is administered as part of a 28 day cycle on days 1 and 15 and the PARP inhibitor is administered on days 3-12 and on days 17-25. In another embodiment, MM-398 is administered as part of a 28 day cycle on days 1 and 15 and the PARP inhibitor is administered on days 5-12 and days 19-25.

In some examples, including the protocols in Table 3, the PARP inhibitor is not administered within 3 days of the administration of liposomal topoisomerase 1 inhibitor such as MM-398 liposomal irinotecan (i.e., the PARP inhibitor is only administered on days that are both at least 2, 3, 4 or 5 days after the administration of the liposomal topoisomerase 1 inhibitor, and 2, 3, 4 or 5 days prior to the next administration of the liposomal topoisomerase 1 inhibitor). Table 3 shows dose timing protocols for administering a therapeutically effective amount of a PARP inhibitor and liposomal irinotecan on certain days of a 28-day antineoplastic treatment cycle.

TABLE 3

Examples of 28-day Treatment Cycles

| Protocol | PARP inhibitor given on days | Liposomal Irinotecan given on days |
|---|---|---|
| 1 | 3-12; 17-25 | 1, 15 |
| 2 | 4-12; 17-25 | 1, 15 |

TABLE 3-continued

| Examples of 28-day Treatment Cycles | | |
|---|---|---|
| Protocol | PARP inhibitor given on days | Liposomal Irinotecan given on days |
| 3 | 5-12; 17-25 | 1, 15 |
| 4 | 6-12; 17-25 | 1, 15 |
| 5 | 3-12; 18-25 | 1, 15 |
| 6 | 4-12; 18-25 | 1, 15 |
| 7 | 5-12; 18-25 | 1, 15 |
| 8 | 6-12; 18-25 | 1, 15 |
| 9 | 3-12; 19-25 | 1, 15 |
| 10 | 4-12; 19-25 | 1, 15 |
| 11 | 5-12; 19-25 | 1, 15 |
| 12 | 6-12; 19-25 | 1, 15 |

In some examples, the PARP inhibitor is administered on one or more of days of a 28-day antineoplastic treatment cycle. For example, the PARP inhibitor can be administered on one or more of days 3, 4, 5, 6, 7, 8, 9, 10, 11 and 12 and 19, 20, 21, 22, 23, 24 and 25 of the 28-day antineoplastic treatment cycle when the liposomal irinotecan (e.g., MM-398) is administered once every two weeks, or on days 1 and 15 of the 28-day antineoplastic treatment cycle.

Methods of treatment and therapeutic uses of PARP inhibitors and topoisomerase inhibitors (e.g., liposomal irinotecan) disclosed herein are useful in the treatment of various forms of cancer. Preferably, the cancer includes a diagnosed solid tumor. In some examples, the cancer (e.g., solid tumor) is of a tumor type with one or more DNA repair pathway deficiencies, such as breast and ovarian tumors with BRCA1 or BRCA2 mutations.

In the methods of this disclosure, the cancer is cervical cancer, ovarian cancer, breast cancers including triple negative breast cancer (TNBC), non-small cell lung cancer (NSCLC), small cell lung cancer (SCLC), gastric cancer, pancreatic cancer, colorectal cancer, or a neuroendocrine tumor.

The methods of this disclosure can further comprise administering to the patient one or more additional agents including, but not limited, to anti-emetics such as a 5-HT3 antagonist; agents for treating of diarrhea, such as loperamide; dexamethasone; or other chemotherapeutic agents.

In one embodiment, the methods of the present disclosure result in a pathologic complete response (pCR), complete response (CR), partial response (PR) or stable disease (SD). In another embodiment the combination therapy with MM-398 and a PARP inhibitor, e.g., veliparib, results in therapeutic synergy.

Further aspects include providing an existing standard of care therapy to the patients, which may or may not include treatment with appropriate single agents. In some instances, the standard of care may include administration of a PARP inhibitor compound.

Thus, in one aspect, the present disclosure provides a method of treating a patient with cancer and having a tumor, the method comprising:

i. parenterally (e.g., intravenously) administering to the patient an effective amount of an irinotecan liposomal formulation; and ii. administering to the patient an effective amount of a PARP inhibitor wherein the PARP inhibitor is administered after an effective irinotecan plasma clearing interval.

The present disclosure provides a method of treating a patient with cancer and having a tumor, the method comprising a treatment regimen that may be repeated at weekly or longer intervals (e.g., Q2W, Q3W, or Q4W), each instance of the treatment comprising:

i. intravenously administering to the patient an effective amount of an irinotecan liposomal formulation of a Top1 inhibitor such as irinotecan, topotecan, lurtotecan, indotecan, and indimitecan; and ii. administering to the patient and effective amount of a PARP inhibitor wherein the PARP inhibitor is administered after an interval following completion of the administration of the Top1 inhibitor, e.g., an effective irinotecan plasma clearing interval.

In a further embodiment, the method comprises:

i. intravenously administering to the patient an effective amount of an irinotecan liposomal formulation having a terminal elimination half-life of about 26.8 hours and a maximal irinotecan plasma concentration of about 38.0 micrograms/ml; and ii. administering to the patient and effective amount of a PARP inhibitor wherein the PARP inhibitor is administered after an interval of 24 hours or up to three days following completion of the administration of the irinotecan.

EXAMPLES

The following non-limiting examples illustrate the methods of the present disclosure.

Example 1: In Vitro Studies

In vitro studies were performed testing combinations of various PARP inhibitors and topoisomerase inhibitors liposomal irinotecan and SN-38.

FIGS. 1A-1D show line graphs that depict cervical cancer cell viability following treatment with SN-38 and/or various PARP inhibitors. Unless otherwise indicated, the data in each of these figures was obtained by measuring cell viability of 5 different cervical cancer cells (ME-180 in FIG. 1A, MS-751 in FIG. 1B, C-33A in FIG. 1C, SW756 in FIG. 1D and SiHa in FIG. 1E) with 1000 cells/well in a 384 well plate treated with SN-38 (topoisomerase 1 inhibitor) and/or one of 3 different PARP inhibitors (veliparib, niraparib, or olaparib) at 0.33 micrograms/mL) for 24 hours, followed by washing and incubation for an additional 72 hours with fresh media.

The combination of the topoisomerase 1 inhibitor SN-38 and various PARP inhibitors (veliparib, olaparib and rucaparib) were tested in vitro with various small cell lung cancer (SCLC), pancreatic cancer and breast cancer cell lines. At 2 nM SN-38 concentration, an additive/synergistic growth inhibition of the cancer cells was observed in combination with olaparib, veliparib and rucaparib (with veliparib observed to be slightly less potent in the combination with SN-38 than olaparib and rucaparib). At all concentrations tested, the static growth of the cancer cell population was achieved. FIGS. 2A-2E are graphs showing the results of in vitro experiments evaluating combinations of the topoisomerase 1 inhibitor SN38 with various PARP inhibitors, formatted according to the tables 4-5 below (plates of 5,000 cells/well, 100 microliters per well; drugs added with 20× at 10 microliters per drug, top up to 100 microliters total with DMEM; then initiate scan every 4 hours up to 68 hours).

TABLE 4

| Treatment | Small Cell Lung Cancer DMS-114 | Small Cell Lung Cancer NCI-H1048 | Pancreatic Cancer CFPAC-1 | Pancreatic Cancer BxPC-3 | TNBC MDA-MB-231 |
|---|---|---|---|---|---|
| SN-38 & Olaparib | Plate 1 | Plate 2 | Plate 3 | Plate 4 | Plate 5 |
| SN-38 & Rucaparib | Plate 1 | Plate 2 | Plate 3 | Plate 4 | Plate 5 |
| SN-38 & Veliparib | Plate 1 | Plate 2 | Plate 3 | Plate 4 | Plate 5 |

TABLE 5

| Target Concentrations | | | | |
|---|---|---|---|---|
| Drug | Active Range based on XTC008 | Estimated tumor range (nM) | Dose Level | Conc' (nM) |
| SN- 38 | 1-50 nM | 3-163 nM | S1 | 2 |
| | | (398); | S2 | 5 |
| | | IRI < 200 nM | S3 | 10 |
| | | | S4 | 20 |
| | | | S5 | 50 |
| Olapano | 100)-10000 nM | 8000 nM | O1 | 2000 |
| | | | O2 | 4000 |
| | | | O3 | 8000 |
| Veliparib | 1000-10000 nM | >2000 nM | V1 | 2000 |
| | | | V2 | 4000 |
| | | | V3 | 8000 |
| Rucaparib | 1-100 nM (Panc) | <6000 nM | R1 | 2000 |
| | | | R2 | 4000 |
| | | | R3 | 8000 |

Figure 2A:
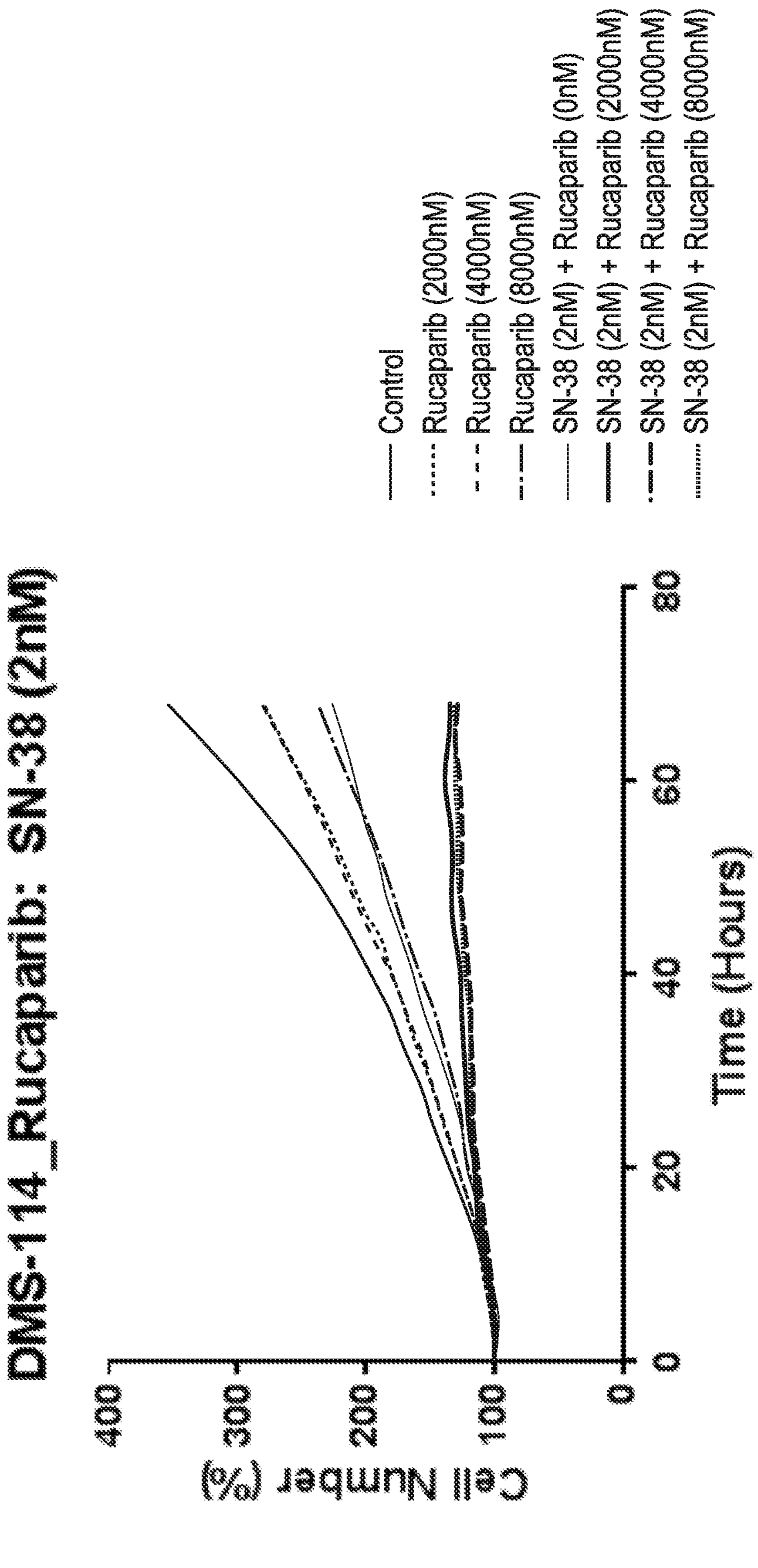
FIG. 2A is a graph showing the results of in vitro measurement of % cell number over time for DMS-114 small cell lung cancer cells treated with the topoisomerase inhibitor SN-38 and the PARP inhibitor rucaparib.

Additive/synergistic effects were observed between SN-38 at 2 nM combined with the tested PARP inhibitors olaparib, veliparib and rucaparib with DMS-114 SCLC cells. FIG. 2A is a graph showing the results of in vitro measurement of % cell number over time for DMS-114 small cell lung cancer cells treated with the topoisomerase inhibitor SN-38 and the PARP inhibitor rucaparib.

Figure 2B:
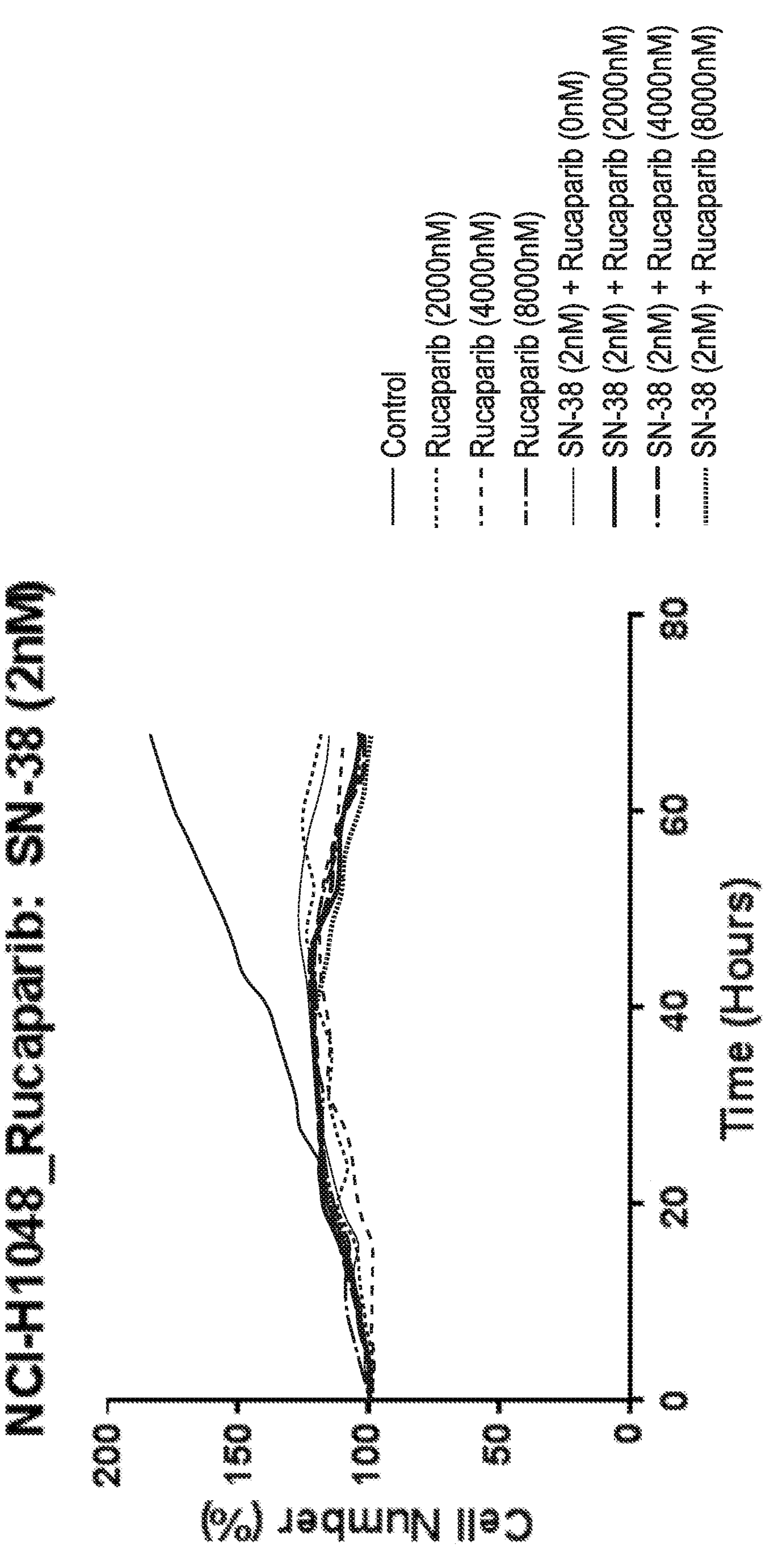
FIG. 2B is a graph showing the results of in vitro measurement of % cell number over time for NCI-H1048 small cell lung cancer cells treated with the topoisomerase inhibitor SN-38 and the PARP inhibitor rucaparib.

The NCI-H1048 SCLC cells were slow-growing and very sensitive to combinations of olaparib and rucaparib with SN-38 at 2 nM. FIG. 2B is a graph showing the results of in vitro measurement of % cell number over time for NCI-H1048 small cell lung cancer cells treated with the topoisomerase inhibitor SN-38 and the PARP inhibitor rucaparib.

Figure 2C:
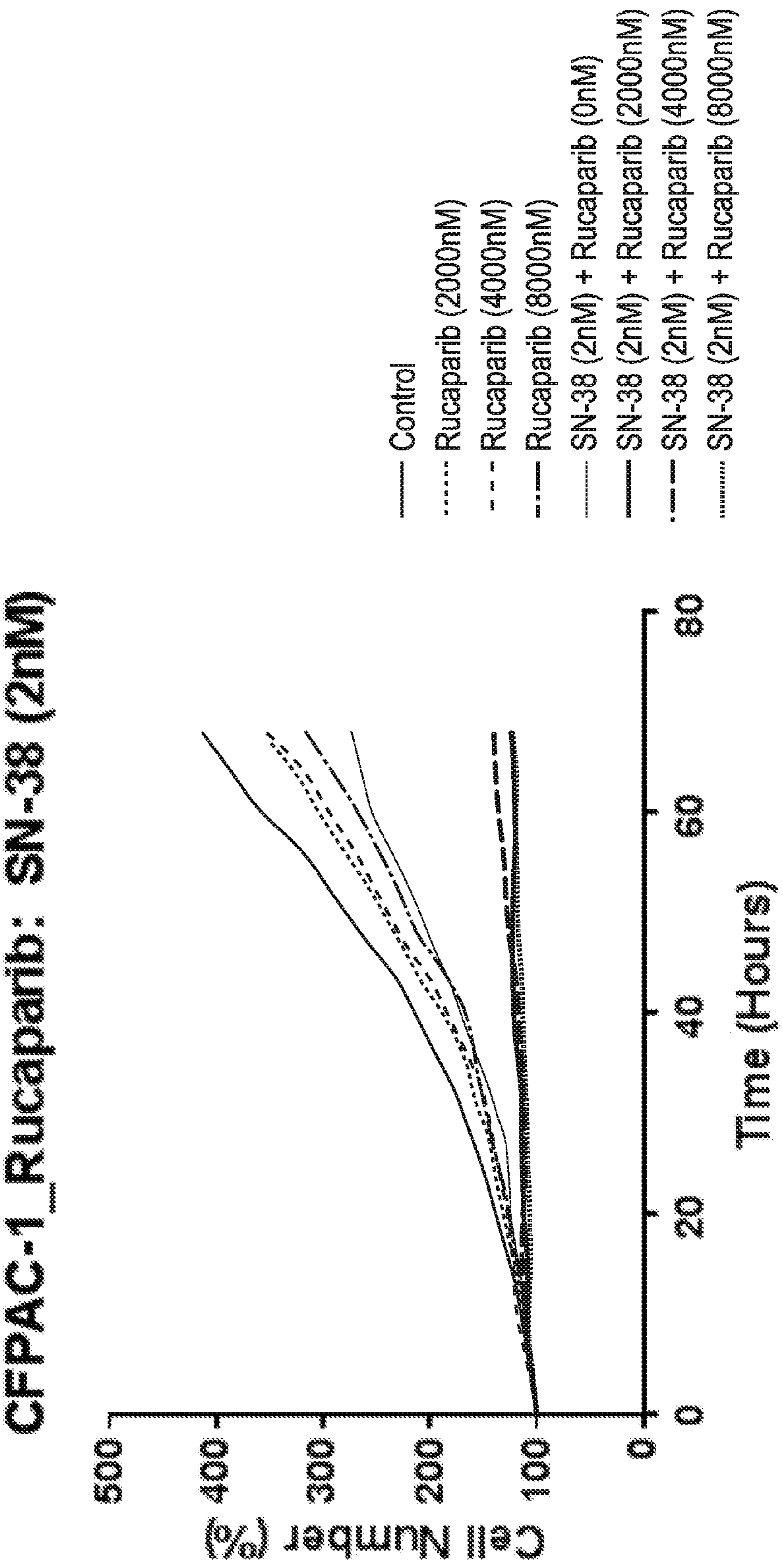
FIG. 2C is a graph showing the results of in vitro measurement of % cell number over time for CFPAC-1 pancreatic cancer cells treated with the topoisomerase inhibitor SN-38 and the PARP inhibitor rucaparib.

Additive/synergistic effects were observed between SN-38 at 2 nM combined with the tested PARP inhibitors olaparib, veliparib and rucaparib with CFPAC-1 pancreatic cancer cells. FIG. 2C is a graph showing the results of in vitro measurement of % cell number over time for CFPAC-1 pancreatic cancer cells treated with the topoisomerase inhibitor SN-38 and the PARP inhibitor rucaparib.

Figure 2D:
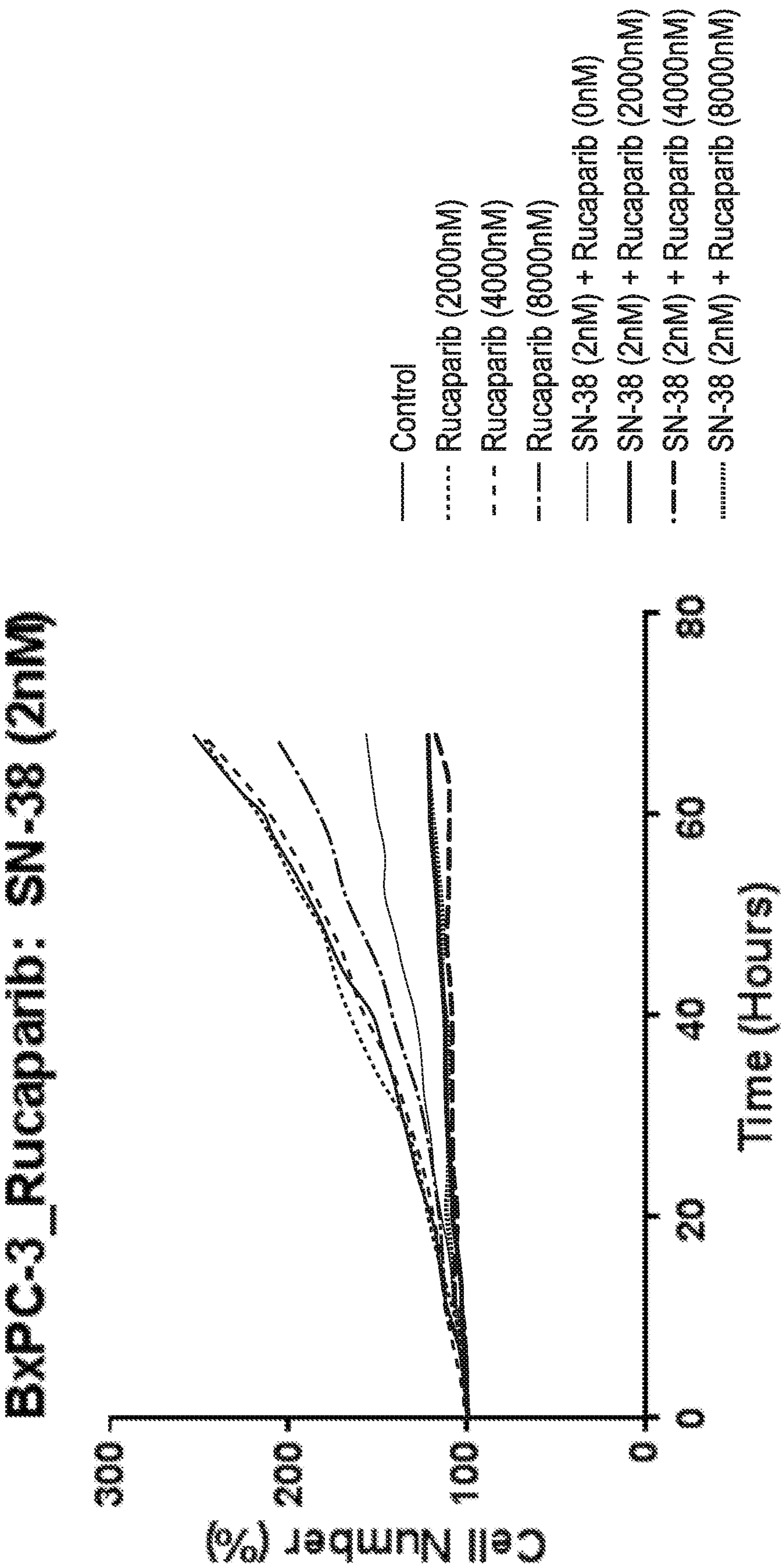
FIG. 2D is a graph showing the results of in vitro measurement of % cell number over time for BxPC-3 pancreatic cancer cells treated with the topoisomerase inhibitor SN-38 and the PARP inhibitor rucaparib.
Figure 2E:
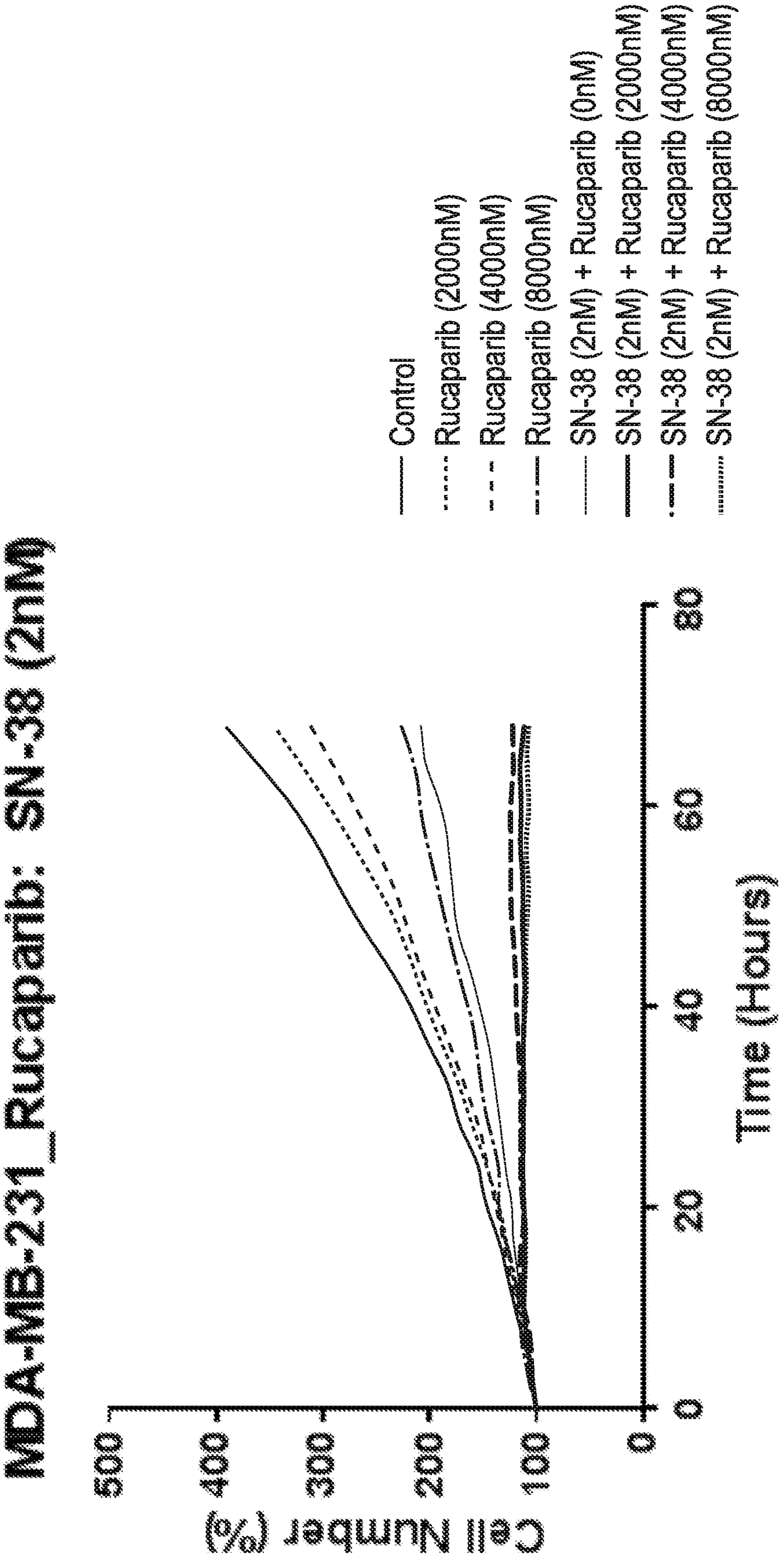
FIG. 2E is a graph showing the results of in vitro measurement of % cell number over time for MDA-MB-231 triple negative breast cancer (TNBC) cancer cells treated with the topoisomerase inhibitor SN-38 and the PARP inhibitor rucaparib.

FIG. 2D is a graph showing the results of in vitro measurement of % cell number over time for BxPC-3 pancreatic cancer cells treated with the topoisomerase inhibitor SN-38 and the PARP inhibitor rucaparib. FIG. 2E is a graph showing the results of in vitro measurement of % cell number over time for MDA-MB-231 triple negative breast cancer (TNBC) cancer cells treated with the topoisomerase inhibitor SN-38 and the PARP inhibitor rucaparib.

Figure 13A:
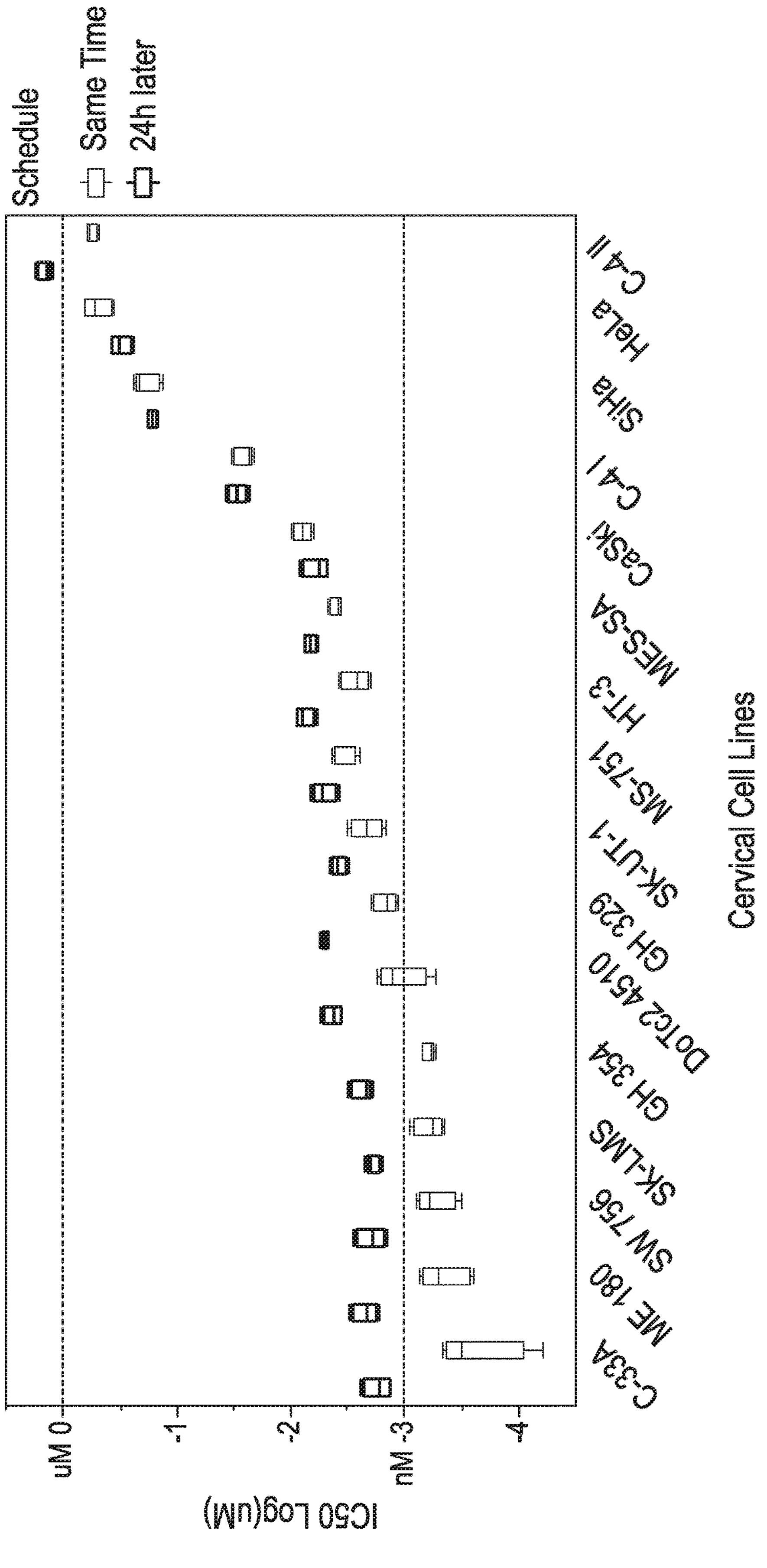
FIG. 13A is a graph showing the in vitro activity (IC50) for multiple cervical cancer cell lines treated with veliparib and SN38, added together or with the veliparib added 24 hours after the SN38.
Figure 13B:
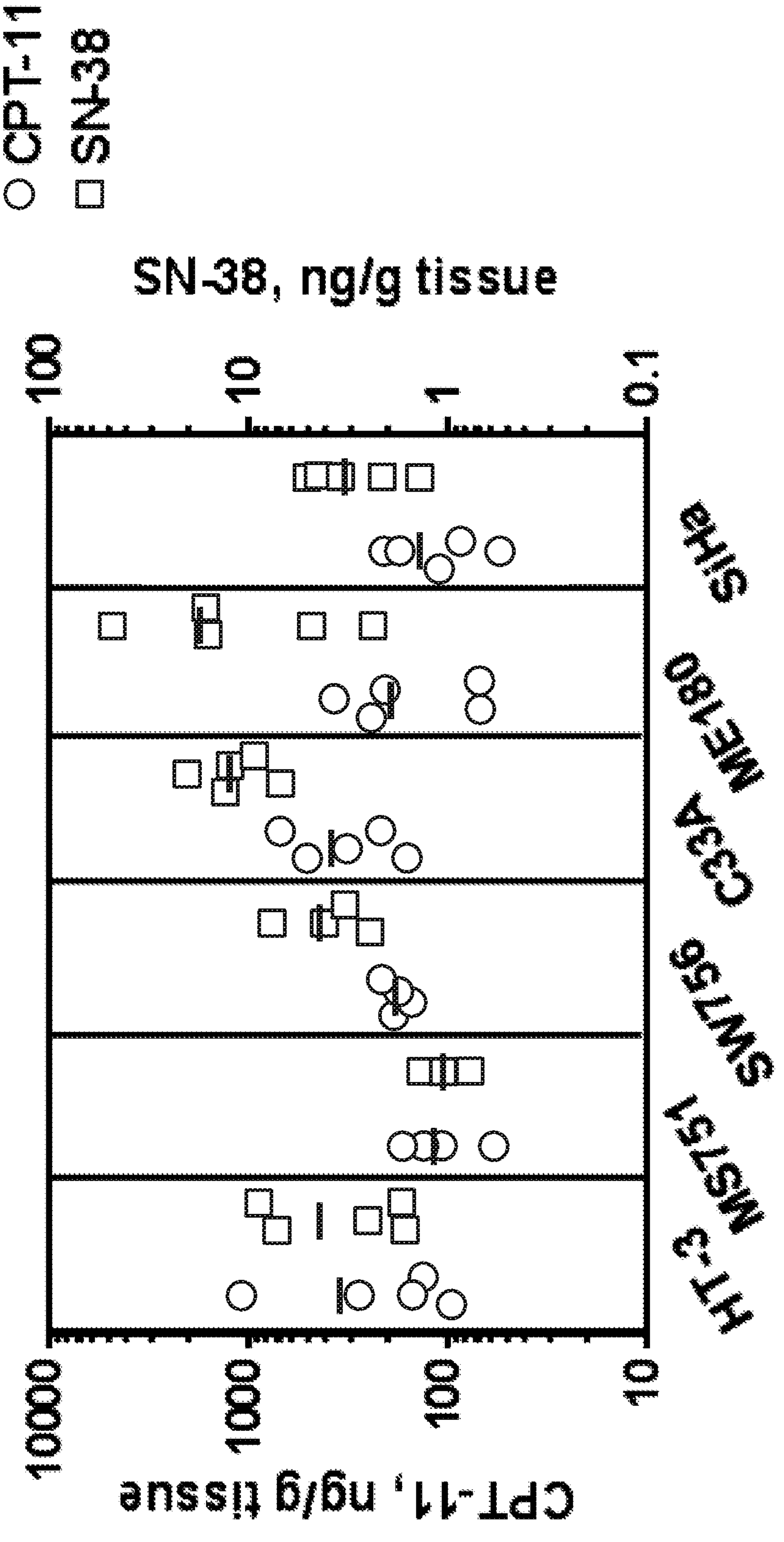
FIG. 13B is a graph showing the cell viability (CTG assay) in nude mice with cervical cancer tumors, injected with a single dose of MM-398 (10 mg/kg) followed by measurement of irinotecan and SN38 content in the tumor measured by LC-MS.

FIG. 13A depicts the in vitro activity of SN-38 in cervical models. Cervical cells lines were treated with veliparib and SN-38 at either the same time or with scheduling with Veliparib being added 24 h after SN-38, and cell viability was measured using CTG assay.

Example 2: Pre-Clinical Dose Tolerability Studies

Various pre-clinical in vivo experiments were conducted to evaluate delayed dosing of veliparib relative to liposomal irinotecan can alleviate systemic toxicity, including a pre-clinical dose tolerability study. The combination of veliparib and irinotecan has been plagued by dose-limiting toxicities that have prevented this combination from being dosed at high (effective) doses of each drug, thereby limiting its clinical utility. To address this problem, pre-clinical studies evaluated administering a liposomal preparation of a topoisomerase 1 inhibitor, followed by the administration of a PARP inhibitor at least 1 day (preferably 2-3 days) after the day on which the liposomal topoisomerase 1 inhibitor was administered.

The advantage of dosing with MM-398 compared to free irinotecan is the extended PK profile and prolonged local tumor exposure of MM-398. Since SN-38 is cleared more quickly from normal tissues than from tumor, delayed dosing of veliparib (e.g. starting veliparib dosing a few days after MM-398 administration) allows for the window of maximum irinotecan-induced toxicity to pass in the absence of concurrent veliparib toxicity. However, the tumor levels of SN-38 are sustained longer than in healthy tissue, such that upon PARP inhibitor dosing subsequent to liposomal Top1 inhibitor (e.g., MM-398) administration, both drugs will act on tumor tissue simultaneously.

Figure 5A:
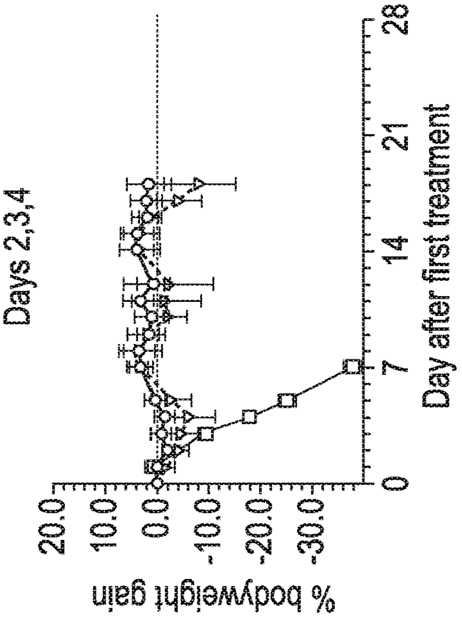
FIG. 5A is a graph showing the results of a murine tolerability study of a combination of MM-398 and veliparib, measuring % change in bodyweight after administration of 15 mg/kg of MM-398 on day 1, and 50 mg/kg of veliparib on days 2, 3, and 4.
Figure 5B:
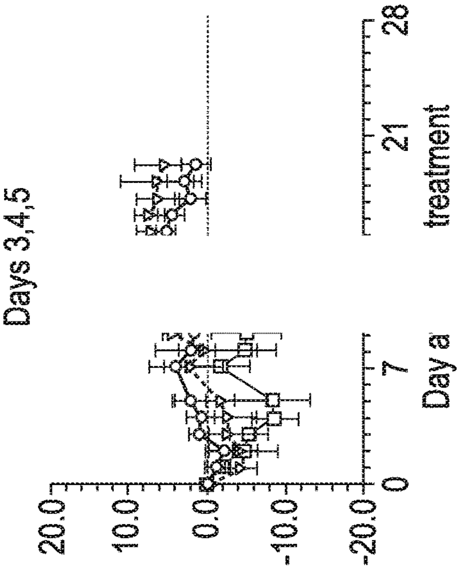
FIG. 5B is a graph showing the results of a murine tolerability study of a combination of MM-398 and veliparib, measuring % change in bodyweight after administration of 28 mg/kg of MM-398 on day 1, and 50 mg/kg of veliparib on days 3, 4, and 5.
Figure 5C:
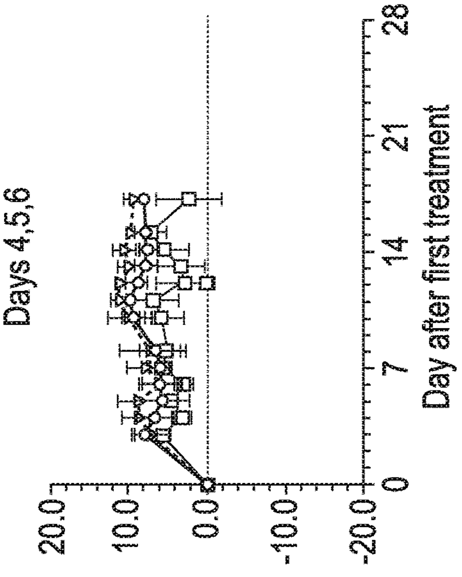
FIG. 5C is a graph showing the results of a murine tolerability study of a combination of MM-398 and veliparib, measuring % change in bodyweight after administration of 50 mg/kg of MM-398 on day 1, and 50 mg/kg of veliparib on days 4, 5, and 6.
Figure 6A:
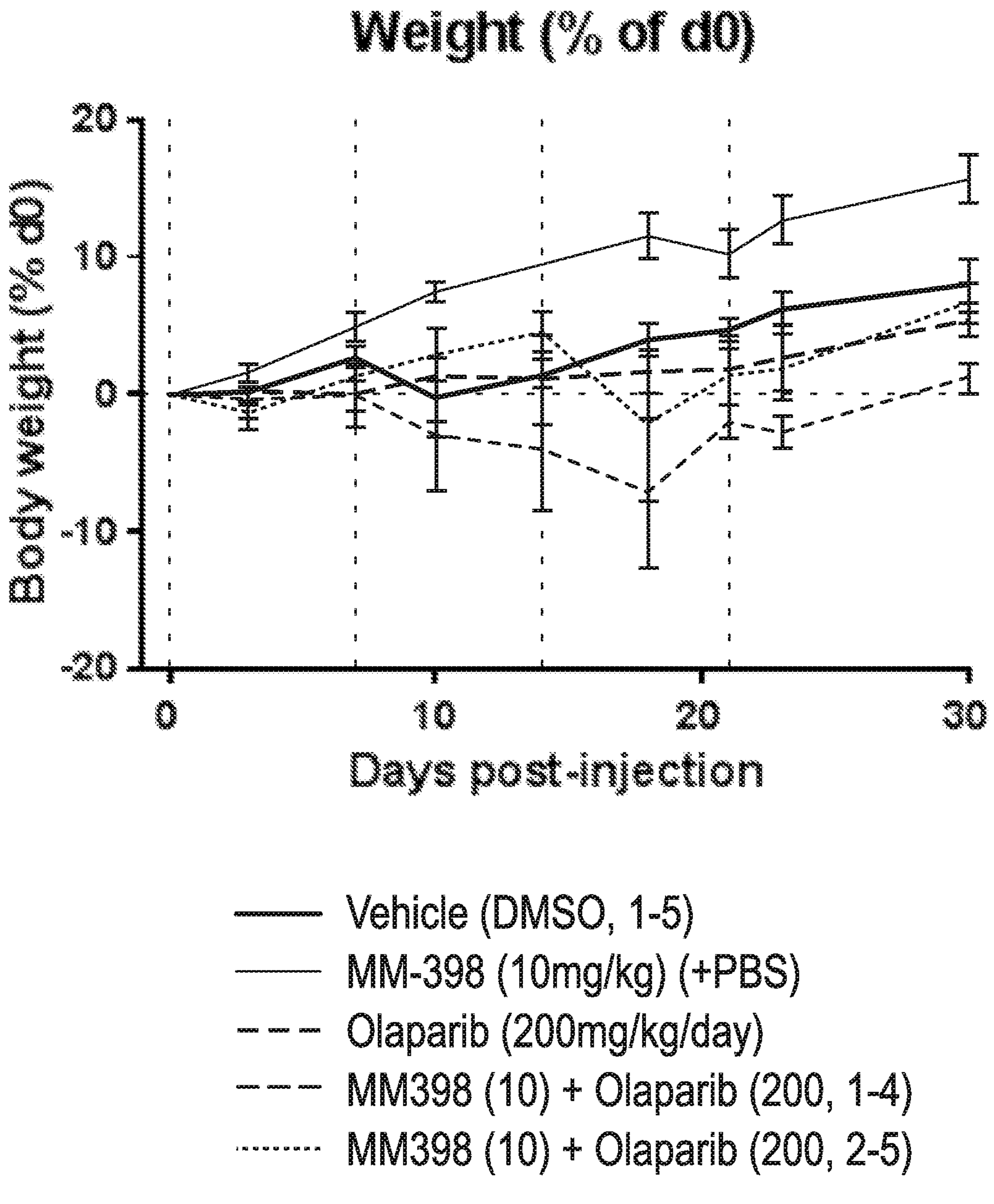
FIG. 6A is a graph comparing the results of a murine tolerability study measuring % change in bodyweight after administration of 10 mg/kg of MM-398 (+PBS); 200 mg/kg/day of Olaparib; 10 mg/kg of MM-398 (+PBS) with 200 mg/kg/day of Olaparib on days 1-4; and 10 mg/kg of MM-398 (+PBS) with 200 mg/kg/day of Olaparib on days 1-5.
Figure 6B:
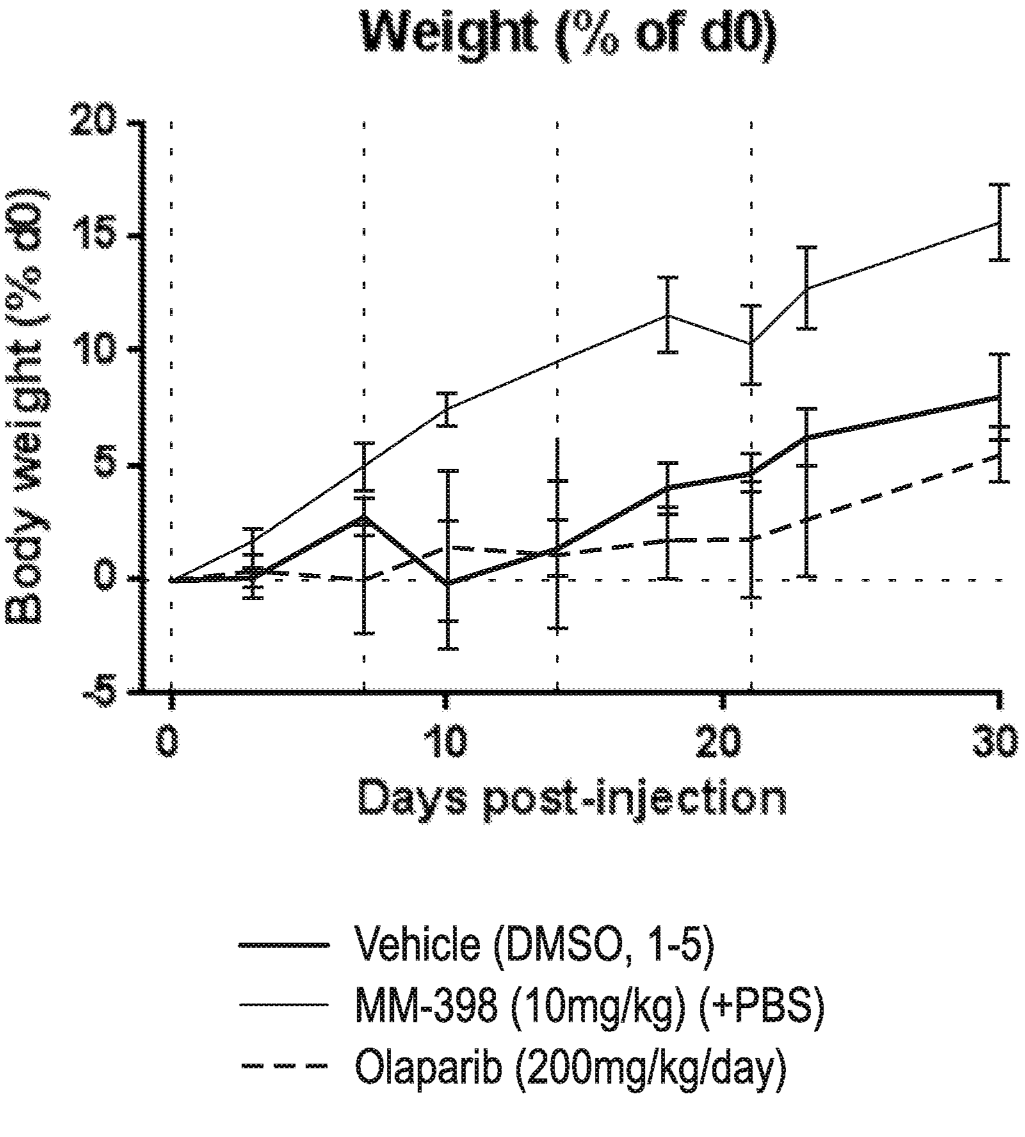
FIG. 6B is a graph comparing the results of a murine tolerability study measuring % change in bodyweight after administration of 10 mg/kg of MM-398 (+PBS) and 200 mg/kg/day of Olaparib.
Figure 6C:
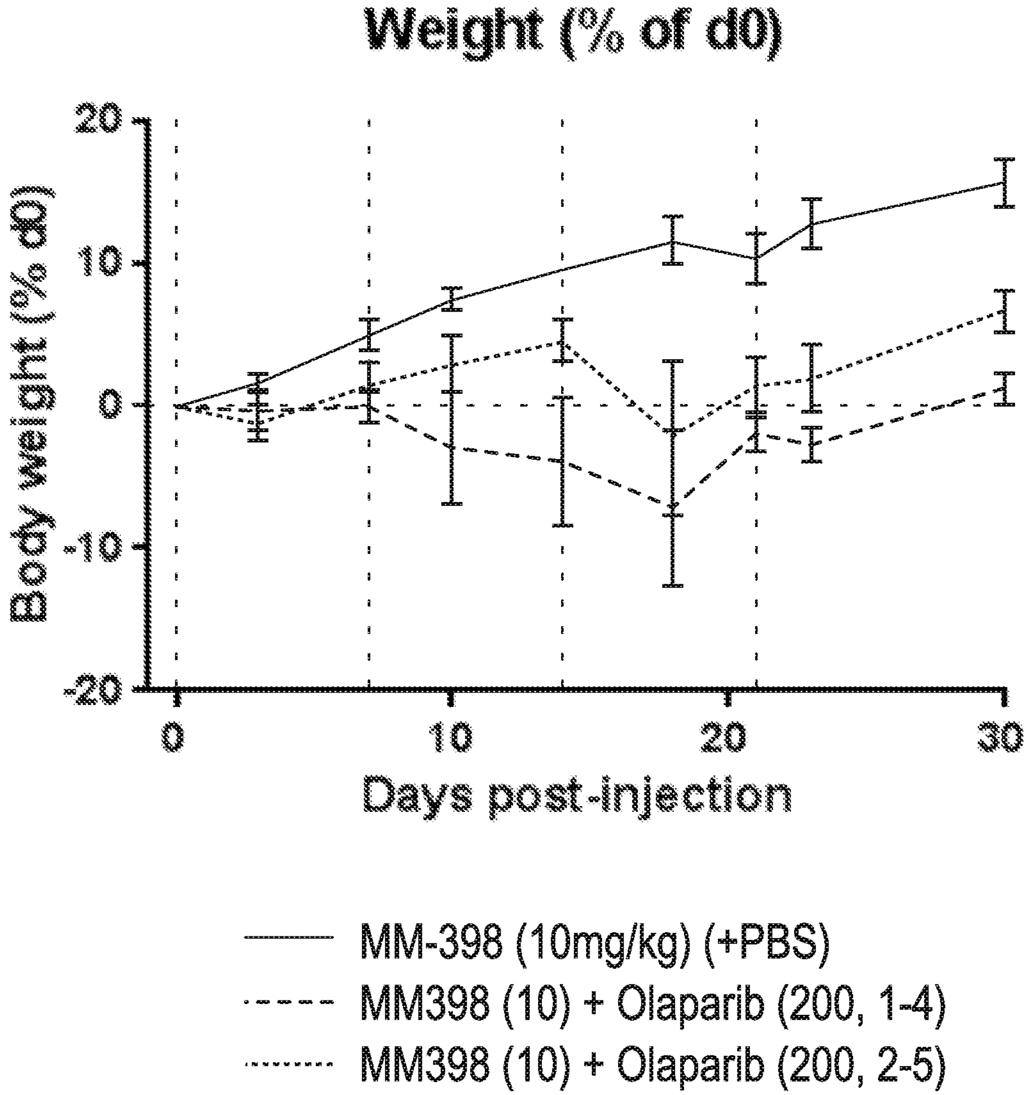
FIG. 6C is a graph comparing the results of a murine tolerability study measuring % change in bodyweight after administration of 10 mg/kg of MM-398 (+PBS); 10 mg/kg of MM-398 (+PBS) with 200 mg/kg/day of Olaparib on days 1-4; and 10 mg/kg of MM-398 (+PBS) with 200 mg/kg/day of Olaparib on days 1-5.
Figure 6D:
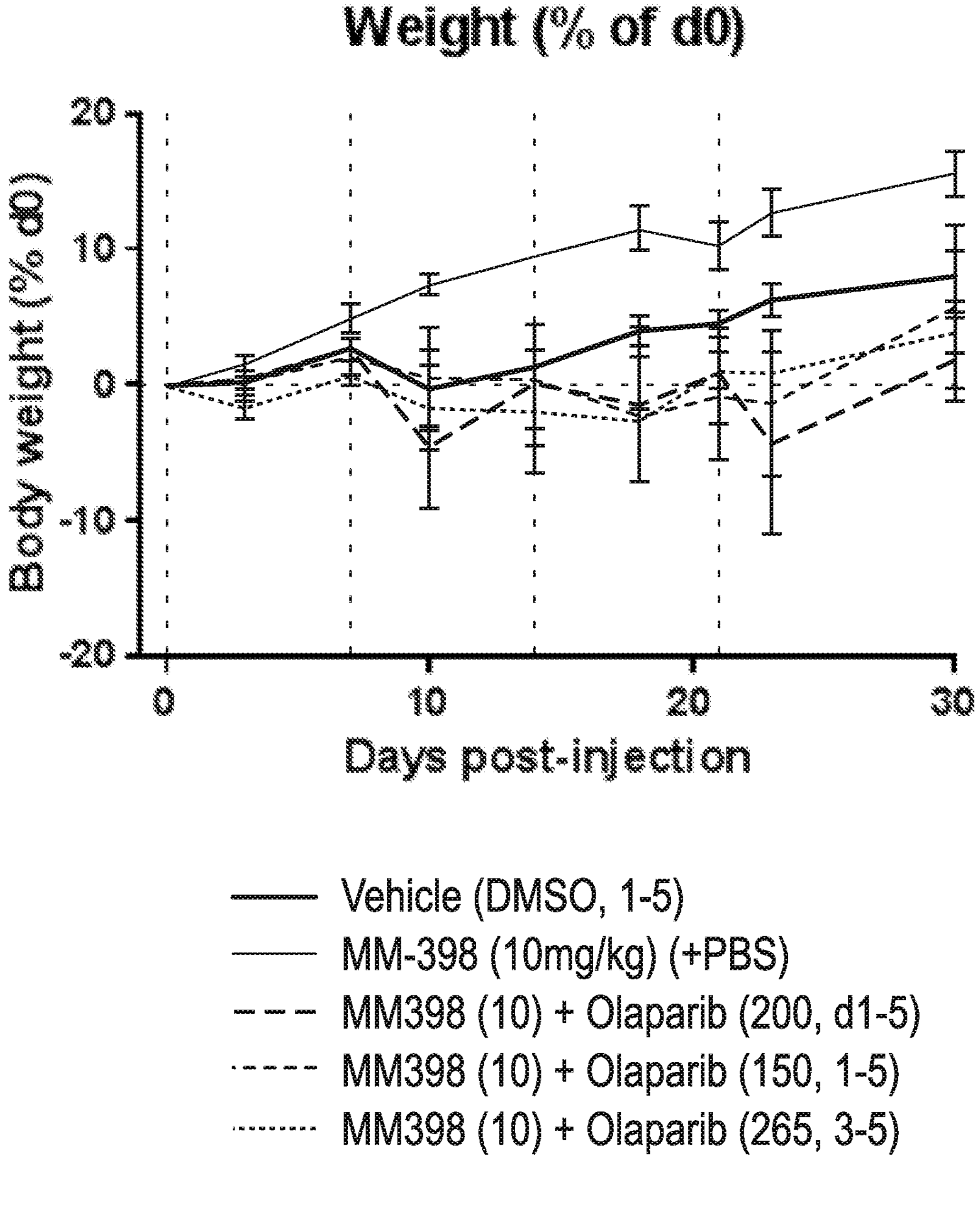
FIG. 6D is a graph comparing the results of a murine tolerability study measuring % change in bodyweight after administration of 10 mg/kg of MM-398 (+PBS); 10 mg/kg of MM-398 (+PBS) with 200 mg/kg/day of Olaparib on days 1-5; 10 mg/kg of MM-398 (+PBS) with 150 mg/kg/day of Olaparib on days 1-5; and 10 mg/kg of MM-398 (+PBS) with 265 mg/kg/day of Olaparib on days 3-5.

To demonstrate that delayed dosing of veliparib relative to nal-IRI can alleviate systemic toxicity, a pre-clinical dose tolerability study was performed. Mice were dosed chronically with nal-IRI once weekly at various doses on Day 1, while veliparib was dosed once daily at a fixed dose for 3 consecutive days each week (either on Days 2-4, Days 3-5, or Days 4-6), and body weight was followed as a gross measure of toxicity. All mice were dosed chronically once weekly on day 1, with veliparib subsequently dosed for 3 consecutive days either on days 2-4, days 3-5, or days 4-6. Mice were weighed daily and % bodyweight gain is indicated on the Y-axis. Weight loss is indicative of intolerability of the combination. Notably, the highest (50 mg/kg) dose of MM-398 liposomal irinotecan was best tolerated (i.e., lowest measured reduction in % bodyweight observed over the experiment) when the veliparib was administered on days 4, 5 and 6 (FIG. 5C). Similarly, the combination of veliparib and MM-398 was best tolerated at lower MM-398 liposomal irinotecan doses when the veliparib was only administered on days 4, 5, and 6 after MM-398 administration. Toxicity of the combination was seen at the highest doses of MM-398 when given in close proximity to the veliparib doses (FIG. 5A). However, this toxicity could be alleviated either by dose reducing MM-398 or delaying the start of veliparib dosing, whereby the highest dose of MM-398 could be successfully dosed with veliparib if given on Days 4-6 following Day 1 dosing of MM-398. The Day 4-6 veliparib dosing schedule (following day 1 dosing of MM398) was followed in subsequent efficacy studies which demonstrated synergy of the combination in two cervical cancer tumor xenograft models, in which veliparib alone was not efficacious (FIG. 7A) and a second model in which neither MM-398 or veliparib were efficacious as single agents (FIG. 7B), however the combination demonstrated tumor growth inhibition (FIG. 7B).

Figure 4:
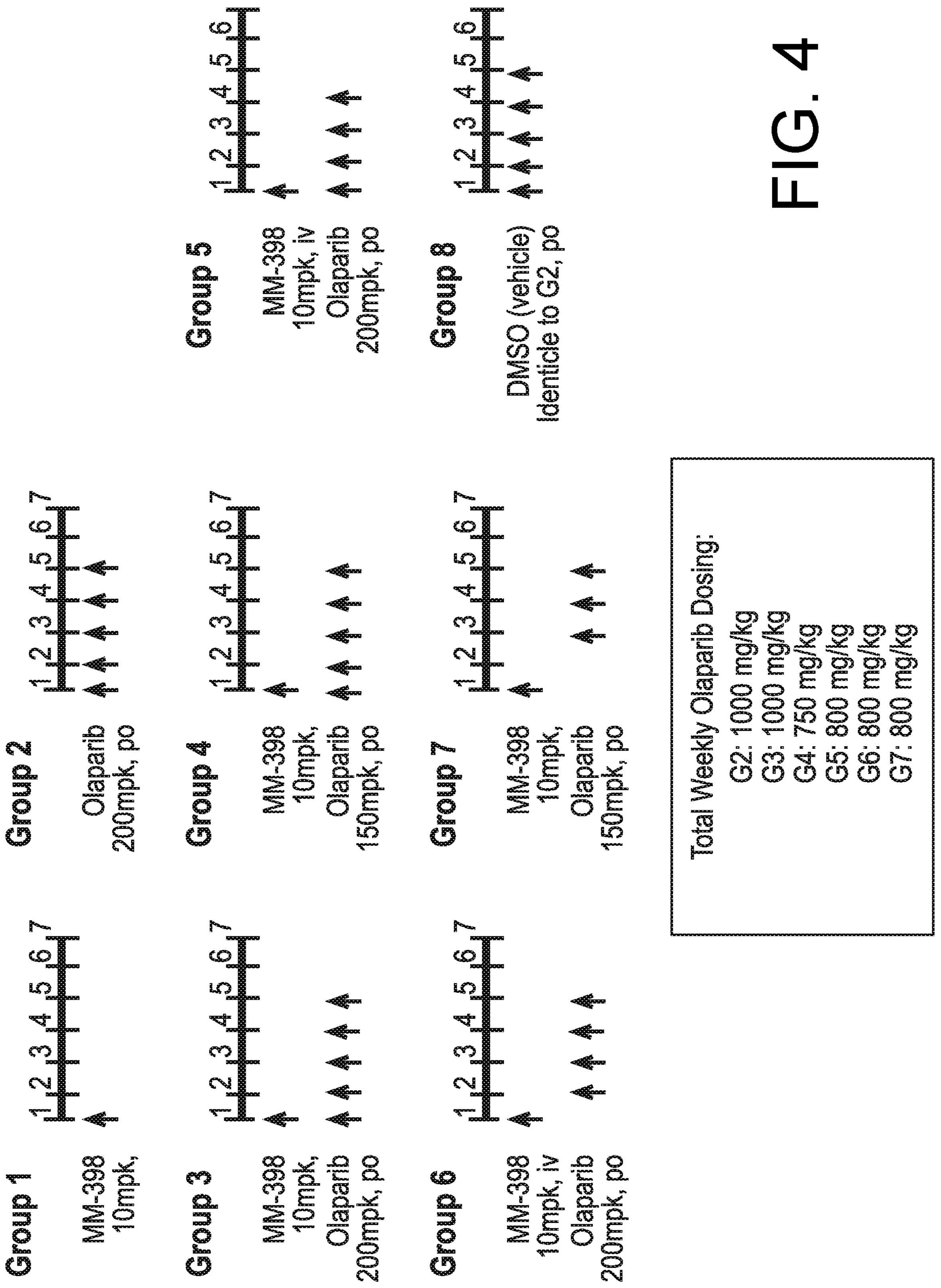
FIG. 4 depicts a graphical representation of a murine tolerability study design comparing MM-398 and olaparib as a monotherapy or in combination using a fixed dose of MM-398 and varying doses of olaparib, with various dosing schedules for different groups.

To exemplify an embodiment demonstrating that delayed dosing of olaparib relative to MM-398 can alleviate systemic toxicity, a pre-clinical dose tolerability study was performed. FIG. 4 depicts a graphical representation of a murine tolerability study design comparing MM-398 and olaparib as a monotherapy or in combination using a fixed dose of MM-398 and varying doses of olaparib, with various dosing schedules for different groups: Group 1: MM-398 alone IV (10 mg/kg); Group 2: olaparib alone oral (200 mg/kg); Group 3: MM-398 (d1)+olaparib (200 mg/kg, d1-5); Group 4: MM-398 (d1)+olaparib (150 mg/kg, d1-5; Group 5: MM-398 (d1)+olaparib (200 mg/kg, d1-4); Group 6: MM-398 (d1)+olaparib (200 mg/kg, d2-5); Group 7: MM-398 (d1)+olaparib (265 mg/kg, d3-5); group 8: DMSO alone oral (FIGS. 6A-6D). Mice that received monotherapy of MM-398, olaparib were dosed 5× weekly. Mice that received a combination of a constant concentration of MM-398 (10 mg/kg) and varying concentration of olaparib were dosed in varying schedules: Group 3: MM-398 (d1)+ olaparib (200 mg/kg, d1-5); Group 4: MM-398 (d1)+olaparib (150 mg/kg, d1-5; Group 5: MM-398 (d1)+olaparib (200 mg/kg, d1-4); Group 6: MM-398 (d1)+olaparib (200 mg/kg, d2-5); Group 7: MM-398 (d1)+olaparib (200 mg/kg, d3-5). Mice were monitored for treatment dependent toxicities by charting body weight and percent survival. Addition of olaparib seemed to be more toxic as compared to monotherapy, however delaying start of olaparib administration to d3 seemed to decrease olaparib specific toxicity as compared to concurrent therapy. Mice were dosed chronically with MM-398 once weekly at various doses on Day 1, while olaparib was dosed once daily at a weekly fixed dose for 5, 4 or 3 consecutive days each week (either on Days 1-5, Days 1-4, Days 2-5 or Days 3-5), and body weight and percent survival were followed as a gross measure of toxicity. Toxicity of the combination was seen at the highest doses of MM-398 when given in close proximity to the olaparib doses (FIG. 4). However, this toxicity could be alleviated either by delaying the start of olaparib dosing, whereby the highest dose of MM-398 could be successfully dosed with olaparib if given on Days 3-5 following Day 1 dosing of MM-398.

Mice were dosed chronically with MM-398 once weekly at various doses on Day 1, while veliparib was dosed once daily at a fixed dose for 3 consecutive days each week (either on Days 2-4, Days 3-5, or Days 4-6) and body weight was followed as a gross measure of toxicity. Toxicity of the combination was seen at the highest doses of nal-IRI when given in close proximity to the veliparib doses. However, this toxicity could be alleviated either by dose reducing nal-IRI or delaying the start of veliparib dosing. This dosing schedule was followed in subsequent mouse efficacy studies which demonstrated synergy of the combination in two cervical cancer tumor xenograft models, in which veliparib alone was not efficacious, and a second model in which neither nal-IRI or veliparib were efficacious as single agents, however the combination demonstrated tumor growth inhibition.

Figure 8A:
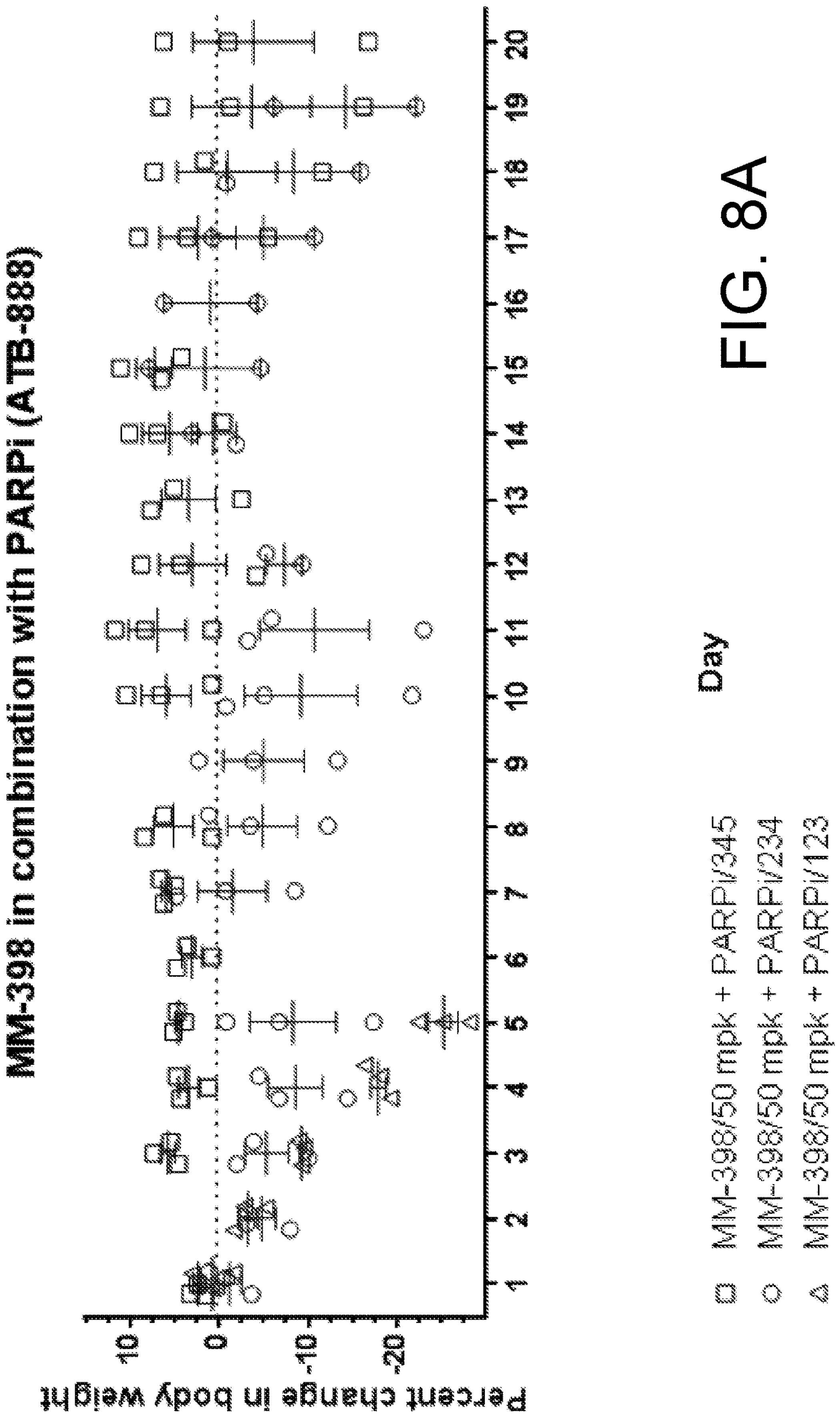
FIG. 8A is a graph that depicts the in vivo tolerability of 50 mg/kg dose of MM-398 in combination with 50 mg/kg veliparib given on days 1, 2, and 3; or 2, 3, and 4; or 3, 4, and 5 after administration of the MM-398.
Figure 8B:
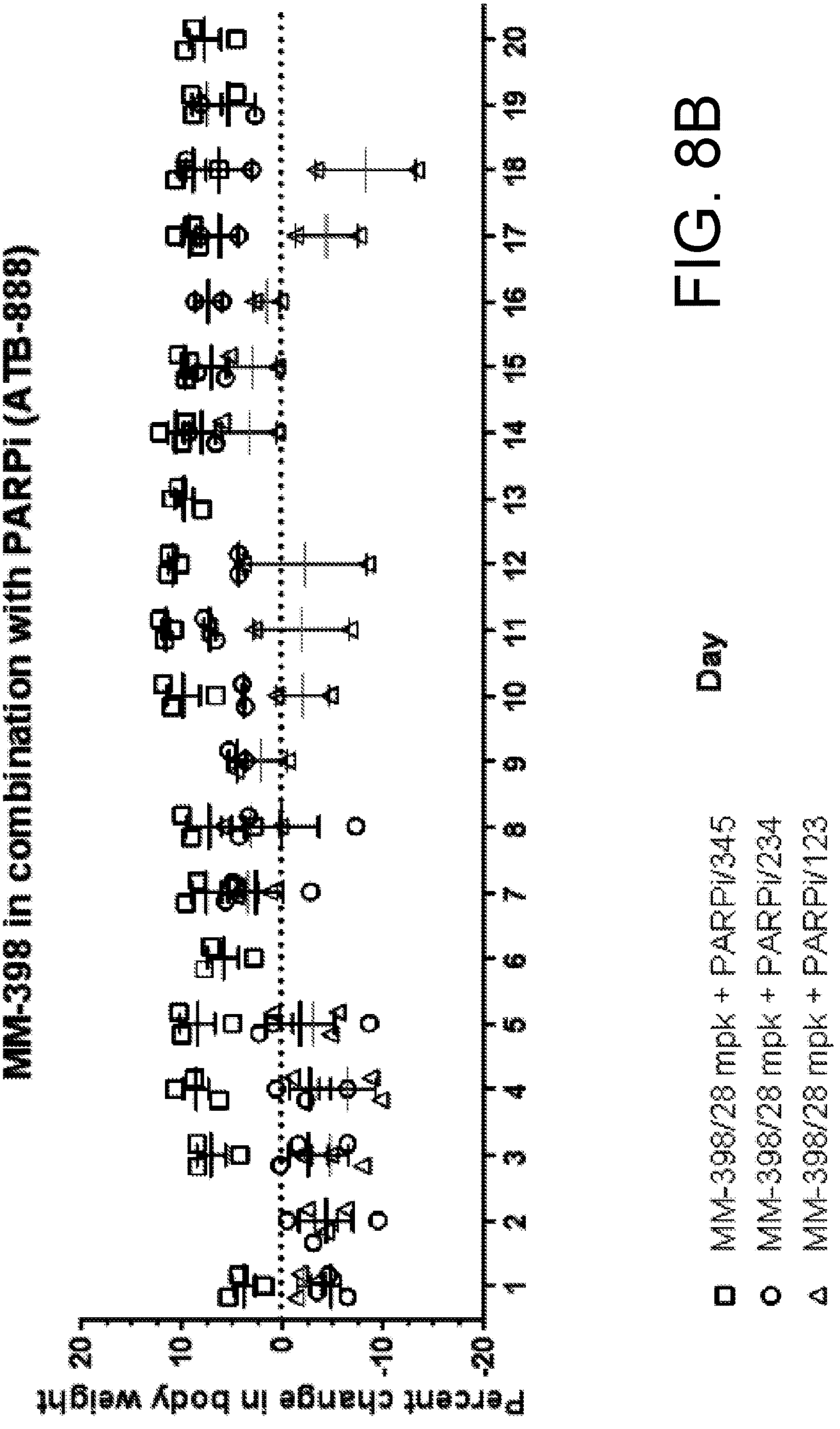
FIG. 8B is a graph that depicts the in vivo tolerability of 28 mg/kg dose of MM-398 in combination with 50 mg/kg veliparib given on days 1, 2, and 3; or 2, 3, and 4; or 3, 4, and 5 after administration of the MM-398.

The tolerability of the combination of MM398 in a mouse model on day 1 was evaluated in combination with the administration of veliparib on days 1-3, days 2-4 and days 3-5. The tolerability of the combined regimen in mice (measured by change in percent bodyweight over 20 days) increased as the first administration of the veliparib occurred on day 2 and day 3, with day 3 initial veliparib dosing providing the most tolerated dosing schedule. FIG. 8A is a graph that further depicts the in vivo tolerability of the 50 milligrams/kilogram (mpk) dose of MM-398 on day 1 in combination with 50 mg/kg veliparib given on days 1, 2, and 3; or days 2, 3, and 4; or days 3, 4, and 5 after administration of the MM-398, as reflected in percent change in body weight with an adjusted lower limit. FIG. 8B is a graph that further depicts the in vivo tolerability of the 28 mpk dose of MM-398 on day 1 in combination with 50 mg/kg veliparib given on days 1, 2, and 3; or days 2, 3, and 4; or days 3, 4, and 5 after administration of the MM-398, as reflected in percent change in body weight with an adjusted lower limit.

Figure 12:
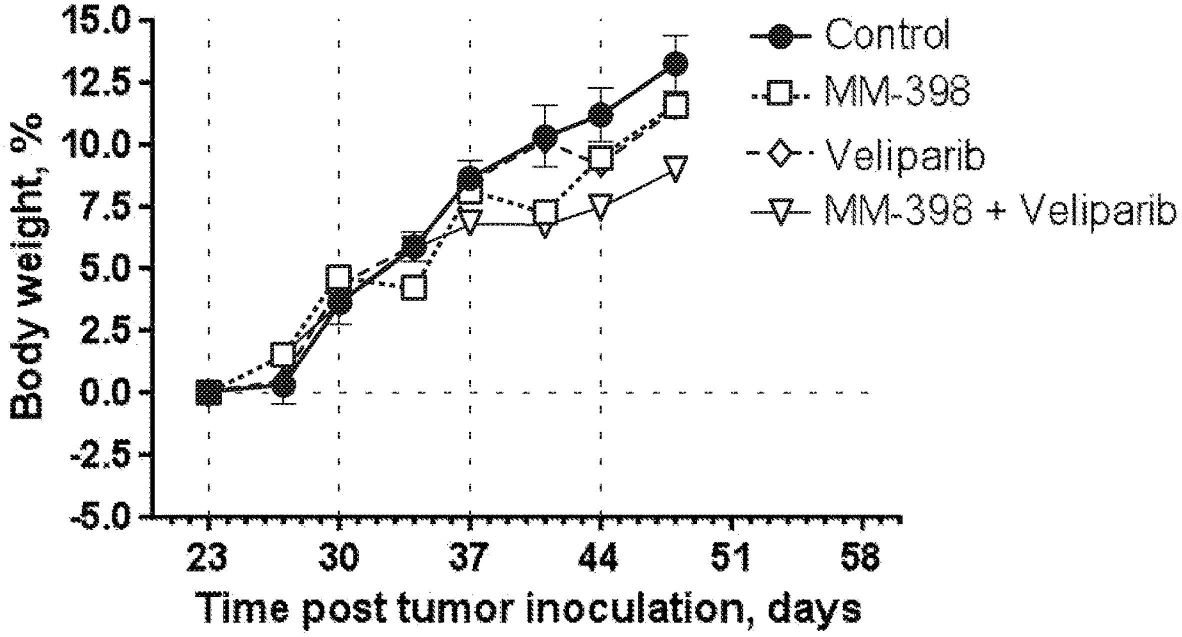
FIG. 12 depicts the effect of MM-398 in combination with veliparib in C33A xenograft model and body weight, where veliparib was dosed 72 h following liposomal irinotecan (5 mg/kg MM398) and/or the PARP inhibitor veliparib (50 mpk) on days 3-5 starting after administration of MM398.

FIG. 12 is a graph showing that treatment of mice with the combination of MM-398 with veliparib in C33A xenograft model described in Example 4 also lead to decreases in body weight as compared to administration of either drug alone.

These studies demonstrated that this toxicity could be alleviated by delaying the start of PARP inhibitor dosing, preferably by 2-3 days after the day on which liposomal irinotecan was administered. A dosing schedule where the PARP inhibitor was only administered on days subsequent to administration of liposomal irinotecan was followed in mouse efficacy studies (Example 3) demonstrating therapeutic synergy of the combination of a PARP inhibitor and liposomal irinotecan in two cervical cancer tumor xenograft models (in which veliparib alone was not efficacious, and a second model in which neither MM-398 or veliparib were efficacious as single agents, however the combination demonstrated tumor growth inhibition).

Example 3: Pre-Clinical Efficacy of Liposomal Irinotecan

In vivo tumor xenograft studies demonstrated that the efficacy of liposomal irinotecan is greater than free irinotecan. In addition, in vivo tumor xenograft studies demonstrated MM-398 is related to high CES activity and/or high tumor levels of CPT-11 following dosing with MM-398. Additionally, MM-398 has demonstrated superior activity compared to equivalent dosing of free irinotecan in several pre-clinical models including breast, colon, ovarian, and pancreatic tumor xenograft models.

Liposomal irinotecan (MM-398) has greater efficacy in various cancer models, compared to non-liposomal irinotecan. Cancer cells were implanted subcutaneously in mice; when tumors were well established and had reached mean volumes of 200 mm3, IV treatment with free irinotecan, MM-398 or control was initiated. The doses of free and nanoliposomal irinotecan used in each study are indicated above, with dose time points indicated by arrows. Tumor permeability as well as tumor tissue carboxylesterase (CES) activity, which is responsible for the enzymatic conversion of CPT-11 to SN-38, are predicted to be critical factors for local tumor exposure of SN-38 following MM-398 dosing. In vivo tumor xenograft studies have demonstrated that efficacy of MM-398 is related to high CES activity and/or high tumor levels of CPT-11 following dosing with MM-398. Additionally, MM-398 has demonstrated superior activity compared to equivalent dosing of free irinotecan in several pre-clinical models including breast, colon, ovarian, and pancreatic tumor xenograft models.

Example 4: Pre-Clinical Activity of Liposomal Irinotecan and PARP Inhibitors

Figure 7A:
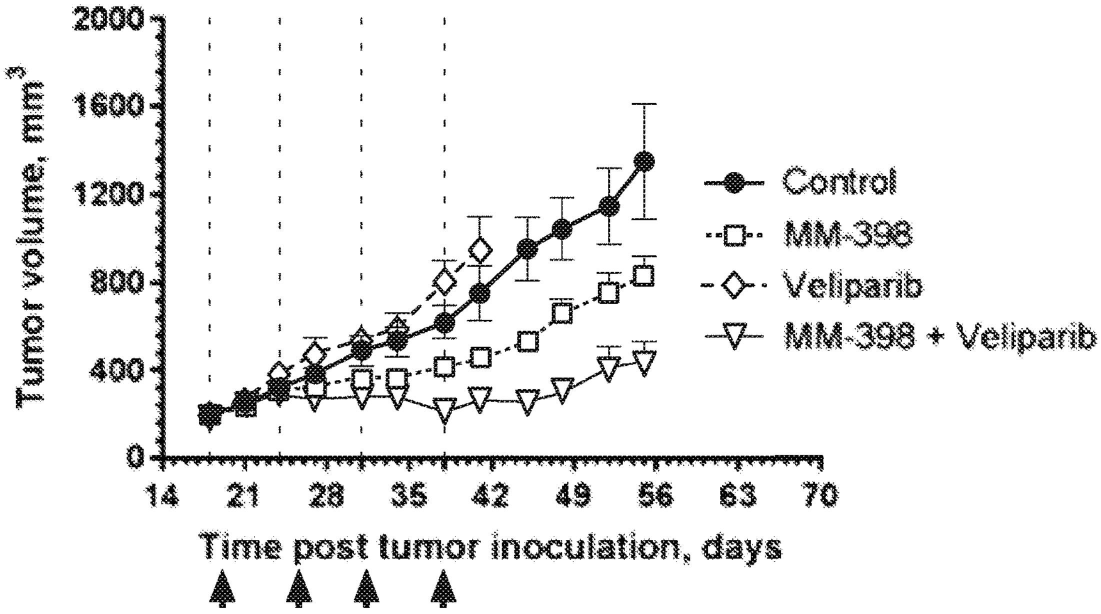
FIG. 7A is a graph showing data from a mouse xenograft study using MS751 cervical cancer cells in a murine model treated with liposomal irinotecan (5 mg/kg MM398) and/or the PARP inhibitor veliparib on days 4-6 after administration of MM398.
Figure 7B:
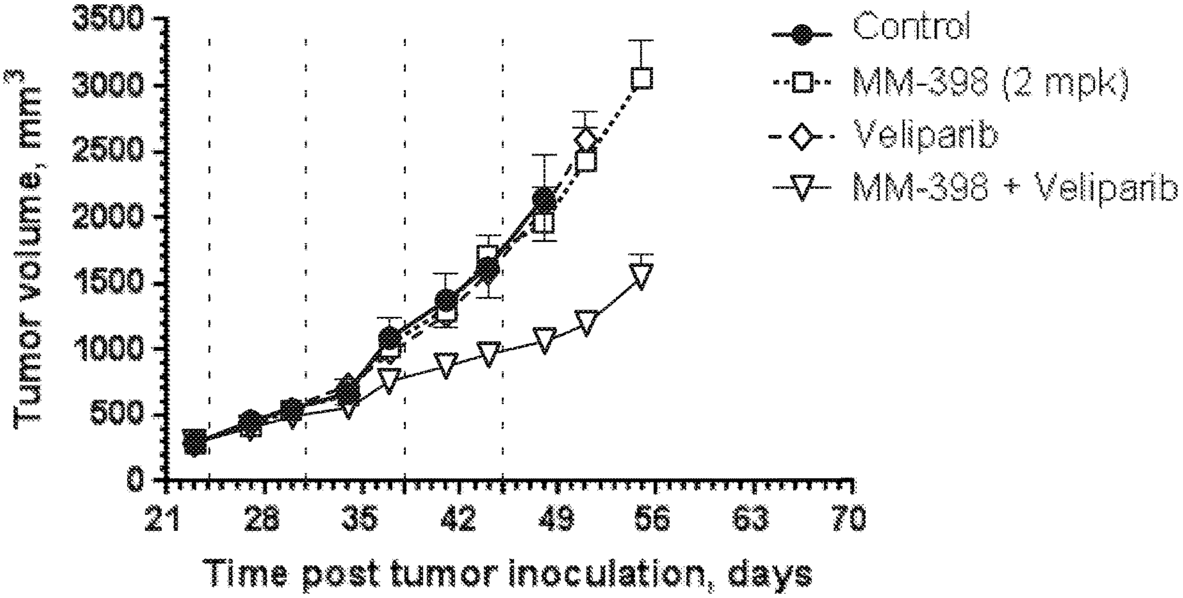
FIG. 7B is a graph showing data from a mouse xenograft study using MS751 cervical cancer cells in a murine model treated with liposomal irinotecan (2 mg/kg MM398) and/or the PARP inhibitor veliparib on days 4-6 after administration of MM398.

Referring to FIG. 7A and FIG. 7B, the antitumor activity of MM-398 was studied in combinations with veliparib (PARPi) in multiple cervical xenograft models. In this study, MS-751 and C33A xenograft models of cervical cancer were employed to probe the effect of administering suboptimal doses of MM-398 in combination with the PARP inhibitor veliparib. Differential tissue levels of MM-398 at 24 and 72 hours indicated that MM-398 and the active metabolite SN-38 cleared faster from the liver, spleen, colon, and plasma, than from tumors. The combination of veliparib and MM-398 gave improvements in key PD biomarkers (cleaved caspase and yH2AX) when compared to veliparib or MM-398 alone. FIGS. 7A and 7B show that the combination of MM-398+veliparib is synergistic. Two different cervical cancer xenograft models were utilized to study the efficacy of MM-398 dosed once weekly on Day 1 (arrows), veliparib dosed at 50 mg/kg orally once daily for 3 consecutive days on Days 4-6 of each week, or the combination dosed on the same schedule as the single agent treatments combined. (A) MS751 cervical cancer xenograft model using MM-398 dosed at 5 mg/kg and (B) C33A cervical cancer xenograft model using MM-398 dosed at 2 mg/kg. In the study, control mice were the same strain, and were harvested prior to tested mice (slightly younger). Data is not presented for mice removed from study for weight loss or for mice removed unintentionally before end date.

Cervical MS-751 Xenograft Model

The MS-751 Xenograft Model details are summarized in Table 6.

TABLE 6

| Mouse strain: | Nude (Tacoma) | | | |
|---|---|---|---|---|
| Tumor | Cervical MS-751, C33A | | | |
| Inoculation: | 5*10^6 (s.c.) in 30% MG | | | |
| Drug: | MM-398 (iv) + Veliparib | Animal per | Dose | |
| Groups: | (oral) | group: | (mpk) | |
| 1 | Saline | 10 | | |
| 2 | MM-398 | 10 | 5 | |
| 3 | veliparib/oral | 10 | 50 | 3/4/5th day |
| 4 | MM-398 + veliparib | 10 | 5 + 50 | 3/4/5th day |

Figure 9A:
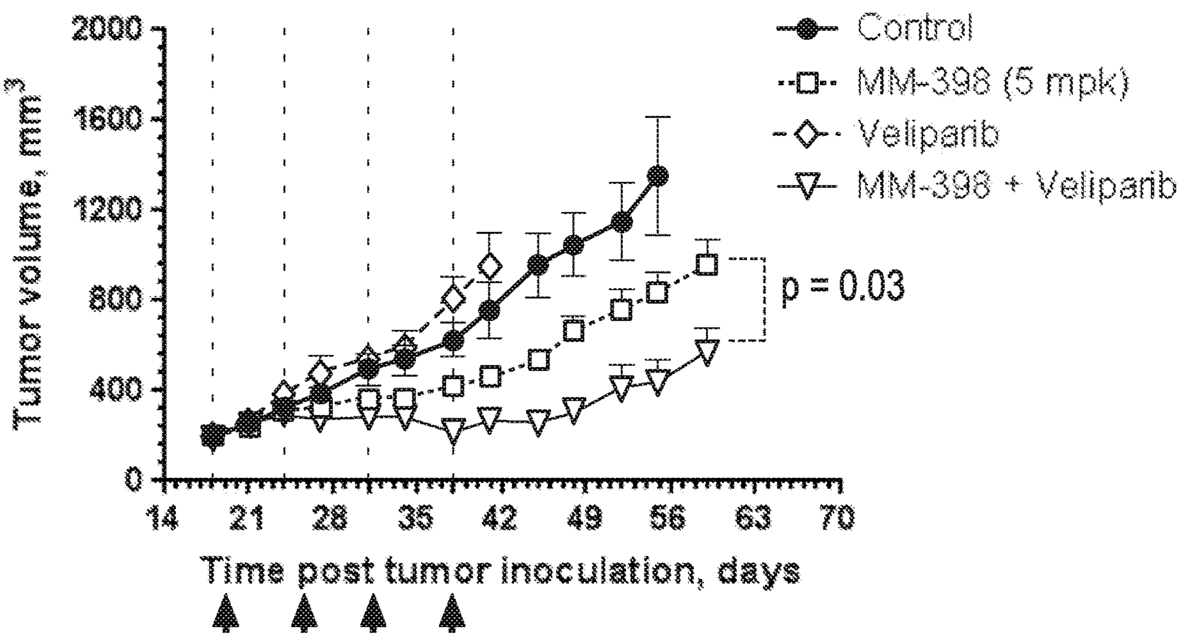
FIG. 9A is a graph showing data from a mouse xenograft study using MS751 cervical cancer cells in a murine model treated with liposomal irinotecan (5 mg/kg MM398) and/or the PARP inhibitor veliparib (50 mpk) on days 3-5 starting after administration of MM398.
Figure 9B:
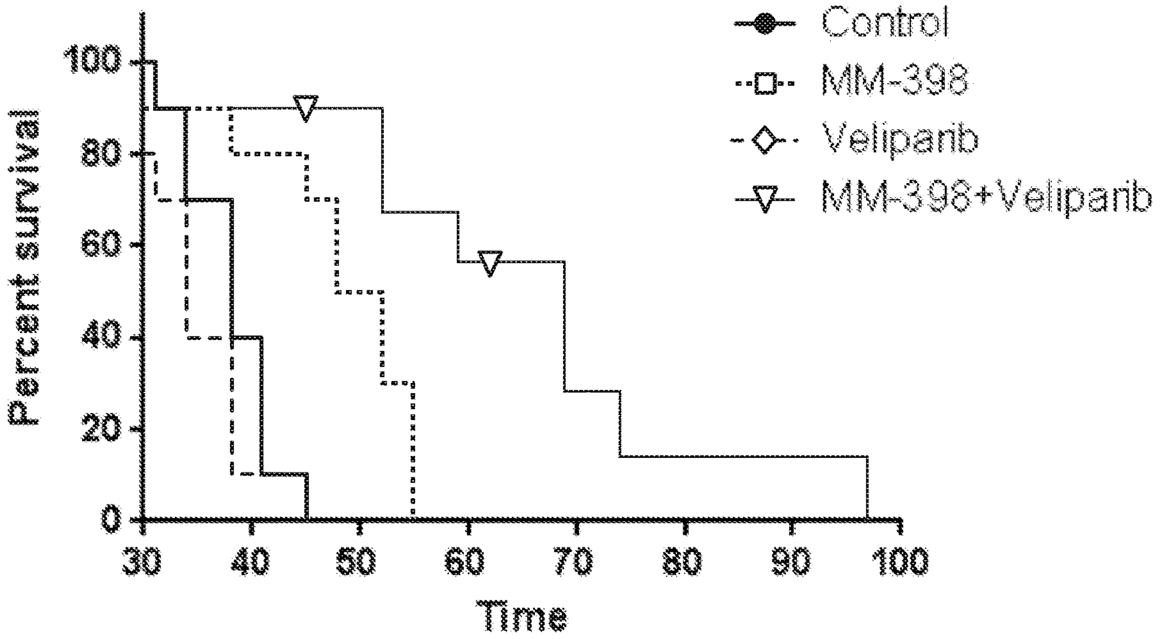
FIG. 9B is a graph showing survival data from a mouse xenograft study using MS751 cervical cancer cells in a murine model treated with liposomal irinotecan (5 mg/kg MM398) and/or the PARP inhibitor veliparib (50 mpk) on days 3-5 starting after administration of MM398.
Figure 9C:
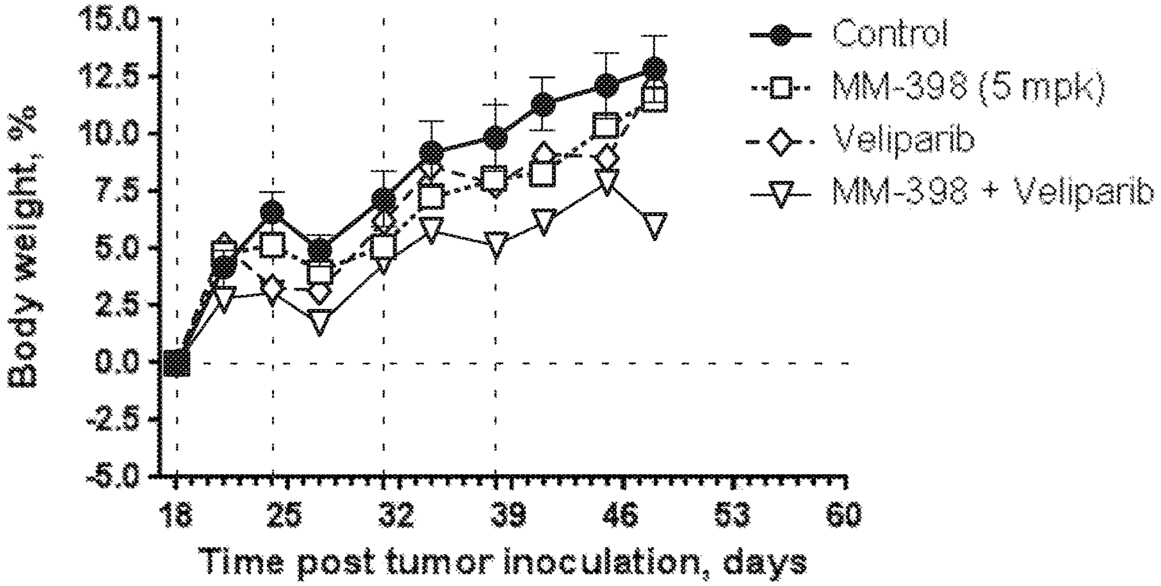
FIG. 9C is a graph that depicts the effect of MM-398 in combinations with veliparib in MS751 xenograft murine model treated with liposomal irinotecan (5 mg/kg MM398) and/or the PARP inhibitor veliparib (50 mpk) on days 3-5 starting after administration of MM398.

FIG. 9A shows that tumor volume decreased when MM-398 (5 mpk dose) was administered in combinations with veliparib in the MS751 xenograft model (p=0.03) as compared to administration of either drug alone. FIG. 9B shows that percent survival was better for mice treated with MM-398 (5 mpk dose) in combinations with veliparib in MS751 xenograft model as compared to treatment with either drug alone either drug administered alone. FIG. 9C shows that treatment with the combination of MMM-398 with veliparib in MS751 xenograft model lead to decreases in body weight as compared to administration of either drug alone.

C33A Cervical Xenograft Model

The C33A Xenograft Model details are summarized in Table 7.

TABLE 7

| Mice: | Female, Ncr Nudes (Taconic), 5-6 weeks. |
|---|---|
| Cell Lines: | C33 A |
| Tumor Inoculation: $5 \times 10^6$ in 100 μl Matrigel (30 vol %) sc | |
| 15 mice per a cell line | |
| Groups: | Dose, mpk: |
| MM-398 alone | 2 |
| Veliparib alone | 50 |
| MM-398 + Veliparib (3-4-5 d) | 2 + 60 |

TABLE 7-continued

| End-life Collection: 72 h after first injection |
|---|
| Frozen (Tumor, Liver, Spleen, Plasma) |
| FFPA (Tumor) |
| Analysis: |
| gamma H2AX and cleaved caspase/ |
| Tunnel in FFPE (Lia) |
| CPT-11 and SN-38 in all tissues for |
| MM-398 flash frozen only (Roswell) |

Figure 10:
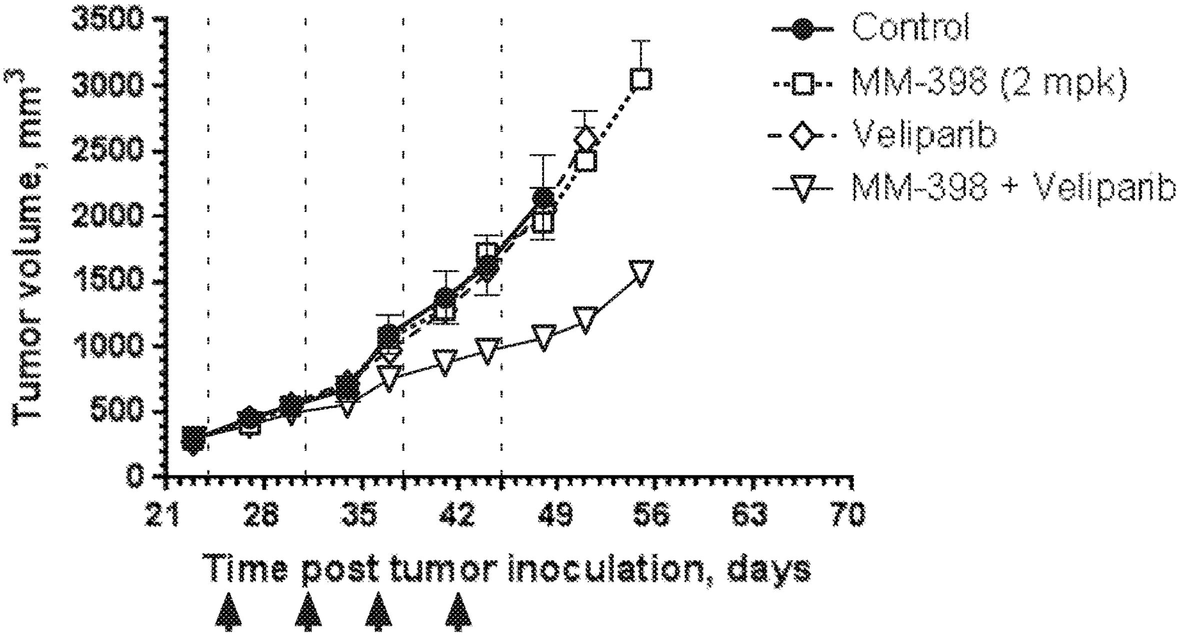
FIG. 10 is a graph showing data from a mouse xenograft study using C33 cervical cancer cells in a murine model treated with liposomal irinotecan (2 mg/kg MM398) and/or the PARP inhibitor veliparib (50 mpk) on days 3-5 starting after administration of MM398.
Figure 11:
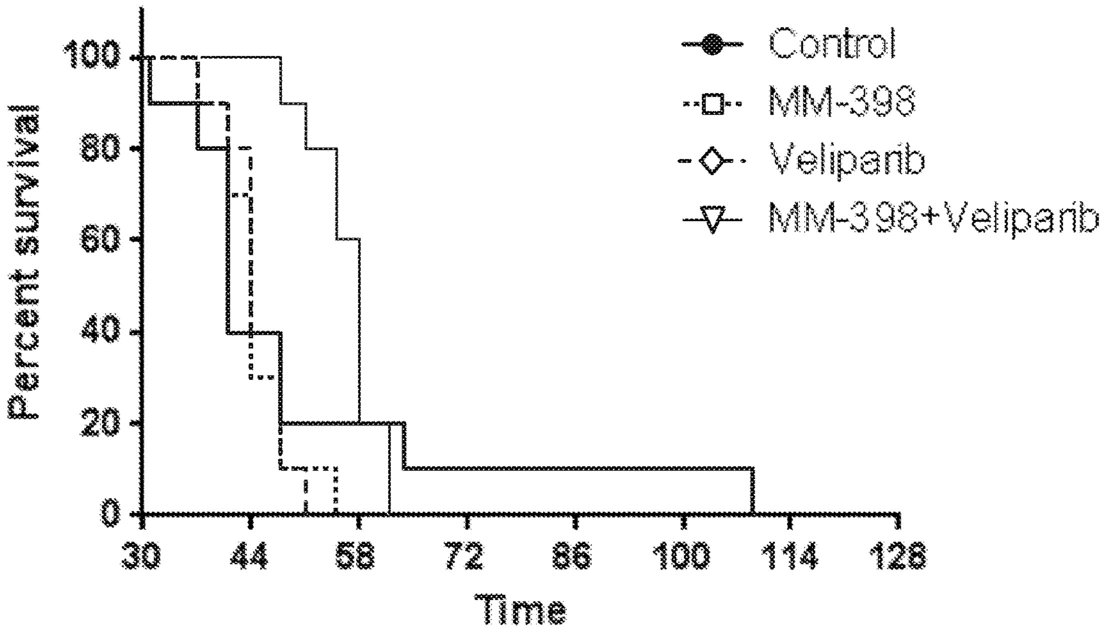
FIG. 11 is a graph showing survival data from a mouse xenograft study using C33 cervical cancer cells in a murine model treated with liposomal irinotecan (5 mg/kg MM398) and/or the PARP inhibitor veliparib (50 mpk) on days 3-5 starting after administration of MM398.

FIG. 10 shows that the combination of MM-398 with veliparib in the C33A xenograft model leads to decreases in tumor volume as compared to either drug alone administered alone. FIG. 11 shows that percent survival was better for mice MM-398 (5 mpk dose) in combinations with veliparib in C33A xenograft model as compared to either drug administered alone.

Example 5: Clinical Use of Liposomal Irinotecan and PARP Inhibitors

Clinical Use of Liposomal Irinotecan and Veliparib

Figure 17:
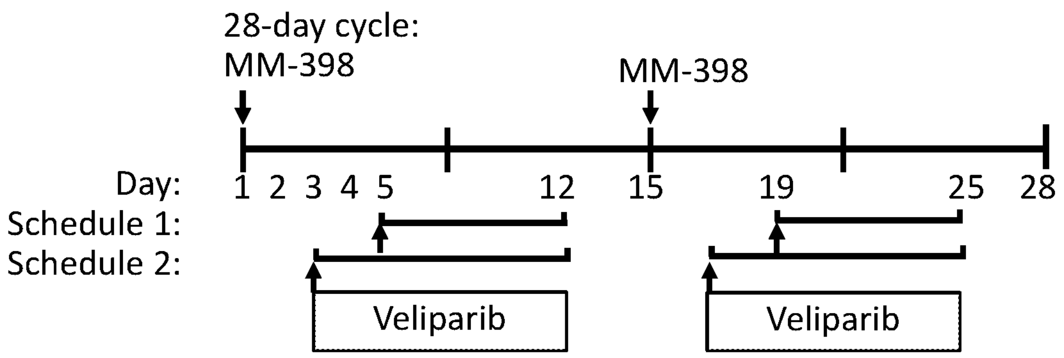
FIG. 17 outlines two different schedules of veliparib dosing that will be explored in combination with MM-398 bi-weekly dosing.

This is a Phase 1 human dose escalation study to characterize the safety, tolerability, MTD and PK of MM-398 in combination with veliparib in order to determine an optimal combination dose and schedule that will be identified as the recommended Phase 2 dose. The schematic shown in FIG. 17 outlines two different schedules of veliparib dosing that will be explored in combination with MM-398 bi-weekly dosing.

MM-398 will be administered by intravenous (IV) infusion over 90 minutes at a dose of 80 mg/$m^2$ every two weeks. MM-398 is administered by intravenous (IV) infusion over 90 minutes at a dose of 80 mg/$m^2$ (salt) irinotecan once every two weeks (days 1 and 15 of each 28-day treatment cycle). Veliparib is co-administered orally twice daily by the patient at home according to the following schedule:

TABLE 8

| Dose Level[1] | Veliparib Dose (mg BID) | Veliparib Dose Days | MM-398 Dose (salt) (mg/$m^2$ q2w) |
|---|---|---|---|
| 1 | 100 | Day 5-12; 19-25 | 80, Day 1, 15 |
| 2 | 200 | Day 5-12; 19-25 | 80, Day 1, 15 |
| 3 | 200 | Day 5-12; 17-25 | 80, Day 1, 15 |
| 4 | 300 | Day 5-12; 19-25 | 80, Day 1, 15 |
| 5 | 400 | Day 5-12; 19-25 | 80, Day 1, 15 |

[1]Additional dose levels and alternate dosing schedules may be explored upon agreement of Sponsor, Medical Monitor and Investigators.
** After the MTD is reached, and for the first cycle only, we plan to enroll approximately 18 patients obtain tumor biopsies according to the schema outlined in the correlates section below.

The study will enroll 3 patients per dose cohort following a traditional 3+3 dose escalation design. Dose limiting toxicities (DLTs) will be evaluated during the first cycle of treatment (28 days) in order to determine the MTD. If there are no DLTs within the safety evaluation period, then the next cohort can be initiated following agreement between the Investigators and Medical Monitor. If a DLT occurs, then the cohort will be expanded to 6 patients. If 2 or more patients have DLTs within a given dose level, then the dose will not be escalated further; however, lower doses may be explored. Additional dosing schedules may also be explored depending on the safety, tolerability, and PK observed.

Given that these individual therapies have been studied in previous clinical trials, it is important that the safety assessment takes into account the expected safety profile of the standard dose regimens. For all treatment regimens, any toxicity that is related to disease progression will not be considered a DLT. The following events, occurring during cycle 1 of the study combination, will be considered DLTs if deemed drug-related:

- grade 3 or 4 neutropenia complicated by fever≥38.5° C. (i.e. febrile neutropenia) and/or documented infection;
- grade 4 neutropenia that does not resolve within 7 days despite optimal therapy (withholding study drug and GCSF administration);
- grade 4 thrombocytopenia that does not resolve within 7 days or any grade 3-4 thrombocytopenia complicated with hemorrhage;
- grade 4 anemia that does not resolve within 7 days despite optimal therapy (withholding study drug and red blood cell transfusions);
- inability to begin subsequent treatment course within 14 days of the scheduled date, due to study drug toxicity;
- any grade 3-4 non-hematologic toxicity (except fatigue/asthenia<2 weeks in duration; vomiting or diarrhea lasting less than 72 hours whether treated with an optimal anti-emetic or anti-diarrheal regimen or not; or alkaline phosphatase changes).
- ≥grade 2 seizure Patients will be treated until disease progression as determined by RECIST v1.1 criteria evaluated by CT scan every 8 weeks from first dose of study drug. The inclusion and exclusion criteria for the clinical trial are summarized in the table 9 below.

TABLE 9

| Inclusion Criteria | Exclusion Criteria |
|---|---|
| Patients must have histologic or cytologic confirmation of cancer for which there is no known standard therapy capable of extending life expectancy. | Active CNS metastasis |
| ECOG Performance Status 0 or 1 | Clinically significant GI disorders, including history of small bowel obstruction unless the obstruction was a surgically treated remote episode |
| Tumor lesion(s) amenable to multiple pass percutaneous biopsies and patient willing to undergo required pre- and post-treatment biopsies | Prior irinotecan therapy; or topotecan therapy or bevacizumab therapy within 6 months of first dose of study treatment |
| Must have adequate: | Prior chemotherapy or biological therapy within 3 weeks, or within a time interval less than 5 half-lives of the agent, prior to first dose of study treatment |
| Bone marrow function | Prior radiotherapy within 4 weeks of first dose of study treatment |
| ANC > 1,500 cells/ul without the use of hematopoietic growth factors | Patients who have had radiation to the pelvis or other bone marrow-bearing sites will be considered on a case by case basis and may be excluded if the bone marrow reserve is not considered adequate (i.e. radiation to > 25% of bone marrow) |
| Platelet count > 100,000 cells/ul | Known hypersensitivity to MM-398 |
| Hemoglobin > 9 g/dL | Active infection |
| Hepatic function | Pregnant or breast feeding |
| Normal serum total bilirubin | |
| AST and ALT ≤ 2.5 × ULN (≤5 × ULN is acceptable if liver metastases are present) | |
| Renal function | |
| Serum creatinine ≤ 1.5 × ULN | |
| Normal ECG | |
| ≥18 years of age | |
| Able to understand and sign informed consent | |
| Prior PARP inhibitor therapy is allowed | |
| Willing to undergo pre-treatment ferumoxytol MRI (patients will be excluded from undergoing ferumoxytol MRI if they have evidence of iron overload, a known hypersensitivity to ferumoxytol or any other IV iron product, a documented history of multiple drug allergies, or those for whom MRI is otherwise contraindicated, including claustrophobia or anxiety related to undergoing MRI) | |

The dose escalation portion of the trial may require up to 30 patients if 6 patients are required at each of 5 dose levels. An additional 18 patients may be used to explore the effect of veliparib on the biologic correlates. Thus, the accrual ceiling will be set at 48 patients.

The study is proposed to include all solid tumor types, however, particular indications that are of high interest for this study includes the following: cervical cancer, ovarian cancer, triple negative breast cancer (TNBC), non-small cell lung cancer (NSCLC), small cell lung cancer (SCLC), gastric cancer, pancreatic cancer, and neuroendocrine tumors.

The methods and uses herein can also be applied to other tumor suitable types including those noted for increased frequency of DNA damage response (DDR) pathway deficiencies (or 'BRCAness') found in sporadic tumors, which are predicted to be sensitive to PARP inhibitors. As mentioned previously, BRCA1 or BRCA2 deficiencies, found particularly in triple negative breast cancer and high-grade serous ovarian cancer, sensitize cells to PARP-inhibitors. Likewise, loss of function of other genes and proteins involved in DDR pathways, including the endonuclease XPF-ERCC1, the homologous recombination repair proteins meiotic recombination protein 11 (MRE11) and Fanconi anemia pathway (FANC) proteins, also sensitize cells to PARP inhibitors. Fanconi anemia pathway deficiencies have been demonstrated in lung, cervical, and breast and ovarian cancers. These and other DDR pathway deficiencies may be predictive biomarkers for PARP inhibitor therapy, and will be explored retrospectively in this study. Veliparib, specifically, has also demonstrated clinical activity in a number of indications, including BRCA-positive and BRCA wild-type breast and ovarian cancer, as well as gastric cancer in combination with FOLFIRI. For the proposed study, indications were chosen not only for their high unmet medical need, but for potential sensitivity to irinotecan and/or veliparib based on the afore-mentioned pre-clinical and/or clinical experience. While the PARP inhibitor olaparib has recently been FDA approved as a monotherapy in BRCA+ ovarian cancer, this study will not limit treatment in the ovarian patient population to BRCA+ patients, as this is a phase I study of a combination therapy and may retrospectively identify patients with other DDR pathway deficiencies in addition to BRCA.

Use of Liposomal Irinotecan and Olaparib

MM-398 is administered by intravenous (IV) infusion over 90 minutes at a dose of 80 $mg/m^2$ (based on the corresponding amount of irinotecan hydrochloride trihydrate, equivalent to 70 $mg/m^2$ irinotecan free base) every two weeks. Olaparib is co-administered orally twice daily by the patient at home according to the following schedule (Table 10).

TABLE 10

| Dose Level[1] | Olaparib Dose (mg BID) | Olaparib Dose Days | MM-398 Dose ($mg/m^2$ q2w)* |
|---|---|---|---|
| 1 | 100 | Day 5-12; 19-25 | 80, Day 1, 15 |
| 2 | 200 | Day 5-12; 19-25 | 80, Day 1, 15 |
| 3 | 200 | Day 5-12; 17-25 | 80, Day 1, 15 |
| 4 | 300 | Day 5-12; 19-25 | 80, Day 1, 15 |
| 5 | 400 | Day 5-12; 19-25 | 80, Day 1, 15 |

*= The 80 $mg/m^2$ MM-398 dose is based on the corresponding amount of irinotecan hydrochloride trihydrate (equivalent to 70 $mg/m^2$ based on irinotecan free base).

Example 6: Measuring Phosphorylated H2AX in Tumor Biopsies

Figure 14:
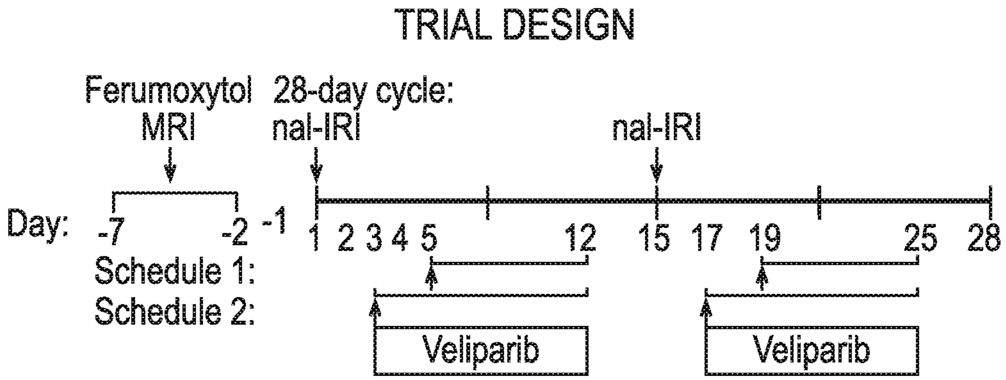
FIG. 14 is a graphical representation of a phase I study design employing the combinations of MM-398 (nal-IRI) and veliparib.

Phosphorylated H2AX (γ-H2AX) plays an important role in the recruitment and/or retention of DNA repair and checkpoint proteins such as BRCA1, MRE11/RAD50/NBS1 complex, MDC1 and 53BP1. DNA damage has been shown to increase H2AX phosphorylation in cancer cells following exposure to camptothecins. If the PARP inhibitor compound(s) is/are able to increase the degree of DNA damage due to irinotecan from MM-398, it may be detectable by measurement of H2AX phosphorylation. An immunofluorescence assay was used in previous clinical studies. Patient peripheral blood mononuclear cells (PBMCs), hair follicles, and/or tumor biopsy samples will be collected if there is readily accessible disease. The association between the pharmacodynamic response measured by γ-H2AX level can be assessed by Fisher's test or the Wilcoxon rank sum test, as appropriate; this evaluation will be done at the MTD+/−a maximum of 2 dose levels (FIG. 14).

TABLE 11

| Schedule for biopsies and surrogate samples | | | | | |
|---|---|---|---|---|---|
| Dose Level | | PARPi Dose (mg BID) | PARPi Dose Days | MM-398 Dose ($mg/m^2$ q2w) | Biopsy in am for PD marker |
| 1 | | 100 | Day 5-12; 19-25 | 80, Day 1, 15 | |
| 2 | | 200 | Day 5-12; 19-25 | 80, Day 1, 15 | |
| 3 | | 200 | Day 3-12; 17-25 | 80, Day 1, 15 | Days 1, 5, 19 |
| 4 | | 300 | Day 3-12; 17-25 | 80, Day 1, 15 | Days 1, 5, 19 |
| 5 | | 400 | Day 3-12; 17-25 | 80, Day 1, 15 | Days 1, 5, 19 |
| Confirm | A | MTD | Day 3-12; 19-25 | 80, Day 1, 15 | Days 1, 5, 19 |
| | B | MTD | Day 5-12; 17-25 | 80, Day 1, 15 | Days 1, 5, 19 |

Figure 15A:
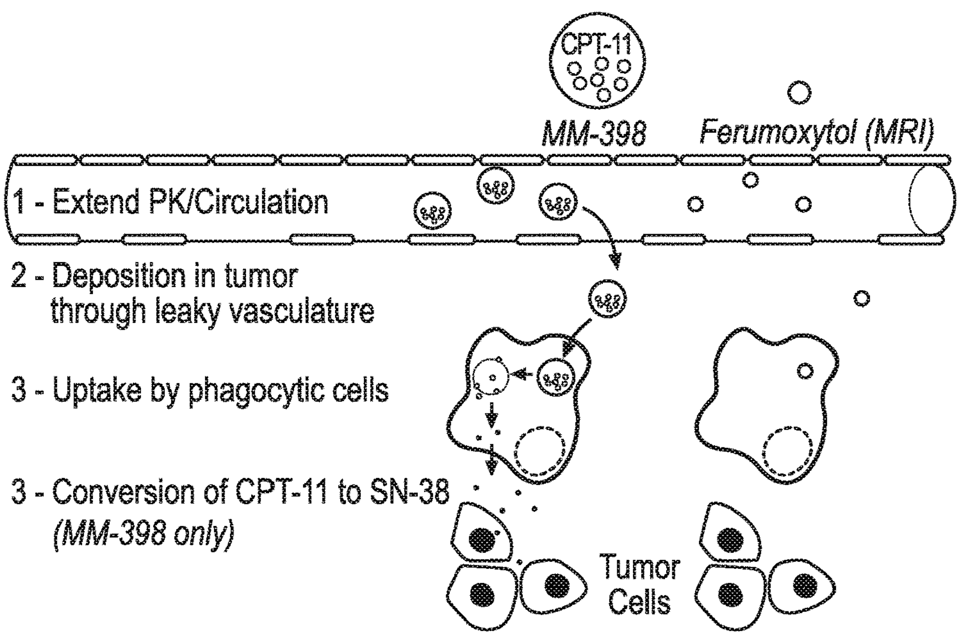
FIG. 15A is a schematic showing a use of ferumoxytol (FMX) as a predictive biomarker for cancer treatment with liposomal irinotecan (e.g., MM-398).
Figure 15B:
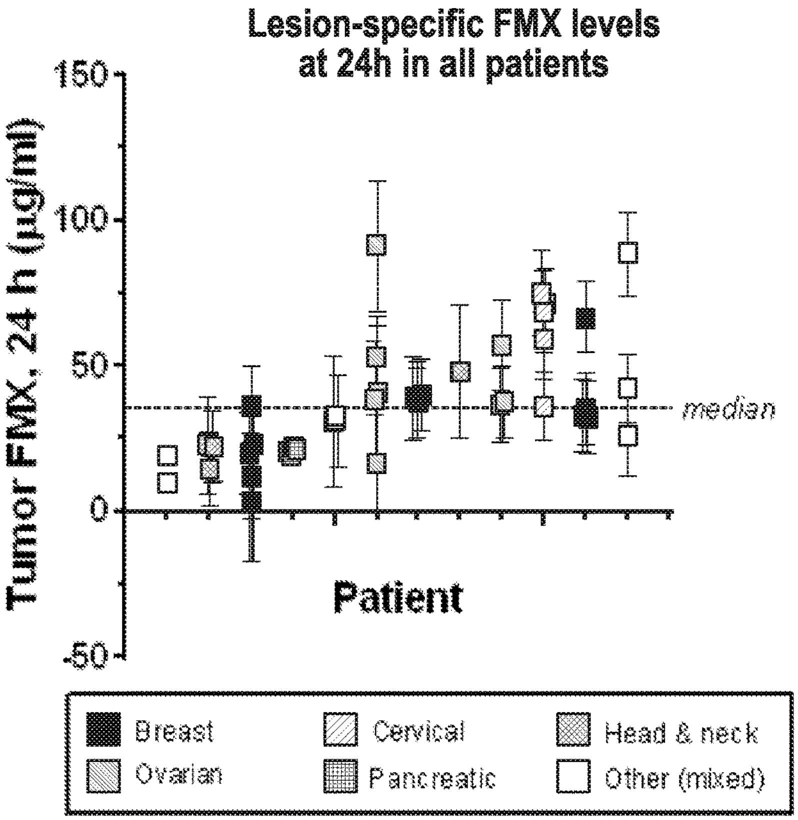
FIG. 15B is a graph showing FMX concentration of individual patient lesions was calculated using a standard curve from MR images obtained 24 h post-FMX injection.
Figure 15C:
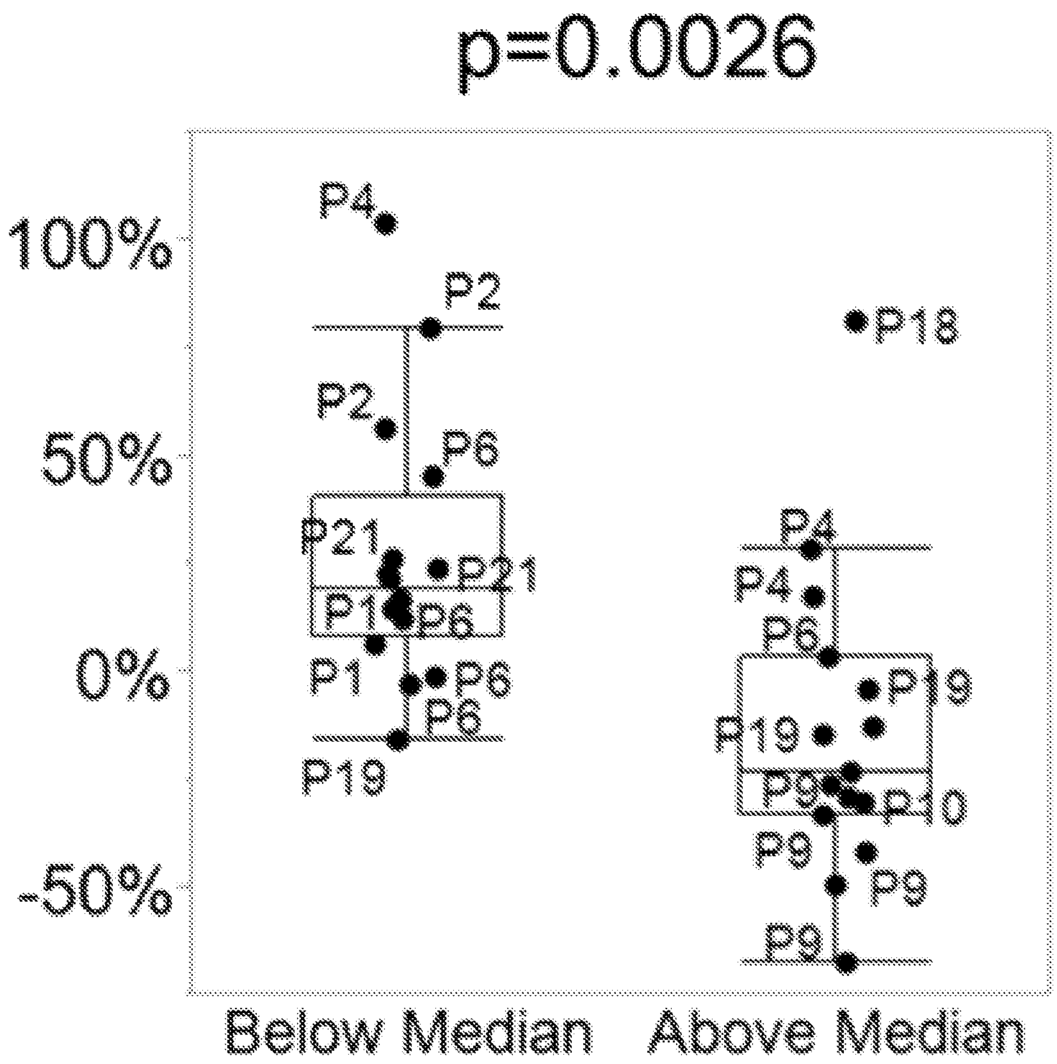
FIG. 15C is a graph showing FMX signal from lesions at 24 h are grouped relative to the median value observed in the FMX MRI evaluable lesions and compared to the best change in lesion size based on CT scans (data available from 9 patients; total of 31 lesions).

Example 7: Administering and Detecting Ferumoxytol to Predict Deposition of Topoisomerase Inhibitor from Liposomal Irinotecan FIGS. 15A-15C show that FMX MRI may be a predictive tool for tumor response to MM-398. FIG. 15A is a schematic showing that MM-398 and FMX have similar properties, including 1) extended PK, 2) the ability to deposit in tumor tissues through the EPR effect (i.e. leaky vasculature), and 3) uptake by macrophages. Therefore, visualization of FMX on MRI may be able to predict MM-398 deposition. (B) FMX concentration of individual patient lesions was calculated using a standard curve from MR images obtained 24 h post-FMX injection. (C) FMX signal from lesions at 24 h are grouped relative to the median value observed in the FMX MRI evaluable lesions and compared to the best change in lesion size based on CT scans (data available from 9 patients; total of 31 lesions).

The phase I study of MM-398 also examined the feasibility of magnetic resonance (MR) imaging to predict tumor-associated macrophage (TAM) content and MM-398 deposition. TAMs appear to play a key role in the deposition, retention and activation of MM-398 within the tumor microenvironment. In this clinical study, ferumoxytol (FMX) a microparticulate preparation of a superparamagnetic iron oxide coated with polyglucose sorbitol carboxymethylether) was used as an imaging contrast agent and MR images were obtained at 1 h, 24 h, and 72 h following FMX injection. FMX is an approved therapy that is indicated for the treatment of iron deficiency anemia in adult patients with chronic kidney disease; however a growing number of cancer patients without iron deficiency are being administered FMX as an imaging agent to visualize macrophage content and vasculature. Like MM-398, FMX is also a nanoparticle with a diameter of approximately 17-31 nm. As tumor permeability was predicted to be an important factor in MM-398 efficacy, FMX was also investigated for use as a surrogate for liposome deposition (FIG. 15A). A benefit of FMX is that this agent helps to identify patients that are less likely to respond to MM-398 because of poor drug uptake. Ferumoxytol as a diagnostic test enables the detection of a patient population that would significantly benefit from MM-398 that would otherwise be uncategorized.

The MRI results from a human clinical trial study demonstrated that the amount of FMX depositing in tumor lesions was able to be quantified (FIG. 15B), and it was subsequently shown that a correlation existed between tumor lesion ferumoxytol uptake by MRI and response to MM-398 (FIG. 15C). This correlation is now being studied further in an expansion of the Phase 1 study, and is included as a correlative imaging study for a trial of MM-398+ veliparib.

FMX is an iron replacement product indicated for the treatment of iron deficiency anemia in adult patients with chronic kidney disease. Although not approved as an indication, ferumoxytol has also been used as an imaging agent in cancer patients and will be utilized as such in this study. At least 2 days prior to Cycle 1 Day 1 (maximum of 8 days prior) a single dose of 5 mg/kg FMX will be administered by intravenous injection. The total single dose will not exceed 510 mg, the maximum approved single dose of FMX. This dosing schedule is less intense than the approved label, which recommends two doses of 510 mg 3 to 8 days apart; however since FMX is being used as imaging agent in this study as opposed to a replacement product for iron deficiency, a lower dose is more appropriate. Three MRIs will be performed for each patient over 2 days. All patients will have a baseline image acquired prior to the FMX infusion, and a second image acquired 1-4 h after the end of FMX administration. All patients will return the following day for a 24 h FMX-MRI using the same protocol and sequences as previously. Each patient will be required to complete their FMX-MRIs on the same scanner to reduce inter-scan variability. The body area to be scanned will be determined by the location of the patient's disease. Each MRI study will be evaluated for image quality and signal characteristics of tumors and reference tissue on T1-, T2- and T2*-weighted sequences. Once a completed set of images from each patient has been received, a qualitative review will be performed and sent to a quantitative lab for analysis. The data will be analyzed in a similar fashion as described above.

pacemakers, pain pumps or other MRI incompatible devices; or history claustrophobia or anxiety related to undergoing MRI)

If a patient consents to FMX-MRI, the patient will receive ferumoxytol infusion and undergo the required FMX-MRI scans approximately 2-6 days prior to beginning MM-398 treatment (the FMX period). FMX will be administered at a dose of 5 mg/kg up to a maximum of 510 mg. All other aspects of administration will be consistent with the latest ferumoxytol prescribing information. A detailed FMX-MRI protocol will be included in the study imaging manual. Briefly, each patient will be required to complete their FMX-MRIs on the same scanner to reduce inter-scan variability. Each MRI study will be evaluated for image quality and signal characteristics of tumors and reference tissue on T1-, T2- and T2*-weighted sequences. Once a completed set of images from each patient has been received, the images will be loaded onto the viewing workstation for qualitative review and then sent to a quantitative lab (handled by central imaging CRO) for analysis.

Multiple MR images will be collected on Day 1-Day 2 of the FMX period at various time points: a baseline image acquired prior to the FMX infusion, a second image occurring 1-4 h after the end of FMX administration, and a third image at approximately 24 h post-FMX, using the same protocol and sequences as on Day 1. The body areas to be scanned will be determined by the location of the patient's disease; detailed instructions will be described in the study imaging manual.

Imaging Correlates Table 12

| Correlative Objective | Imaging Technique | Organ(s) Scanned and Timing of Scans |
|---|---|---|
| Ferumoxytol (FMX) uptake | MRI | Sites of disease; 3 scans completed approximately 2-6 days prior to Cycle 1 Day 1. Scan time points: baseline (immediately prior to FMX infusion) 1 h (post-FMX infusion) 24 h (post-FMX infusion) |
| Histone gamma-H2AX (Pommier, DTB-CCR; Doroshow, Leidos) | Immunofluorescence microscopy ELISA (in development) | Tumor biopsy before treatment, and during treatment. Hair follicles during treatment. PBMC before treatment and during treatment |

Imaging Correlate Study

Patients will be eligible to participate in the FMX imaging study if they do not meet any of the following criteria:

- Evidence of iron overload as determined by:
  - Fasting transferrin saturation of >45% and/or
  - Serum ferritin levels>1000 ng/ml
- A history of allergic reactions to any of the following:
  - compounds similar to ferumoxytol or any of its components as described in full prescribing information for ferumoxytol injection
  - any IV iron replacement product (e.g. parenteral iron, dextran, iron-dextran, or parenteral iron polysaccharide preparations)
  - multiple drugs
- Unable to undergo MRI or for whom MRI is otherwise contraindicated (e.g. presence of errant metal, cardiac Example 8: Clinical Use of Liposomal Irinotecan in Combination with 5-Fluorouracil and Leucovorin Clinical efficacy of MM-398 has also been demonstrated in gemcitabine-refractory metastatic pancreatic cancer patients: in a randomized, Phase 3, international study (NAPOLI-1), MM-398 was given in combination with 5-fluorouracil/leucovorin (5-FU/LV) and significantly prolonged overall survival (OS) compared to 5-FU/LV treatment alone. The median OS for the MM-398-containing arm was 6.1 months compared to 4.2 months for the control arm (HR=0.67, p=0.0122). Because the active pharmaceutical ingredient in MM-398 is irinotecan, the safety profile was, as anticipated, qualitatively similar to irinotecan, where the most common adverse events (≥30%) are nausea, vomiting, abdominal pain, diarrhea, constipation, anorexia, neutropenia, leukopenia (including lymphocytopenia), anemia, asthenia, fever, body weight decreasing, and alopecia (irinotecan package insert). Table 14 provides a summary of Grade 3 or higher safety data of patients treated with MM-398 plus 5-FU/LV from the NAPOLI-1 study. Table 13 provides toxicities observed in the Phase I monotherapy study, for comparison.

TABLE 13

Summary of the most common (>10%) grade 3 or greater adverse events from the 13 patients treated with MM-398 monotherapy at a dose of 80 mg/$m^2$ every 2 weeks during the phase I study. Adverse Events ≥ Grade 3 in Study MM-398-01-01-02

| | n (%) |
|---|---|
| Diarrhea | 4 (30.8) |
| Hypokalemia | 3 (23.1) |
| Abdominal pain | 2 (15.4) |
| Anemia | 2 (15.4) |
| Nausea | 2 (15.4) |
| Neutropenia | 2 (15.4) |

TABLE 14

Summary of Grade 3 or higher AEs from the NAPOLI-1 phase III study.

| | MM-398 + 5-FU/LV[1] (N = 117) | 5-FU/LV[2] (N = 134) |
|---|---|---|
| GRADE ≥ 3 NON-HEMATOLOGIC AEs IN > 5% PATIENTS, %[3] | % | % |
| Fatigue | 14 | 4 |
| Diarrhea | 13 | 5 |
| Vomiting | 11 | 3 |
| Nausea | 8 | 3 |
| Asthenia | 8 | 7 |
| Abdominal pain | 7 | 6 |
| Decreased appetite | 4 | 2 |
| Hypokalemia | 3 | 2 |
| Hypernatremia | 3 | 2 |
| GRADE 23 HEMATOLOGIC AES BASED ON LABORATORY VALUES, %[3,4] | | |
| Neutrophil count decreased | 20 | 2 |
| Hemoglobin decreased | 6 | 5 |
| Platelet count decreased | 2 | 0 |

[1]Dose: 80 mg/$m^2$ MM-398 + 2400 mg/$m^2$ over 46 h/400 mg/$m^2$ 5-FU/LV q2w
[2]Dose: 2000 mg/$m^2$ over 24 h/200 mg/$m^2$ 5-FU/LV weekly × 4, q6w
[3]Per CTCAE Version 4
[4]Includes only patients who had at least one post-baseline assessment

Example 9: Cell Survival for Various TNBC Cell Lines Following SN-38 and PARP Inhibitor Combination Treatment Tables 15a, 15b, 16a, and 16b provide the results of in vitro measurements of cell survival for various triple negative breast cancer (TNBC) cancer cell lines to determine the cell viability following treatment with SN-38 and/or a PARP inhibitor. Tables 15a and 15b provide IC50 data, and Tables 16a and 16b provide Maximum Kill data.

TABLE 15a

IC50 log10 (μM)

| Exp. | | Cell Line | | |
|---|---|---|---|---|
| 1 | Treatment | BT20 | SUM159PT | HCC38 |
| | SN38 | −0.18 | −2.35 | −2.80 |
| | Niraparib | 2.14 | 0.35 | 1.23 |
| | SN38 & Niraparib (3 ug/ml) | −0.67 | −3.99 | −0.12 |
| | SN38 & Niraparib (1 ug/ml) | −0.70 | −3.42 | −4.09 |
| | SN38 & Niraparib (0.3 ug/ml) | −0.71 | −2.85 | −4.23 |
| | SN38 & Niraparib (0.1 ug/ml) | −0.61 | −2.87 | −4.05 |
| Exp. | | Cell Line | | |
| 2 | Treatment | BT20 | SUM149PT | SUM159PT |
| | SN38 | −0.69 | 0.24 | −2.39 |
| | Olaparib | 1.24 | 2.40 | 0.18 |
| | SN38 & Olaparib (3 ug/ml) | −1.48 | −0.19 | −3.70 |
| | SN38 & Olaparib (1 ug/ml) | −1.49 | −0.34 | −3.31 |
| | SN38 & Olaparib (0.3 ug/ml) | −1.44 | −0.18 | −2.92 |
| | SN38 & Olaparib (0.1 ug/ml) | −1.29 | −0.11 | −2.92 |
| Exp. | | Cell Line | | |
| 3 | Treatment | BT20 | SUM149PT | SUM159PT |
| | SN38 | −0.37 | 0.27 | −2.66 |
| | Rucaparib | 1.27 | 1.68 | −0.07 |
| | SN38 & Rucaparib (3 ug/ml) | −1.33 | −0.16 | −3.64 |
| | SN38 & Rucaparib (1 ug/ml) | −1.47 | −0.23 | −3.28 |
| | SN38 & Rucaparib (0.3 ug/ml) | −1.48 | −0.49 | −3.23 |
| | SN38 & Rucaparib (0.1 ug/ml) | −1.24 | −0.10 | −3.11 |
| Exp. | | Cell Line | | |
| 4 | Treatment | BT20 | SUM159PT | HCC38 |
| | SN38 | −0.24 | −2.33 | −2.75 |
| | Talazoparib | 1.45 | −1.03 | −1.23 |
| | SN38 & Talazoparib (3 ug/ml) | −1.88 | −4.01 | −3.41 |
| | SN38 & Talazoparib (1 ug/ml) | −1.70 | −4.01 | −4.01 |
| | SN38 & Talazoparib (0.3 ug/ml) | −1.10 | −4.01 | −5.46 |
| | SN38 & Talazoparib (0.1 ug/ml) | −1.36 | −4.01 | −2.87 |

TABLE 15b

IC50 log10 (μM)

| | | Cell Line | | |
|---|---|---|---|---|
| Exp. 1 | Treatment | HCC1187 | HCC1806 | BT549 |
| | SN38 | −0.68 | −2.08 | −0.10 |
| | Niraparib | 2.11 | 1.27 | 2.03 |
| | SN38 & Niraparib (3 ug/ml) | −1.58 | −2.80 | −0.39 |
| | SN38 & Niraparib (1 ug/ml) | −1.45 | −2.62 | −0.64 |
| | SN38 & Niraparib (0.3 ug/ml) | −1.61 | −2.55 | −0.74 |
| | SN38 & Niraparib (0.1 ug/ml) | −1.41 | −2.52 | −0.55 |

TABLE 15b-continued

IC50 log10 (μM)

| Exp. 2 | Treatment | Cell Line HCC70 | HCC1187 | BT549 |
|---|---|---|---|---|
| | SN38 | −0.07 | −0.64 | −0.04 |
| | Olaparib | $-4.2 \times 10^{7}$ | 2.41 | 2.04 |
| | SN38 & Olaparib (3 ug/ml) | −0.58 | −1.77 | −0.55 |
| | SN38 & Olaparib (1 ug/ml) | −0.49 | −1.67 | −0.48 |
| | SN38 & Olaparib (0.3 ug/ml) | −0.50 | −1.35 | −0.35 |
| | SN38 & Olaparib (0.1 ug/ml) | −0.48 | −1.56 | −0.04 |

| Exp. 3 | Treatment | Cell Line HCC38 | HCC1954 | BT549 |
|---|---|---|---|---|
| | SN38 | −2.89 | −0.97 | −0.05 |
| | Rucaparib | −0.07 | 1.60 | 1.75 |
| | SN38 & Rucaparib (3 ug/ml) | 4.93 | −1.22 | −0.48 |
| | SN38 & Rucaparib (1 ug/ml) | −3.88 | −1.33 | −0.57 |
| | SN38 & Rucaparib (0.3 ug/ml) | −4.01 | −1.51 | −0.49 |
| | SN38 & Rucaparib (0.1 ug/ml) | −3.29 | −1.57 | −0.52 |

| Exp. 4 | Treatment | Cell Line HCC1187 | HCC1954 | SKBR3 |
|---|---|---|---|---|
| | SN38 | −0.98 | −0.65 | −1.38 |
| | Talazoparib | 2.28 | 3.64 | $-2.8 \times 10^{4}$ |
| | SN38 & Talazoparib (3 ug/ml) | −1.79 | −1.64 | −2.05 |
| | SN38 & Talazoparib (1 ug/ml) | −1.79 | −1.51 | −2.65 |
| | SN38 & Talazoparib (0.3 ug/ml) | −1.94 | −1.45 | −2.23 |
| | SN38 & Talazoparib (0.1 ug/ml) | −1.92 | −1.29 | −2.41 |

TABLE 16a

Maximum Kill Percent

| Exp. 1 | Treatment | Cell Line BT20 | SUM159PT | HCC38 |
|---|---|---|---|---|
| | SN38 | 100 | 97 | 96 |
| | Niraparib | 100 | 97 | 100 |
| | SN38 & Niraparib (3 ug/ml) | 100 | 100 | |
| | SN38 & Niraparib (1 ug/ml) | 100 | 100 | 93 |
| | SN38 & Niraparib (0.3 ug/ml) | 100 | 99 | 100 |
| | SN38 & Niraparib (0.1 ug/ml) | 100 | 100 | 100 |

| Exp. 2 | Treatment | Cell Line BT20 | SUM149PT | SUM159PT |
|---|---|---|---|---|
| | SN38 | 100 | 96 | 97 |
| | Olaparib | 98 | 100 | 94 |
| | SN38 & Olaparib (3 ug/ml) | 98 | 97 | 100 |
| | SN38 & Olaparib (1 ug/ml) | 99 | 96 | 97 |
| | SN38 & Olaparib (0.3 ug/ml) | 100 | 98 | 99 |
| | SN38 & Olaparib (0.1 ug/ml) | 100 | 96 | 99 |

| Exp. 3 | Treatment | Cell Line BT20 | SUM149PT | SUM159PT |
|---|---|---|---|---|
| | SN38 | 100 | 95 | 99 |
| | Rucaparib | 100 | 99 | 97 |
| | SN38 & Rucaparib (3 ug/ml) | 92 | 97 | 99 |
| | SN38 & Rucaparib (1 ug/ml) | 100 | 97 | 99 |
| | SN38 & Rucaparib (0.3 ug/ml) | 94 | 95 | 100 |
| | SN38 & Rucaparib (0.1 ug/ml) | 96 | 100 | 97 |

| Exp. 4 | Treatment | Cell Line BT20 | SUM159PT | HCC38 |
|---|---|---|---|---|
| | SN38 | 100 | 96 | 92 |
| | Talazoparib | 100 | 94 | 92 |
| | SN38 & Talazoparib (3 ug/ml) | 100 | | |

TABLE 16a-continued

Maximum Kill Percent

| | |
|---|---|
| SN38 & Talazoparib (1 ug/ml) | 90 |
| SN38 & Talazoparib (0.3 ug/ml) | 93 |
| SN38 & Talazoparib (0.1 ug/ml) | 93 |

TABLE 16b

Maximum Kill Percent

| Exp. 1 | Treatment | Cell Line HCC1187 | HCC1806 | BT549 |
|---|---|---|---|---|
| | SN38 | 90 | 93 | 95 |
| | Niraparib | 98 | 100 | 100 |
| | SN38 & Niraparib (3 ug/ml) | 89 | 91 | 94 |
| | SN38 & Niraparib (1 ug/ml) | 93 | 92 | 92 |
| | SN38 & Niraparib (0.3 ug/ml) | 89 | 92 | 92 |
| | SN38 & Niraparib (0.1 ug/ml) | 89 | 93 | 94 |

| Exp. 2 | Treatment | Cell Line HCC70 | HCC1187 | BT549 |
|---|---|---|---|---|
| | SN38 | 97 | 100 | 93 |
| | Olaparib | 50 | 87 | 100 |
| | SN38 & Olaparib (3 ug/ml) | 98 | 100 | |
| | SN38 & Olaparib (1 ug/ml) | 100 | 91 | 96 |
| | SN38 & Olaparib (0.3 ug/ml) | 100 | 99 | 94 |
| | SN38 & Olaparib (0.1 ug/ml) | 100 | 99 | 96 |

| Exp. 3 | Treatment | Cell Line HCC38 | HCC1954 | BT549 |
|---|---|---|---|---|
| | SN38 | 92 | 94 | 94 |
| | Rucaparib | 87 | 100 | 100 |
| | SN38 & Rucaparib (3 ug/ml) | | 96 | 93 |
| | SN38 & Rucaparib (1 ug/ml) | 98 | 94 | 92 |

TABLE 16b-continued

| Maximum Kill Percent | | | | |
|---|---|---|---|---|
| | SN38 & Rucaparib (0.3 ug/ml) | 98 | 95 | 93 |
| | SN38 & Rucaparib (0.1 ug/ml) | 97 | 93 | 94 |
| | | Cell Line | | |
| Exp. 4 | Treatment | HCC1187 | HCC1954 | SKBR3 |
| | SN38 | 88 | 100 | 88 |
| | Talazoparib | | 100 | |
| | SN38 & Talazoparib (3 ug/ml) | 89 | 93 | 90 |
| | SN38 & Talazoparib (1 ug/ml) | 89 | 94 | 89 |
| | SN38 & Talazoparib (0.3 ug/ml) | 89 | 94 | 100 |
| | SN38 & Talazoparib (0.1 ug/ml) | 100 | 96 | 87 |

Figure 3A:
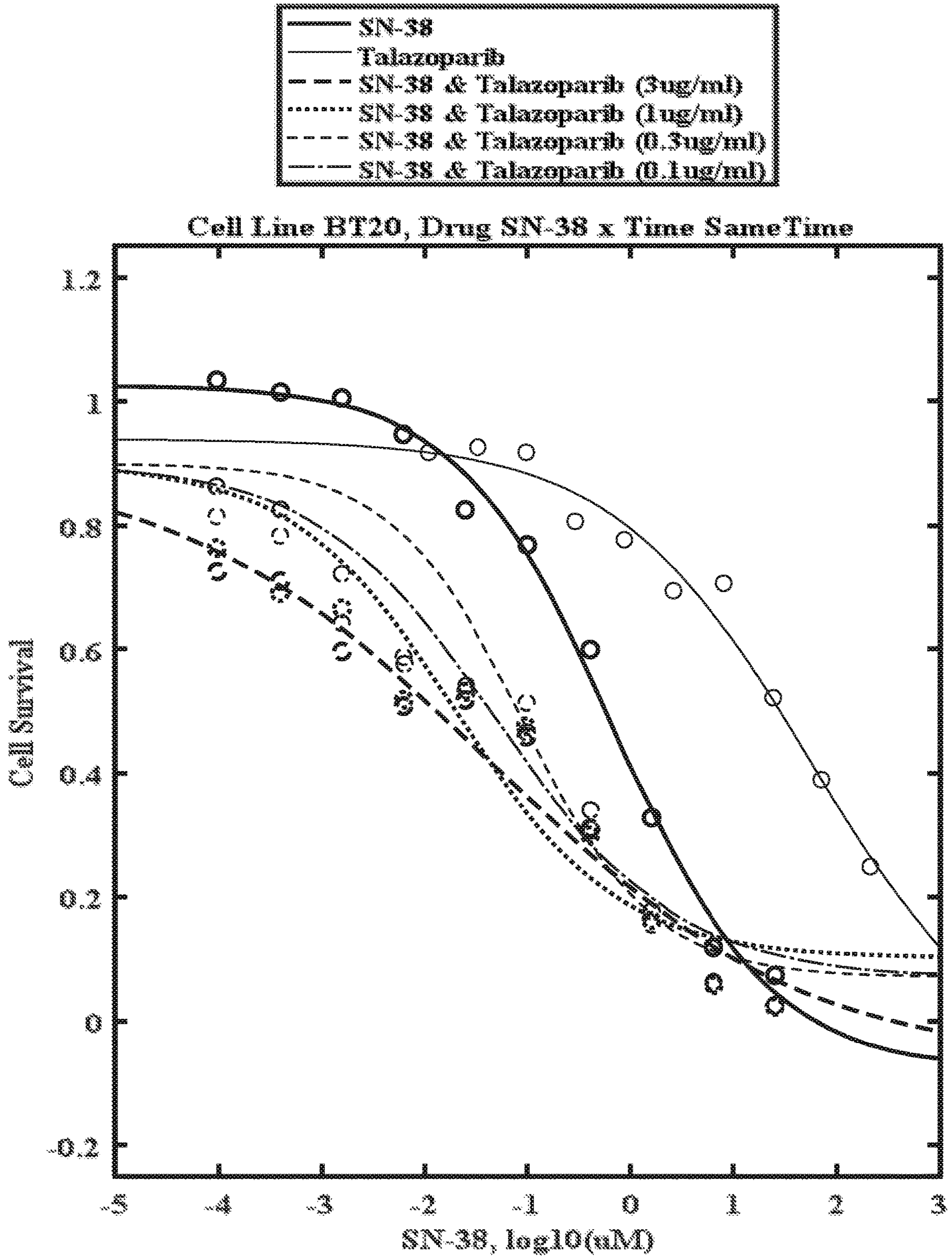
FIG. 3A is a graph showing the results of in vitro measurement of cell survival for BT-20 triple negative breast cancer (TNBC) cancer cells treated with the topoisomerase inhibitor SN-38 and the PARP inhibitor talazoparib.
Figure 3B:
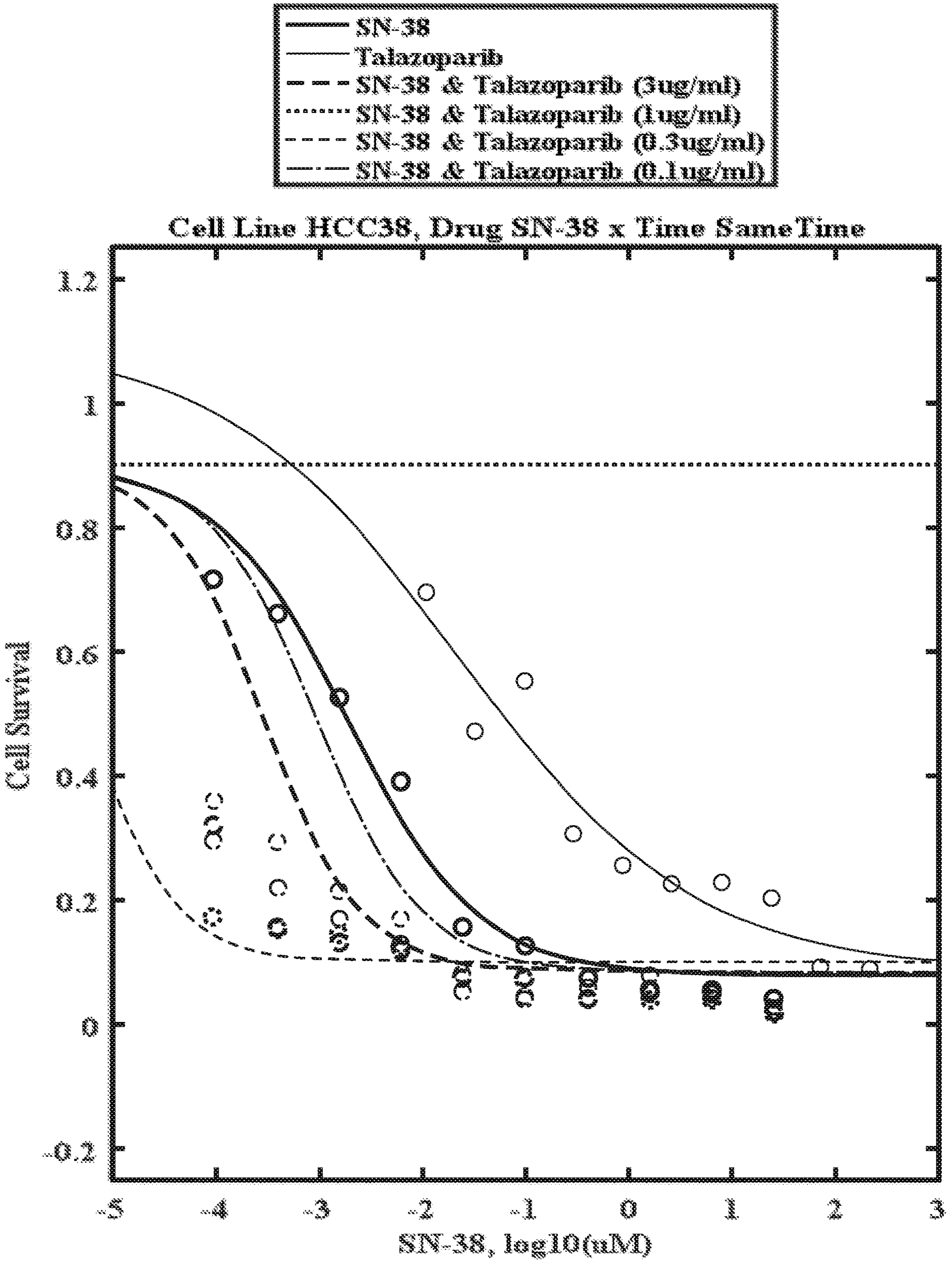
FIG. 3B is a graph showing the results of in vitro measurement of cell survival for HCC38 triple negative breast cancer (TNBC) cancer cells treated with the topoisomerase inhibitor SN-38 and the PARP inhibitor talazoparib.

The experiments that generated these data were performed in 384 well format. Cells were plated at 1000 cells/well and then incubated for 24 hours. Then SN-38 and/or one of four different PARP inhibitors (talazoparib niraparib, olaparib or rucaparib) was added and incubated for an additional 24 hours then the wells were washed with PBS to remove the drug and fresh media was added back into the wells. The plates were then allowed to incubate for 72 hours period. After the 72 hour incubation period the media was removed and cell viability was determined using the CellTiter-Glo® cell viability assay (Promega, Madison Wis.) according to the product instructions. FIGS. 3A and 3B are line graphs that depict cell viability in BT20 and HCC38 breast cancer cell lines, respectively, following treatment with SN-38 and/or talazoparib.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features set forth herein. The disclosure of each and every U.S., international or other patent or patent application or publication referred to herein is hereby incorporated herein by reference in its entirety.

The invention claimed is:

1. A method of treating a patient having a solid tumor, the method comprising:

i) administering to the patient liposomal irinotecan once every two weeks; and ii) administering a Poly(ADP-ribose) Polymerase (PARP) inhibitor daily for 3 to 10 days between consecutive administrations of the liposomal irinotecan wherein the PARP inhibitor is administered starting at least 2 days after the liposomal irinotecan and ending at least 1 day prior to the administration of additional liposomal irinotecan, wherein the patient has been diagnosed with small cell lung cancer.

2. The method of claim 1, wherein each administration of liposomal irinotecan is administered as a dose providing the equivalent of 70 $mg/m^2$ irinotecan free base.

3. The method of claim 1, wherein the PARP inhibitor is selected from the group consisting of niraparib, olaparib, veliparib, rucaparib and talazoparib.

4. The method according to claim 1, wherein the PARP inhibitor is administered on each of consecutive days 5 to 10.

5. The method of claim 4, wherein the PARP inhibitor is selected from the group consisting of niraparib, olaparib, veliparib, rucaparib and talazoparib.

6. A method of treating a patient with cancer and having a tumor, the method comprising:

i) administering to the patient an effective amount of liposomal irinotecan, wherein the liposomal irinotecan is a unilamellar lipid bilayer vesicle, which encapsulates irinotecan sucrosofate salt and the vesicle comprises 1,2-distearoyl-sn-glycero-3-phosphocholine, cholesterol, and methoxy-terminated polyethylene glycol (MW 2000)-distearoylphosphatidylethanolamine, at a weight ratio of 6.81 mg:2.22 mg:0.12 mg; and ii) administering to the patient an effective amount of a PARP inhibitor selected from the group consisting of niraparib, olaparib, veliparib, rucaparib and talazoparib, wherein the PARP inhibitor is administered after an effective irinotecan plasma clearing interval, wherein the patient has been diagnosed with small cell lung cancer.

7. The method of claim 6, wherein the effective irinotecan plasma clearing interval is from about 48 to about 120 hours.

8. The method of claim 6, wherein the effective irinotecan plasma clearing interval is 2, 3, 4 or 5 days.

9. The method of claim 6, wherein the effective amount of liposomal irinotecan is a dose providing the equivalent of 70 $mg/m^2$ irinotecan free base administered during a 90 minute infusion.

10. The method of claim 6, wherein each administration of the PARP inhibitor is administered at a dose of from about 20 mg/day to about 800 mg/day.

11. A method of treating a patient diagnosed with small cell lung cancer and having a solid tumor, the method comprising administering to the patient an antineoplastic therapy in a 28-day treatment cycle, the antineoplastic therapy consisting of:

i) intravenously administering to the patient an effective amount of a liposomal irinotecan only on days 1 and 15 of the treatment cycle, the liposomal irinotecan having an irinotecan terminal elimination half-life of about 26.8 hours and a maximal irinotecan plasma concentration of about 38.0 micrograms/ml; and ii) administering an effective amount of a PARP inhibitor to the patient on days 5-12 and 19-25 or 3-12 and 17-25 of the treatment cycle.

12. The method of claim 11, wherein the PARP inhibitor is selected from the group consisting of niraparib, olaparib, veliparib, rucaparib and talazoparib.

13. The method of claim 11, wherein the therapeutically effective amount of the liposomal irinotecan is a dose providing the equivalent of 70 $mg/m^2$ irinotecan free base administered during a 90 minute infusion.

14. The method of claim 11, further comprising administering one or more subsequent 28-day treatment cycles of the antineoplastic therapy to the patient in the absence of disease progression or unacceptable toxicity during the prior treatment cycle of the antineoplastic therapy.

15. The method of claim 11, wherein each administration of the PARP inhibitor is administered at a dose of from about 20 mg/day to about 800 mg/day.

* * * * *